(12) United States Patent
Morgan et al.

(10) Patent No.: US 12,187,712 B2
(45) Date of Patent: Jan. 7, 2025

(54) CARDIAC SARCOMERE INHIBITORS

(71) Applicant: Cytokinetics, Inc., South San Francisco, CA (US)

(72) Inventors: Bradley P. Morgan, South San Francisco, CA (US); Mark Vanderwal, Oakland, CA (US); Chihyuan Chuang, Millbrae, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 945 days.

(21) Appl. No.: 17/255,379

(22) PCT Filed: Jun. 25, 2019

(86) PCT No.: PCT/US2019/038908
§ 371 (c)(1),
(2) Date: Jul. 15, 2021

(87) PCT Pub. No.: WO2020/005888
PCT Pub. Date: Jan. 2, 2020

(65) Prior Publication Data
US 2021/0276991 A1    Sep. 9, 2021

Related U.S. Application Data

(60) Provisional application No. 62/690,249, filed on Jun. 26, 2018.

(51) Int. Cl.
C07D 413/14    (2006.01)
C07D 271/06    (2006.01)
C07D 413/12    (2006.01)

(52) U.S. Cl.
CPC ......... *C07D 413/14* (2013.01); *C07D 271/06* (2013.01); *C07D 413/12* (2013.01)

(58) Field of Classification Search
CPC ... C07D 413/14; C07D 413/12; C07D 271/06
See application file for complete search history.

(56) References Cited

U.S. PATENT DOCUMENTS

| | | |
|---|---|---|
| 5,846,514 A | 12/1998 | Foster |
| 5,919,785 A | 7/1999 | Dinsmore |
| 6,334,997 B1 | 1/2002 | Foster |
| 8,592,426 B2 | 11/2013 | Aebi et al. |
| 9,181,200 B2 | 11/2015 | Oslob |
| 9,199,945 B2 | 12/2015 | Oslob |
| 9,663,516 B2 | 5/2017 | Oslob |
| 9,925,177 B2 | 3/2018 | Oslob |
| 10,836,755 B2 | 11/2020 | Chuang et al. |
| 11,414,424 B2 | 8/2022 | Chuang et al. |
| 11,472,796 B2 | 10/2022 | Chuang et al. |
| 11,919,909 B2 | 3/2024 | Morgan |
| 2005/0014749 A1 | 1/2005 | Chen et al. |
| 2006/0173183 A1 | 8/2006 | Powers |
| 2006/0241110 A1 | 10/2006 | Morgan |
| 2007/0078126 A1 | 4/2007 | Morgan et al. |
| 2009/0192168 A1 | 7/2009 | Muci et al. |
| 2011/0275673 A1 | 11/2011 | Xiang et al. |
| 2013/0018055 A1 | 1/2013 | Aebi et al. |
| 2013/0296335 A1 | 11/2013 | Morgan et al. |
| 2016/0176868 A1 | 6/2016 | Oslob et al. |
| 2016/0289211 A1 * | 10/2016 | Ashcraft ............ C07D 417/06 |
| 2019/0256504 A1 | 8/2019 | Chuang |
| 2019/0276435 A1 | 9/2019 | Shepard et al. |
| 2020/0000822 A1 | 1/2020 | Kruse et al. |
| 2020/0048235 A1 | 2/2020 | Zhang et al. |
| 2020/0054636 A1 | 2/2020 | Semigran et al. |
| 2020/0109148 A1 | 4/2020 | Chuang |
| 2021/0147399 A1 | 5/2021 | Chuang et al. |

(Continued)

FOREIGN PATENT DOCUMENTS

| | | |
|---|---|---|
| WO | 2003059265 A2 | 7/2003 |
| WO | 2003059265 A3 | 6/2004 |

(Continued)

OTHER PUBLICATIONS

Anonymous (2022). "Empowering Muscle Empowering Lives: Sarcomere Directed Therapies," Cytokinetics, 57 pages.
CAS (Nov. 12, 2007). "STN Registry Database entry for CAS RN 953060-71-4," entry date of Nov. 12, 2007, accessed Jul. 15, 2021, 5 pages.
CAS Registry No. 1384080-08-3. (Jul. 23, 2012). "1,2,4-Oxadiazole-5-carboxylic acid, 3-[4-[(acetylamino)methyl] phenyl]-,methyl ester," 3 pages.
CAS Registry No. 1384080-74-3. (Jul. 23, 2012). "1,2,4-Oxadiazole-5-carboxylic acid, 3-[4-[(acetylamino)methyl] phenyl]-,ethyl ester," 2 Pages.

(Continued)

*Primary Examiner* — Timothy R Rozof
(74) *Attorney, Agent, or Firm* — MORRISON & FOERSTER LLP

(57) ABSTRACT

Provided are compounds of Formula (I):

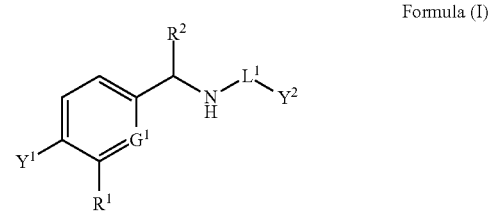

Formula (I)

or a pharmaceutically acceptable salt thereof, wherein $R^1$, $R^2$, $Y^1$, $Y^2$, $L^1$, and $G^1$ are as defined herein. Also provided is a pharmaceutically acceptable composition comprising a compound of Formula (I), or a pharmaceutically acceptable salt thereof. Also provided are methods of using a compound of Formula (I), or a pharmaceutically acceptable salt thereof.

39 Claims, No Drawings

(56) References Cited

U.S. PATENT DOCUMENTS

| | | | |
|---|---|---|---|
| 2021/0253563 | A1 | 8/2021 | Morgan et al. |
| 2021/0323913 | A1 | 10/2021 | Martin et al. |
| 2022/0265612 | A1 | 8/2022 | Qiao |
| 2022/0274969 | A1 | 9/2022 | Tom et al. |
| 2022/0306642 | A1 | 9/2022 | Morgan et al. |
| 2022/0315571 | A1 | 10/2022 | Tom et al. |
| 2023/0045540 | A1 | 2/2023 | Mchugh et al. |
| 2023/0058927 | A1 | 2/2023 | Malik et al. |
| 2023/0119665 | A1 | 4/2023 | Chuang et al. |
| 2023/0338378 | A1 | 10/2023 | Perera et al. |

FOREIGN PATENT DOCUMENTS

| | | | |
|---|---|---|---|
| WO | 2004064730 | A2 | 8/2004 |
| WO | 2004064760 | A2 | 8/2004 |
| WO | 2006009726 | A2 | 1/2006 |
| WO | 2006116150 | A1 | 11/2006 |
| WO | 2007078815 | A2 | 7/2007 |
| WO | 2007117180 | A1 | 10/2007 |
| WO | 2008130320 | A2 | 10/2008 |
| WO | 2008130320 | A3 | 12/2008 |
| WO | 2010033701 | A2 | 3/2010 |
| WO | 2010130796 | A1 | 11/2010 |
| WO | 2012101011 | A2 | 8/2012 |
| WO | 2013048928 | A1 | 4/2013 |
| WO | 2013108227 | A1 | 7/2013 |
| WO | 2014205223 | A1 | 12/2014 |
| WO | 2014205234 | A1 | 12/2014 |
| WO | 2015089337 | A1 | 6/2015 |
| WO | 2017055469 | A1 | 4/2017 |
| WO | 2017103219 | A1 | 6/2017 |
| WO | 2017103223 | A1 | 6/2017 |
| WO | 2017222951 | A1 | 12/2017 |
| WO | 2018063955 | A1 | 4/2018 |
| WO | 2018089433 | A1 | 5/2018 |
| WO | 2018117034 | A1 | 6/2018 |
| WO | 2019144041 | A1 | 7/2019 |
| WO | 2019182925 | A1 | 9/2019 |
| WO | 2019226213 | A2 | 11/2019 |
| WO | 2019226213 | A3 | 1/2020 |
| WO | 2020005887 | A1 | 1/2020 |
| WO | 2020005888 | A1 | 1/2020 |
| WO | 2020047323 | A1 | 3/2020 |
| WO | 2020047447 | A1 | 3/2020 |
| WO | 2022047004 | A1 | 3/2022 |

OTHER PUBLICATIONS

CAS Registry No. 1826330-24-8 (Dec. 10, 2015). "2-Pyridinamine, 5-Methyl-N-[[4-[3-(Trifluoromethyl)-1H-Pyrazol-1-yl]Phenyl]Methyl]—," 1 page.

CAS Registry No. 1826379-58-1 (Dec. 10, 2015). "2-Pyridinamine, 4-Methyl-N-[[4-[3-(Trifluoromethyl)-1H-Pyrazol-1-yl]Phenyl]Methyl]—," 1 page.

CAS Registry No. 1829209-70-2 (Dec. 14, 2015). "2-Pyridinamine, 3-Methyl-N-[[4-[3-(Trifluoromethyl)-1H-Pyrazol-1-yl]Phenyl]Methyl]—," 1 page.

CAS Registry No. 1829877-40-8. (Dec. 15, 2015). "2-Pyridinamine, 6-Methyl-N-[[4-[3-(Trifluoromethyl)-1H-Pyrazol-1-yl]Phenyl]Methyl]—," 1 page.

CAS Registry No. 2093706-41-1. (Apr. 30, 2017). "2-Pyrazinecarbonitrile, 5-[[[4-[3-(Trifluoromethyl)-1H-Pyrazol-1-yl] Phenyl]Methyl]Amino]—," Enamine LLC, 1 page.

Examination Report mailed on Aug. 17, 2023, for European Patent Application No. 19703917. 5 pages.

International Preliminary Report on Patentability mailed Jan. 27, 2022, for Patent Application No. PCT/US2020/042387, filed Jul. 16, 2020, 8 pages.

International Preliminary Report on Patentability mailed Jan. 27, 2022, for Patent Application No. PCT/US2020/042389, filed Jul. 16, 2020, 8 pages.

International Preliminary Report on Patentability mailed Jan. 27, 2022, for Patent Application No. PCT/US2020/042390, filed Jul. 16, 2020, 8 pages.

International Search Report and Written Opinion of the International Searching Authority mailed on May 17, 2022, for PCT Patent Application No. PCT/US2022/018725, filed on Mar. 3, 2022, 12 pages.

Martin, R. et al. (2009). "Total Synthesis of Pentabromo- and Pentachloropseudilin, and Synthetic Analogues—Allosteric Inhibitors of Myosin ATPase," Angew Chem Int Ed Engl. 48(43):8042-8046.

U.S. Appl. No. 18/355,195, filed Jul. 19, 2023, for Stephen B. Heitner et al.

U.S. Appl. No. 18/365,038, filed Aug. 3, 2023, for Malik Fady et al.

Berge, S.M. et al. (Jan. 1977). "Pharmaceuticals Salts," J. Pharmaceutical Sciences 66:1-19.

Caputo, S. et al. (Nov. 28, 2017). "Diversity-Oriented Synthesis of Various Enantiopure Heterocycles by Coupling Organocatalysis with Multicomponent Reactions," European J. of Chem. 2017(45):6619-6628.

CAS (Dec. 5, 2011). "STN Registry Database Entry for CAS RN 1348860-91-2," accessed Feb. 13, 2021, 1 page.

Dahl, L.K. et al. (Jun. 1, 1962). "Effects of Chronic Excess Salt Ingestion Evidence That Genetic Factors Play an Important Role in Susceptibility to Experimental Hypertension," J Exp Med. 115(6):1173-1190.

Database Registry (Jun. 18, 2008). RN-1028938-65-9 Emory MLSC database: "2, 5-Piperazinediones, 4-[(4-chlorophenyl)methyl]-3-(4-methoxyphenyl)-1-(2-phenylethyl)—," Chemical Abstracts Service, 1 page.

Database Registry (Jun. 24, 2008). RN-1030378-92-7 Emory MLSC database: "1-Piperazineacetamide, 3-(2-fluorophenyl)-N-(2-methylcyclohexyl)-4-[(4-methylphenyl)methyl]-2,5-dioxo," Chemical Abstracts Service, 1 page.

Database Registry (Nov. 4, 2011). RN-1340679-26-6 ChemDiv, Inc.: "2, 5-Piperazinedione, 1-(-3_methylbutyl)-4-(phenylmethyl)-3-(3-pyridinyl)," Chemical Abstracts Service, 3 pages.

Dean, D.C. (2000). "Recent Advances in the Synthesis and Applications of Radiolabeled Compounds for the Drug Discovery and Development," Curr. Pharm. Des. 6(10): Preface Only, 1 page.

Evans, A.E. (Mar. 1981, e-pub. Jan. 9, 2007). "Synthesis of Radiolabeled Compounds," J Radio Anal. Chem. 64(1-2):9-32.

Fillmore, N. et al. (2018). "Uncoupling of Glycolysis from Glucose Oxidation Accompanies the Development of Heart Failure with Preserved Ejection Fraction," Mol. Med. 24(3):1-12.

Geisterfer-Lowrance, A.A.T. et al. (May 3, 1996). "A Mouse Model of Familial Hypertrophic Cardiomyopathy," Science 272(5262):731-734.

Green, E. M. et al. (Feb. 5, 2016). "A Small-Molecule Inhibitor of Sarcomere Contractility Suppresses Hypertrophic Cardiomyopathy in Mice," Science 351(6273):617-621.

Guazzi, M. et al. (Sep. 26, 2017). "Cardiopulmonary Exercise Testing: What is its Value?," J. Am. Coll. Cardiol. 70(13):1618-1636.

Hargrave, J.D. et al. (Nov. 21, 2010, e-pub. Sep. 8, 2010). "Rhodium-Catalysed Conjugate Addition of Arylboronic Acids to Enantiopure Dehydroamino Acid Derivatives," Org. Biomol. Chem. 8(22):5120-5125.

Hartung, A. et al. (Dec. 11, 2012). "One-Pot Ugi/Aza-Michael Synthesis of Highly Substituted 2,5-Diketopiperazines with Anti-Proliferative Properties," Molecules Online 17(12):14685-14699.

International Preliminary Report on Patentability mailed Jan. 7, 2021, for Patent Application No. PCT/US2019/038907, filed Jun. 25, 2019, 7 pages.

International Preliminary Report on Patentability mailed Jan. 7, 2021, for Patent Application No. PCT/US2019/038908, filed Jun. 25, 2019, 8 pages.

International Preliminary Report on Patentability mailed Jul. 30, 2020, for Patent Application No. PCT/US2019/014344, filed Jan. 18, 2019, 11 pages.

(56) References Cited

OTHER PUBLICATIONS

International Search Report and Written Opinion of the International Searching Authority mailed Aug. 28, 2019, for PCT Patent Application No. PCT/US2019/038907, filed Jun. 25, 2019, 12 pages.
International Search Report and Written Opinion of the International Searching Authority mailed Aug. 28, 2019, for PCT Patent Application No. PCT/US2019/038908, filed Jun. 25, 2019, 14 pages.
International Search Report and Written Opinion of the International Searching Authority mailed May 20, 2019, for PCT Patent Application No. PCT/US2019/014344, filed Jan. 18, 2019, 19 pages.
International Search Report and Written Opinion of the International Searching Authority mailed Nov. 10, 2020, for PCT Patent Application No. PCT/US2020/042387, filed Jul. 16, 2020, 13 pages.
International Search Report and Written Opinion of the International Searching Authority mailed Nov. 5, 2020, for PCT Patent Application No. PCT/US2020/042389, filed Jul. 16, 2020, 13 pages.
International Search Report and Written Opinion of the International Searching Authority mailed Nov. 6, 2020, for PCT Patent Application No. PCT/US2020/042390, filed Jul. 16, 2020, 14 pages.
Invitation to Pay Additional Fees mailed Mar. 28, 2019, for PCT Patent Application No. PCT/US2019/014344, filed Jan. 18, 2019, 14 pages.
Ito, N. (Jan. 2003). "A Medium-Term Rat Liver Bioassay for Rapid In Vivo Detection of Carcinogenic Potential of Chemicals," Cancer Science 94(1):3-8.
Jackson, P. et al. (Aug. 22, 2018). "Appendage and Scaffold Diverse Fully Functionalized Small-Molecule Probes via a Minimalist Terminal Alkyne-Aliphatic Diazirine Isocyanide," J. Org. Chem. 83(18):11245-11253.
Jiang, J. et al. (Oct. 4, 2013, e-pub. Jul. 14, 2014). "Allele-Specific Silencing of Mutant Myh6 Allele in Mice Suppresses Hypertrophic Cardiomyopathy," Science 342(6154):111-114, 11 pages.
Kabalka, G.W. et al. (1989). "The Synthesis of Radiolabeled Compounds via Organometallic Intermediates," Tetrahedron 45(21):6601-6621.
Kaim, L.E. et al. (2007, e-pub. Jan. 24, 2007). "New Indolizine Template from the Ugi Reaction," Synlett 2(1):227-230.
Kim-Mitsuyama, S. et al. (Oct. 2004). "Additive Beneficial Effects of the Combination of a Calcium Channel Blocker and an Angiotensin Blocker on a Hypertensive Rat-Heart Failure Model," Hypertens Res. 27(10):771-779.
Lee, M. et al. (May 25, 2016). "Convenient asymmetric synthesis of 1,3,4,6-tetrasubstituted 2,5-diketopiperazines," Arkivoc 2016(4):100-113.
Lee, M. et al. (May 19, 2016). "Stereoselective Nucleophile Substitution of [alpha]-Bromo Tertiary Amides for Asymmetric Synthesis of Highly Substituted 2,5-Diketopiperazines," Bull. Korean Chem. Soc. 37(6):981-984.
Lesma, G. et al. (Jun. 18, 2014). "Asymmetric Ugi 3CR on isatin-derived ketimine: synthesis of chiral 3,3-disubstituted 3-aminooxindole derivatives," Beilstein Journal of Organic Chemistry 10:1383-1389.
Malhotra, R. et al. (Aug. 2016, e-pub. Jun. 8, 2016). "Cardiopulmonary Exercise Testing in Heart Failure," JACC Heart Fail 4(8):607-616.
Mamoun, O. et al. (1995, e-pub. Sep. 23, 2006). "Synthesis of Methyl 3-Amino-3-pyrrolidinecarboxylates: A Convenient Access to Cucurbitine and Analogues," Synthetic Communications 25(9):1295-1302.

Parker, M.F.L. et al. (Jan. 23, 2014). "Acceleration of an Aromatic Claisen Rearrangement Via a Designed Spiroligozyme Catalyst that Mimics the Ketosteroid Isomerase Catalytic Dyad," J. American Chem. Soc. 136(10):3817-3827.
Pettersson, M. et al. (Oct. 1, 2015). "Design, Synthesis and Evaluation of 2,5-Diketopiperazines as Inhibitors of the MDM2-p53 Interaction," PLOS One 10(10):e0137867, 19 pages.
Philipson, D. J. et al. (2017, e-pub. Aug. 31, 2017). "Emerging Pharmacologic and Structural Therapies for Hypertrophic Cardiomyopathy," Heart Fail Rev. 22(6):879-888.
Pyne, S.G. et al. (1993). "Asymmetric Synthesis of Chiral Cyclic Amino Acids by Diels-Alder Reactions of (2S)- and (2R)-4-Methyleneoxazolidin-5-ones," Aust. J Chem. 46(1):73-93.
Rowin, E.J. et al. (Nov. 2017). "Role of Exercise Testing in Hypertrophic Cardiomyopathy," JACC: Cariovasc Imaging. 10(11):1374-1386.
Sakata, Y. et al. (Jan. 2001). "Renin Angiotensin System-Dependent Hypertrophy as a Contributor to Heart Failure in Hypertensive Rats: Different Characteristics From Renin Angiotensin System-Independent Hypertrophy," J. Am. Coll. Cardiol. 37(1):293-299.
Santra, S. et al. (Apr. 1, 2011, e-pub. Feb. 25, 2011). "A Rapid, One-Pot, Microwave-Influenced Synthesis of Spiro-2,5-diketopiperazines via a Cascade Ugi/6-Exo-Trig Aza-Michael Reaction," Journal of Organic Chemistry 76(7):2261-2264.
Taub, P.R. et al. (Oct. 1, 2013). "Perturbations in Skeletal Muscle Sarcomere Structure in Patients with Heart Failure and Type 2 Diabetes: Restorative Effects of (−)-epicatechin-rich Cocoa," Clinical Science 125(8):383-389.
U.S. Appl. No. 17/013,472, filed Sep. 4, 2020, by Chuang Chihyuan et al.
U.S. Appl. No. 17/255,336, filed Jun. 25, 2019, by Bradley Morgan et al.
Walvoord, R.R. et al. (Nov. 4, 2014). "Quantification of Electrophilic Activation by Hydrogen-Bonding Organocatalysts", J. American Chem. Soc. 136(45):16055-16065.
Williams, R. et al. (Nov. 3, 1992). "Asymmetric synthesis of S-(−)-Cucurbitine," Tetrahedron Letters 33(45):6755-6758.
Williams, R.M. et al. (Nov. 1982). "A New and Efficient Cyclization Reaction to Construct the Bicyclomycin Ring System: Synthesis of N,N'-Dimethyl-4-desmethylenebicyclomycin," Journal of the American Chemical Society 104(22):6092-6099.
Yates, P. et al. (Jan. 1, 1983). "Synthesis of Piperazine-2,5-diones Related to Bicyclomycin: 3-acetoxy-1,4-dibenzyl-3-[1-(2-methoxyethyl)-and 1-(2-hydroxyethyl)ethenyl]piperazine-2,5-dione. 1. Route Via Acyclic Intermediates," Canadian Journal of Chemistry 61(3):519-528.
Yoshifuji, S. et al. (Aug. 1995). "Stereospecific Synthesis of (R)- and (S)-Baclofen and (R)- and (S)-PCPGABA [4-Amino-2-(4-chlorophenyl)butyric Acid] via (R)- and (S)-3-(4-Chlorophenyl)pyrrolidines," Chem Pharm Bull 42(8) 1302-1306.
CAS Registry No. 1279871-13-4. (Apr. 14, 2011). "Carbamic acid, N-(3,4-dihydro-7-phenyl-2H-1-benzopyran-4-yl)-, 1, 1-dimethylethyl ester," 2 pages.
CAS Registry No. 2649643-74-1. (Jul. 6, 2021). "1H-Pyrrole-3-carboxamide, N-[(1S)-2,3-dihydro-5-phenyl-1H-inden-1- yl]-1-ethyl-2,5-dihydro-4-hydroxy-5-oxo-," 3 pages.
Chuang, C et al. (Oct. 4, 2021). "Discovery of Aficamten (CK-274), A Next Generation Cardiac Myosin Inhibitor for the Treatment of Hypertrophic Cardiomyopathy," Journal of Medicinal Chemistry 64(19): 14142-14152.

* cited by examiner

CARDIAC SARCOMERE INHIBITORS

CROSS REFERENCE TO RELATED APPLICATIONS

This application is a national stage application under 35 U.S.C. § 371 of International Application No. PCT/US2019/038908, filed internationally on Jun. 25, 2019, which claims priority to U.S. Provisional Application No. 62/690,249, filed Jun. 26, 2018, entitled "CARDIAC SARCOMERE INHIBITORS," the contents of which are hereby incorporated by reference in their entirety for all purposes.

FIELD

Provided herein are heterocyclic compounds, pharmaceutical compositions comprising such compounds, and methods of treating various cardiac diseases and conditions with such compounds.

BACKGROUND

The disclosure relates to certain chemical entities that selectively modulate the cardiac sarcomere, and specifically to certain chemical entities, pharmaceutical compositions and methods for treating various cardiac diseases and conditions.

The cardiac sarcomere is composed of a network of contractile and structural proteins that regulate cardiac muscle function. The components of the cardiac sarcomere present targets for the treatment of various cardiac diseases and conditions, for example by increasing contractility or facilitating complete relaxation to modulate systolic and diastolic function, respectively. The force and speed of cardiac muscle contraction is a major determinant of organ function and is modulated by the cyclical interactions of actin and myosin. Regulation of actin and myosin binding is determined by a network of myofilament regulatory proteins and the level of intracellular $Ca^{2+}$. The troponin complex and tropomyosin are thin filament proteins which govern the availability of actin binding sites, and the essential and regulatory light chains, and myosin binding protein C modulate the position and mechanical properties of myosin.

Abnormalities in the cardiac sarcomere have been identified as the driving cause for a variety of cardiac diseases and conditions, such as hypertrophic cardiomyopathy (HCM) and heart failure with preserved ejection fraction (HFpEF). Mutations in the proteins of the sarcomere cause disease by rendering the cardiac muscle either 'hyper' or 'hypo' contractile. Modulators of the cardiac sarcomere can be used to rebalance contractility and stop or reverse the course of disease.

Current agents that target the cardiac sarcomere, such as inotropes (drugs that increase the contractile ability of the heart) are poorly selective for cardiac tissue, which leads to recognized adverse effects that limit their use. These adverse effects include cell damage caused by an increased rate of energy expenditure, exacerbation of relaxation abnormalities, and potential arrhythmogenic side effects that may result from increased cytosolic $Ca^{2+}$ and cyclic AMP concentrations in the inotropically stimulated myocardium. Given the limitations of current agents, new approaches are needed to improve cardiac function in HCM and HFpEF.

There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes. The selectivity of agents directed at the cardiac sarcomere (for example, by targeting cardiac myosin) has been identified as an important means to achieve this improved therapeutic index. The present disclosure provides such agents (particularly cardiac sarcomere inhibitors) and methods for their use. These agents are selective allosteric inhibitors of cardiac myosin that have little to no effect on smooth muscle myosin. Benefits of these compounds include a wider therapeutic index, less impact on cardiac relaxation, better pharmacokinetics, and better safety.

The present disclosure provides chemical entities, pharmaceutical compositions and methods for the treatment of heart failure including HCM and HFpEF. The compositions are inhibitors of the cardiac sarcomere, for example, inhibitors of cardiac myosin.

BRIEF SUMMARY

In one aspect, provided is a compound of Formula (I), or a pharmaceutically acceptable salt thereof:

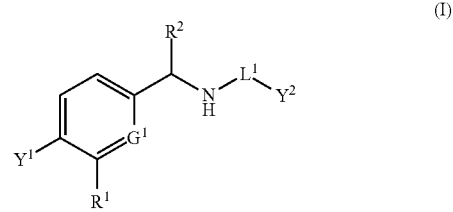

or a pharmaceutically acceptable salt thereof, wherein:
  $R^1$ is H or halo;
  $G^1$ is —N— or —C($R^b$)—, wherein $R^b$ is H or halo, or $R^b$ is taken together with $R^2$ and the atoms to which they are attached to form a 5- or 6-membered cycloalkyl or heterocycloalkyl ring;
  $R^2$ is H or —CH$_3$, or $R^2$ is taken together with $R^b$ and the atoms to which they are attached to form a 5- or 6-membered cycloalkyl or heterocycloalkyl ring;
  $L^1$, $Y^1$, and $Y^2$ are defined by (i) or (ii):
  (i) $L^1$ is absent;
    $Y^1$ is $R^x$; and
    $Y^2$ is $R^z$;
  or
  (ii) $L^1$ is

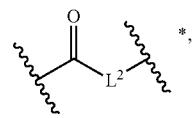

wherein $L^2$ is absent, —O—, —NH—, or —OCH$_2$—*, and wherein * indicates the attachment to $Y^2$
  $Y^1$ is

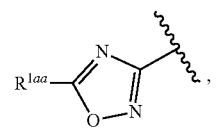

wherein R$^{1aa}$ is H, alkyl, cycloalkyl, cycloalkenyl, heterocycloalkyl, heterocycloalkenyl, aryl, or heteroaryl; and Y$^2$ is —CH$_3$, phenyl, or R$^z$;

R$^x$ is

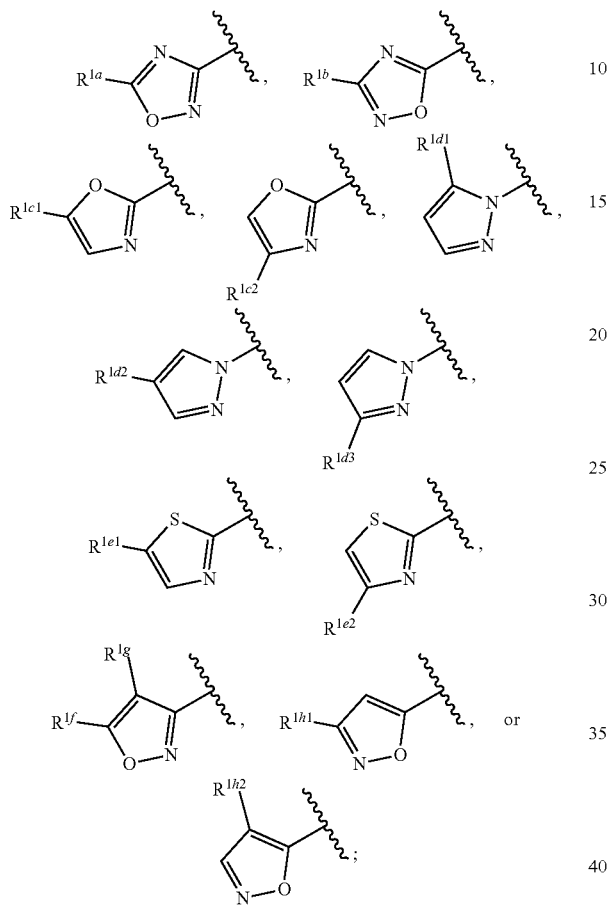

R$^{1a}$, R$^{1b}$, R$^{1c1}$, R$^{1c2}$, R$^{1f}$, R$^{1g}$, R$^{1h1}$, and R$^{1h2}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl;

R$^{1d1}$, R$^{1d2}$, and R$^{1d3}$ are each independently alkyl, alkenyl, alkynyl, haloalkyl, —C(O)O— alkyl, cycloalkyl, cycloalkenyl, cycloalkynyl, heterocycloalkyl, heterocycloalkenyl, aryl, or heteroaryl;

R$^{1e1}$ and R$^{1e2}$ are each independently H, alkyl, alkenyl, alkynyl, haloalkyl, —C(O)O— alkyl, or a cycloalkyl, cycloalkenyl, cycloalkynyl, heterocycloalkyl, heterocycloalkenyl, or heteroaryl ring;

R$^z$ is

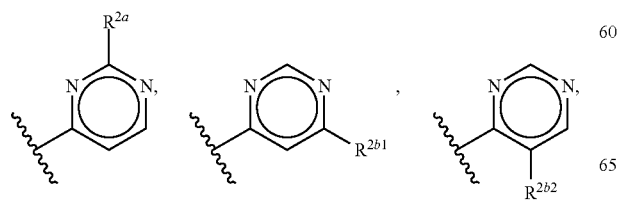

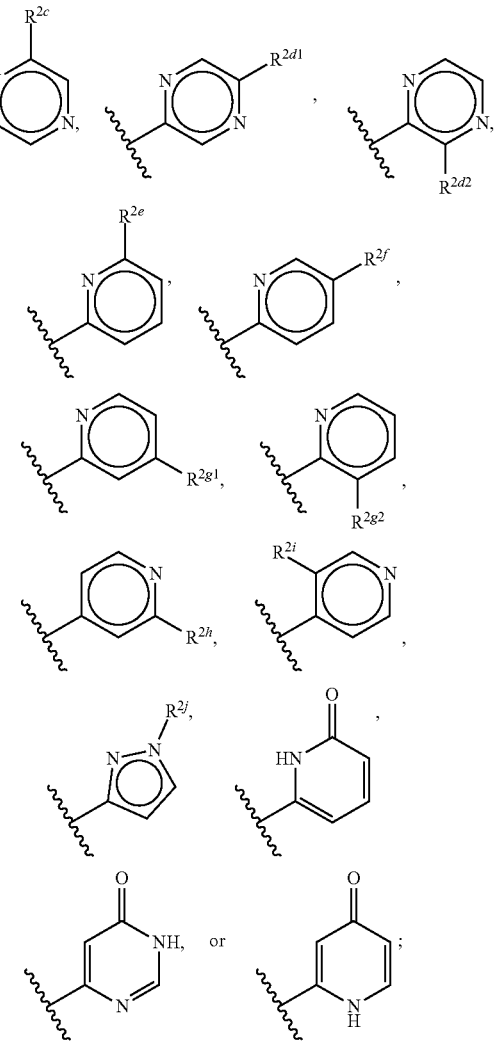

R$^{2a}$, R$^{2b1}$, R$^{2b2}$, R$^{2c}$, R$^{2d1}$, R$^{2d2}$, R$^{2h}$, R$^{2i}$, and R$^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$;

R$^{2e}$, R$^{2f}$, R$^{2g1}$, and R$^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and R$^c$ and R$^d$ are each independently H or alkyl;

wherein, when Y$^1$ is

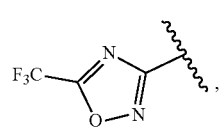

at least one of (a)-(c) applies:

(a) R$^2$ is —CH$_3$;

(b) R$^1$ is halo; and (c) G$^1$ is —C(R$^b$)—, wherein R$^b$ is halo; and when Y¹ is

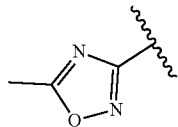 [SMILES: *c1noc(C)n1]

and Y² is

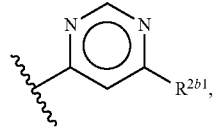

$R^{2b1}$ is selected from the group consisting of H, halo, —OH, —CN, —NR$^c$R$^d$, alkyl, alkenyl, alkynyl, —O—C$_2$-C$_6$alkyl, haloalkyl, cycloalkyl, and —C(O)NR$^c$R$^d$.

In some embodiments, the compound of Formula (I) is a compound of Formula (Ia):

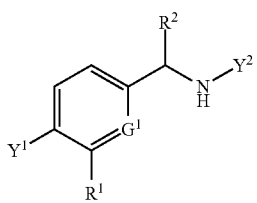

(Ia)

or a pharmaceutically acceptable salt thereof, wherein:
  $R^1$ is H or halo;
  $G^1$ is —N— or —C(R$^b$)—, wherein R$^b$ is H or halo, or R$^b$ is taken together with R$^2$ and the atoms to which they are attached to form a 5- or 6-membered cycloalkyl or heterocycloalkyl ring;
  $R^2$ is H or —CH$_3$, or R$^2$ is taken together with R$^b$ and the atoms to which they are attached to form a 5- or 6-membered cycloalkyl or heterocycloalkyl ring;
  $Y^1$ is R$^x$;
  $R^x$ is

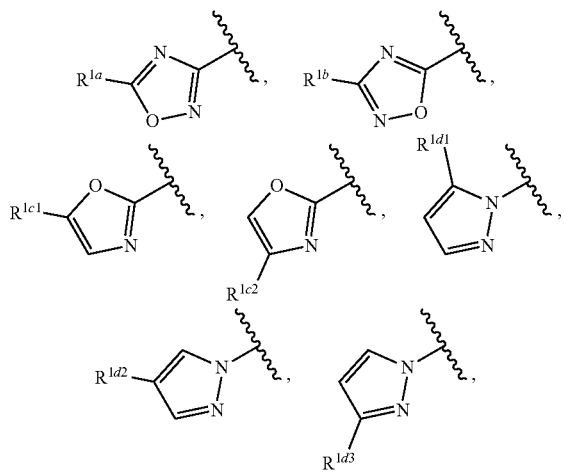

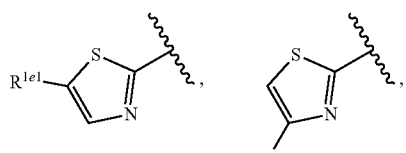

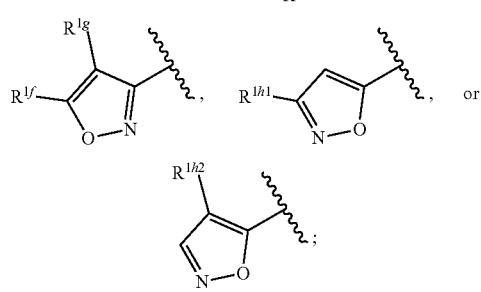

$R^{1a}$, $R^{1b}$, $R^{1c1}$, $R^{1c2}$, $R^{1f}$, $R^{1g}$, $R^{1h1}$, and $R^{1h2}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl;

$R^{1d1}$, $R^{1d2}$, and $R^{1d3}$ are each independently alkyl, alkenyl, alkynyl, haloalkyl, —C(O)O— alkyl, cycloalkyl, cycloalkenyl, cycloalkynyl, heterocycloalkyl, heterocycloalkenyl, aryl, or heteroaryl;

$R^{1e1}$ and $R^{1e2}$ are each independently H, alkyl, alkenyl, alkynyl, haloalkyl, —C(O)O— alkyl, or a cycloalkyl, cycloalkenyl, cycloalkynyl, heterocycloalkyl, heterocycloalkenyl, or heteroaryl ring;

$Y^2$ is R$^z$;

$R^z$ is

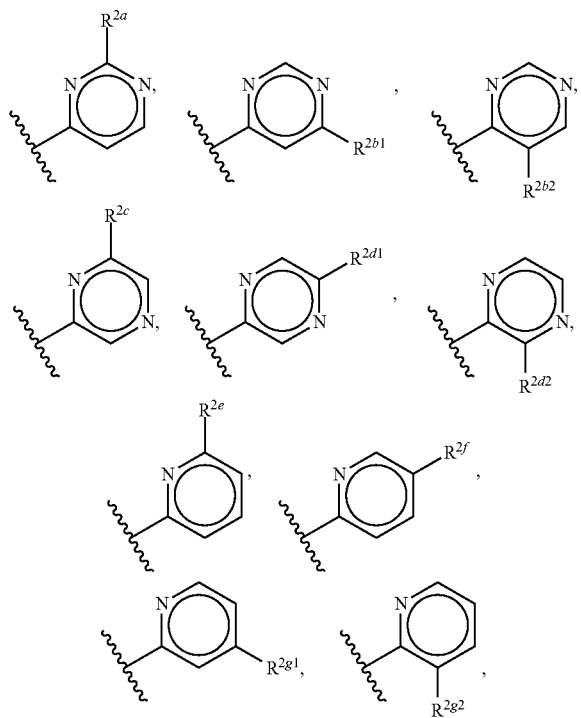

-continued

[chemical structures: pyridine with R²ʰ, pyridine with R²ⁱ, pyrazole with R²ʲ, pyridinone, pyrimidinone (NH), pyridinone (NH)]

R²ᵃ, R²ᵇ¹, R²ᵇ², R²ᶜ, R²ᵈ¹, R²ᵈ², R²ʰ, R²ⁱ, and R²ʲ are each independently selected from the group consisting of H, halo, —OH, —CN, —NRᶜRᵈ, alkyl, alkenyl, alkynyl, —O-alkyl, haloalkyl, cycloalkyl, and —C(O)NRᶜRᵈ;

R²ᵉ, R²ᶠ, R²ᵍ¹, and R²ᵍ² are each independently selected from the group consisting of halo, —OH, —CN, —NRᶜRᵈ, alkyl, alkenyl, alkynyl, —O-alkyl, haloalkyl, cycloalkyl, and —C(O)NRᶜRᵈ; and Rᶜ and Rᵈ are each independently H or alkyl;

wherein, when Y¹ is

[chemical structure: F₃C-oxadiazole]

at least one of (a)-(c) applies:
(a) R² is —CH₃;
(b) R¹ is halo; and
(c) G¹ is —C(Rᵇ)—, wherein Rᵇ is halo; and
when Y¹ is

[chemical structure: methyl-oxadiazole]

and Y² is

[chemical structure: pyrimidine with R²ᵇ¹]

R²ᵇ¹ is selected from the group consisting of H, halo, —OH, —CN, —NRᶜRᵈ, alkyl, alkenyl, alkynyl, —O—C₂-C₆alkyl, haloalkyl, cycloalkyl, and —C(O)NRᶜRᵈ.

In some embodiments, the compound of Formula (I) is a compound of Formula (Ib):

(Ib)

[chemical structure of Formula (Ib)]

or a pharmaceutically acceptable salt thereof, wherein:

R¹ᵃᵃ is H, alkyl, cycloalkyl, cycloalkenyl, heterocycloalkyl, heterocycloalkenyl, aryl, or heteroaryl;

R¹ is H or halo;

G¹ is —N— or —C(Rᵇ)—, wherein Rᵇ is H or halo, or Rᵇ is taken together with R² and the atoms to which they are attached to form a 5- or 6-membered cycloalkyl or heterocycloalkyl ring;

R² is H or —CH₃, or R² is taken together with Rᵇ and the atoms to which they are attached to form a 5- or 6-membered cycloalkyl or heterocycloalkyl ring;

L² is absent, —O—, —NH—, or —OCH₂—*; wherein * indicates the attachment to Y²

Y² is CH₃, phenyl, or Rᶻ;

Rᶻ is

[chemical structures: pyrimidines with R²ᵃ, R²ᵇ¹, R²ᵇ²; pyrazines with R²ᶜ, R²ᵈ¹, R²ᵈ²; pyridines with R²ᵉ, R²ᶠ, R²ᵍ¹, R²ᵍ², R²ʰ, R²ⁱ]

-continued

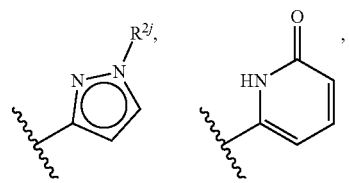

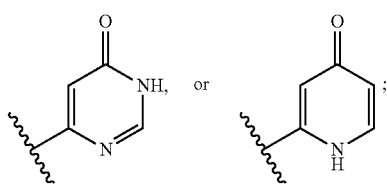

$R^{2a}$, $R^{2b1}$, $R^{2b2}$, $R^{2c}$, $R^{2d1}$, $R^{2d2}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$;

$R^{2e}$, $R^{2f}$, $R^{2g1}$, and $R^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and $R^c$ and $R^d$ are each independently H or alkyl.

In some embodiments of Formula (I), (Ia), or (Ib), $R^1$ is H. In some embodiments, $R^1$ is halo.

In some embodiments of Formula (I), (Ia), or (Ib), $G^1$ is —N—. In some embodiments, $G^1$ is —C(R$^b$)—, and $R^b$ is H or halo. In some embodiments, $G^1$ is —C(R$^b$)—, and $R^b$ is taken together with $R^2$ and the atoms to which they are attached to form a 5- or 6-membered cycloalkyl or heterocycloalkyl ring.

In some embodiments of Formula (I), (Ia), or (Ib), $R^2$ is H. In other embodiments, $R^2$ is —CH$_3$.

In some embodiments of Formula (I) or (Ia), $Y^1$ is

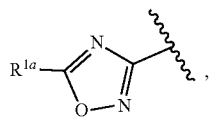

and $R^1$ is H, alkyl, haloalkyl, —C(O)O-alkyl, cycloalkyl, cycloalkenyl, heterocycloalkyl, heterocycloalkenyl, aryl, or heteroaryl.

In some embodiments of Formula (I) or (Ia), $Y^1$ is

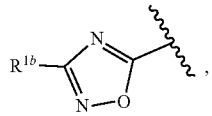

and $R^{1b}$ is H, alkyl, haloalkyl, —C(O)O-alkyl, cycloalkyl, cycloalkenyl, heterocycloalkyl, heterocycloalkenyl, aryl, or heteroaryl.

In some embodiments of Formula (I) or (Ia), $Y^1$ is

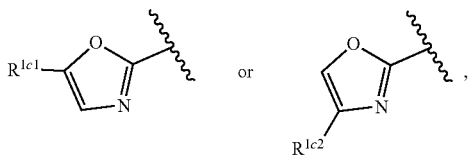

and $R^{1c1}$ and $R^{1c2}$ are each independently H, alkyl, haloalkyl, —C(O)O-alkyl, cycloalkyl, cycloalkenyl, heterocycloalkyl, heterocycloalkenyl, aryl, or heteroaryl.

In some embodiments of Formula (I) or (Ia), $Y^1$ is

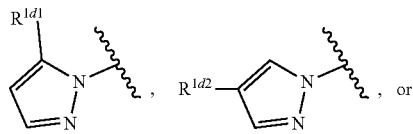

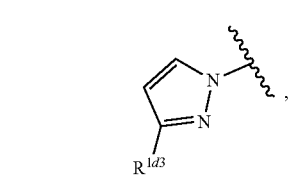

and $R^{1d1}$, $R^{1d2}$, and $R^{1d3}$ are each independently alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl.

In some embodiments of Formula (I) or (Ia), $Y^1$ is

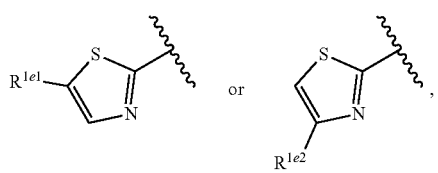

and $R^{1e1}$ and $R^{1e2}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, or heteroaryl.

In some embodiments of Formula (I) or (Ia), $Y^1$ is

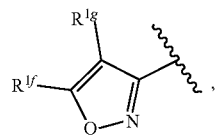

and $R^{1f}$ and $R^{1g}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl.

In some embodiments of Formula (I) or (Ia), $Y^1$ is

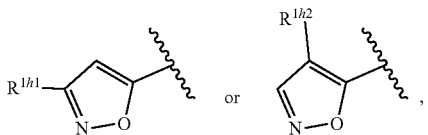

and $R^{1h1}$ and $R^{1h2}$ are each independently H, alkyl, haloalkyl, —C(O)O-alkyl, cycloalkyl, cycloalkenyl, heterocycloalkyl, heterocycloalkenyl, aryl, or heteroaryl.

In some embodiments of Formula (I) or (Ia), $Y^1$ is selected from the group consisting of

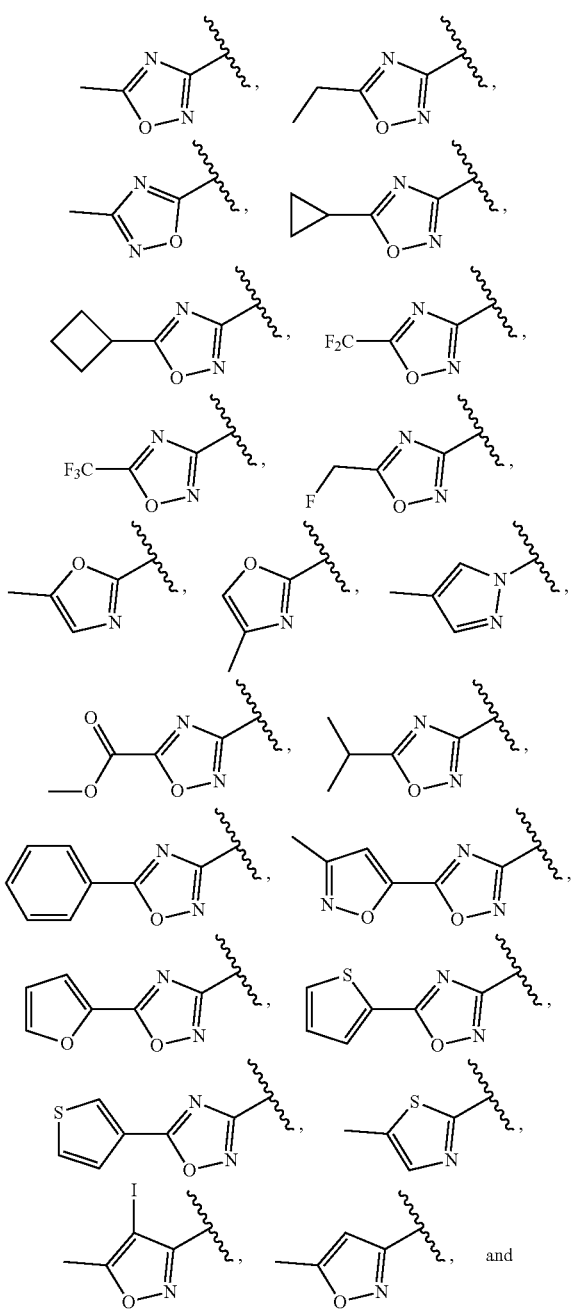

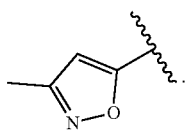

It is understood that any descriptions of variables for Formula (I), (Ia), and (Ib) may be combined with each and every variable, the same as if each and every combination were specifically and individually listed. For example, a description of $R^1$ may be combined with each description of $R^2$, $G^1$, $L^1$, $Y^1$, or $Y^2$, either individually or collectively the same as if each combination were specifically and individually listed.

In some embodiments of Formula (I) or (Ib), $R^{1aa}$ is alkyl.

In some embodiments of Formula (I) or (Ib), $L^2$ is absent. In some embodiments, $L^2$ is —O—. In some embodiments, $L^2$ is —NH—. In other embodiments, $L^2$ is —OCH$_2$—*, wherein * indicates the attachment to $Y^2$.

In some embodiments of Formula (I), (Ia), or (Ib), $Y^2$ is

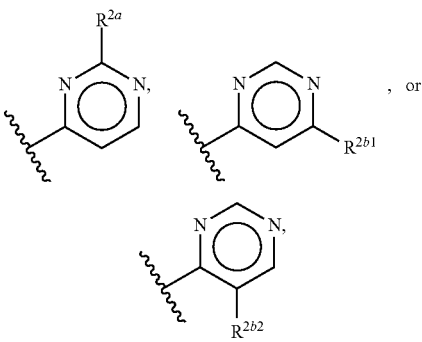

and $R^{2a}$, $R^{2b1}$, and $R^{2b2}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$.

In some embodiments of Formula (I), (Ia), or (Ib), $Y^2$ is

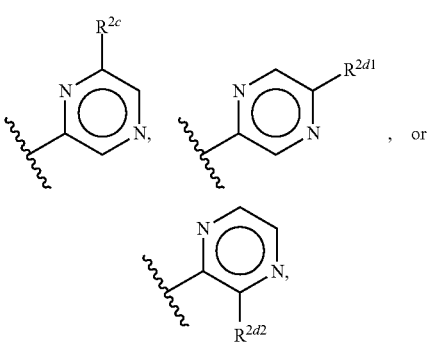

and $R^{2c}$, $R^{2d1}$, and $R^{2d2}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$.

In some embodiments of Formula (I), (Ia), or (Ib), Y² is

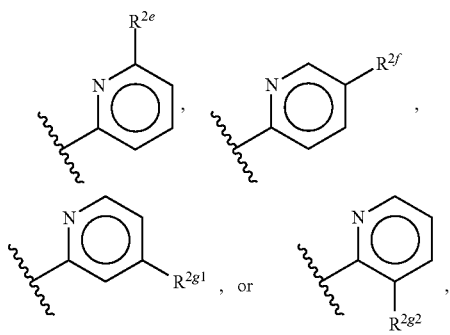

and R²ᵉ, R²ᶠ, R²ᵍ¹, and R²ᵍ² are each independently selected from the group consisting of halo, —OH, —CN, —NRᶜRᵈ, alkyl, alkenyl, alkynyl, —O-alkyl, haloalkyl, cycloalkyl, and —C(O)NRᶜRᵈ.

In some embodiments of Formula (I), (Ia), or (Ib), Y² is

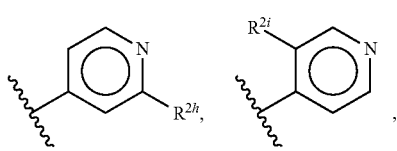

and R²ʰ and R²ⁱ are each independently selected from the group consisting of H, halo, —OH, —CN, —NRᶜRᵈ, alkyl, alkenyl, alkynyl, —O-alkyl, haloalkyl, cycloalkyl, and —C(O)NRᶜRᵈ.

In some embodiments of Formula (I), (Ia), or (Ib), Y² is

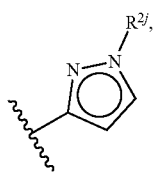

and R²ʲ is selected from the group consisting of H, halo, —OH, —CN, —NRᶜRᵈ, alkyl, alkenyl, alkynyl, —O—alkyl, haloalkyl, cycloalkyl, and —C(O)NRᶜRᵈ.

In some embodiments of Formula (I), (Ia), or (Ib), Y² is selected from the group consisting of

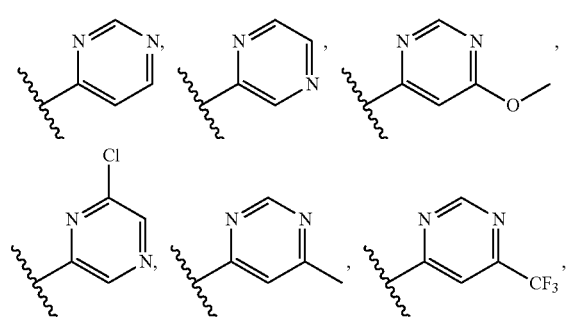

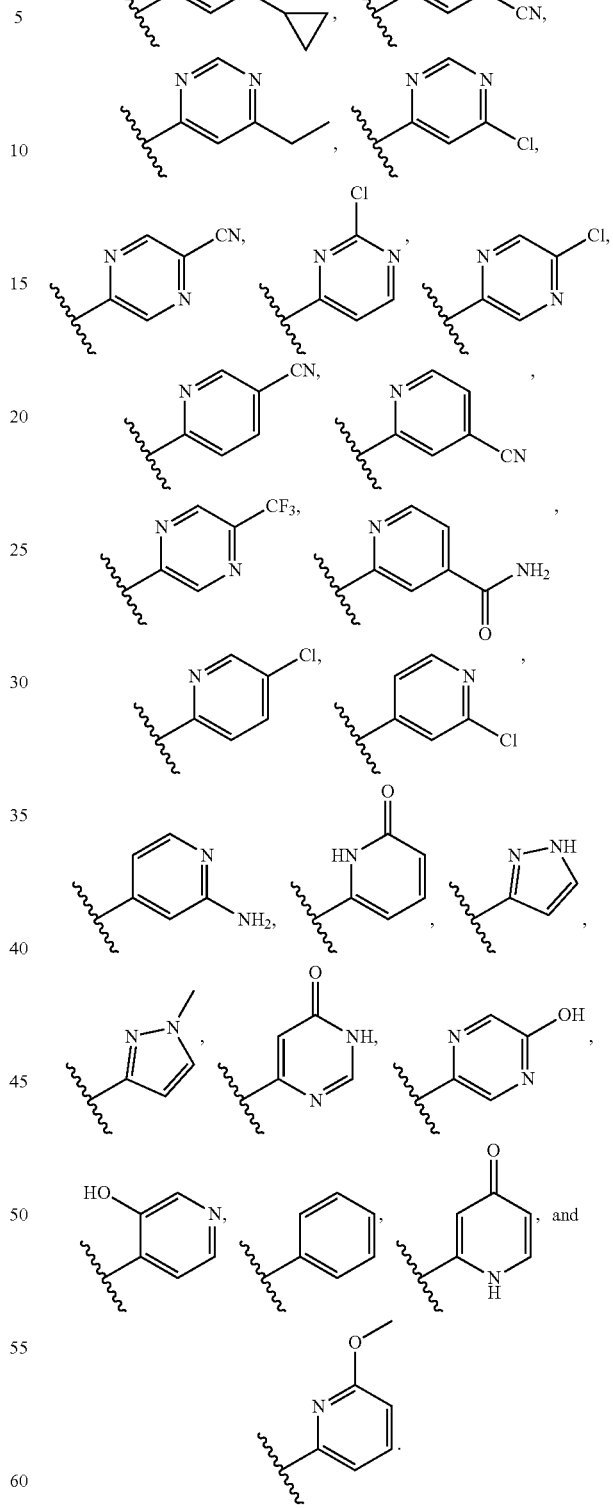

In some embodiments of Formula (I) or (Ib), Y² is CH₃.
In some embodiments of Formula (I) or (Ib), Y² is phenyl.
Provided in some embodiments are compounds selected from the group consisting of compounds of Table 1, or a pharmaceutically acceptable salt thereof.

Provided in some aspects is a pharmaceutical composition containing a compound of Formula (I) or any variation thereof (e.g., a compound of Formula (I-1), (I-2), (Ia), (Ia-1), (Ia-2), (Ib), (Ib-1), or (Ib-2)), or a pharmaceutically acceptable salt thereof, and a pharmaceutically acceptable excipient.

Provided in some aspects are methods of treating heart disease in a subject in need thereof, the method comprising administering to the subject a compound of Formula (I) or any variation thereof (e.g., a compound of Formula (I-1), (I-2), (Ia), (Ia-1), (Ia-2), (Ib), (Ib-1), or (Ib-2)), or a pharmaceutically acceptable salt thereof, or a pharmaceutical composition containing a compound of Formula (I) or any variation thereof, or a pharmaceutically acceptable salt thereof. In some embodiments, the heart disease is hypertrophic cardiomyopathy (HCM). In some embodiments, the HCM is obstructive or nonobstructive or is caused by sarcomeric and/or non-sarcomeric mutations. In some embodiments, the heart disease is heart failure with preserved ejection fraction (HFpEF). In some embodiments, the heart disease is selected from the group consisting of diastolic dysfunction, primary or secondary restrictive cardiomyopathy, myocardial infarction and angina pectoris, and left ventricular outflow tract obstruction. In some embodiments, the heart disease is hypertensive heart disease, congenital heart disease, cardiac ischemia, coronary heart disease, diabetic heart disease, congestive heart failure, right heart failure, cardiorenal syndrome, or infiltrative cardiomyopathy. In some embodiments, the heart disease is a condition that is or is related to cardiac senescence and/or diastolic dysfunction due to aging. In some embodiments, the heart disease is a condition that is or is related to left ventricular hypertrophy and/or concentric left ventricular remodeling.

Provided in other aspects are methods of treating a disease or condition associated with HCM in a subject in need thereof, wherein the method comprises administering to the subject a compound of Formula (I) or any variation thereof (e.g., a compound of Formula (I-1), (I-2), (Ia), (Ia-1), (Ia-2), (Ib), (Ib-1), or (Ib-2)), or a pharmaceutically acceptable salt thereof, or a pharmaceutical composition containing a compound of Formula (I) or any variation thereof, or a pharmaceutically acceptable salt thereof. In some embodiments, the disease or condition is selected from the group consisting of Fabry's Disease, Danon Disease, mitochondrial cardiomyopathies, and Noonan Syndrome.

Provided in some aspects are methods of treating a disease or condition that is associated with secondary left ventricular wall thickening in a subject in need thereof, wherein the method comprises administering to the subject a compound of Formula (I) or any variation thereof (e.g., a compound of Formula (I-1), (I-2), (Ia), (Ia-1), (Ia-2), (Ib), (Ib-1), or (Ib-2)), or a pharmaceutically acceptable salt thereof, or a pharmaceutical composition containing a compound of Formula (I) or any variation thereof, or a pharmaceutically acceptable salt thereof. In some embodiments, the disease or condition is selected from the group consisting of hypertension, valvular heart diseases (such as aortic stenosis and Mitral valve regurgitation), metabolic syndromes (such as diabetes and obesity), end stage renal disease, scleroderma, sleep apnea, amyloidosis, Fabry's disease, Friedreich Ataxia, Danon disease, Noonan syndrome, and Pompe disease.

Provided in other aspects are methods of treating a disease or condition that is associated with small left ventricular cavity and cavity obliteration, hyperdynamic left ventricular contraction, myocardial ischemia, or cardiac fibrosis. Also provided are methods of treating muscular dystrophies (e.g., Duchenne muscular dystrophy) or glycogen storage diseases.

Also provided are methods of inhibiting the cardiac sarcomere, wherein the method involves contacting the cardiac sarcomere with a compound of Formula (I) or any variation thereof (e.g., a compound of Formula (I-1), (I-2), (Ia), (Ia-1), (Ia-2), (Ib), (Ib-1), or (Ib-2)), or a pharmaceutically acceptable salt thereof, or a pharmaceutical composition containing a compound of Formula (I) or any variation thereof, or a pharmaceutically acceptable salt thereof.

DETAILED DESCRIPTION

Definitions

As used in the present specification, the following words and phrases are generally intended to have the meanings as set forth below, except to the extent that the context in which they are used indicates otherwise.

Throughout this application, unless the context indicates otherwise, references to a compound of Formula (I) includes all subgroups of Formula (I) defined herein, such as Formula (I-1), (I-2), (Ia), (Ia-1), (Ia-2), (Ib), (Ib-1), or (Ib-2), including all substructures, subgenera, preferences, embodiments, examples and particular compounds defined and/or described herein. References to a compound of Formula (I) and subgroups thereof, such as Formula (I-1), (I-2), (Ia), (Ia-1), (Ia-2), (Ib), (Ib-1), or (Ib-2), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I) and subgroups thereof, such as Formula (I-1), (I-2), (Ia), (Ia-1), (Ia-2), (Ib), (Ib-1), or (Ib-2), include polymorphs, solvates, co-crystals, isomers, tautomers and/or oxides thereof. In some embodiments, references to a compound of Formula (I) and subgroups thereof, such as Formula (I-1), (I-2), (Ia), (Ia-1), (Ia-2), (Ib), (Ib-1), or (Ib-2), include polymorphs, solvates, and/or co-crystals thereof. In some embodiments, references to a compound of Formula (I) and subgroups thereof, such as Formula (I-1), (I-2), (Ia), (Ia-1), (Ia-2), (Ib), (Ib-1), or (Ib-2), include isomers, tautomers and/or oxides thereof. In some embodiments, references to a compound of Formula (I) and subgroups thereof, such as Formula (I-1), (I-2), (Ia), (Ia-1), (Ia-2), (Ib), (Ib-1), or (Ib-2), include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo [2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Cycloalkynyl" indicates a non-aromatic carbocyclic ring, containing the indicated number of carbon atoms (e.g., 3 to 10, or 3 to 8, or 3 to 6 ring carbon atoms) and at least one carbon-carbon triple bond. Cycloalkynyl groups may be monocyclic or polycyclic (e.g., bicyclic, tricyclic). Examples of cycloalkynyl groups include cyclopentyne, cyclohexyne, cycloheptyne, cyclooctyne, cyclononyne.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo [b]thiophen-2(3H)-one, benzo[b]thiophen-3(2H)-one, benzo[c]thiophen-1(3H)-one, benzo[c]isothiazol-3(1H)-one, benzo [d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluoro, chloro, bromo or iodo.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocycloalkyl, heterocycloalkenyl, aralkyl, aminosulfonyl, sulfonylamino, sulfonyl, oxo and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2H$, $^3H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.,* 2000; 6(10); Kabalka, G. et al., The Synthesis of Radiolabeled Compounds via Organometallic Intermediates, *Tetrahedron,* 1989, 45(21), 6601-21; and Evans, E., Synthesis of radiolabeled compounds, *J. Radioanal. Chem.,* 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, the term "therapeutic" refers to the ability to modulate the cardiac sarcomere. As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of the cardiac sarcomere. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

"ATPase" refers to an enzyme that hydrolyzes ATP. ATPases include proteins comprising molecular motors such as the myosins.

As used herein, "selective binding" or "selectively binding" refers to preferential binding to a target protein in one type of muscle or muscle fiber as opposed to other types. For example, a compound selectively binds to fast skeletal troponin C if the compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

It is understood that embodiments described herein as "comprising" include "consisting of" and "consisting essentially of" embodiments.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

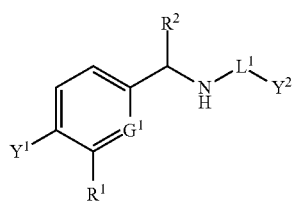

or a pharmaceutically acceptable salt thereof, wherein:
$R^1$ is H or halo;
$G^1$ is —N— or —C($R^b$)—, wherein $R^b$ is H or halo, or $R^b$ is taken together with $R^2$ and the atoms to which they are attached to form a 5- or 6-membered cycloalkyl or heterocycloalkyl ring;
$R^2$ is H or —CH$_3$, or $R^2$ is taken together with $R^b$ and the atoms to which they are attached to form a 5- or 6-membered cycloalkyl or heterocycloalkyl ring;
$L^1$, $Y^1$, and $Y^2$ are defined by (i) or (ii):
(i) $L^1$ is absent;
    $Y^1$ is $R^x$; and
    $Y^2$ is $R^z$;
or
(ii) $L^1$ is

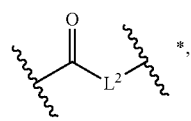

wherein $L^2$ is absent, —O—, —NH—, or —OCH$_2$—*, and wherein * indicates the attachment to $Y^2$
$Y^1$ is

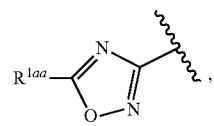

wherein $R^{1aa}$ is H, alkyl, cycloalkyl, cycloalkenyl, heterocycloalkyl, heterocycloalkenyl, aryl, or heteroaryl; and $Y^2$ is —CH$_3$, phenyl, or R$^z$;

R$^x$ is

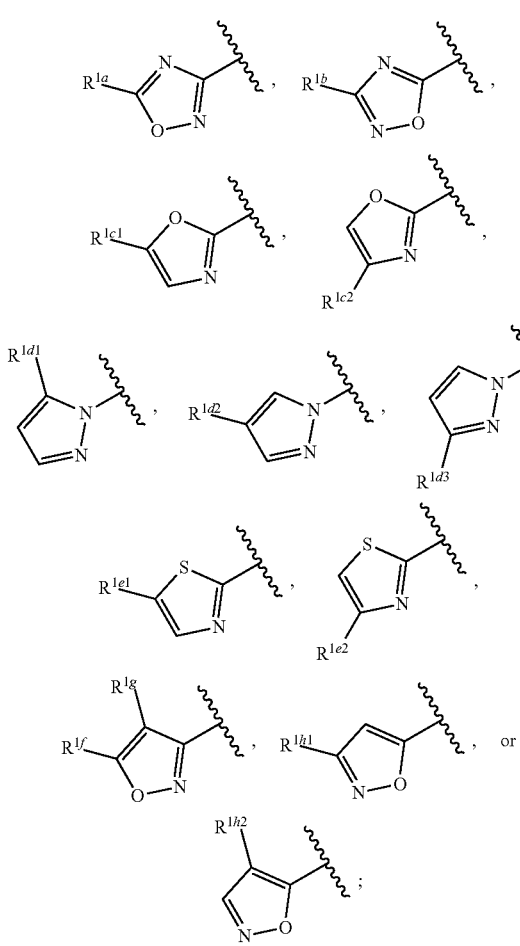

R$^{1a}$, R$^{1b}$, R$^{1c1}$, R$^{1c2}$, R$^{1f}$, R$^{1g}$, R$^{1h1}$, and R$^{1h2}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl;

R$^{1d1}$, R$^{1d2}$, and R$^{1d3}$ are each independently alkyl, alkenyl, alkynyl, haloalkyl, —C(O)O— alkyl, cycloalkyl, cycloalkenyl, cycloalkynyl, heterocycloalkyl, heterocycloalkenyl, aryl, or heteroaryl;

R$^{1e1}$ and R$^{1e2}$ are each independently H, alkyl, alkenyl, alkynyl, haloalkyl, —C(O)O— alkyl, or a cycloalkyl, cycloalkenyl, cycloalkynyl, heterocycloalkyl, heterocycloalkenyl, or heteroaryl ring;

R$^z$ is

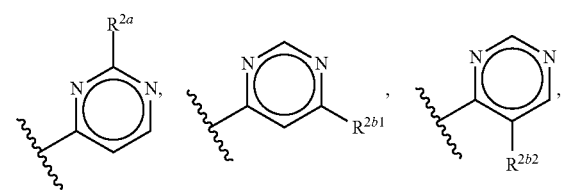

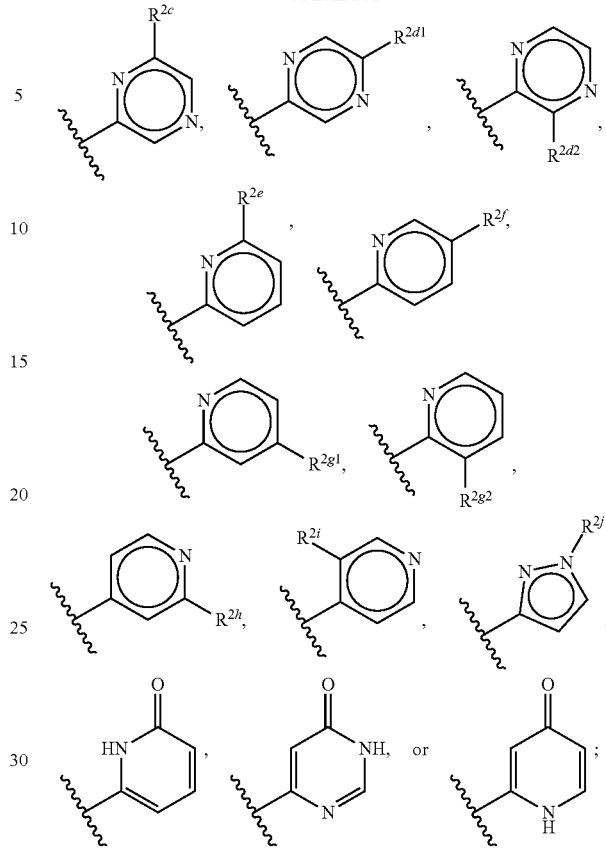

R$^{2a}$, R$^{2b1}$, R$^{2b2}$, R$^{2c}$, R$^{2d1}$, R$^{2d2}$, R$^{2h}$, R$^{2i}$, and R$^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$;

R$^{2e}$, R$^{2f}$, R$^{2g1}$, and R$^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and R$^c$ and R$^d$ are each independently H or alkyl;

wherein, when $Y^1$ is

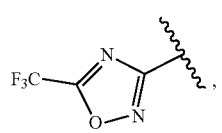

at least one of (a)-(c) applies:
(a) R$^2$ is —CH$_3$;
(b) R$^1$ is halo; and
(c) G$^1$ is —C(R$^b$)—, wherein R$^b$ is halo; and when $Y^1$ is

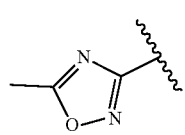 [SMILES: *c1noc(C)n1]

and Y² is

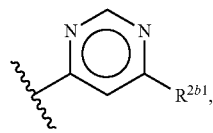

R²ᵇ¹ is selected from the group consisting of H, halo, —OH, —CN, —NRᶜRᵈ, alkyl, alkenyl, alkynyl, —O—C₂-C₆alkyl, haloalkyl, cycloalkyl, and —C(O)NRᶜRᵈ.

In another aspect, the compound of Formula (I) is a compound of Formula (I-1):

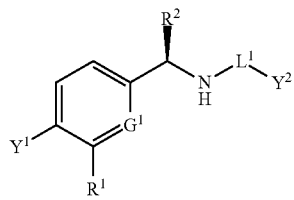

(I-1)

or a pharmaceutically acceptable salt thereof, wherein R¹, R², G¹, L¹, Y¹, and Y² are as defined for Formula (I) or any variation or embodiment thereof.

In another aspect, the compound of Formula (I) is a compound of Formula (I-2):

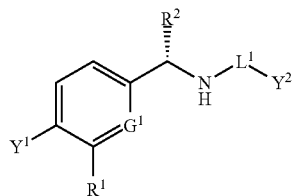

(I-2)

or a pharmaceutically acceptable salt thereof, wherein R¹, R², G¹, L¹, Y¹, and Y² are as defined for Formula (I) or any variation or embodiment thereof.

In another aspect, the compound of Formula (I) is a compound of Formula (Ia):

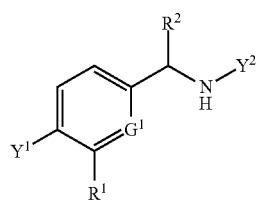

(Ia)

or a pharmaceutically acceptable salt thereof, wherein:
R¹ is H or halo;
G¹ is —N— or —C(Rᵇ)—, wherein Rᵇ is H or halo, or Rᵇ is taken together with R² and the atoms to which they are attached to form a 5- or 6-membered cycloalkyl or heterocycloalkyl ring;

R² is H or —CH₃, or R² is taken together with Rᵇ and the atoms to which they are attached to form a 5- or 6-membered cycloalkyl or heterocycloalkyl ring;
Y¹ is Rˣ;
Rˣ is

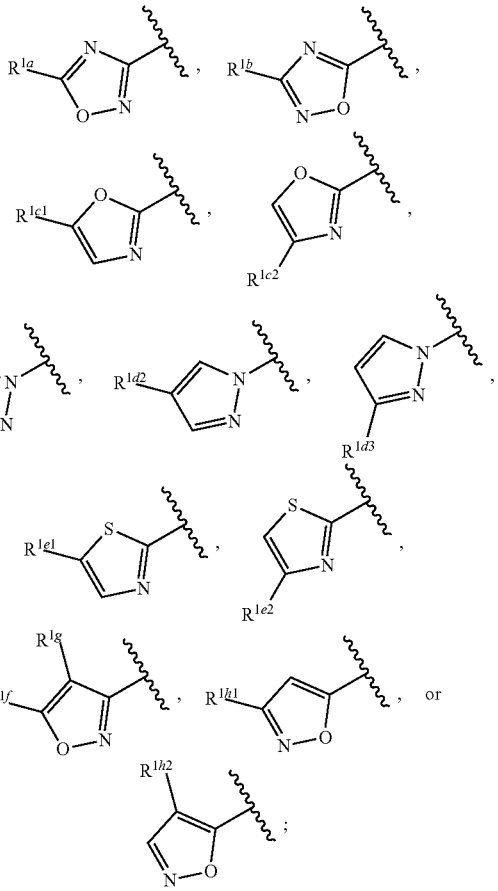

R¹ᵇ, R¹ᶜ¹, R¹ᶜ², R¹ᶠ, R¹ᵍ, R¹ʰ¹, and R¹ʰ² are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl;
R¹ᵈ¹, R¹ᵈ², and R¹ᵈ³ are each independently alkyl, alkenyl, alkynyl, haloalkyl, —C(O)O— alkyl, cycloalkyl, cycloalkenyl, cycloalkynyl, heterocycloalkyl, heterocycloalkenyl, aryl, or heteroaryl;
R¹ᵉ¹ and R¹ᵉ² are each independently H, alkyl, alkenyl, alkynyl, haloalkyl, —C(O)O— alkyl, or a cycloalkyl, cycloalkenyl, cycloalkynyl, heterocycloalkyl, heterocycloalkenyl, or heteroaryl ring;
Y² is Rᶻ;
Rᶻ is

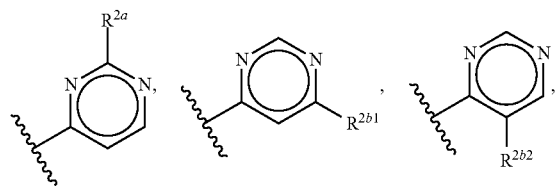

-continued

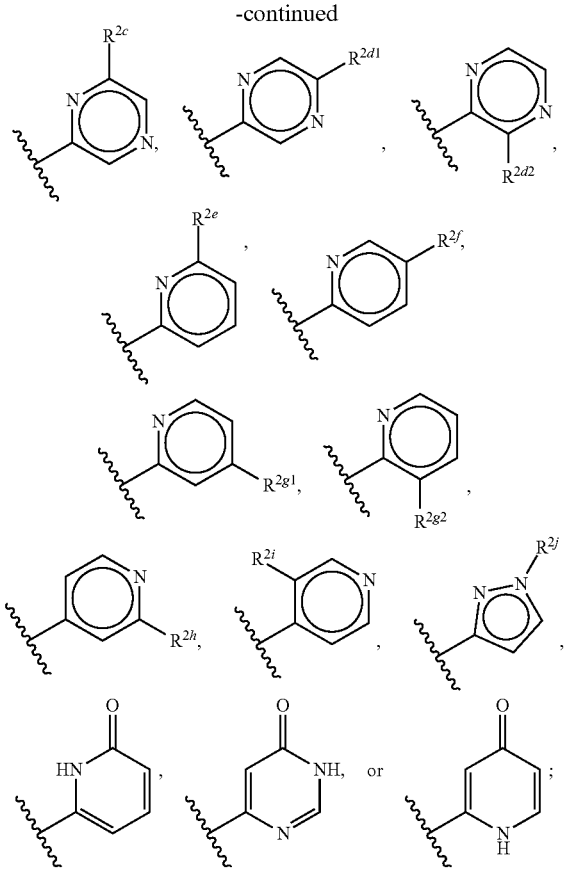

$R^{2a}$, $R^{2b1}$, $R^{2b2}$, $R^{2c}$, $R^{2d1}$, $R^{2d2}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$;

$R^{2e}$, $R^{2f}$, $R^{2g1}$, and $R^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and $R^c$ and $R^d$ are each independently H or alkyl;

wherein, when $Y^1$ is

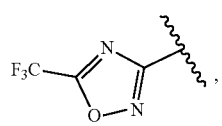

at least one of (a)-(c) applies:
(a) $R^2$ is —CH$_3$;
(b) $R^1$ is halo; and
(c) $G^1$ is —C($R^b$)—, wherein $R^b$ is halo; and when $Y^1$ is

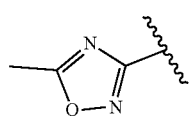 [SMILES: *c1noc(C)n1]

and $Y^2$ is

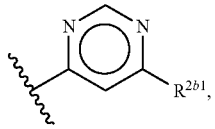

$R^{2b1}$ is selected from the group consisting of H, halo, —OH, —CN, —NR$^c$R$^d$, alkyl, alkenyl, alkynyl, —O—C$_2$-C$_6$alkyl, haloalkyl, cycloalkyl, and —C(O)NR$^c$R$^d$.

In another aspect, the compound of Formula (I) is a compound of Formula (Ia-1):

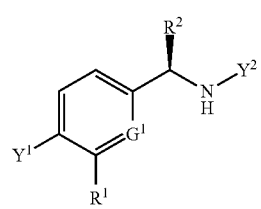

(Ia-1)

or a pharmaceutically acceptable salt thereof, wherein $R^1$, $R^2$, $G^1$, $Y^1$, and $Y^2$ are as defined for Formula (I) or Formula (Ia) or any variation or embodiment thereof.

In another aspect, the compound of Formula (I) is a compound of Formula (Ia-2):

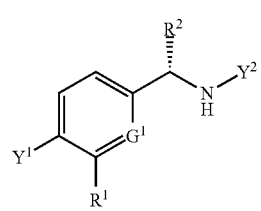

(Ia-2)

or a pharmaceutically acceptable salt thereof, wherein $R^1$, $R^2$, $G^1$, $Y^1$, and $Y^2$ are as defined for Formula (I) or Formula (Ia) or any variation or embodiment thereof.

In another aspect, the compound of Formula (I) is a compound of Formula (Ib):

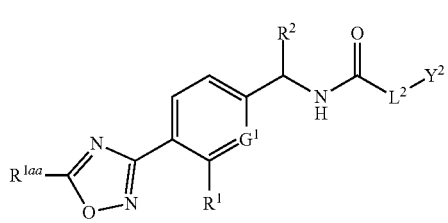

(Ib)

or a pharmaceutically acceptable salt thereof, wherein:
$R^{1aa}$ is H, alkyl, cycloalkyl, cycloalkenyl, heterocycloalkyl, heterocycloalkenyl, aryl, or heteroaryl; $R^1$ is H or halo; $G^1$ is —N— or —C($R^b$)—, wherein $R^b$ is H or halo, or $R^b$ is taken together with $R^2$ and the atoms to which they are attached to form a 5- or 6-membered cycloalkyl or heterocycloalkyl ring;

R² is H or —CH₃, or R² is taken together with Rᵇ and the atoms to which they are attached to form a 5- or 6-membered cycloalkyl or heterocycloalkyl ring;

L² is absent, —O—, —NH—, or —OCH₂—*; wherein * indicates the attachment to Y²

Y² is CH₃, phenyl, or Rᶻ;

Rᶻ is

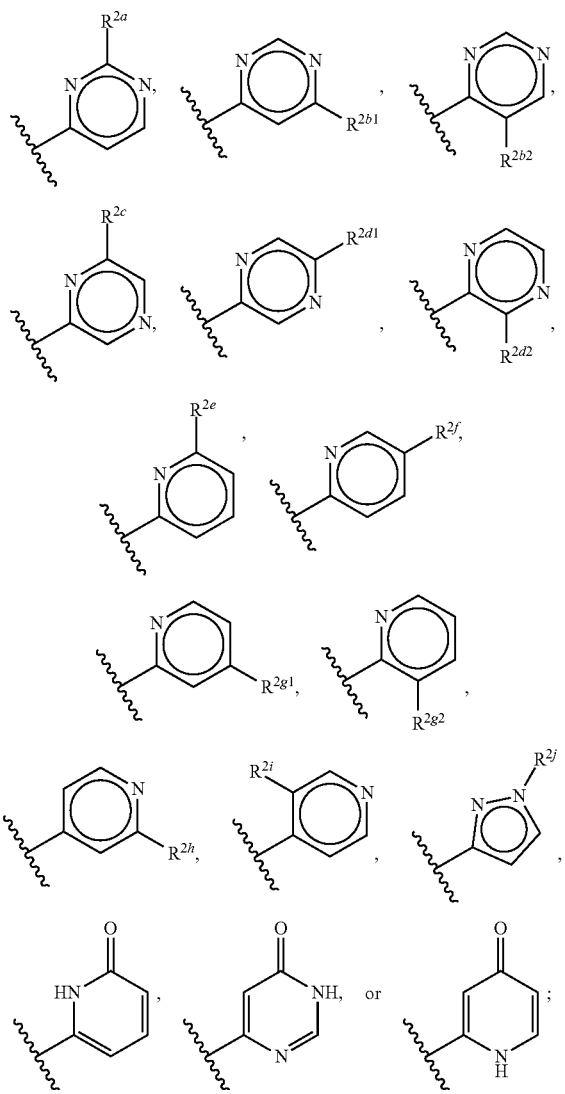

$R^{2a}$, $R^{2b1}$, $R^{2b2}$, $R^{2c}$, $R^{2d1}$, $R^{2d2}$, $R^{2h}$, $R^{2i}$, and $R^{2j}$ are each independently selected from the group consisting of H, halo, —OH, —CN, —NRᶜRᵈ, alkyl, alkenyl, alkynyl, —O-alkyl, haloalkyl, cycloalkyl, and —C(O)NRᶜRᵈ;

$R^{2e}$, $R^{2f}$, $R^{2g1}$, and $R^{2g2}$ are each independently selected from the group consisting of halo, —OH, —CN, —NRᶜRᵈ, alkyl, alkenyl, alkynyl, —O-alkyl, haloalkyl, cycloalkyl, and —C(O)NRᶜRᵈ; and Rᶜ and Rᵈ are each independently H or alkyl.

In another aspect, the compound of Formula (I) is a compound of Formula (Ib-1):

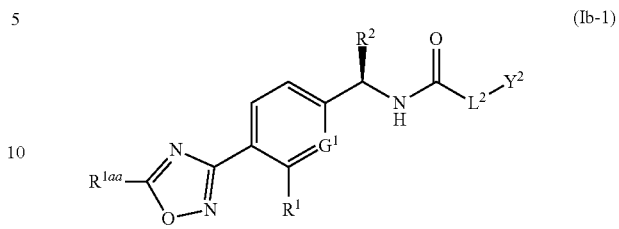

(Ib-1)

or a pharmaceutically acceptable salt thereof, wherein $R^{1aa}$, $R^1$, $R^2$, $G^1$, $L^2$, and $Y^2$ are as defined for Formula (I) or Formula (Ib) or any variation or embodiment thereof.

In another aspect, the compound of Formula (I) is a compound of Formula (Ib-1):

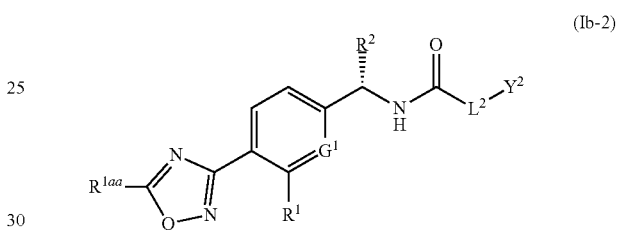

(Ib-2)

or a pharmaceutically acceptable salt thereof, wherein $R^{1aa}$, $R^1$, $R^2$, $G^1$, $L^2$, and $Y^2$ are as defined for Formula (I) or Formula (Ib) or any variation or embodiment thereof.

In some embodiments of Formula (I), (I-1), (I-2), (Ia), (Ia-1), (Ia-2), (Ib), (Ib-1), or (Ib-2), R¹ is H. In some embodiments, R¹ is halo. In certain embodiments, R¹ is Cl. In some embodiments, R¹ is F. In some embodiments, R¹ is Br. In other embodiments, R¹ is I.

In some embodiments of Formula (I), (I-1), (I-2), (Ia), (Ia-1), (Ia-2), (Ib), (Ib-1), or (Ib-2), G¹ is —N—. In some embodiments, G¹ is —C(Rᵇ)—, and Rᵇ is H or halo. In some embodiments, G¹ is —C(H)—. In some embodiments, G¹ is —C(Cl)—. In some embodiments, G¹ is —C(F)—. In some embodiments, G¹ is —C(Br)—. In other embodiments, G¹ is —C(I)—. In some embodiments, G¹ is —C(Rᵇ)—, and Rᵇ is taken together with R² and the atoms to which they are attached to form a 5- or 6-membered cycloalkyl or heterocycloalkyl ring. In some embodiments, G¹ is —C(Rᵇ)—, and Rᵇ is taken together with R² and the atoms to which they are attached to form a 5-membered cycloalkyl ring. For instance, in some embodiments, Rᵇ is taken together with R² to form —CH₂CH₂—. In some embodiments, G¹ is —C(Rᵇ)—, and Rᵇ is taken together with R² and the atoms to which they are attached to form a 6-membered cycloalkyl ring. For instance, in some embodiments, Rᵇ is taken together with R² to form —CH₂CH₂CH₂—. In other embodiments, G¹ is —C(Rᵇ)—, and Rᵇ is taken together with R² and the atoms to which they are attached to form a 5- or 6-membered heterocycloalkyl ring containing one or more heteroatoms selected from the group consisting of N, O, and S.

In some embodiments of Formula (I), (I-1), (I-2), (Ia), (Ia-1), (Ia-2), (Ib), (Ib-1), or (Ib-2), R² is H. In other embodiments, R² is —CH₃.

In some embodiments of Formula (I), (I-1), (I-2), (Ia), (Ia-1), or (Ia-2), $R^x$ is

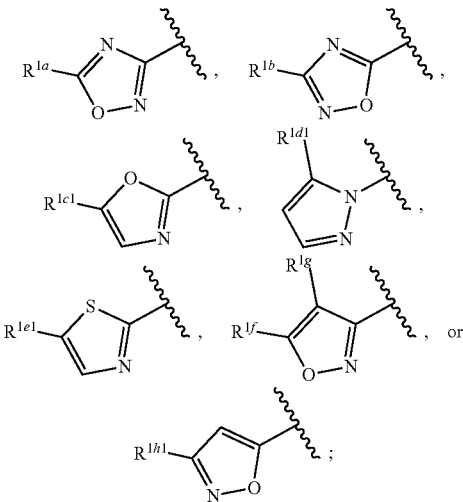

wherein $R^{1a}$, $R^{1b}$, $R^{1c1}$, $R^{1f}$, $R^{1g}$, and $R^{1h1}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl; $R^{1d1}$ is alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl; and $R^{1e1}$ is H, alkyl, alkenyl, alkynyl, haloalkyl, —C(O)O-alkyl, or a cycloalkyl, cycloalkenyl, cycloalkynyl, heterocycloalkyl, heterocycloalkenyl, or heteroaryl ring. In some embodiments of Formula (I), (I-1), (I-2), (Ia), (Ia-1), or (Ia-2), $Y^1$ is

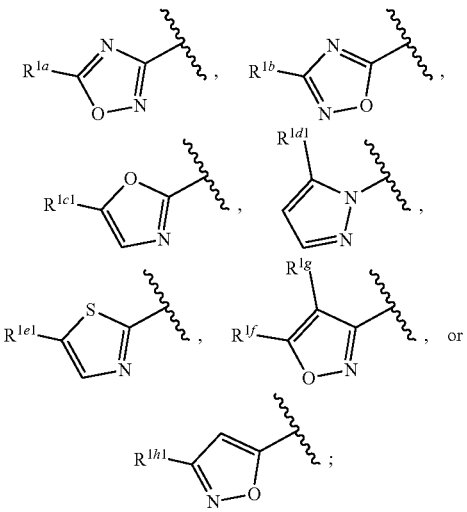

wherein $R^{1a}$, $R^{1b}$, $R^{1c1}$, $R^{1f}$, $R^{1g}$, and $R^{1h1}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl; $R^{1d1}$ is alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl; and $R^{1e1}$ is H, alkyl, alkenyl, alkynyl, haloalkyl, —C(O)O-alkyl, or a cycloalkyl, cycloalkenyl, cycloalkynyl, heterocycloalkyl, heterocycloalkenyl, or heteroaryl ring.

In some embodiments of Formula (I), (I-1), (I-2), (Ia), (Ia-1), or (Ia-2), $Y^1$ is

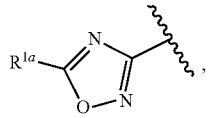

and $R^{1a}$ is H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl. In some embodiments, $Y^1$ is

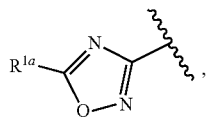

and $R^{1a}$ is H. In some embodiments, $Y^1$ is

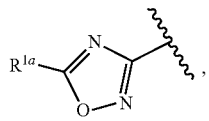

and $R^{1a}$ is a $C_1$-$C_6$alkyl. For example, in some embodiments, $R^{1a}$ is methyl, ethyl, n-propyl, isopropyl, butyl, isobutyl, secbutyl, or tertbutyl. In some embodiments, $Y^1$ is

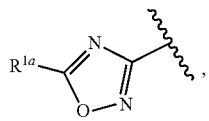

and $R^{1a}$ is a $C_1$-$C_6$haloalkyl. For example, in some embodiments, $R^{1a}$ is fluoromethyl, fluoroethyl, trifluoromethyl, difluoromethyl, or trifluoromethyl. In some embodiments, $Y^1$ is

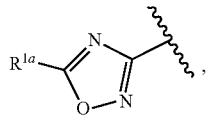

and $R^{1a}$ is —C(O)O—$C_1$-$C_6$alkyl. For example, in some embodiments, $R^{1a}$ is —C(O)OCH$_3$, —C(O)OEt, —C(O)OPr, —C(O)OiPr, or —C(O)OtBu. In some embodiments, $Y^1$ is

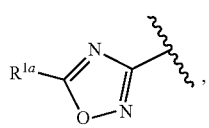

and $R^{1a}$ is $C_3$-$C_8$cycloalkyl, $C_3$-$C_8$cycloalkenyl, or $C_3$-$C_8$cycloalkynyl. For example, in some embodiments, $R^{1a}$ is cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $Y^1$ is

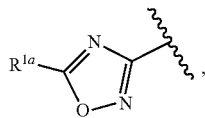

and $R^{1a}$ is a 5-12 membered heterocycloalkyl or a 5-12 membered heterocycloalkenyl. For example, in some embodiments, $R^{1a}$ is tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In some embodiments, $Y^1$ is

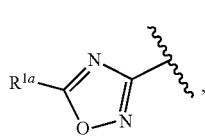

and $R^{1a}$ is a 6-12 membered aryl. For example, in some embodiments, $R^{1a}$ is $R^{1a}$ is phenyl or napthyl. In other embodiments, $Y^1$ is

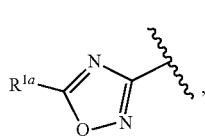

and $R^{1a}$ is a 5-12 membered heteroaryl. For example, in some embodiments, $R^{1a}$ is a pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl. In some embodiments, $Y^1$ is selected from the group consisting of

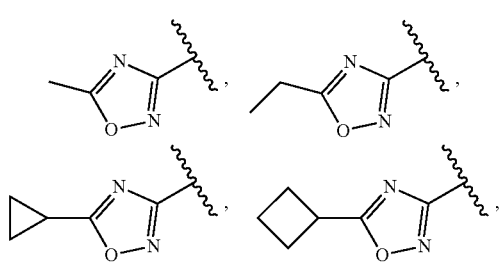

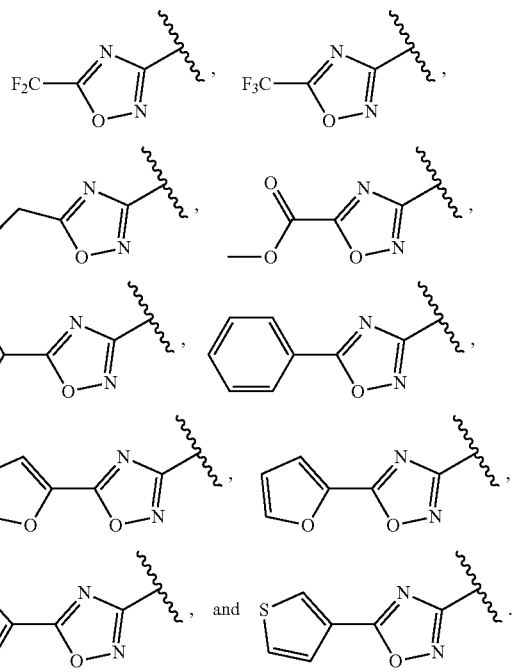

In some embodiments, when $Y^1$ is

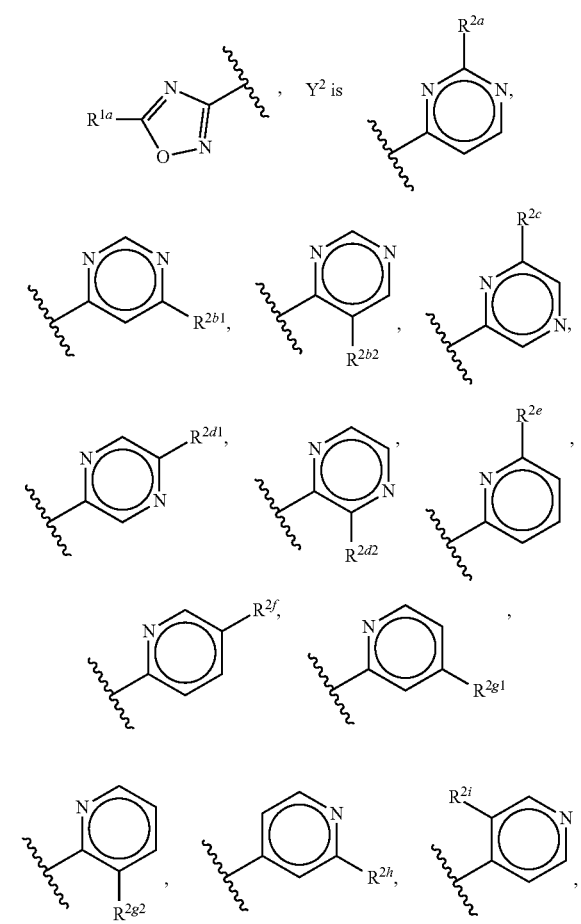

-continued

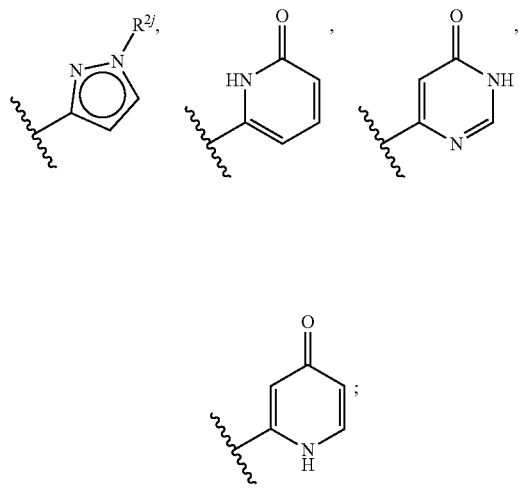

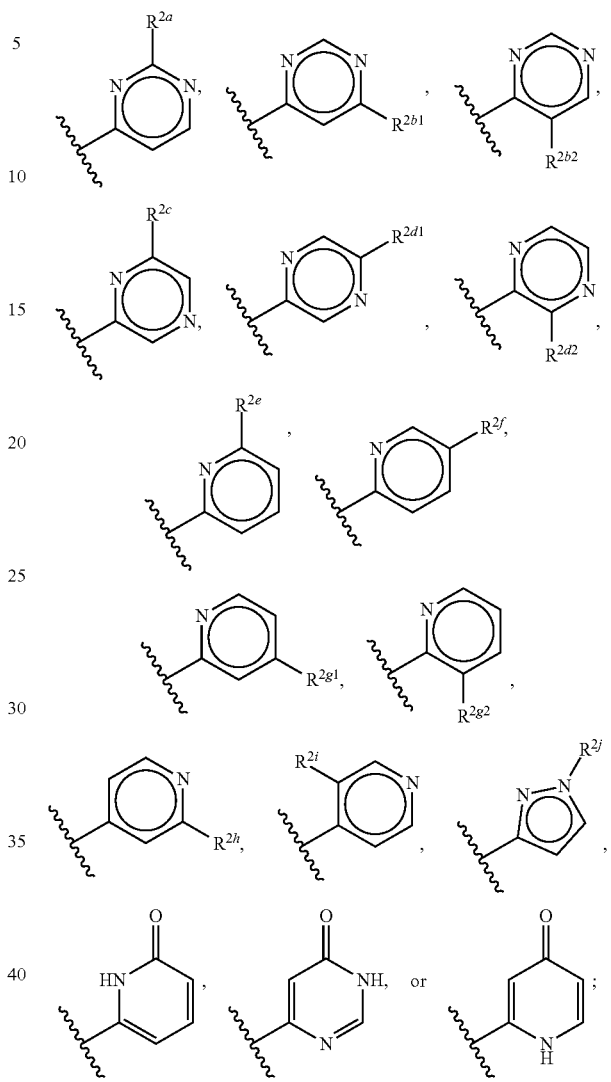

wherein $R^{2a}$, $R^{2c}$, $R^{2d1}$, $R^{2d2}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$; $R^{2d1}$ and $R^{2d2}$ are each independently selected from the group consisting of H, halo, —OH, —CN, —NR$^c$R$^d$, alkyl, alkenyl, alkynyl, haloalkyl, cycloalkyl, and —C(O)NR$^c$R$^d$; $R^{2e}$, $R^{2f}$, $R^{2g1}$, and $R^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and R$^c$ and R$^d$ are each independently H or alkyl. In some embodiments, when $Y^1$ is

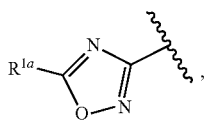

$Y^2$ is

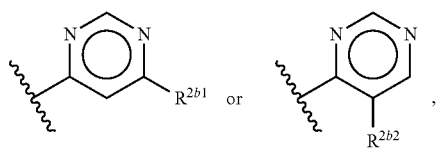

wherein $R^{2b1}$ and $R^{2b2}$ are each independently selected from the group consisting of H, halo, —OH, —CN, —NR$^c$R$^d$, $C_1$-$C_6$alkyl, $C_2$-$C_6$alkenyl, $C_2$-$C_6$alkynyl, —O—$C_2$-$C_6$alkyl, $C_1$-$C_6$haloalkyl, $C_3$-$C_8$cycloalkyl, and —C(O)NR$^c$R$^d$. In some embodiments, when $Y^1$ is

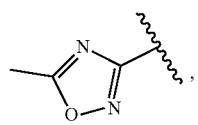

wherein $R^{2a}$, $R^{2c}$, $R^{2d1}$, $R^{2d2}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$; $R^{2b1}$ and $R^{2b2}$ are each independently selected from the group consisting of H, halo, —OH, —CN, —NR$^c$R$^d$, alkyl, alkenyl, alkynyl, haloalkyl, cycloalkyl, and —C(O)NR$^c$R$^d$; $R^{2e}$, $R^{2f}$, $R^{2g1}$, and $R^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and R$^c$ and R$^d$ are each independently H or alkyl. In some embodiments, when $Y^1$ is

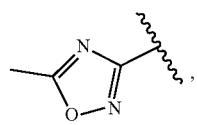 [SMILES: *c1noc(C)n1]

$Y^2$ is

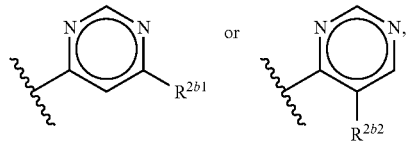

wherein $R^{2b1}$ and $R^{2b2}$ are each independently selected from the group consisting of H, halo, —OH, —CN, —NR$^c$R$^d$, $C_1$-$C_6$alkyl, $C_2$-$C_6$alkenyl, $C_2$-$C_6$alkynyl, —O—$C_2$-$C_6$alkyl, $C_1$-$C_6$haloalkyl, $C_3$-$C_8$cycloalkyl, and —C(O)NR$^c$R$^d$.

In some embodiments of Formula (I), (I-1), (I-2), (Ia), (Ia-1), or (Ia-2), $Y^1$ is

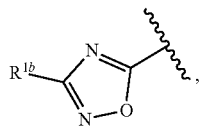

and $R^{1b}$ is H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl. In some embodiments, $Y^1$ is

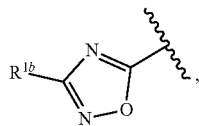

and $R^{1b}$ is H. In some embodiments, $Y^1$ is

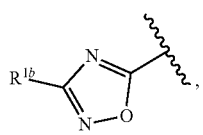

and $R^{1b}$ is a $C_1$-$C_6$alkyl. For example, in some embodiments, $R^{1b}$ is methyl, ethyl, n-propyl, isopropyl, butyl, isobutyl, secbutyl, or tertbutyl. In some embodiments, $Y^1$ is

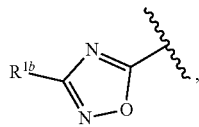

and $R^{1b}$ is a $C_1$-$C_6$haloalkyl. For example, in some embodiments, $R^{1b}$ is fluoromethyl, fluoroethyl, trifluoromethyl, difluoromethyl, or trifluoromethyl. In some embodiments, $Y^1$ is

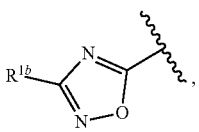

and $R^{1b}$ is a —C(O)O—$C_1$-$C_6$alkyl. For example, in some embodiments, $R^{1b}$ is —C(O)OCH$_3$, —C(O)OEt, —C(O)OPr, —C(O)OiPr, or —C(O)OtBu. In some embodiments, $Y^1$ is

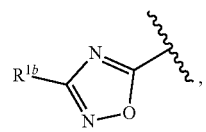

and $R^{1b}$ is a $C_3$-$C_8$cycloalkyl, $C_3$-$C_8$cycloalkenyl, or $C_3$-$C_8$cycloalkynyl. For example, in some embodiments, $R^{1b}$ is cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $Y^1$ is

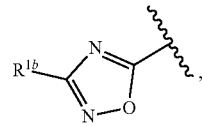

and $R^{1b}$ is a 5-12 membered heterocycloalkyl or a 5-12 membered heterocycloalkenyl. For example, in some embodiments, $R^{1b}$ is tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In some embodiments, $Y^1$ is

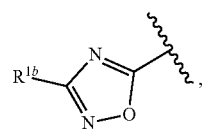

and $R^{1b}$ is 6-12 membered aryl. For example, in some embodiments, $R^{1b}$ is phenyl or napthyl. In other embodiments, $Y^1$ is

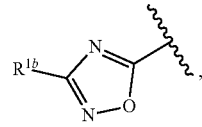

and $R^{1b}$ is a 5-12 membered heteroaryl. For example, in some embodiments, $R^{1b}$ is a pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl. In some embodiments, $Y^1$ is

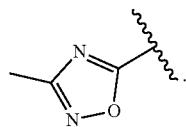 [SMILES: *c1nc(C)no1]

In some embodiments of Formula (I), (I-1), (I-2), (Ia), (Ia-1), or (Ia-2), $Y^1$ is

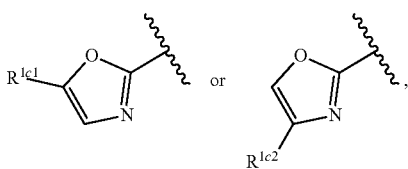

and $R^{1c1}$ and $R^{1c2}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl. In some embodiments, $Y^1$ is

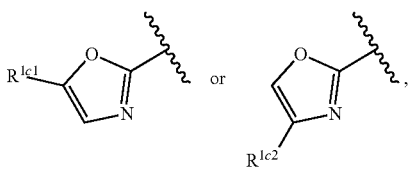

and $R^{1c1}$ and $R^{1c2}$ are each H. In some embodiments, $Y^1$ is

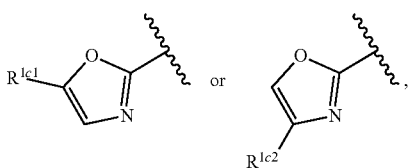

and $R^{1c1}$ and $R^{1c2}$ are each independently $C_1$-$C_6$alkyl. For example, in some embodiments, $R^{1c1}$ and $R^{1c2}$ are each independently methyl, ethyl, n-propyl, isopropyl, butyl, isobutyl, secbutyl, or tertbutyl. In some embodiments, $Y^1$ is

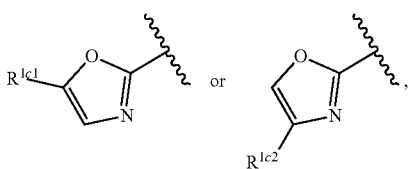

and $R^{1c1}$ and $R^{1c2}$ are each independently $C_1$-$C_6$haloalkyl. For example, in some embodiments, $R^{1c1}$ and $R^{1c2}$ are each independently fluoromethyl, fluoroethyl, trifluoromethyl, difluoromethyl, or trifluoromethyl. In some embodiments, $Y^1$ is

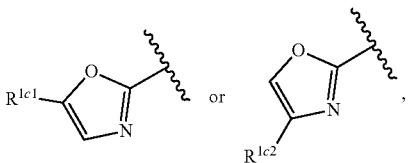

and $R^{1c1}$ and $R^{1c2}$ are each independently —C(O)O—$C_1$-$C_6$alkyl. For example, in some embodiments, $R^{1c1}$ and $R^{1c2}$ are each independently —C(O)OCH$_3$, —C(O)OEt, —C(O)OPr, —C(O)OiPr, or —C(O)OtBu. In some embodiments, $Y^1$ is

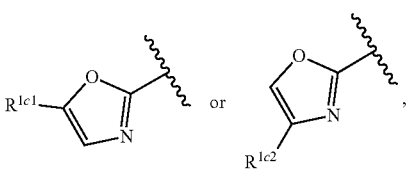

and $R^{1c1}$ and $R^{1c2}$ are each independently $C_3$-$C_8$cycloalkyl, $C_3$-$C_8$cycloalkenyl, or $C_3$-$C_8$cycloalkynyl. For example, in some embodiments, $R^{1c1}$ and $R^{1c2}$ are each independently cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $Y^1$ is

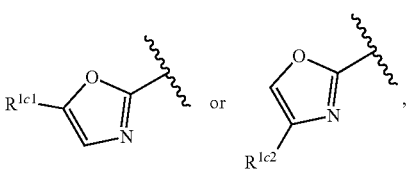

and $R^{1c1}$ and $R^{1c2}$ are each independently a 5-12 membered heterocycloalkyl or a 5-12 membered heterocycloalkenyl. For example, in some embodiments, $R^{1c1}$ and $R^{1c2}$ are each independently tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In some embodiments, $Y^1$ is

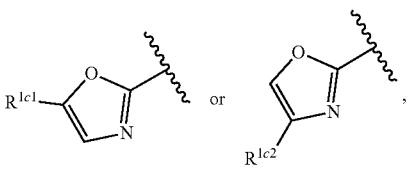

and $R^{1c1}$ and $R^{1c2}$ are each independently a 6-12 membered aryl. For example, in some embodiments, $R^{1c1}$ and $R^{1c2}$ are each independently phenyl or napthyl. In other embodiments, $Y^1$ is

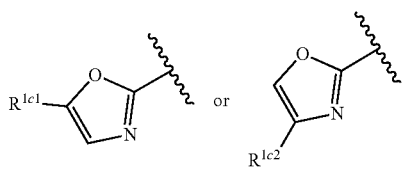 or , and $R^{1c1}$ and $R^{1c2}$ are each independently a 5-12 membered heteroaryl. For example, in some embodiments, $R^{1c1}$ and $R^{1c2}$ are each independently a pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl. In some embodiments, $Y^1$ is

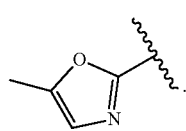 [SMILES: *c1ncc(C)o1]

In other embodiments, $Y^1$ is

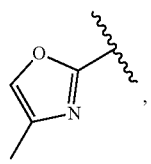 [SMILES: *c1nc(C)co1]

In some embodiments of Formula (I), (I-1), (I-2), (Ia), (Ia-1), or (Ia-2), $Y^1$ is

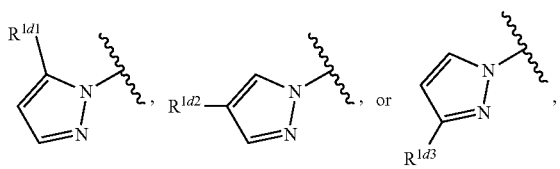

and $R^{1d1}$, $R^{1d2}$, and $R^{1d3}$ are each independently alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl. In some embodiments, $Y^1$ is

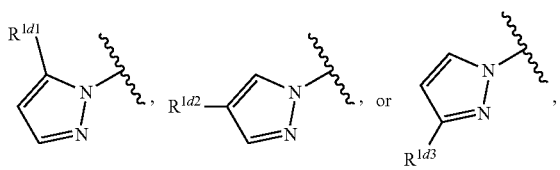

and $R^{1d1}$, $R^{1d2}$, and $R^{1d3}$ are each independently a $C_1$-$C_6$alkyl. For example, in some embodiments, $R^{1d1}$, $R^{1d2}$, and $R^{1d3}$ are each independently methyl, ethyl, n-propyl, isopropyl, butyl, isobutyl, secbutyl, or tertbutyl. In some embodiments,

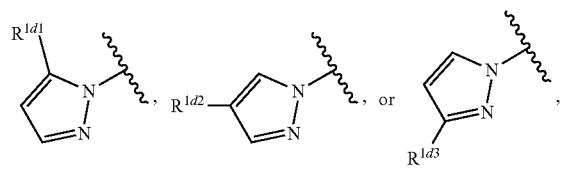

and $R^{1d1}$, $R^{1d2}$, and $R^{1d3}$ are each independently a $C_1$-$C_6$haloalkyl. For example, in some embodiments, $R^{1d1}$, $R^{1d2}$, and $R^{1d3}$ are each independently fluoromethyl, fluoroethyl, trifluoromethyl, difluoromethyl, or trifluoromethyl. In some embodiments, $Y^1$ is

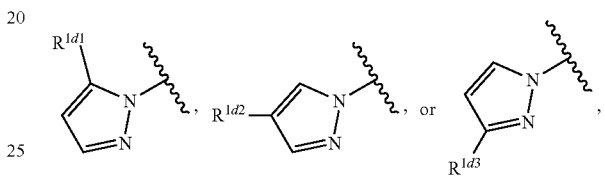

and $R^{1d1}$, $R^{1d2}$, and $R^{1d3}$ are each independently —C(O)O—$C_1$-$C_6$alkyl. For example, in some embodiments, $R^{1d1}$, $R^{1d2}$, and $R^{1d3}$ are each independently —C(O)OCH$_3$, —C(O)OEt, —C(O)OPr, —C(O)OiPr, or —C(O)OtBu. In some embodiments, $Y^1$ is

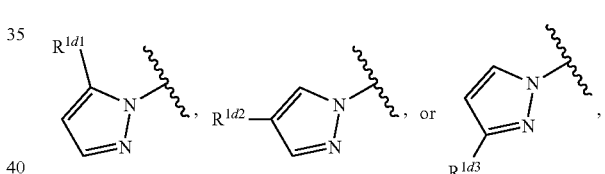

and $R^{1d1}$, $R^{1d2}$, and $R^{1d3}$ are each independently $C_3$-$C_8$cycloalkyl, $C_3$-$C_8$cycloalkenyl, or $C_3$-$C_8$cycloalkynyl. For example, in some embodiments, $R^{1d}$ is cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $Y^1$ is

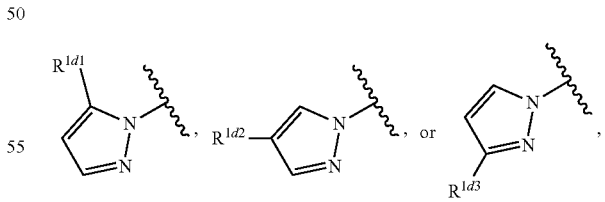

and $R^{1d1}$, $R^{1d2}$, and $R^{1d3}$ are each independently a 5-12 membered heterocycloalkyl or a 5-12 membered heterocycloalkenyl. For example, in some embodiments, $R^{1d1}$, $R^{1d2}$, and $R^{1d3}$ are each independently tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In some embodiments, $Y^1$ is

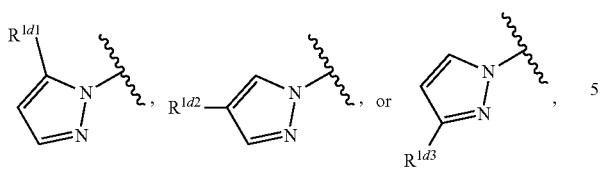

and $R^{1d1}$, $R^{1d2}$, and $R^{1d3}$ are each independently a 6-12 membered aryl. For example, in some embodiments, $R^{1d}$ is phenyl or napthyl. In other embodiments, $Y^1$ is

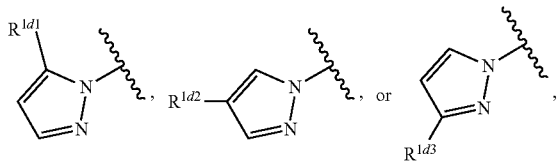

and $R^{1d1}$, $R^{1d2}$, and $R^{1d3}$ are each independently a 5-12 membered heteroaryl. For example, in some embodiments, $R^{1d1}$, $R^{1d2}$, and $R^{1d3}$ are each independently a pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl. In some embodiments, $Y^1$ is

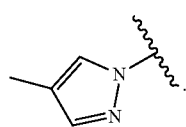

In some embodiments of Formula (I), (I-1), (I-2), (Ia), (Ia-1), or (Ia-2), $Y^1$ is

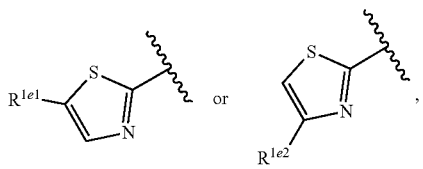

and $R^{1e1}$ and $R^{1e2}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, or heteroaryl. In some embodiments, $Y^1$ is

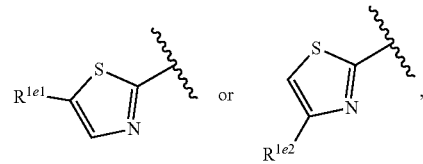

and $R^{1e1}$ and $R^{1e2}$ are each H. In some embodiments, $Y^1$ is

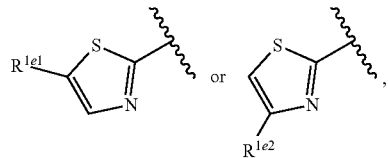

and $R^{1e1}$ and $R^{1e2}$ are each independently a $C_1$-$C_6$alkyl. For example, in some embodiments, $R^{1e1}$ and $R^{1e2}$ are each independently methyl, ethyl, n-propyl, isopropyl, butyl, isobutyl, secbutyl, or tertbutyl. In some embodiments, $Y^1$ is

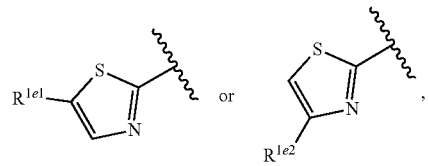

and $R^{1e1}$ and $R^{1e2}$ are each independently a $C_1$-$C_6$haloalkyl. For example, in some embodiments, $R^{1e1}$ and $R^{1e2}$ are each independently fluoromethyl, fluoroethyl, trifluoromethyl, difluoromethyl or trifluoromethyl. In some embodiments, $Y^1$ is

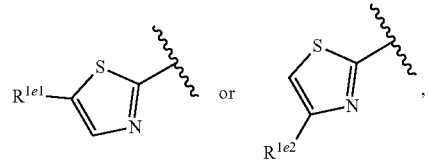

and $R^{1e1}$ and $R^{1e2}$ are each independently —C(O)O—$C_1$-$C_6$alkyl. For example, in some embodiments, $R^{1e1}$ and $R^{1e2}$ are each independently —C(O)OCH$_3$, —C(O)OEt, —C(O)OPr, —C(O)OiPr, or —C(O)OtBu. In some embodiments, $Y^1$ is

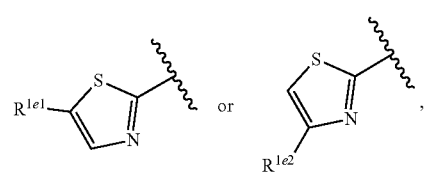

and $R^{1e1}$ and $R^{1e2}$ are each independently $C_3$-$C_8$cycloalkyl, $C_3$-$C_8$cycloalkenyl, or $C_3$-$C_8$cycloalkynyl. For example, in some embodiments, $R^{1e1}$ and $R^{1e2}$ are each independently cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $Y^1$ is

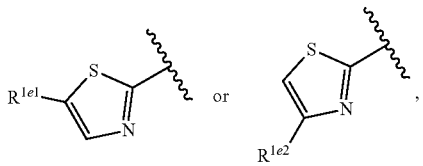

and $R^{1e1}$ and $R^{1e2}$ are each independently a 5-12 membered heterocycloalkyl or a 5-12 membered heterocycloalkenyl. For example, in some embodiments, $R^{1e1}$ and $R^{1e2}$ are each independently tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In other embodiments, $Y^1$ is

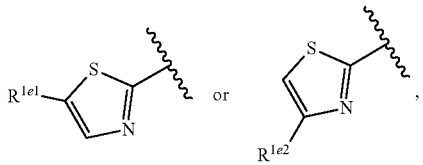

and $R^{1e1}$ and $R^{1e2}$ are each independently a 5-12 membered heteroaryl. For example, in some embodiments, $R^{1e1}$ and $R^{1e2}$ are each independently a pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl. In some embodiments, $Y^1$ is

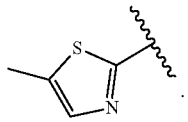

In some embodiments of Formula (I), (I-1), (I-2), (Ia), (Ia-1), or (Ia-2), $Y^1$ is

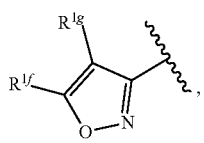

and $R^{1f}$ and $R^{1g}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl. In some embodiments, $Y^1$ is

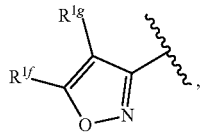

and one of $R^{1f}$ and $R^{1g}$ is H. In other embodiments, $Y^1$ is

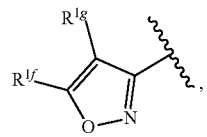

and both $R^{1f}$ and $R^{1g}$ are H. In some embodiments, $Y^1$ is

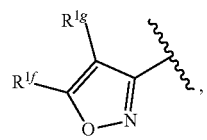

and one of $R^{1f}$ and $R^{1g}$ is a $C_1$-$C_6$alkyl. For example, in some embodiments, one of $R^{1f}$ and $R^{1g}$ is methyl, ethyl, n-propyl, isopropyl, butyl, isobutyl, secbutyl, or tertbutyl. In some embodiments, $Y^1$ is

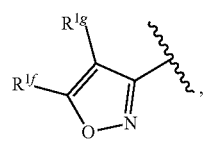

and one of $R^{1f}$ and $R^{1g}$ is a $C_1$-$C_6$haloalkyl. For example, in some embodiments, one of $R^{1f}$ and $R^{1g}$ is fluoromethyl, fluoroethyl, trifluoromethyl, difluoromethyl, or trifluoromethyl. In some embodiments, $Y^1$ is

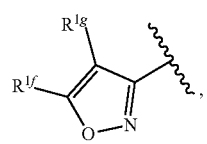

and one of $R^{1f}$ and $R^{1g}$ is —C(O)O—$C_1$-$C_6$alkyl. For example, in some embodiments, one of $R^{1f}$ and $R^{1g}$ is —C(O)OCH$_3$, —C(O)OEt, —C(O)OPr, —C(O)OiPr, or —C(O)OtBu. In some embodiments, $Y^1$ is

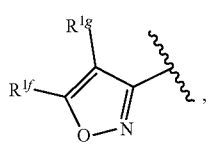

and one of $R^{1f}$ and $R^{1g}$ is a $C_3$-$C_8$cycloalkyl, $C_3$-$C_8$cycloalkenyl, or $C_3$-$C_8$cycloalkynyl. For example, in some embodiments, one of $R^{1f}$ and $R^{1g}$ is cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $Y^1$ is

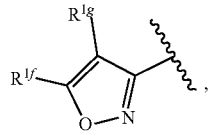

and one of $R^{1f}$ and $R^{1g}$ is a 5-12 membered heterocycloalkyl or a 5-12 membered heterocycloalkenyl. For example, in some embodiments, one of $R^{1f}$ and $R^{1g}$ is tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In some embodiments, $Y^1$ is

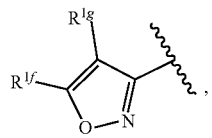

and one of $R^{1f}$ and $R^{1g}$ is a 6-12 membered aryl. For example, in some embodiments, one of $R^{1f}$ and $R^{1g}$ is phenyl or napthyl. In other embodiments, $Y^1$ is

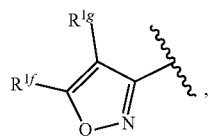

and one of $R^{1f}$ and $R^{1g}$ is a 5-12 membered heteroaryl. For example, in some embodiments, one of $R^{1f}$ and $R^{1g}$ is a pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl. In some embodiments, $Y^1$ is

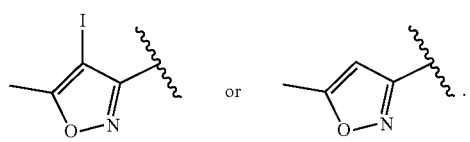

In some embodiments of Formula (I), (I-1), (I-2), (Ia), (Ia-1), or (Ia-2), $Y^1$ is

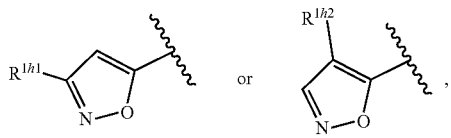

and $R^{1h1}$ and $R^{1h2}$ are each independently H, alkyl, haloalkyl, —C(O)O-alkyl, cycloalkyl, cycloalkenyl, heterocycloalkyl, heterocycloalkenyl, aryl, or heteroaryl. In some embodiments, $Y^1$ is

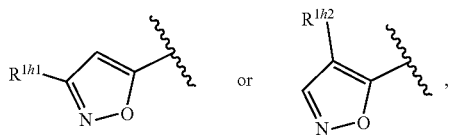

and $R^{1h1}$ and $R^{1h2}$ are each H. In some embodiments, $Y^1$ is

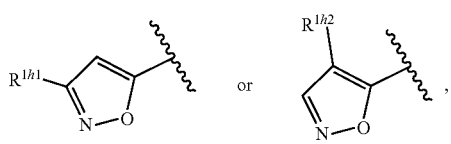

and $R^{1h1}$ and $R^{1h2}$ are each independently a $C_1$-$C_6$alkyl. For example, in some embodiments, $R^{1h1}$ and $R^{1h2}$ are each independently methyl, ethyl, n-propyl, isopropyl, butyl, isobutyl, secbutyl, or tertbutyl. In some embodiments, $Y^1$ is

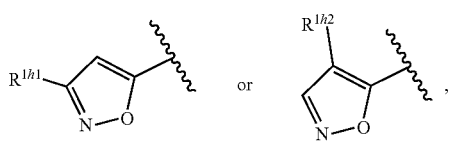

and $R^{1h1}$ and $R^{1h2}$ are each independently a $C_1$-$C_6$haloalkyl. For example, in some embodiments, $R^{1h1}$ and $R^{1h2}$ are each independently fluoromethyl, fluoroethyl, trifluoromethyl, difluoromethyl, or trifluoromethyl.

In some embodiments, $Y^1$ is

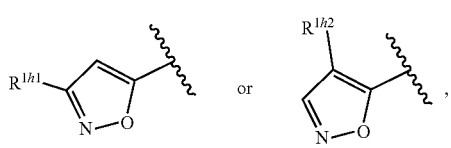

and $R^{1h1}$ and $R^{1h2}$ are each independently —C(O)O—$C_1$-$C_6$alkyl. For example, in some embodiments, $R^{1h1}$ and $R^{1h2}$ are each independently —C(O)OCH$_3$, —C(O)OEt, —C(O)OPr, —C(O)OiPr, or —C(O)OtBu. In some embodiments, $Y^1$ is

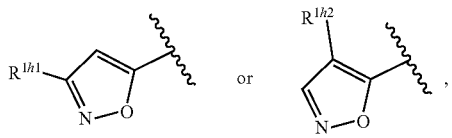

and $R^{1h1}$ and $R^{1h2}$ are each independently $C_3$-$C_8$cycloalkyl, $C_3$-$C_8$cycloalkenyl, or $C_3$-$C_8$cycloalkynyl. For example, in some embodiments, $R^{1h1}$ and $R^{1h2}$ are each independently cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $Y^1$ is

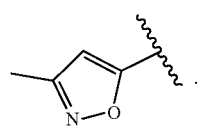 [SMILES: *c1cc(C)no1]

and $R^{1h1}$ and $R^{1h2}$ are each independently a 5-12 membered heterocycloalkyl or a 5-12 membered heterocycloalkenyl. For example, in some embodiments, $R^{1h1}$ and $R^{1h2}$ are each independently tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In some embodiments, $Y^1$ is and $R^{1h1}$ and $R^{1h2}$ are each independently a 6-12 membered aryl. For example, in some embodiments, $R^{1h1}$ and $R^{1h2}$ are each independently phenyl or napthyl. In other embodiments, $Y^1$ is and $R^{1h1}$ and $R^{1h2}$ are each independently a 5-12 membered heteroaryl. For example, in some embodiments, $R^{1h1}$ and $R^{1h2}$ are each independently pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl. In some embodiments, $Y^1$ is In some embodiments of Formula (I), (I-1), (I-2), (Ia), (Ia-1), or (Ia-2), $Y^1$ is selected from the group consisting of

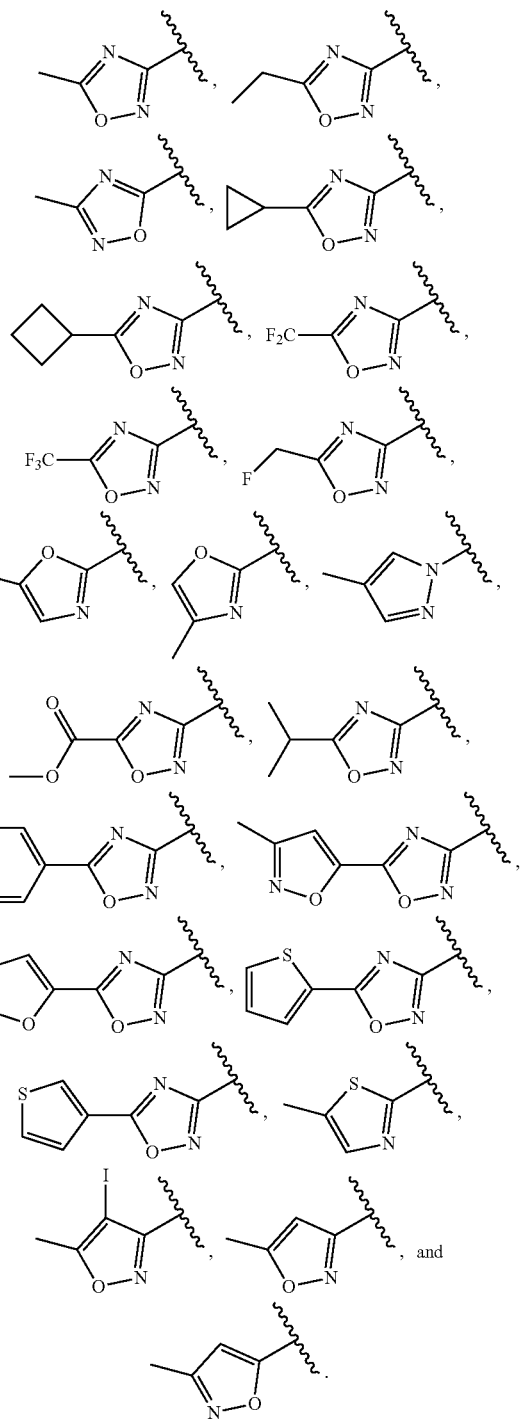

In some embodiments of Formula (I), (I-1), or (I-2), $L^1$ is absent. In other embodiments, $L^1$ is

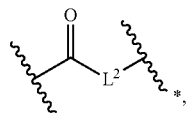

wherein $L^2$ is absent, —O—, —NH—, or —OCH$_2$—*, and wherein * indicates the attachment to $Y^2$. In some embodiments, $L^1$ is —C(O)—. In some embodiments, $L^1$ is

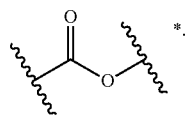 [SMILES: *OC(*)=O]

In some embodiments, $L^1$ is

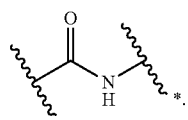

In other embodiments, $L^1$ is

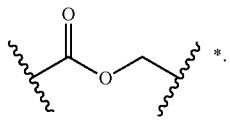 [SMILES: *COC(*)=O]

In some embodiments of Formula (I), (I-1), (I-2), (Ib), (Ib-1), or (Ib-2), $Y^1$ is

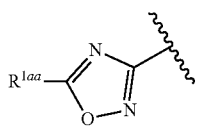

and $R^{1aa}$ is $C_1$-$C_6$alkyl. For example, in some embodiments, $R^{1aa}$ is methyl, ethyl, n-propyl, isopropyl, butyl, isobutyl, secbutyl, or tertbutyl. In some embodiments, $R^{1aa}$ is H. In some embodiments, $R^{1aa}$ is $C_3$-$C_8$cycloalkyl, $C_3$-$C_8$cycloalkenyl, or $C_3$-$C_8$cycloalkynyl. For example, in some embodiments, $R^{1aa}$ is cyclopropyl, cyclobutyl, cyclopentyl, cyclohexyl, cyclopropenyl, cyclobutenyl, cyclopentenyl, cyclohexenyl, cyclopentyne, cyclohexyne, cycloheptyne, or cyclooctyne. In some embodiments, $R^{1aa}$ is a 5-12 membered heterocycloalkyl or a 5-12 membered heterocycloalkenyl. For example, in some embodiments, $R^{1aa}$ is tetrahydrofuranyl, pyrrolidinyl, piperazinyl, piperidinyl, morpholinyl, thiomorpholinyl, 1,1-dioxothiomorpholinyl, dihydroindolyl, indazolyl, quinolizinyl, imidazolidinyl, imidazolinyl, indolinyl, 1,2,3,4-tetrahydroisoquinolinyl, or thiazolidinyl. In some embodiments, $R^{1aa}$ is a 6-12 membered aryl. For example, in some embodiments, $R^{1aa}$ is phenyl or napthyl. In other embodiments, $R^{1aa}$ is a 5-12 membered heteroaryl. For example, in some embodiments, $R^{1aa}$ is pyrrolyl, furanyl, thiophenyl, imidazolyl, pyrazolyl, thiazolyl, oxazolyl, isoxazolyl, isothiazolyl, triazolyl, oxadiazolyl, thiadiazolyl, tetrazolyl, pyridinyl, pyrazinyl, pyrimidinyl, pyridazinyl, indolyl, benzofuranyl, benzothiophenyl, indazolyl, benzimidazolyl, benzothiazolyl, benzoxazolyl, indolizinyl, isoindolyl, purinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, phenoxazinyl, phenothiazinyl, or phthalimidyl.

In some embodiments of Formula (I), (I-1), (I-2), (Ib), (Ib-1), or (Ib-2), $L^2$ is absent. In some embodiments, $L^2$ is —O—. In some embodiments, $L^2$ is —NH—. In other embodiments, $L^2$ is —OCH$_2$—*, wherein * indicates the attachment to $Y^2$.

In some embodiments of Formula (I), (I-1), (I-2), (Ia), (Ia-1), (Ia-2), (Ib), (Ib-1), or (Ib-2),

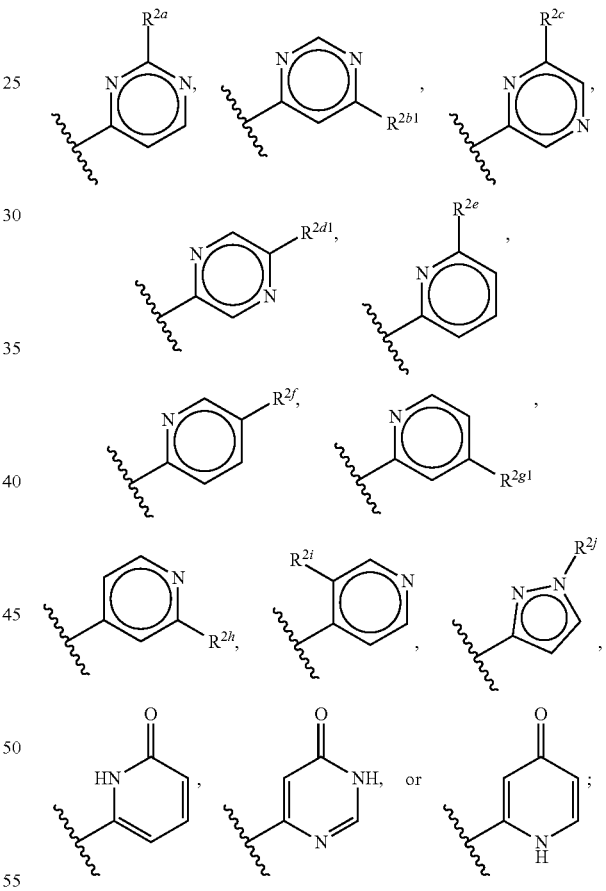

wherein $R^{2a}$, $R^{2b1}$, $R^{2c}$, $R^{2d1}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$; $R^{2e}$, $R^{2f}$, and $R^{2g1}$, are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and $R^c$ and $R^d$ are each independently H or alkyl. In some embodiments of Formula (I), (I-1), (I-2), (Ia), (Ia-1), (Ia-2), (Ib), (Ib-1), or (Ib-2),

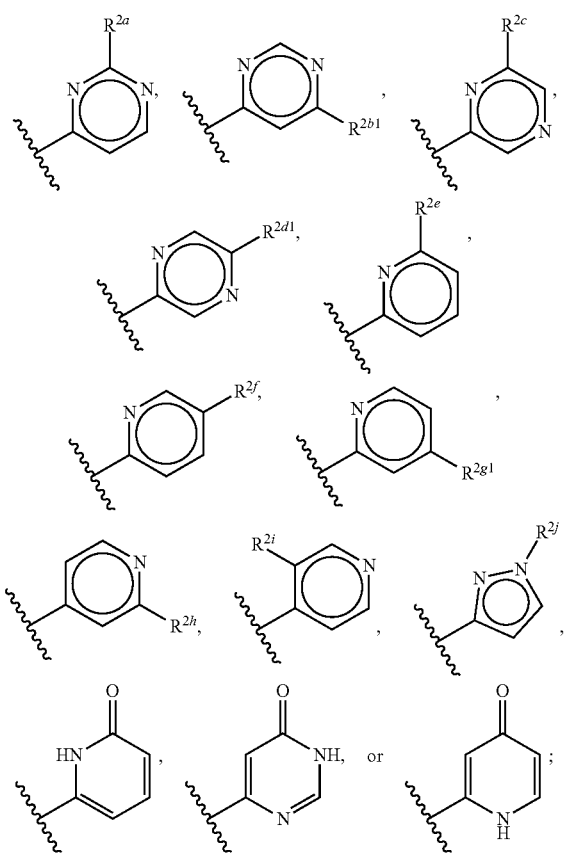

wherein $R^{2a}$, $R^{2b1}$, $R^{2e}$, $R^{2d1}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$; $R^{2e}$, $R^{2f}$, and $R^{2g1}$, are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and R$^c$ and R$^d$ are each independently H or alkyl.

In some embodiments of Formula (I), (I-1), (I-2), (Ia), (Ia-1), (Ia-2), (Ib), (Ib-1), or (Ib-2), $Y^2$ is

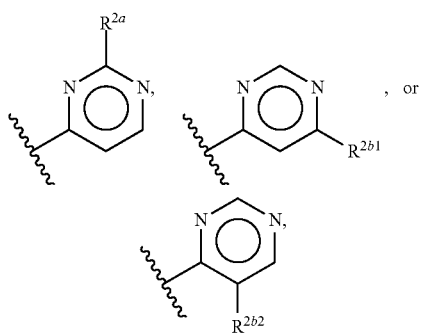

and $R^{2a}$, $R^{2b1}$, and $R^{2b2}$ are each independently selected from the group consisting of H, halo, —OH, —CN, —NR$^c$R$^d$, $C_1$-$C_6$alkyl, $C_2$-$C_6$alkenyl, $C_2$-$C_6$alkynyl, —O—$C_1$-$C_6$alkyl, $C_1$-$C_6$haloalkyl, $C_3$-$C_8$cycloalkyl, and —C(O)NR$^c$R$^d$. In some embodiments, $R^{2a}$, $R^{2b1}$, or $R^{2b2}$ is H. In some embodiments, $R^{2a}$, $R^{2b1}$, or $R^{2b2}$ is halo. In some embodiments, $R^{2a}$, $R^{2b1}$, or $R^{2b2}$ is F. In some embodiments, $R^{2a}$, $R^{2b1}$, or $R^{2b2}$ is Cl. In some embodiments, $R^{2a}$, $R^{2b1}$, or $R^{2b2}$ is Br. In other embodiments, $R^{2a}$, $R^{2b1}$, or $R^{2b2}$ is I. In some embodiments, $R^{2a}$, $R^{2b1}$, or $R^{2b2}$ is —CN. In some embodiments, $R^{2a}$, $R^{2b1}$, or $R^{2b2}$ is $C_1$-$C_6$alkyl, $C_2$-$C_6$alkenyl, or $C_2$-$C_6$alkynyl. In some embodiments, $R^{2a}$, $R^{2b1}$, or $R^{2b2}$ is methyl, ethyl, n-propyl, isopropyl, butyl, isobutyl, secbutyl, or tertbutyl. In some embodiments, $R^{2a}$, $R^{2b1}$, or $R^{2b2}$ is methyl. In some embodiments, $R^{2a}$, $R^{2b1}$, or $R^{2b2}$ is ethyl. In some embodiments, $R^{2a}$, $R^{2b1}$, or $R^{2b2}$ is $C_1$-$C_6$haloalkyl. In some embodiments, $R^{2a}$, $R^{2b1}$, or $R^{2b2}$ is fluoromethyl, fluoroethyl, trifluoromethyl, difluoromethyl, or trifluoromethyl. In some embodiments, $R^{2a}$, $R^{2b1}$, or $R^{2b2}$ is $CF_3$. In some embodiments, $R^{2a}$, $R^{2b1}$, or $R^{2b2}$ is $C_3$-$C_8$cycloalkyl. In some embodiments, $R^{2a}$, $R^{2b1}$, or $R^{2b2}$ is cyclopropyl, cyclobutyl, cyclopentyl, or cyclohexyl. In some embodiments, $R^{2a}$, $R^{2b1}$, or $R^{2b2}$ is cyclopropyl. In some embodiments, $R^{2a}$, $R^{2b1}$, or $R^{2b2}$ is $NH_2$ or —C(O)NH$_2$. In some embodiments, $R^{2a}$, $R^{2b1}$, or $R^{2b2}$ is —OH, methoxy, ethoxy, propoxy, isopropoxy, or tertbutoxy. In some embodiments, $Y^2$ is selected from the group consisting of

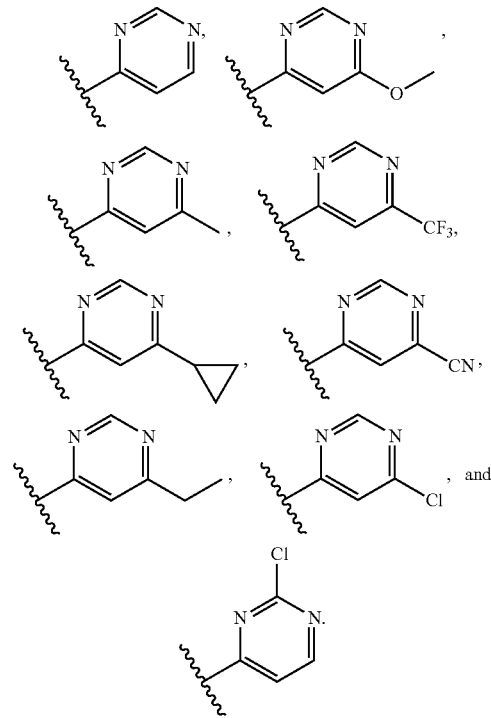

In some embodiments of Formula (I), (I-1), (1-2), (Ia), (Ia-1), (Ia-2), (Ib), (Ib-1), or (Ib-2), $Y^2$ is

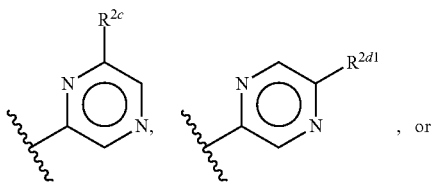

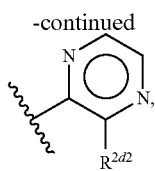

and $R^{2c}$, $R^{2d1}$, and $R^{2b2}$ are each independently selected from the group consisting of H, halo, —OH, —CN, —NR$^c$R$^d$, C$_1$-C$_6$alkyl, C$_2$-C$_6$alkenyl, C$_2$-C$_6$alkynyl, —O—C$_1$-C$_6$alkyl, C$_1$-C$_6$haloalkyl, C$_3$-C$_5$cycloalkyl, and —C(O)NR$^c$R$^d$. In some embodiments, $R^{2c}$, $R^{2d1}$, or $R^{2d2}$ is H. In some embodiments, $R^{2c}$, $R^{2d1}$, or $R^{2d2}$ is halo. In some embodiments, $R^{2c}$, $R^{2d1}$, or $R^{2d2}$ is F. In some embodiments, $R^{2c}$, $R^{2d1}$, or $R^{2b2}$ is Cl. In some embodiments, $R^{2c}$, $R^{2d1}$, or $R^{2d2}$ is Br. In other embodiments, $R^{2c}$, $R^{2d1}$, or $R^{2b2}$ is I. In some embodiments, $R^{2c}$, $R^{2d1}$, or $R^{2d2}$ is —CN. In some embodiments, $R^{2c}$, $R^{2d1}$, or $R^{2d2}$ is C$_1$-C$_6$alkyl, C$_2$-C$_6$alkenyl, or C$_2$-C$_6$alkynyl. In some embodiments, $R^{2c}$, $R^{2d1}$, or $R^{2d2}$ is methyl, ethyl, n-propyl, isopropyl, butyl, isobutyl, secbutyl, or tertbutyl. In some embodiments, $R^{2c}$, $R^{2d1}$, or $R^{2d2}$ is methyl. In some embodiments, $R^{2c}$, $R^{2d1}$, or $R^{2d2}$ is ethyl. In some embodiments, $R^{2c}$, $R^{2d1}$ or $R^{2b2}$ is C$_1$-C$_6$haloalkyl. In some embodiments, $R^{2c}$, $R^{2d1}$ or $R^{2b2}$ is fluoromethyl, fluoroethyl, trifluoromethyl, difluoromethyl, or trifluoromethyl. In some embodiments, $R^{2c}$, $R^{2d1}$, or $R^{2d2}$ is CF$_3$. In some embodiments, $R^{2c}$, $R^{2d1}$, or $R^{2d2}$ is C$_3$-C$_8$cycloalkyl. In some embodiments, $R^{2c}$, $R^{2d1}$, or $R^{2d2}$ is cyclopropyl, cyclobutyl, cyclopentyl, or cyclohexyl. In some embodiments, $R^{2c}$, $R^{2d1}$, or $R^{2d2}$ is cyclopropyl. In some embodiments, $R^{2c}$, $R^{2d1}$, or $R^{2d2}$ is NH$_2$ or —C(O)NH$_2$. In some embodiments, $R^{2c}$, $R^{2d1}$, or $R^{2d2}$ is —OH, methoxy, ethoxy, propoxy, isopropoxy, or tertbutoxy. In some embodiments, $Y^2$ is selected from the group consisting of and $R^{2e}$, $R^{2f}$, $R^{2g1}$, and $R^{2g2}$ are each independently selected from the group consisting of halo, —OH, —CN, —NR$^c$R$^d$, C$_1$-C$_6$alkyl, C$_2$-C$_6$alkenyl, C$_2$-C$_6$alkynyl, —O—C$_1$-C$_6$alkyl, C$_1$-C$_6$haloalkyl, C$_3$-C$_8$cycloalkyl, and —C(O)NR$^c$R$^d$. In some embodiments, $R^{2e}$, $R^{2f}$, $R^{2g1}$, or $R^{2g2}$ is halo. In some embodiments, $R^{2e}$, $R^{2f}$, $R^{2g1}$, or $R^{2g2}$ is F. In some embodiments, $R^{2e}$, $R^{2f}$, $R^{2g1}$, or $R^{2g2}$ is Cl. In some embodiments, $R^{2e}$, $R^{2f}$, $R^{2g1}$, or $R^{2g2}$ is Br. In other embodiments, $R^{2e}$, $R^{2f}$, $R^{2g1}$, or $R^{2g2}$ is I. In some embodiments, $R^{2e}$, $R^{2f}$, $R^{2g1}$, or $R^{2g2}$ is —CN. In some embodiments, $R^{2e}$, $R^{2f}$, $R^{2g1}$, or $R^{2g2}$ is C$_1$-C$_6$alkyl, C$_2$-C$_6$alkenyl, or C$_2$-C$_6$alkynyl. In some embodiments, $R^{2e}$, $R^{2f}$, $R^{2g1}$, or $R^{2g2}$ is methyl, ethyl, n-propyl, isopropyl, butyl, isobutyl, secbutyl, or tertbutyl. In some embodiments, $R^{2e}$, $R^{2f}$, $R^{2g1}$, or $R^{2g2}$ is methyl. In some embodiments, $R^{2e}$, $R^{2f}$, $R^{2g1}$, or $R^{2g2}$ is ethyl. In some embodiments, $R^{2e}$, $R^{2f}$, $R^{2g1}$, or $R^{2g2}$ is C$_1$-C$_6$haloalkyl. In some embodiments, $R^{2e}$, $R^{2f}$, $R^{2g1}$, or $R^{2g2}$ is fluoromethyl, fluoroethyl, trifluoromethyl, difluoromethyl, or trifluoromethyl. In some embodiments, $R^{2e}$, $R^{2f}$, $R^{2g1}$, or $R^{2g2}$ is CF$_3$. In some embodiments, $R^{2e}$, $R^{2f}$, $R^{2g1}$, or $R^{2g2}$ is C$_3$-C$_8$cycloalkyl. In some embodiments, $R^{2e}$, $R^{2f}$, $R^{2g1}$, or $R^{2g2}$ is cyclopropyl, cyclobutyl, cyclopentyl, or cyclohexyl. In some embodiments, $R^{2e}$, $R^{2f}$, $R^{2g1}$, or $R^{2g2}$ is cyclopropyl. In some embodiments, $R^{2e}$, $R^{2f}$, $R^{2g1}$, or $R^{2g2}$ is NH$_2$ or —C(O)NH$_2$. In some embodiments, $R^{2e}$, $R^{2f}$, $R^{2g1}$, or $R^{2g2}$ is —OH, methoxy, ethoxy, propoxy, isopropoxy, or tertbutoxy. In some embodiments, $Y^2$ is selected from the group consisting of

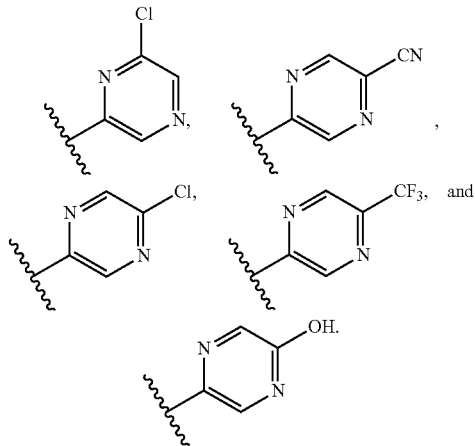

In some embodiments of Formula (I), (I-1), (I-2), (Ia), (Ia-1), (Ia-2), (Ib), (Ib-1), or (Ib-2), $Y^2$ is

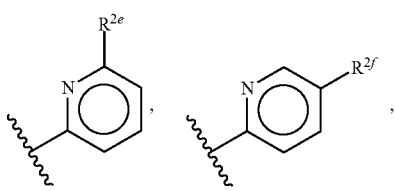

In some embodiments of Formula (I), (I-1), (I-2), (Ia), (Ia-1), (Ia-2), (Ib), (Ib-1), or (Ib-2), $Y^2$ is

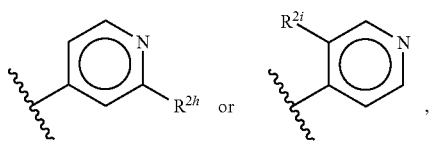

and $R^{2h}$ and $R^{2i}$ are each independently selected from the group consisting of H, halo, —OH, —CN, —NR$^c$R$^d$, $C_1$-$C_6$alkyl, $C_2$-$C_6$alkenyl, $C_2$-$C_6$alkynyl, —O—$C_1$-$C_6$alkyl, $C_1$-$C_6$haloalkyl, $C_3$-$C_8$cycloalkyl, and —C(O)NR$^c$R$^d$. In some embodiments, $R^{2h}$ or $R^{2i}$ is H. In some embodiments, $R^{2h}$ or $R^{2i}$ is halo. In some embodiments, $R^{2h}$ or $R^{2i}$ is F. In some embodiments, $R^{2h}$ or $R^{2i}$ is Cl. In some embodiments, $R^{2h}$ or $R^{2i}$ is Br. In other embodiments, $R^{2h}$ or $R^{2i}$ is I. In some embodiments, $R^{2h}$ or $R^{2i}$ is —CN. In some embodiments, $R^{2h}$ or $R^{2i}$ is $C_1$-$C_6$alkyl, $C_2$-$C_6$alkenyl, or $C_2$-$C_6$alkynyl. In some embodiments, $R^{2h}$ or $R^{2i}$ is methyl, ethyl, n-propyl, isopropyl, butyl, isobutyl, secbutyl, or tertbutyl. In some embodiments, $R^{2h}$ or $R^{2i}$ is methyl. In some embodiments, $R^{2h}$ or $R^{2i}$ is ethyl. In some embodiments, $R^{2h}$ or $R^{2i}$ is $C_1$-$C_6$haloalkyl. In some embodiments, $R^{2h}$ or $R^{2i}$ is fluoromethyl, fluoroethyl, trifluoromethyl, difluoromethyl, or trifluoromethyl. In some embodiments, $R^{2h}$ or $R^{2i}$ is CF$_3$. In some embodiments, $R^{2h}$ or $R^{2i}$ is $C_3$-$C_8$cycloalkyl. In some embodiments, $R^{2h}$ or $R^{2i}$ is cyclopropyl, cyclobutyl, cyclopentyl, or cyclohexyl. In some embodiments, $R^{2h}$ or $R^{2i}$ is cyclopropyl. In some embodiments, $R^{2h}$ or $R^{2i}$ is NH$_2$ or —C(O)NH$_2$. In some embodiments, $R^{2h}$ or $R^{2i}$ is —OH, methoxy, propoxy, isopropoxy, or tertbutoxy. In some embodiments, $Y^2$ is selected from the group consisting of

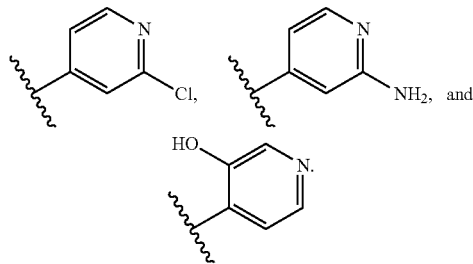

In some embodiments of Formula (I), (I-1), (I-2), (Ia), (Ia-1), (Ia-2), (Ib), (Ib-1), or (Ib-2), $Y^2$ is

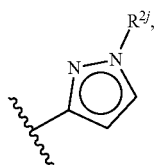

and $R^{2j}$ is selected from the group consisting of H, halo, —OH, —CN, —NR$^c$R$^d$, $C_1$-$C_6$alkyl, $C_2$-$C_6$alkenyl, $C_2$-$C_6$alkynyl, —O—$C_1$-$C_6$alkyl, $C_1$-$C_6$haloalkyl, $C_3$-$C_8$cycloalkyl, and —C(O)NR$^c$R$^d$. In some embodiments, $R^{2j}$ is H. In some embodiments, $R^{2j}$ is halo. In some embodiments, $R^{2j}$ is F. In some embodiments, $R^{2j}$ is Cl. In some embodiments, $R^{2j}$ is Br. In other embodiments, $R^{2j}$ is I. In some embodiments, $R^{2j}$ is —CN. In some embodiments, $R^{2j}$ is $C_1$-$C_6$alkyl, $C_2$-$C_6$alkenyl, or $C_2$-$C_6$alkynyl. In some embodiments, $R^{2j}$ is methyl, ethyl, n-propyl, isopropyl, butyl, isobutyl, secbutyl, or tertbutyl. In some embodiments, $R^{2j}$ is methyl. In some embodiments, $R^{2j}$ is ethyl. In some embodiments, $R^{2j}$ is $C_1$-$C_6$haloalkyl. In some embodiments, $R^{2j}$ is fluoromethyl, fluoroethyl, trifluoromethyl, difluoromethyl, or trifluoromethyl. In some embodiments, $R^{2j}$ is CF$_3$. In some embodiments, $R^{2j}$ is $C_3$-$C_8$cycloalkyl. In some embodiments, $R^{2j}$ is cyclopropyl, cyclobutyl, cyclopentyl, or cyclohexyl. In some embodiments, $R^{2j}$ is cyclopropyl. In some embodiments, $R^{2j}$ is NH$_2$ or —C(O)NH$_2$. In some embodiments, $R^{2j}$ is —OH, methoxy, ethoxy, propoxy, isopropoxy, or tertbutoxy. In some embodiments, $Y^2$ is

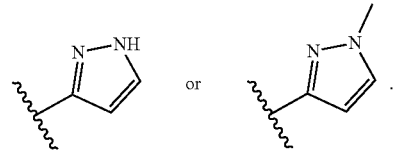

In some embodiments of Formula (I), (I-1), (I-2), (Ia), (Ia-1), (Ia-2), (Ib), (Ib-1), or (Ib-2), $Y^2$ is selected from the group consisting of

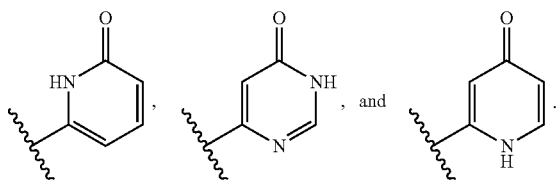

In some embodiments of Formula (I), (I-1), (I-2), (Ia), (Ia-1), (Ia-2), (Ib), (Ib-1), or (Ib-2), $Y^2$ is selected from the group consisting of

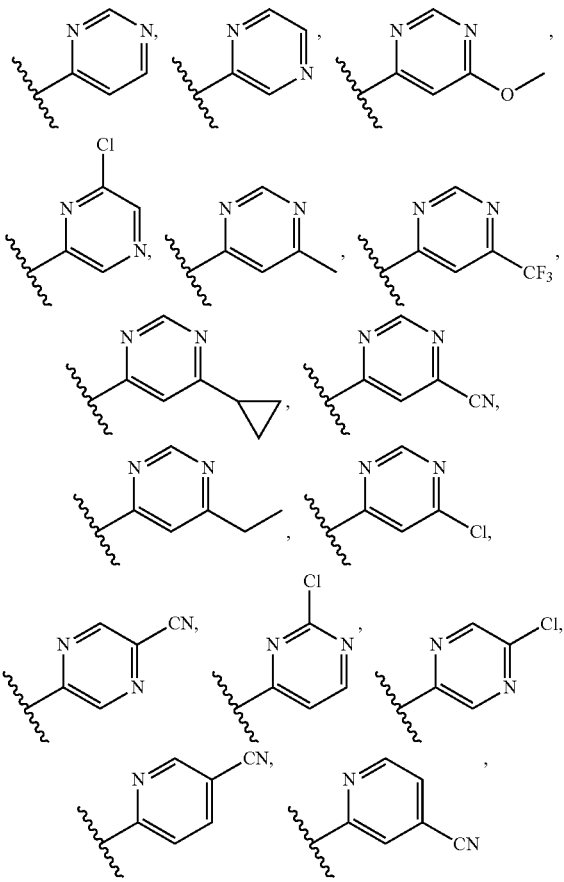

-continued

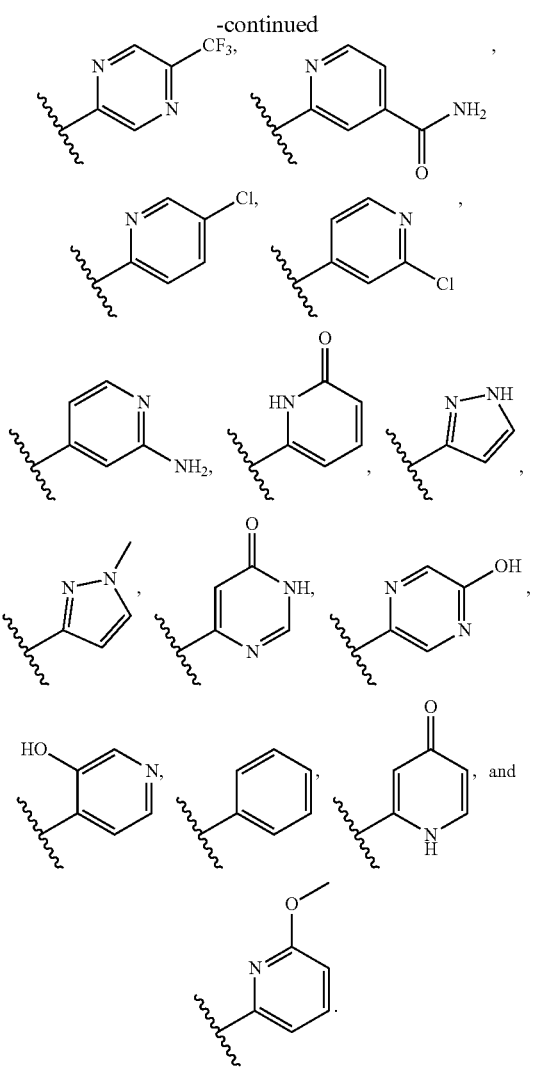

In some embodiments of Formula (I), (I-1), (I-2), (Ib), (Ib-1), or (Ib-2), $Y^2$ is $CH_3$. In some embodiments of Formula (I), (I-1), (I-2), (Ib), (Ib-1), or (Ib-2), $Y^2$ is phenyl.

It is understood that each description of $Y^1$ may be combined with each description of $Y^2$, $L^1$, $G^1$, $R^1$ and/or $R^2$ the same as if each and every combination were specifically and individually listed. Each description of $Y^2$ may also be combined with each description of $Y^1$, $L^1$, $G^1$, $R^1$ and/or $R^2$ the same as if each and every combination were specifically and individually listed. It is similarly understood that each description of $R^1$ and/or $R^2$ may be combined with each description of $Y^1$, $Y^2$, $L^1$, and/or $G^1$ the same as if each and every combination were specifically and individually listed.

In some embodiments of Formula (I), (I-1), (I-2), (Ib), (Ib-1), or (Ib-2), $Y^1$ is

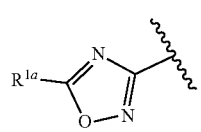

and $Y^2$ is

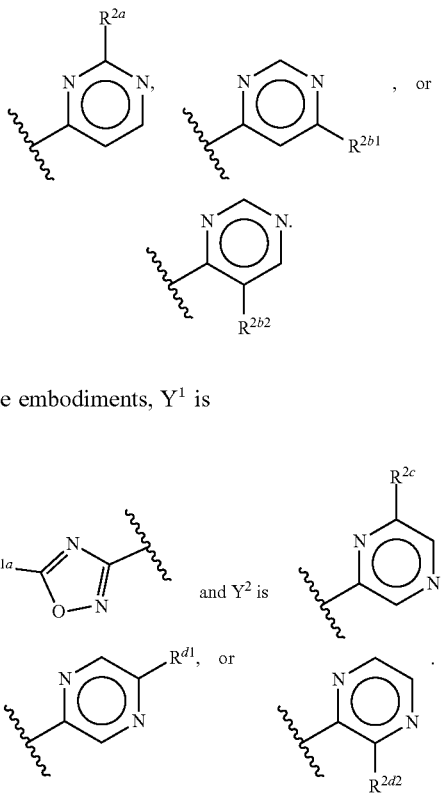

In some embodiments, $Y^1$ is

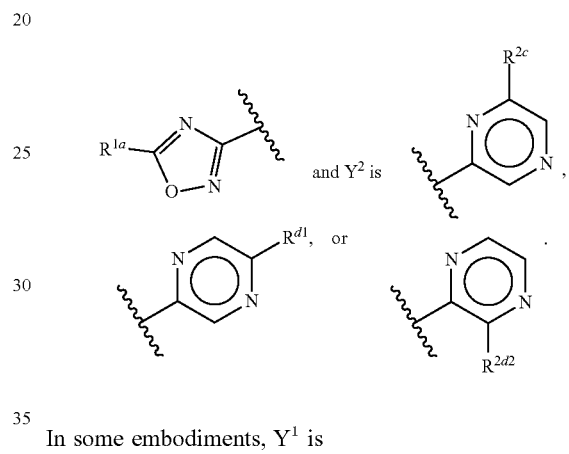

In some embodiments, $Y^1$ is

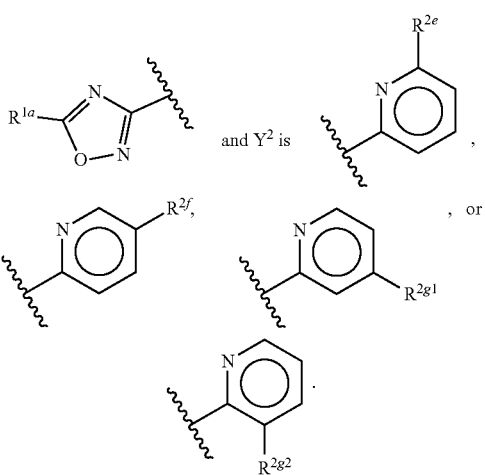

In some embodiments, $Y^1$ is

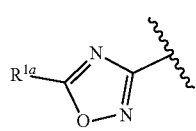

and Y² is

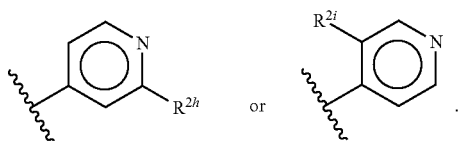

In some embodiments, Y¹ is

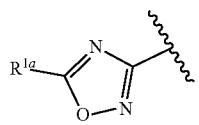

and Y² is

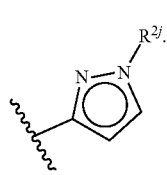

In some embodiments, Y¹ is

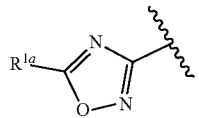

and Y² is

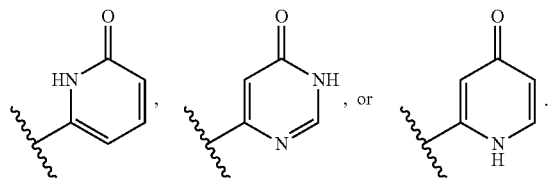

In some of any of the foregoing embodiments, R¹ is H. In some of any of the foregoing embodiments, R¹ is F, Cl, Br, or I. In some of any of the foregoing embodiments, R² is H. In some of any of the foregoing embodiments, R² is CH₃. In some of any of the foregoing embodiments, G¹ is —N—. In some of any of the foregoing embodiments, G¹ is —C(H)—. In some of any of the foregoing embodiments, G¹ is —C(F)—, —C(Cl)—, —C(Br)—, or —C(I)—. In some of any of the foregoing embodiments, G¹ is —C(R$^b$)—, wherein R$^b$ is taken together with R² and the atoms to which they are attached to form a 5- or 6-membered cycloalkyl ring.

In some embodiments of Formula (I), (I-1), (I-2), (Ib), (Ib-1), or (Ib-2), Y¹ is

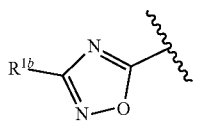

and Y² is

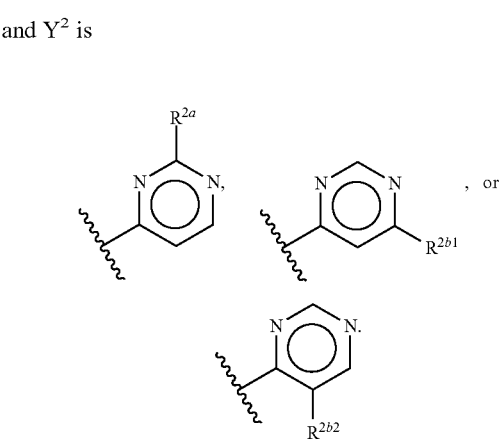

In some embodiments, Y¹ is

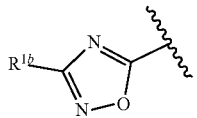

and Y² is

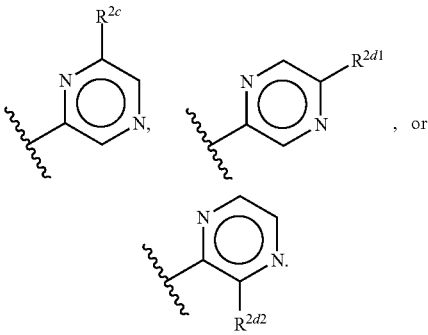

In some embodiments, Y¹ is

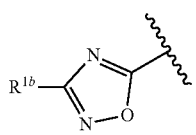

and $Y^2$ is

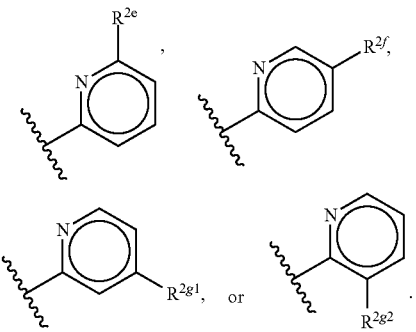

In some embodiments, $Y^1$ is

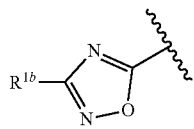

and $Y^2$ is

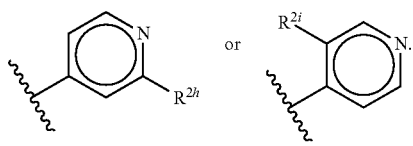

In some embodiments, $Y^1$ is

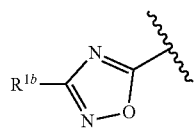

and $Y^2$ is

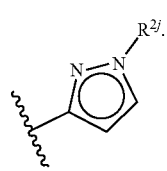

In some embodiments, $Y^1$ is

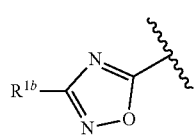

and $Y^2$ is

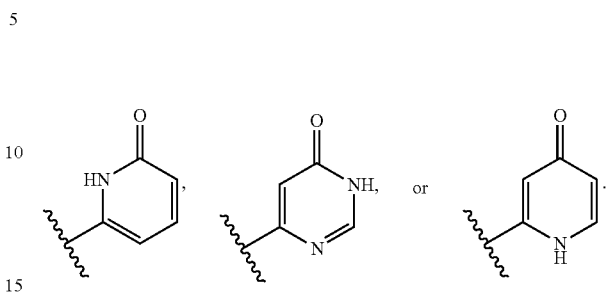

In some of any of the foregoing embodiments, $R^1$ is H. In some of any of the foregoing embodiments, $R^1$ is F, Cl, Br, or I. In some of any of the foregoing embodiments, $R^2$ is H. In some of any of the foregoing embodiments, $R^2$ is $CH_3$. In some of any of the foregoing embodiments, $G^1$ is —N—. In some of any of the foregoing embodiments, $G^1$ is —C(H)—. In some of any of the foregoing embodiments, $G^1$ is —C(F)—, —C(Cl)—, —C(Br)—, or —C(I)—. In some of any of the foregoing embodiments, $G^1$ is —C($R^b$)—, wherein $R^b$ is taken together with $R^2$ and the atoms to which they are attached to form a 5- or 6-membered cycloalkyl ring.

In some embodiments of Formula (I), (I-1), (I-2), (Ib), (Ib-1), or (Ib-2), $Y^1$ is

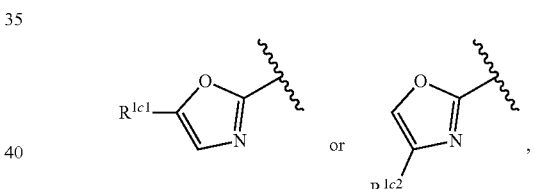

and $Y^2$ is

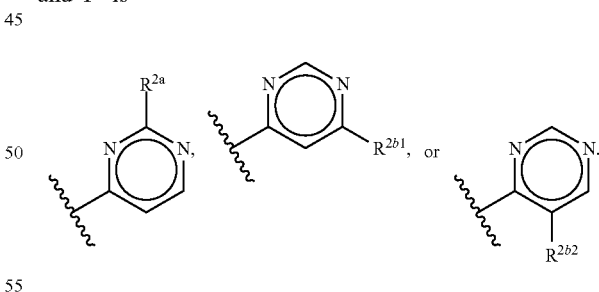

In some embodiments, $Y^1$ is

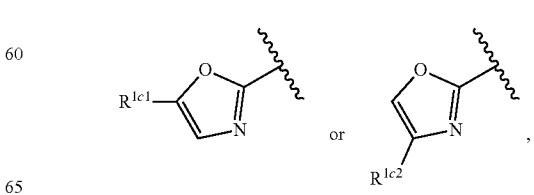

and Y² is

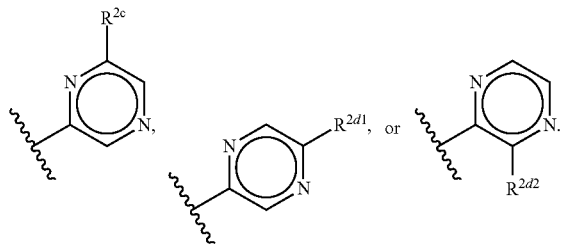

In some embodiments, Y¹ is

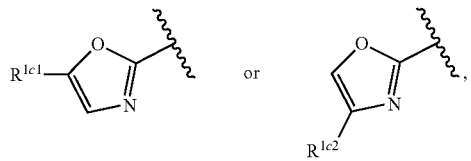

and Y² is

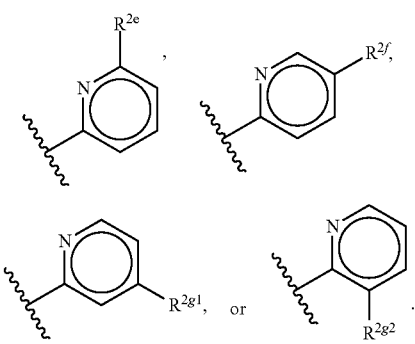

In some embodiments, Y¹ is

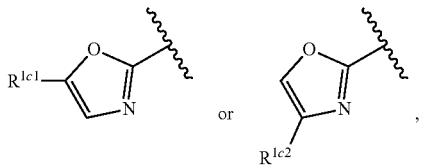

and Y² is

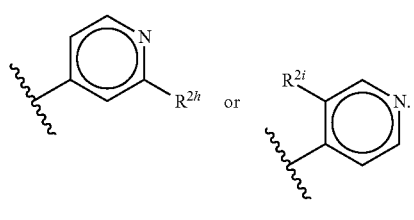

In some embodiments, Y¹ is

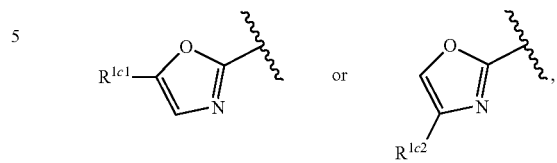

and Y² is

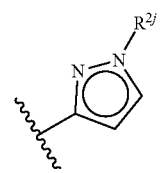

In some embodiments, Y¹ is

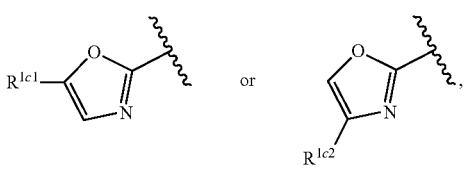

and Y² is

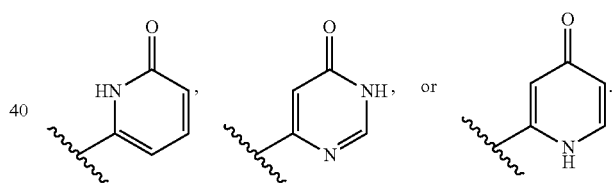

In some of any of the foregoing embodiments, R¹ is H. In some of any of the foregoing embodiments, R¹ is F, Cl, Br, or I. In some of any of the foregoing embodiments, R² is H. In some of any of the foregoing embodiments, R² is CH₃. In some of any of the foregoing embodiments, G¹ is —N—. In some of any of the foregoing embodiments, G¹ is —C(H)—. In some of any of the foregoing embodiments, G¹ is —C(F)—, —C(Cl)—, —C(Br)—, or —C(I)—. In some of any of the foregoing embodiments, G¹ is —C(R$^b$)—, wherein R$^b$ is taken together with R² and the atoms to which they are attached to form a 5- or 6-membered cycloalkyl ring.

In some embodiments of Formula (I), (I-1), (I-2), (Ib), (Ib-1), or (Ib-2), Y¹ is

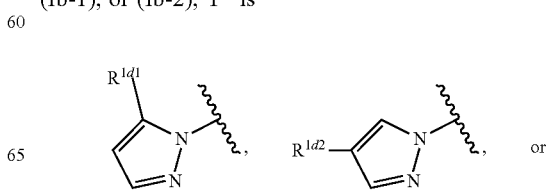

-continued
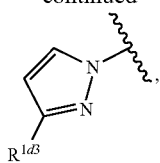
and Y² is
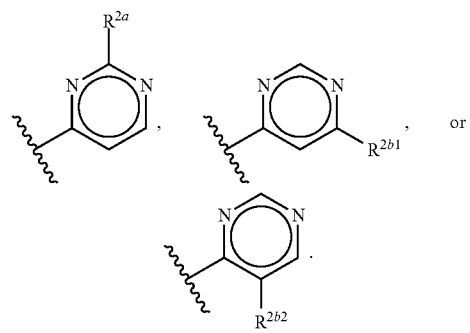
In some embodiments, Y¹ is
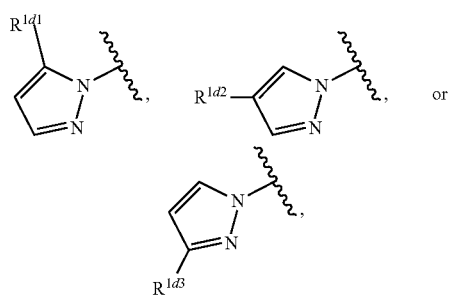
and Y² is
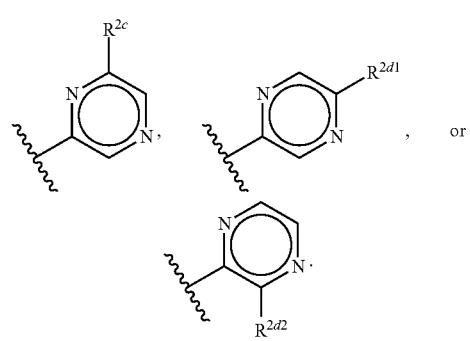
In some embodiments, Y¹ is
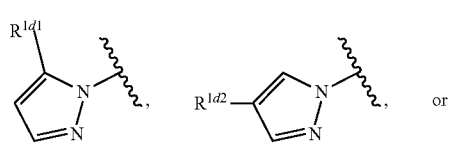
-continued
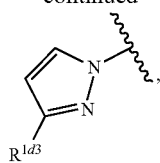
and Y² is
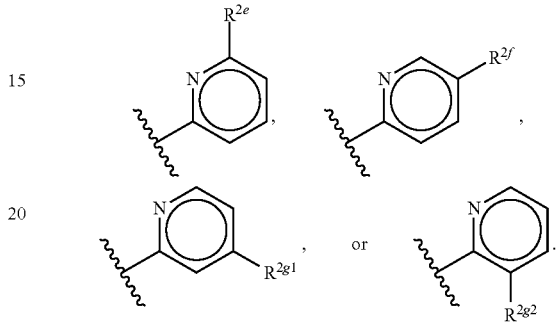
In some embodiments, Y¹ is
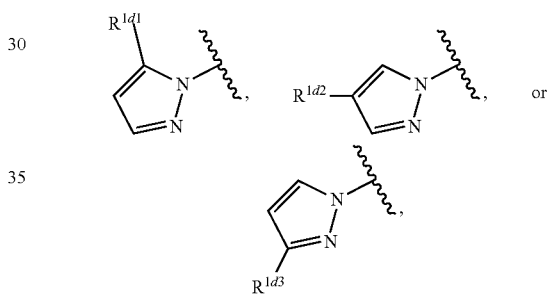
and Y² is
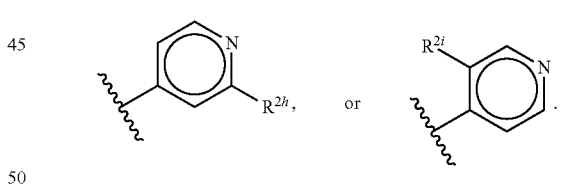
In some embodiments, Y¹ is
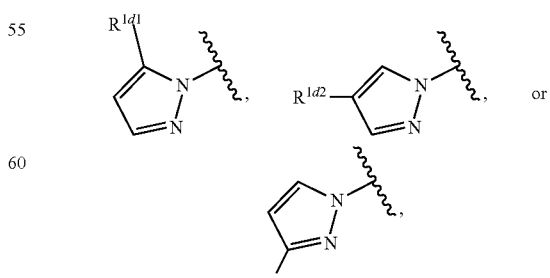

and Y² is

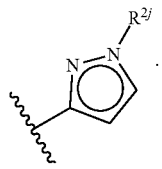

In some embodiments, Y¹ is

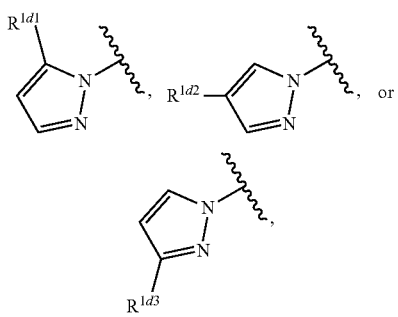

and Y² is

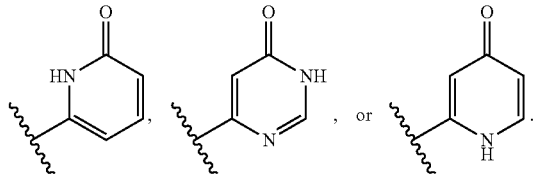

In some of any of the foregoing embodiments, R¹ is H. In some of any of the foregoing embodiments, R¹ is F, Cl, Br, or I. In some of any of the foregoing embodiments, R² is H. In some of any of the foregoing embodiments, R² is CH₃. In some of any of the foregoing embodiments, G¹ is —N—. In some of any of the foregoing embodiments, G¹ is —C(H)—. In some of any of the foregoing embodiments, G¹ is —C(F)—, —C(Cl)—, —C(Br)—, or —C(I)—. In some of any of the foregoing embodiments, G¹ is —C(R$^b$)—, wherein R$^b$ is taken together with R² and the atoms to which they are attached to form a 5- or 6-membered cycloalkyl ring.

In some embodiments of Formula (I), (I-1), (I-2), (Ib), (Ib-1), or (Ib-2), Y¹ is

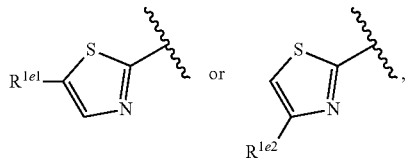

and Y² is

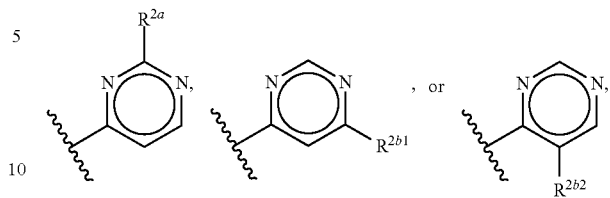

In some embodiments, Y¹ is

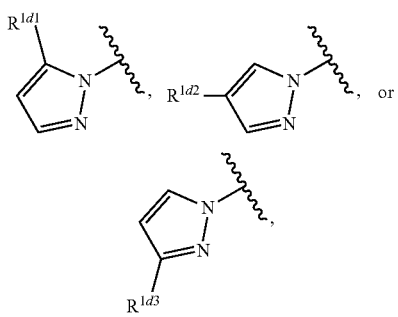

and Y² is

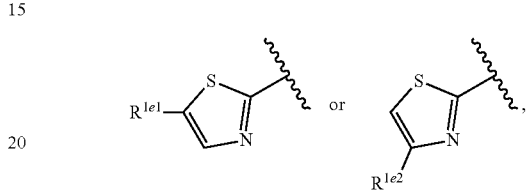

In some embodiments, Y¹ is

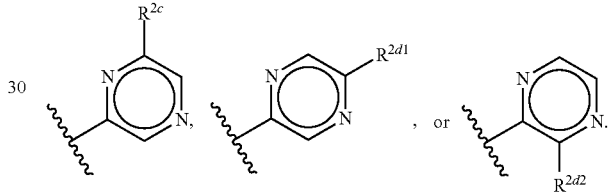

and Y² is

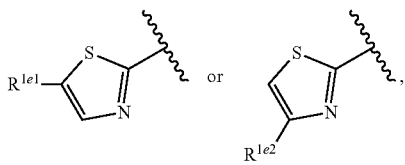

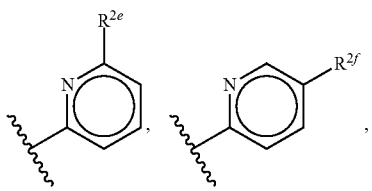

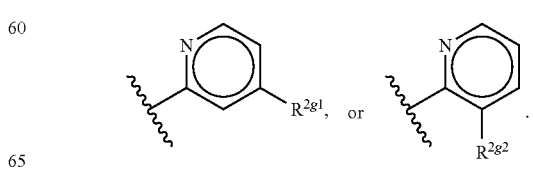

In some embodiments, Y$^1$ is

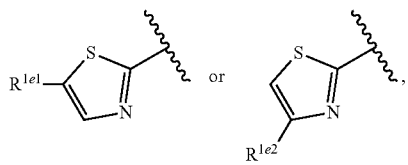

and Y$^2$ is

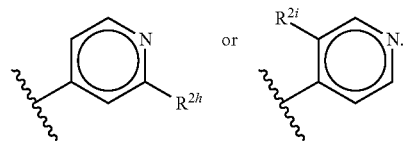

In some embodiments, Y$^1$ is

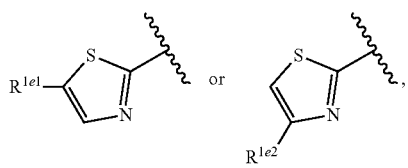

and Y$^2$ is

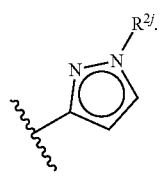

In some embodiments, Y$^1$ is

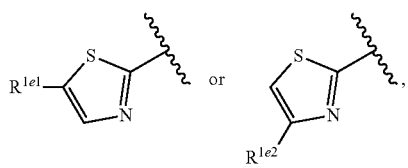

and Y$^2$ is

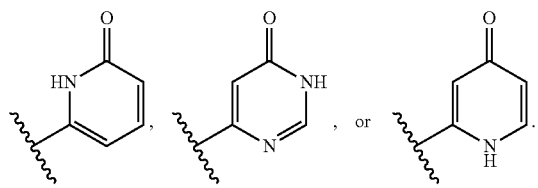

In some of any of the foregoing embodiments, R$^1$ is H. In some of any of the foregoing embodiments, R$^1$ is F, Cl, Br, or I. In some of any of the foregoing embodiments, R$^2$ is H. In some of any of the foregoing embodiments, R$^2$ is CH$_3$. In some of any of the foregoing embodiments, G$^1$ is —N—. In some of any of the foregoing embodiments, G$^1$ is —C(H)—. In some of any of the foregoing embodiments, G$^1$ is —C(F)—, —C(Cl)—, —C(Br)—, or —C(I)—. In some of any of the foregoing embodiments, G$^1$ is —C(R$^b$)—, wherein R$^b$ is taken together with R$^2$ and the atoms to which they are attached to form a 5- or 6-membered cycloalkyl ring.

In some embodiments of Formula (I), (I-1), (1-2), (Ib), (Ib-1), or (Ib-2), Y$^1$ is

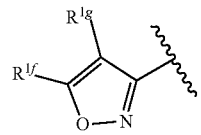

and Y$^2$ is

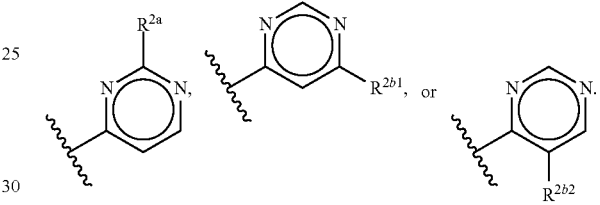

In some embodiments, Y$^1$ is

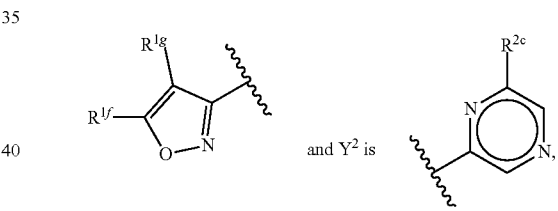

and Y$^2$ is

In some embodiments, Y$^1$ is

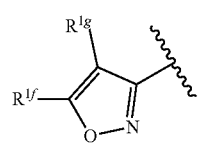

and Y² is

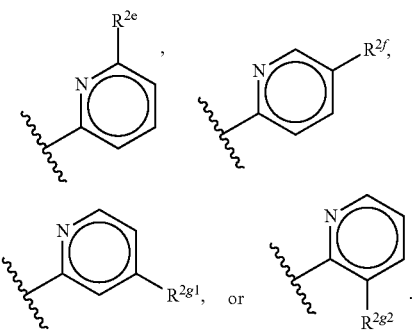

In some embodiments, Y¹ is

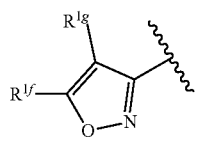

and Y² is

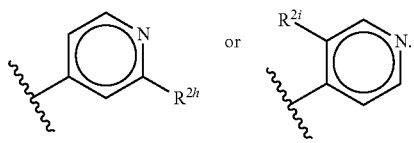

In some embodiments, Y¹ is

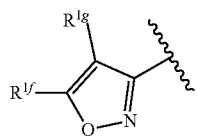

and Y² is

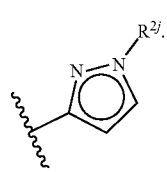

In some embodiments, Y¹ is

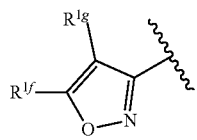

and Y² is

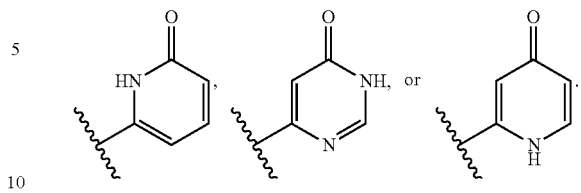

In some of any of the foregoing embodiments, R¹ is H. In some of any of the foregoing embodiments, R¹ is F, Cl, Br, or I. In some of any of the foregoing embodiments, R² is H. In some of any of the foregoing embodiments, R² is CH₃. In some of any of the foregoing embodiments, G¹ is —N—. In some of any of the foregoing embodiments, G¹ is —C(H)—. In some of any of the foregoing embodiments, G¹ is —C(F)—, —C(Cl)—, —C(Br)—, or —C(I)—. In some of any of the foregoing embodiments, G¹ is —C(R$^b$)—, wherein R$^b$ is taken together with R² and the atoms to which they are attached to form a 5- or 6-membered cycloalkyl ring.

In some embodiments of Formula (I), (I-1), (1-2), (Ib), (Ib-1), or (Ib-2), Y¹ is

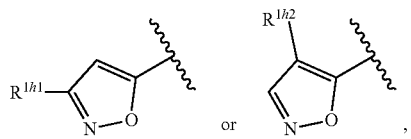

and Y² is

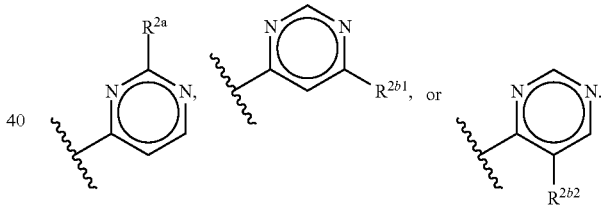

In some embodiments, Y¹ is

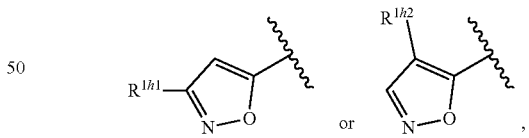

and Y² is

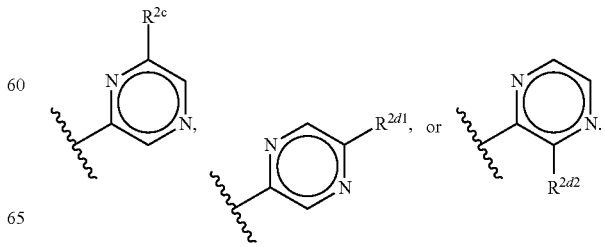

In some embodiments, Y¹ is

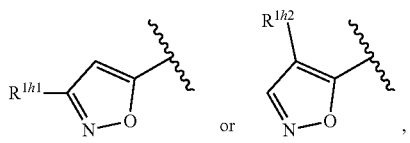 or , and Y² is

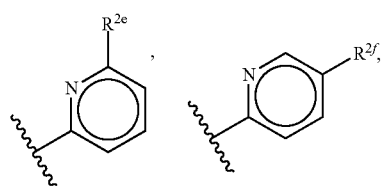

In some embodiments, Y¹ is

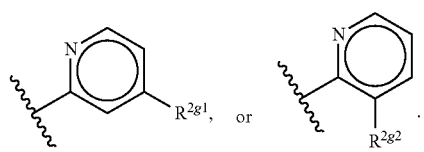 or , and Y² is

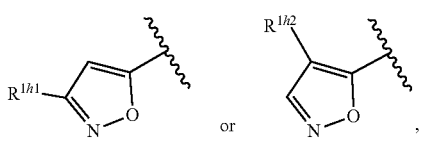

In some embodiments, Y¹ is

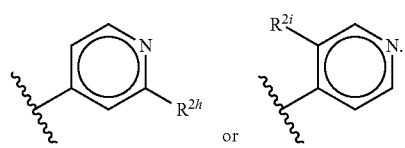 or , and Y² is

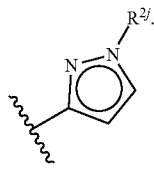

In some embodiments, Y¹ is

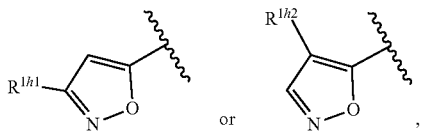 or , and Y² is

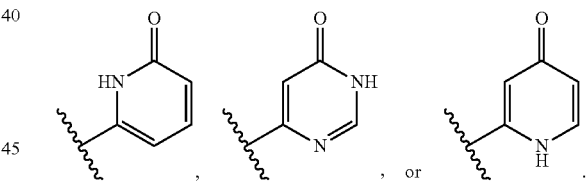

In some of any of the foregoing embodiments, R¹ is H. In some of any of the foregoing embodiments, R¹ is F, Cl, Br, or I. In some of any of the foregoing embodiments, R² is H. In some of any of the foregoing embodiments, R² is CH₃. In some of any of the foregoing embodiments, G¹ is —N—. In some of any of the foregoing embodiments, G¹ is —C(H)—. In some of any of the foregoing embodiments, G¹ is —C(F)—, —C(Cl)—, —C(Br)—, or —C(I)—. In some of any of the foregoing embodiments, G¹ is —C(R^b)—, wherein R^b is taken together with R² and the atoms to which they are attached to form a 5- or 6-membered cycloalkyl ring.

In some embodiments, provided herein are compounds and salts thereof described in Table 1.

TABLE 1

| Cmpd No. | Structure | Name |
|---|---|---|
| 1 | 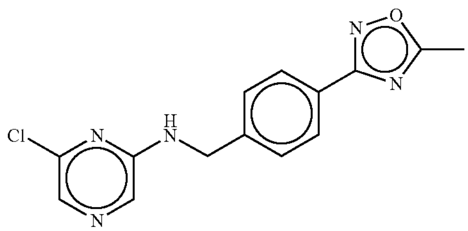 | 6-chloro-N-(4-(5-methyl-1,2,4-oxadiazol-3-yl)benzyl)pyrazin-2-amine |
| 2 | 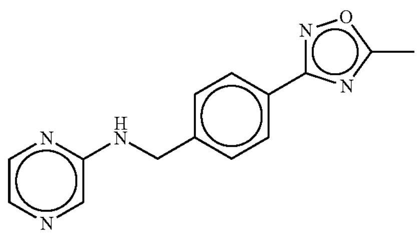 | N-(4-(5-methyl-1,2,4-oxadiazol-3-yl)benzyl)pyrazin-2-amine |
| 3 | 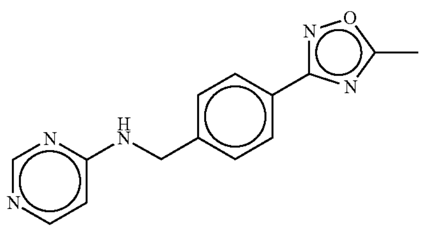 | N-(4-(5-methyl-1,2,4-oxadiazol-3-yl)benzyl)pyrimidin-4-amine |
| 4 | 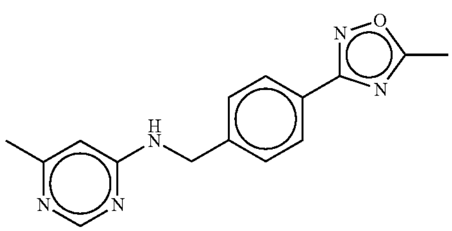 | 6-methyl-N-(4-(5-methyl-1,2,4-oxadiazol-3-yl)benzyl)pyrimidin-4-amine |
| 5 | 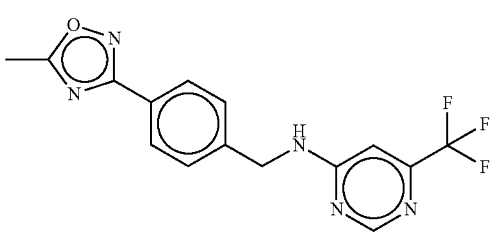 | N-(4-(5-methyl-1,2,4-oxadiazol-3-yl)benzyl)-6-(trifluoromethyl)pyrimidin-4-amine |
| 6 | 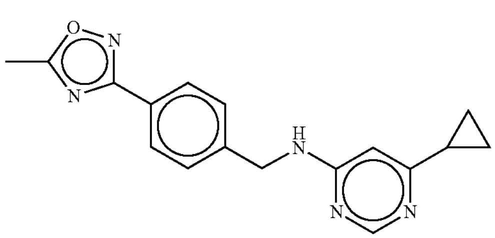 | 6-cyclopropyl-N-(4-(5-methyl-1,2,4-oxadiazol-3-yl)benzyl)pyrimidin-4-amine |

TABLE 1-continued

| Cmpd No. | Structure | Name |
|---|---|---|
| 7 | 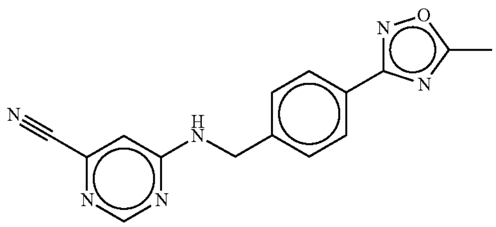 | 6-((4-(5-methyl-1,2,4-oxadiazol-3-yl)benzyl)amino)pyrimidine-4-carbonitrile |
| 8 | 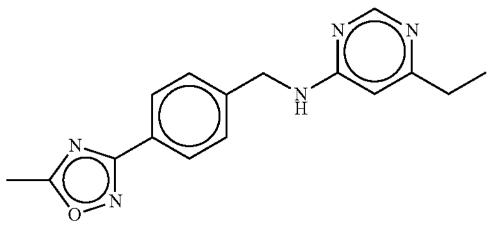 | 6-ethyl-N-(4-(5-methyl-1,2,4-oxadiazol-3-yl)benzyl)pyrimidin-4-amine |
| 9 | 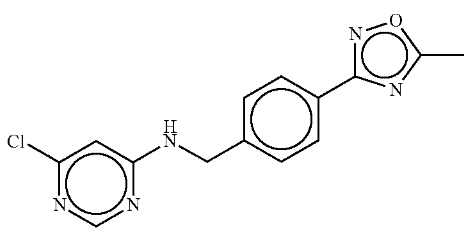 | 6-chloro-N-(4-(5-methyl-1,2,4-oxadiazol-3-yl)benzyl)pyrimidin-4-amine |
| 10 | 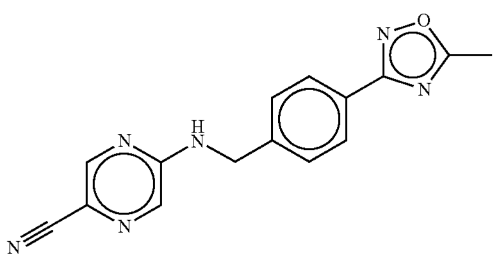 | 5-((4-(5-methyl-1,2,4-oxadiazol-3-yl)benzyl)amino)pyrazine-2-carbonitrile |
| 11 | 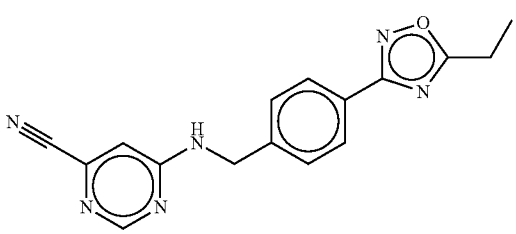 | 6-((4-(5-ethyl-1,2,4-oxadiazol-3-yl)benzyl)amino)pyrimidine-4-carbonitrile |
| 12 | 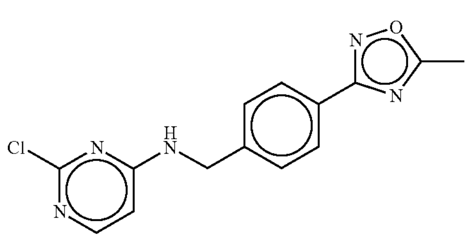 | 2-chloro-N-(4-(5-methyl-1,2,4-oxadiazol-3-yl)benzyl)pyrimidin-4-amine |

TABLE 1-continued

| Cmpd No. | Structure | Name |
|---|---|---|
| 13 | 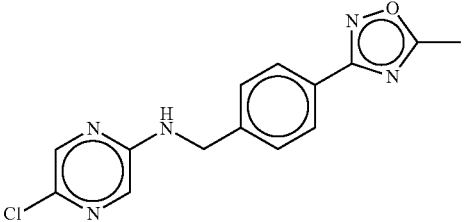 | 5-chloro-N-(4-(5-methyl-1,2,4-oxadiazol-3-yl)benzyl)pyrazin-2-amine |
| 14 | 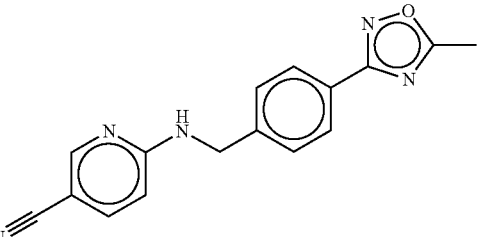 | 6-((4-(5-methyl-1,2,4-oxadiazol-3-yl)benzyl)amino)nicotinonitrile |
| 15 | 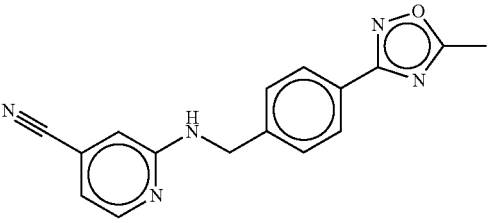 | 2-((4-(5-methyl-1,2,4-oxadiazol-3-yl)benzyl)amino)isonicotinonitrile |
| 16 | 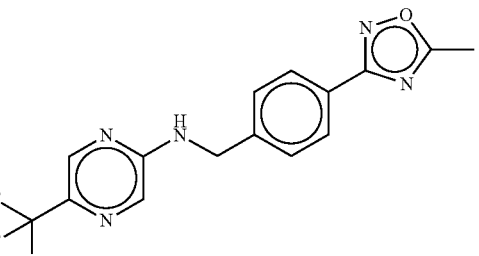 | N-(4-(5-methyl-1,2,4-oxadiazol-3-yl)benzyl)-5-(trifluoromethyl)pyrazin-2-amine |
| 17 | 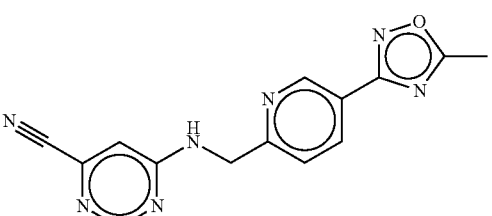 | 6-(((5-(5-methyl-1,2,4-oxadiazol-3-yl)pyridin-2-yl)methyl)amino)pyrimidine-4-carbonitrile |
| 18 | 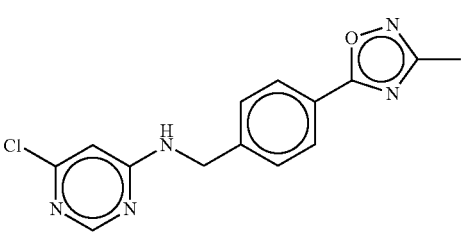 | 6-chloro-N-(4-(3-methyl-1,2,4-oxadiazol-5-yl)benzyl)pyrimidin-4-amine |

TABLE 1-continued

| Cmpd No. | Structure | Name |
|---|---|---|
| 19 | 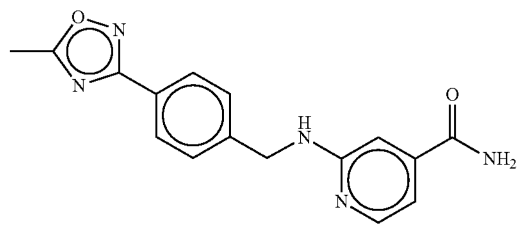 | 2-((4-(5-methyl-1,2,4-oxadiazol-3-yl)benzyl)amino)isonicotinamide |
| 20 | 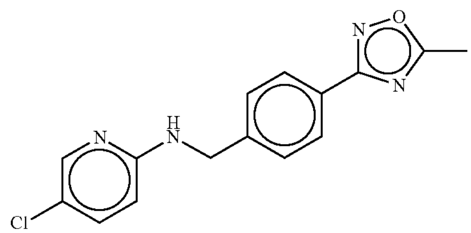 | 5-chloro-N-(4-(5-methyl-1,2,4-oxadiazol-3-yl)benzyl)pyridin-2-amine |
| 21 | 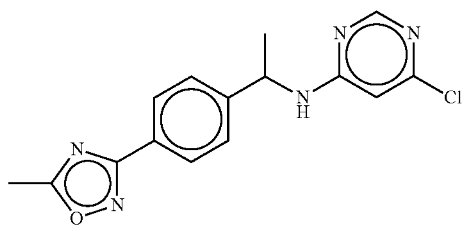 | 6-chloro-N-(1-(4-(5-methyl-1,2,4-oxadiazol-3-yl)phenyl)ethyl)pyrimidin-4-amine |
| 22 | 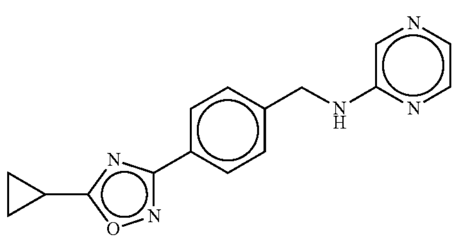 | N-(4-(5-cyclopropyl-1,2,4-oxadiazol-3-yl)benzyl)pyrazin-2-amine |
| 23 | 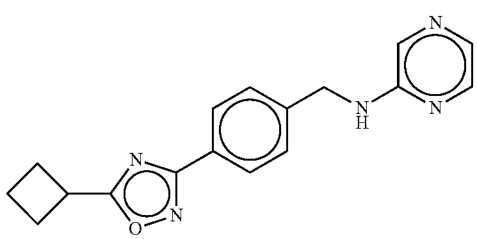 | N-(4-(5-cyclobutyl-1,2,4-oxadiazol-3-yl)benzyl)pyrazin-2-amine |
| 24 | 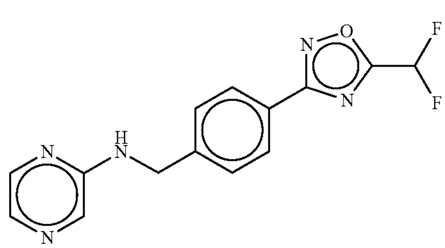 | N-(4-(5-(difluoromethyl)-1,2,4-oxadiazol-3-yl)benzyl)pyrazin-2-amine |

TABLE 1-continued

| Cmpd No. | Structure | Name |
|---|---|---|
| 25 | 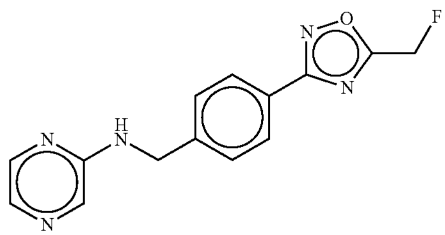 | N-(4-(5-(fluoromethyl)-1,2,4-oxadiazol-3-yl)benzyl)pyrazin-2-amine |
| 26 | 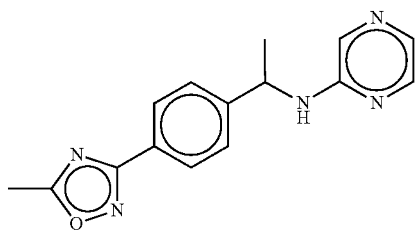 | N-(1-(4-(5-methyl-1,2,4-oxadiazol-3-yl)phenyl)ethyl)pyrazin-2-amine |
| 27 | 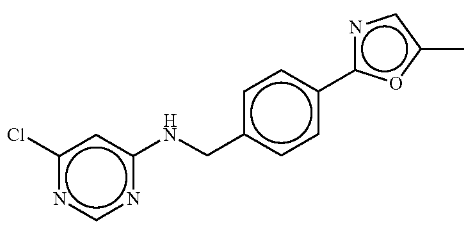 | 6-chloro-N-(4-(5-methyloxazol-2-yl)benzyl)pyrimidin-4-amine |
| 28 | 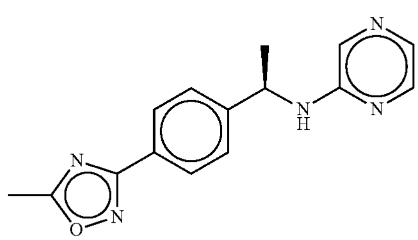 | (R)-N-(1-(4-(5-methyl-1,2,4-oxadiazol-3-yl)phenyl)ethyl)pyrazin-2-amine |
| 29 | 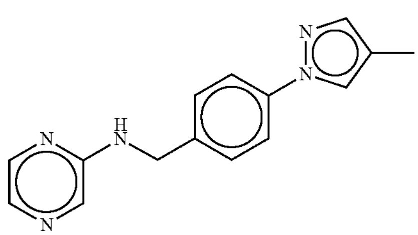 | N-(4-(4-methyl-1H-pyrazol-1-yl)benzyl)pyrazin-2-amine |
| 30 | 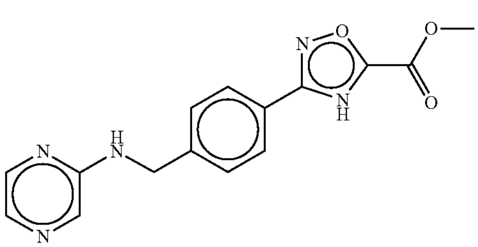 | methyl 3-(4-((pyrazin-2-ylamino)methyl)phenyl)-1,2,4-oxadiazole-5-carboxylate |

TABLE 1-continued

| Cmpd No. | Structure | Name |
|---|---|---|
| 31 | 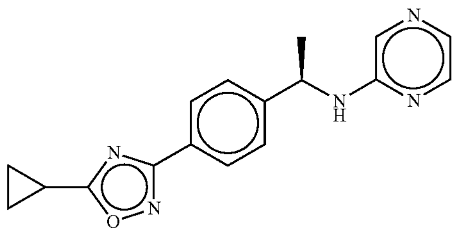 | (R)-N-(1-(4-(5-cyclopropyl-1,2,4-oxadiazol-3-yl)phenyl)ethyl)pyrazin-2-amine |
| 32 | 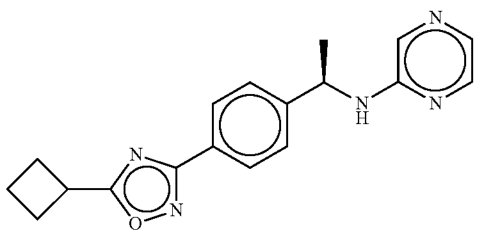 | (R)-N-(1-(4-(5-cyclobutyl-1,2,4-oxadiazol-3-yl)phenyl)ethyl)pyrazin-2-amine |
| 33 | 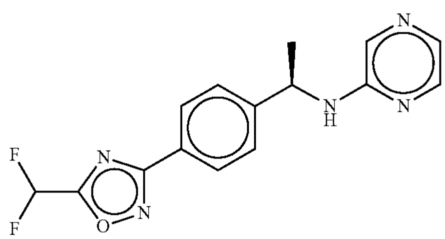 | (R)-N-(1-(4-(5-(difluoromethyl)-1,2,4-oxadiazol-3-yl)phenyl)ethyl)pyrazin-2-amine |
| 34 | 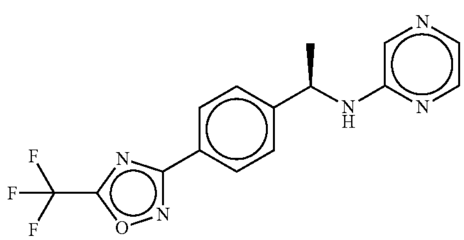 | (R)-N-(1-(4-(5-(trifluoromethyl)-1,2,4-oxadiazol-3-yl)phenyl)ethyl)pyrazin-2-amine |
| 35 | 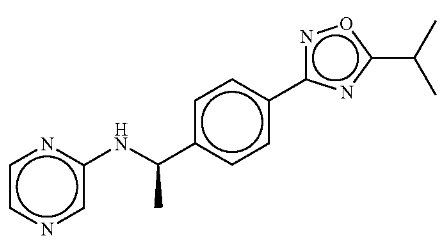 | (R)-N-(1-(4-(5-isopropyl-1,2,4-oxadiazol-3-yl)phenyl)ethyl)pyrazin-2-amine |
| 36 | 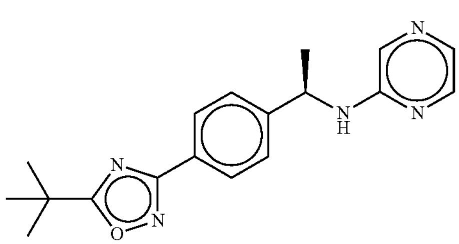 | (R)-N-(1-(4-(5-(tert-butyl)-1,2,4-oxadiazol-3-yl)phenyl)ethyl)pyrazin-2-amine |

TABLE 1-continued

| Cmpd No. | Structure | Name |
|---|---|---|
| 37 | 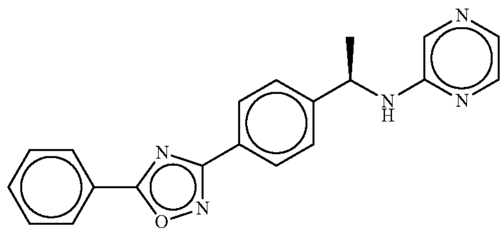 | (R)-N-(1-(4-(5-phenyl-1,2,4-oxadiazol-3-yl)phenyl)ethyl)pyrazin-2-amine |
| 38 | 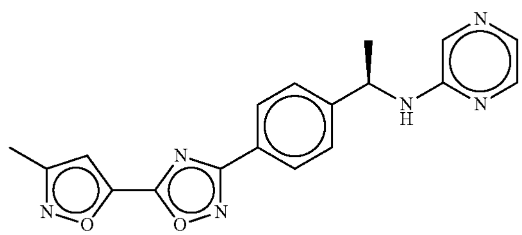 | (R)-N-(1-(4-(5-(3-methylisoxazol-5-yl)-1,2,4-oxadiazol-3-yl)phenyl)ethyl)pyrazin-2-amine |
| 39 | 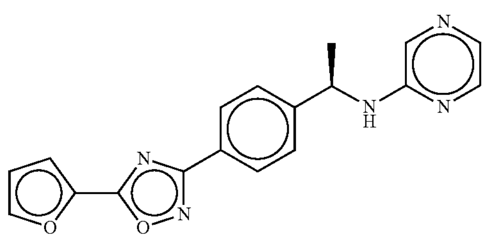 | (R)-N-(1-(4-(5-(furan-2-yl)-1,2,4-oxadiazol-3-yl)phenyl)ethyl)pyrazin-2-amine |
| 40 | 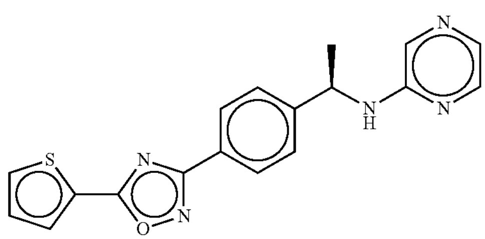 | (R)-N-(1-(4-(5-(thiophen-2-yl)-1,2,4-oxadiazol-3-yl)phenyl)ethyl)pyrazin-2-amine |
| 41 | 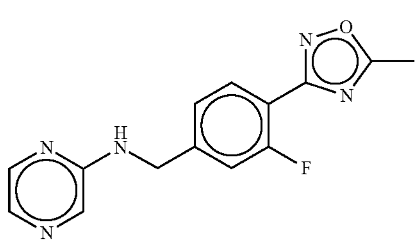 | N-(3-fluoro-4-(5-methyl-1,2,4-oxadiazol-3-yl)benzyl)pyrazin-2-amine |
| 42 | 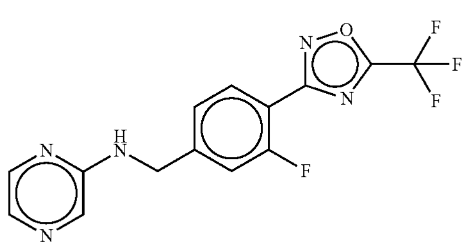 | N-(3-fluoro-4-(5-(trifluoromethyl)-1,2,4-oxadiazol-3-yl)benzyl)pyrazin-2-amine |

TABLE 1-continued

| Cmpd No. | Structure | Name |
|---|---|---|
| 43 | 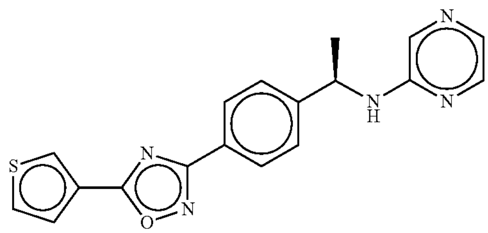 | (R)-N-(1-(4-(5-(thiophen-3-yl)-1,2,4-oxadiazol-3-yl)phenyl)ethyl)pyrazin-2-amine |
| 44 | 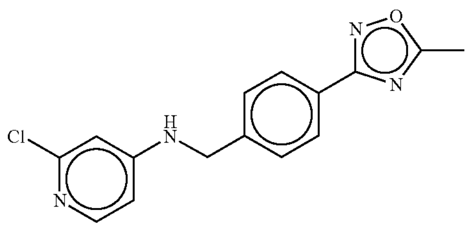 | 2-chloro-N-(4-(5-methyl-1,2,4-oxadiazol-3-yl)benzyl)pyridin-4-amine |
| 45 | 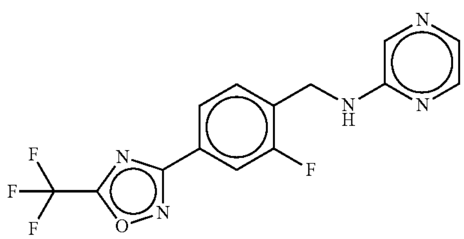 | N-(2-fluoro-4-(5-(trifluoromethyl)-1,2,4-oxadiazol-3-yl)benzyl)pyrazin-2-amine |
| 46 | 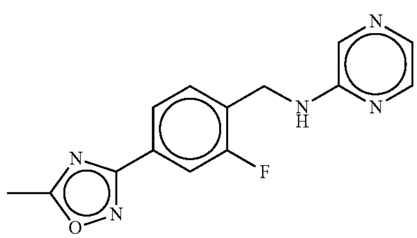 | N-(2-fluoro-4-(5-methyl-1,2,4-oxadiazol-3-yl)benzyl)pyrazin-2-amine |
| 47 | 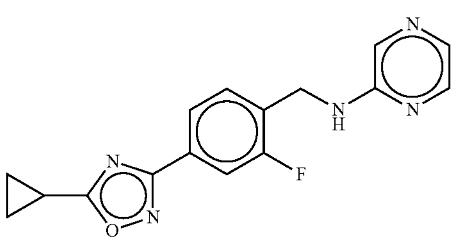 | N-(4-(5-cyclopropyl-1,2,4-oxadiazol-3-yl)-2-fluorobenzyl)pyrazin-2-amine |
| 48 | 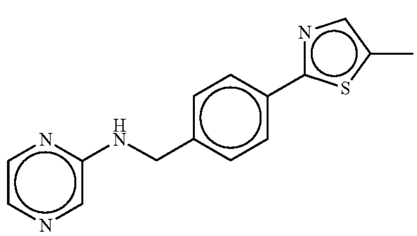 | N-(4-(5-methylthiazol-2-yl)benzyl)pyrazin-2-amine |

TABLE 1-continued

| Cmpd No. | Structure | Name |
|---|---|---|
| 49 | 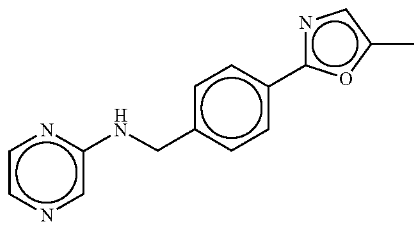 | N-(4-(5-methyloxazol-2-yl)benzyl)pyrazin-2-amine |
| 50 | 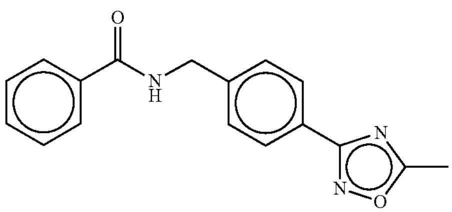 | N-(4-(5-methyl-1,2,4-oxadiazol-3-yl)benzyl)benzamide |
| 51 | 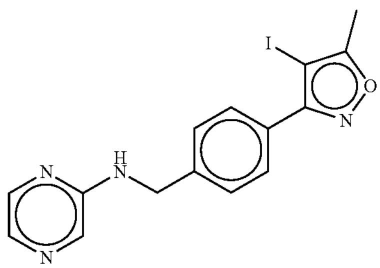 | N-(4-(4-iodo-5-methylisoxazol-3-yl)benzyl)pyrazin-2-amine |
| 52 | 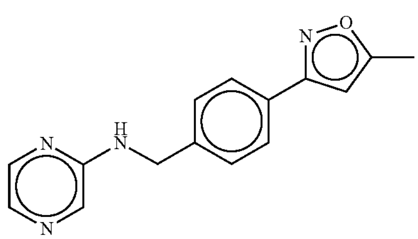 | N-(4-(5-methylisoxazol-3-yl)benzyl)pyrazin-2-amine |
| 53 | 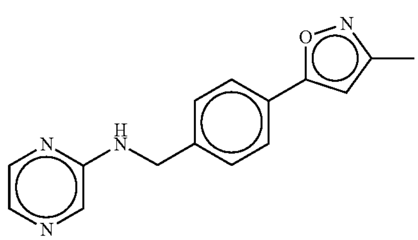 | N-(4-(3-methylisoxazol-5-yl)benzyl)pyrazin-2-amine |
| 54 | 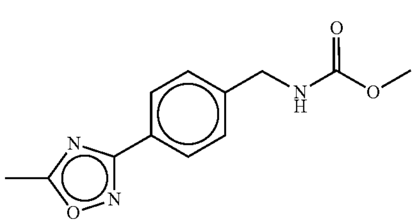 | methyl (4-(5-methyl-1,2,4-oxadiazol-3-yl)benzyl)carbamate |

TABLE 1-continued

| Cmpd No. | Structure | Name |
|---|---|---|
| 55 | 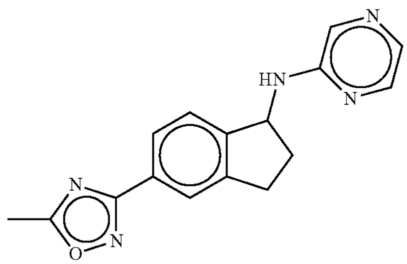 | N-(5-(5-methyl-1,2,4-oxadiazol-3-yl)-2,3-dihydro-1H-inden-1-yl)pyrazin-2-amine |
| 56 | 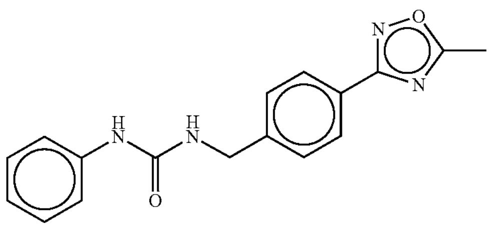 | 1-(4-(5-methyl-1,2,4-oxadiazol-3-yl)benzyl)-3-phenylurea |
| 57 | 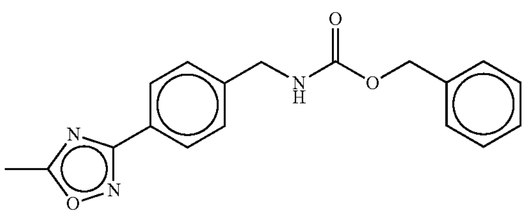 | benzyl (4-(5-methyl-1,2,4-oxadiazol-3-yl)benzyl)carbamate |
| 58 | 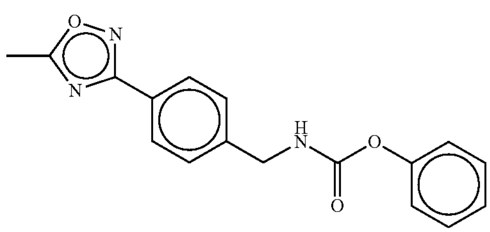 | phenyl (4-(5-methyl-1,2,4-oxadiazol-3-yl)benzyl)carbamate |
| 59 | 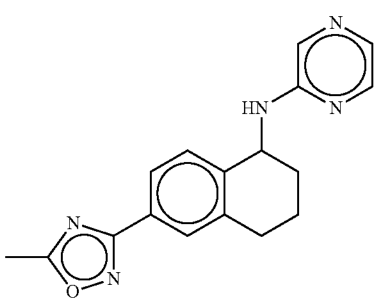 | N-(6-(5-methyl-1,2,4-oxadiazol-3-yl)-1,2,3,4-tetrahydronaphthalen-1-yl)pyrazin-2-amine |
| 60 | 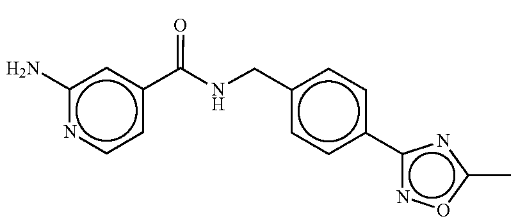 | 2-amino-N-(4-(5-methyl-1,2,4-oxadiazol-3-yl)benzyl)isonicotinamide |

TABLE 1-continued

| Cmpd No. | Structure | Name |
|---|---|---|
| 61 | 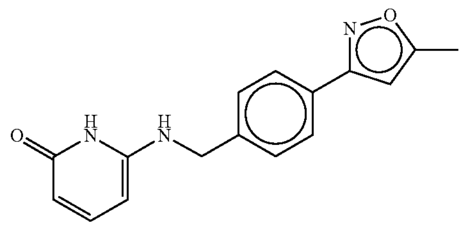 | 6-((4-(5-methylisoxazol-3-yl)benzyl)amino)pyridin-2(1H)-one |
| 62 | 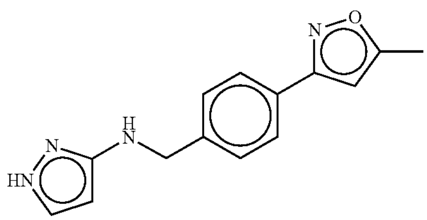 | N-(4-(5-methylisoxazol-3-yl)benzyl)-1H-pyrazol-3-amine |
| 63 | 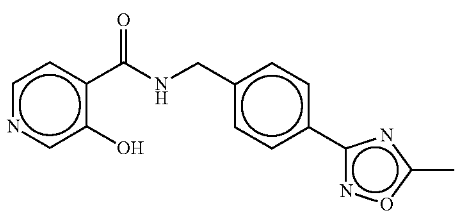 | 3-hydroxy-N-(4-(5-methyl-1,2,4-oxadiazol-3-yl)benzyl)isonicotinamide |
| 64 | 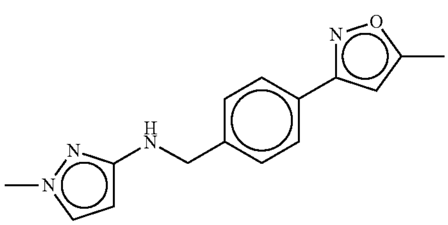 | 1-methyl-N-(4-(5-methylisoxazol-3-yl)benzyl)-1H-pyrazol-3-amine |
| 65 | 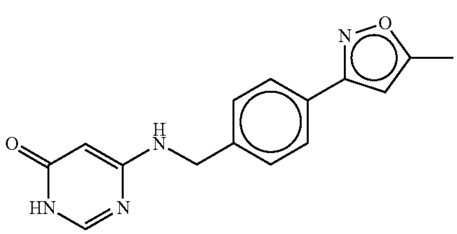 | 6-((4-(5-methylisoxazol-3-yl)benzyl)amino)pyrimidin-4(3H)-one |
| 66 | 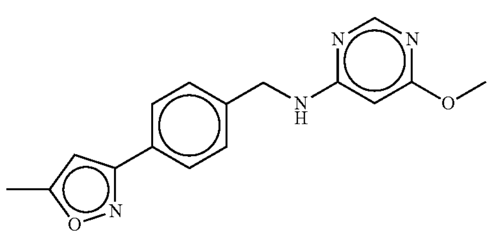 | 6-methoxy-N-(4-(5-methylisoxazol-3-yl)benzyl)pyrimidin-4-amine |

TABLE 1-continued

| Cmpd No. | Structure | Name |
|---|---|---|
| 67 | 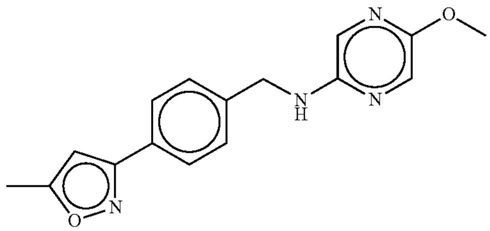 | 5-methoxy-N-(4-(5-methylisoxazol-3-yl)benzyl)pyrazin-2-amine |
| 68 | 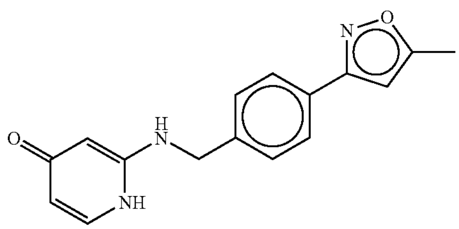 | 2-((4-(5-methylisoxazol-3-yl)benzyl)amino)pyridin-4(1H)-one |
| 69 | 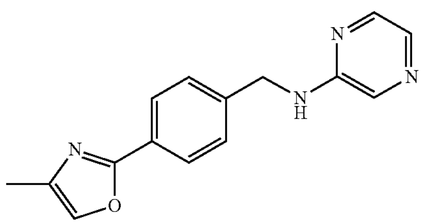 [SMILES: Cc1coc(-c2ccc(CNc3cnccn3)cc2)n1] | N-(4-(4-methyloxazol-2-yl)benzyl)pyrazin-2-amine |
| 70 | 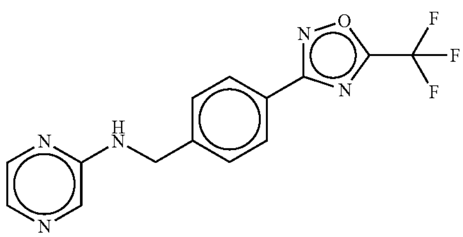 | N-(4-(5-(trifluoromethyl)-1,2,4-oxadiazol-3-yl)benzyl)pyrazin-2-amine |
| 71 | 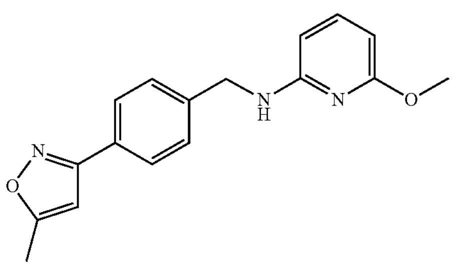 [SMILES: COc1cccc(NCc2ccc(-c3cc(C)on3)cc2)n1] | 6-methoxy-N-[[4-(5-methyl-1,2-oxazol-3-yl)phenyl]methyl]pyridin-2-amine |

In some variations, any of the compounds described herein, such as a compound of Formula (I), (I-1), (I-2), (Ia), (Ia-1), (Ia-2), (Ib), (Ib-1), or (Ib-2), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (I-1), (I-2), (Ia), (Ia-1), (Ia-2), (Ib), (Ib-1), or (Ib-2), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 has two or more stereocenters, also provided are any enantiomer or diastereomer of the compound. For example, if a compound of Table 1 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 1 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 1 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 1 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $R^1$, $R^2$, $G^1$, $L^1$, $Y^1$, and $Y^2$ provided herein can be combined with every other variation or embodiment of $R^1$, $R^2$, $G^1$, $L^1$, $Y^1$, and $Y^2$, as if each combination had been individually and specifically described.

As used herein, when any variable occurs more than one time in a chemical formula, its definition on each occurrence is independent of its definition at every other occurrence.

Formula (I) includes all subformulae thereof. For example, Formula (I) includes compounds of (I-1), (I-2), (Ia), (Ia-1), (Ia-2), (Ib), (Ib-1), and (Ib-2).

The compound names provided herein, including in Table 1, are provided by ChemBioDraw Professional 15.0.0.106. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (I-1), (I-2), (Ia), (Ia-1), (Ia-2), (Ib), (Ib-1), or (Ib-2), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Use

The compounds and pharmaceutical compositions herein may be used to treat or prevent a disease or condition in an individual or subject.

When used in a prophylactic manner, the compounds disclosed and/or described herein may prevent a disease or disorder from developing or lessen the extent of a disease or disorder that may develop in an individual or subject at risk of developing the disease or disorder.

Without being bound by theory, the compounds and pharmaceutical compositions disclosed herein are believed to act by inhibiting myosin. This inhibition potentially decreases the number of independent myosin heads interacting with actin filaments reducing the amount of contraction. Reducing contraction of cardiac muscle can be important for the treatment of heart diseases in which over-contraction is an issue. In some embodiments, provided are methods of treating or preventing heart disease in an individual or subject, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof. In some embodiments, provided are methods of treating or preventing heart disease in a subject in need thereof comprising administering to the subject a therapeutically effective amount of at least one chemical entity as described herein. In some embodiments, provided are methods of treating heart disease in a subject in need thereof comprising administering to the subject a therapeutically effective amount of at least one chemical entity as described herein. In some embodiments, provided are methods of treating an established or diagnosed heart disease in a subject in need thereof comprising administering to the subject a therapeutically effective amount of at least one chemical entity as described herein. In some embodiments, provided are methods of preventing heart disease in a subject in need thereof comprising administering to the subject a therapeutically effective amount of at least one chemical entity as described herein.

Also provided herein is the use of a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for treatment of a heart disease in a subject. In some aspects, provided is a compound or composition as described herein for use in a method of treatment of the human or animal body by therapy. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in a method of treatment of the human or animal body by therapy. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating or preventing heart disease. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating heart disease. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating an established or diagnosed heart disease. In other embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in preventing heart disease. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating a disease or condition associated with HCM. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating a disease or condition associated with secondary left ventricular wall thickening. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in ameliorating a symptom associated with heart disease. In other embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in reducing the risk of a symptom associated with heart disease. In other embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis. In certain embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating a disease or condition associated with small left ventricular cavity and cavity obliteration, hyperdynamic left ventricular contraction, myocardial ischemia, or cardiac fibrosis. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating muscular dystrophies. In some embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in treating a glycogen storage disease. In other embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in modulating the cardiac sarcomere, such as inhibiting the cardiac sarcomere. In yet other embodiments, provided herein are compounds of Formula (I), (I-1), (I-2), (Ia), (Ia-1), (Ia-2), (Ib), (Ib-1), or (Ib-2), or a compound of Table 1, or a pharmaceutically acceptable salt thereof, for use in potentiating cardiac myosin.

In some embodiments, the subject is a mammal. In some embodiments, the subject is a mouse, rat, dog, cat, pig, sheep, horse, cow, or human. In some embodiments, the subject is a human. In some embodiments, the subject has an established or diagnosed heart disease. In some embodiments, the subject has established or diagnosed hypertrophic cardiomyopathy (HCM). In some embodiments, the subject is at risk for developing heart disease. In some embodiments, the subject has a mutation that increases risk for heart disease. In some embodiments, the subject has a mutation that increases risk for hypertrophic cardiomyopathy (HCM). In some embodiments, the mutation is a sarcomeric mutation. In some embodiments, the mutation is a mutation in myosin heavy chain R (MHC-0), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, muscle LIM protein (MLP), or protein kinase AMP-activated non-catalytic subunit gamma 2 (PRKAG2). In some embodiments, the mutation is a mutation in MHC-β. In some embodiments, the subject has established or diagnosed hypertrophic cardiomyopathy without a confirmed genetic etiology.

In some embodiments, the subject has a high risk of progressive symptoms. In some embodiments, the subject has a high risk of atrial fibrillation, ventricular tachyarrhythmias, stroke, and/or sudden death. In some embodiments, the subject has a reduced exercise capacity. In some embodiments, the reduced exercise capacity is as compared to an age-matched control population. In some embodiments, the subject is eligible for surgical intervention or percutaneous ablation to treat the heart disease.

In some embodiments, the heart disease is hypertrophic cardiomyopathy (HCM). In some embodiments, the heart disease is obstructive HCM. In some embodiments, the heart disease is nonobstructive HCM. In some embodiments, the HCM is associated with a sarcomeric mutation. In some embodiments, the HCM is associated with a non-sarcomeric mutation. In some embodiments, the heart disease is obstructive or nonobstructive HCM caused by sarcomeric and/or non-sarcomeric mutations. In some embodiments, the sarcomeric mutation is a mutation in a myosin heavy chain R (MHC-0), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, or muscle LIM protein (MLP). In some embodiments, the sarcomeric mutation is a mutation in MHC-β. In some embodiments, the non-sarcomeric mutation is a mutation in protein kinase AMP-activated non-catalytic subunit gamma 2 (PRKAG2).

In some embodiments, provided herein are methods of treating a disease or condition associated with HCM, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof. In some embodiments, the disease or condition is Fabry's Disease, Danon Disease, mitochondrial cardiomyopathies, or Noonan Syndrome.

Also provided herein is the use of a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for treatment of a disease or condition associated with HCM.

In some embodiments, the heart disease is heart failure with preserved ejection fraction (HFpEF). In some embodiments, the heart disease is diastolic dysfunction. In some embodiments, the heart disease is cardiomyopathy. In some embodiments, the heart disease is primary or secondary restrictive cardiomyopathy. In some embodiments, the heart disease is condition or symptoms caused by coronary artery disease. In some embodiments, the heart disease is myocardial infarction or angina pectoris. In some embodiments, the heart disease is left ventricular outflow tract obstruction. In some embodiments, the heart disease is hypertensive heart disease. In some embodiments, the heart disease is congenital heart disease. In some embodiments, the heart disease is cardiac ischemia and/or coronary heart disease. In some embodiments, the heart disease is diabetic heart disease. In other embodiments, the heart disease is congestive heart failure. In some embodiments, the heart disease is right heart failure. In other embodiments, the heart disease is cardiorenal syndrome. In some embodiments, the heart disease is infiltrative cardiomyopathy. In some embodiments, the heart disease is a condition that is or is related to cardiac senescence or diastolic dysfunction due to aging. In some embodiments, the heart disease is a condition that is or is related to left ventricular hypertrophy and/or concentric left ventricular remodeling.

In some embodiments, the provided are methods of treating a disease or condition associated with secondary left ventricular wall thickening in an individual or subject, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof. In some embodiments, the disease is hypertension, valvular heart diseases (aortic stenosis, Mitral valve regurgitation), metabolic syndromes (diabetes, obesity), end stage renal disease, scleroderma, sleep apnea, amyloidosis, Fabry's disease, Friedreich Ataxia, Danon disease, Noonan syndrome, or Pompe disease.

Also provided herein is the use of a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for treatment of a disease or condition associated with secondary left ventricular wall thickening.

In some embodiments, provided are methods of ameliorating a symptom associated with heart disease in a subject, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof, wherein the symptom is one or more selected from poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of reducing the risk of a symptom associated with heart disease in a subject, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof, wherein the symptom is one or more selected from sudden cardiac death, poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis in an individual or subject, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof.

In some embodiments, provided are methods of treating a disease or condition associated with small left ventricular cavity and cavity obliteration, hyperdynamic left ventricular contraction, myocardial ischemia, or cardiac fibrosis in an individual or subject, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof.

Also provided herein is the use of a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for treatment of a disease or condition associated with small left ventricular cavity and cavity obliteration, hyperdynamic left ventricular contraction, myocardial ischemia, or cardiac fibrosis.

In some embodiments, the provided are methods of treating muscular dystrophies in an individual or subject (e.g., Duchenne muscular dystrophy), comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof. Also provided herein is the use of a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for treatment of muscular dystrophies (e.g., Duchenne muscular dystrophy).

In some embodiments, the provided are methods of treating a glycogen storage disease in an individual or subject, comprising administering to the individual or subject in need thereof a compound of Formula (I), (I-1), (I-2), (Ia), (Ia-1), (Ia-2), (Ib), (Ib-1), or (Ib-2), or a compound of Table 1, or a pharmaceutically acceptable salt thereof. Also provided herein is the use of a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for treatment of a glycogen storage disease.

Also provided are methods for modulating the cardiac sarcomere in an individual or subject which method comprises administering to an individual or subject in need thereof a therapeutically effective amount of at least one chemical entity as described herein. In some embodiments, provided are methods of inhibiting the cardiac sarcomere, comprising contacting the cardiac sarcomere with at least one chemical entity as described herein, such as a compound of Formula (I), (I-1), (I-2), (Ia), (Ia-1), (Ia-2), (Ib), (Ib-1), or (Ib-2), or a compound of Table 1, or a pharmaceutically acceptable salt thereof. Additionally provided herein is the use of at least one chemical entity as described herein, such as a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for inhibiting the cardiac sarcomere of an individual or subject.

Also provided are methods for potentiating cardiac myosin in an individual or subject which method comprises administering to an individual or subject in need thereof a therapeutically effective amount of at least one chemical entity as described herein such as a compound of Formula (I), (I-1), (I-2), (Ia), (Ia-1), (Ia-2), (Ib), (Ib-1), or (Ib-2), or a compound of Table 1, or a pharmaceutically acceptable salt thereof. Additionally provided herein is the use of at least one chemical entity as described herein, such as a compound of Formula (I), (I-1), (I-2), (Ia), (Ia-1), (Ia-2), (Ib), (Ib-1), or (Ib-2), or a compound of Table 1, or a pharmaceutically acceptable salt thereof in the manufacture of a medicament for potentiating cardiac myosin in an individual or subject.

In some embodiments, the methods provided herein further comprise monitoring the effectiveness of the treatment. Examples of indicators include, but are not limited to improvement in one or more of the following: New York Heart Association (NYHA) Functional Classification, exercise capacity, cardiac elasticity, diastolic left ventricular relaxation, left atrial pressure, paroxysmal or permanent atrial fibrillation, left atrial and pulmonary capillary wedge pressures, left ventricular diastolic pressures, syncope, ventricular relaxation during diastole, ventricular fibrosis, left ventricular hypertrophy, left ventricular mass, left ventricular wall thickness, left ventricular mid-cavity obstruction systolic anterior motion of mitral valve, left ventricular outflow tract obstruction, chest pain, exertional dyspnea, pre-syncope, abnormal exercise capacity, and fatigue. These indicators can be monitored by techniques known in the art including self-reporting; ECG, including ambulatory ECG; echocardiography; cardiac MRI; CT; biopsy; cardiopulmonary exercise testing (CPET); and actigraphy.

In some embodiments, the compound reduces the contractility of a cardiomyocyte. In some embodiments, the compound reduces the contractility of a cardiomyocyte by greater than 40%, such as greater than 45%, 50%, 60%, 70%, 80%, or 90%. In some embodiments, the compound reduced the contractility of a cardiomyocyte 40%-90%, such as 40%-80%, 40-70%, 50%-90%, 50%-80% or 50%-70%. In some embodiments, the compound does not significantly alter calcium transients in the cardiomyocyte. In some embodiments, the compound decreases the ATPase activity in a cardiomyocyte. Methods of measuring contractility, ATPase activity, and calcium transients are known in the art, for example, by calcium labeling, electrophysiological recordings, and microscopic imaging. In some embodiments, the compound does not significantly inhibit or induce a cytochrome P450 (CYP) protein.

In some embodiments, the subject has a left ventricular wall that is thicker than normal prior to treatment. In some embodiments, the subject has a left ventricular wall thickness that is greater than 15 mm, such as greater than 18 mm, 20 mm, 22 mm, 25 mm, or 30 mm prior to treatment. In some embodiments, the left ventricular wall thickness is reduced by greater than 5%, such as greater than 8%, 10%, 12%, 15%, 20%, or 30% following treatment. Left ventricular wall thickness can be measured by methods known in the art, such as by echocardiography, CT scan, or a cardiac MRI.

In some embodiments, the subject has abnormal cardiac fibrosis prior to treatment. In some embodiments, the abnormal cardiac fibrosis is reduced by greater than 5%, such as greater than 8%, 10%, 12%, 15%, 20%, or 30% following treatment. Cardiac fibrosis can be measured by methods known in the art, such as by biopsy or a cardiac MRI.

In some embodiments, the subject has reduced exercise capacity prior to treatment. In some embodiments, the exercise capacity of the subject is increased by greater than 5%, such as greater than 8%, 10%, 12%, 15%, 20% or 30% following treatment. In some embodiments, the exercise capacity is measured by cardiopulmonary exercise testing (CPET). CPET measures changes in oxygen consumption ($VO_2$ max). Methods of measuring CPET and $VO_2$ max are well known in the art (Malhotra et al., JACC: Heart Failure, 2016, 4(8): 607-616; Guazzi et al., J Amer College Cardiol, 2017, 70 (13): 1618-1636; Rowin et al., JACC: Cariovasc Imaging, 2017, 10(11):1374-1386). In some embodiments, $VO_2$ max is improved by more than 1 mL/kg/m$^2$, such as more than 1.2 mL/kg/m$^2$, 1.4 mL/kg/m$^2$, 1.5 mL/kg/m$^2$, 1.7 mL/kg/m$^2$, 2 mL/kg/m$^2$, 2.2 mL/kg/m$^2$, 2.5 mL/kg/m$^2$, 3 mL/kg/m$^2$, 3.2 mL/kg/m$^2$, or 3.5 mL/kg/m$^2$ following treatment.

In some embodiments, the subject has a New York Heart Association (NYHA) Functional Classification of II, III, or IV prior to treatment. In some embodiments, the subject has a New York Heart Association (NYHA) Functional Classification of III or IV prior to treatment. In some embodiments, the subject has a New York Heart Association (NYHA) Functional Classification of IV prior to treatment. In some embodiments, the subject remains in the same NYHA functional class or has a reduced NYHA functional class following treatment.

In some embodiments, $VO_2$ max is improved by more than 1 mL/kg/m$^2$, such as more than 1.2 mL/kg/m$^2$, 1.4 mL/kg/m$^2$, 1.5 mL/kg/m$^2$, 1.7 mL/kg/m$^2$, or 2 mL/kg/m$^2$ and the subject has a reduced NYHA functional class following treatment. In some embodiments, $VO_2$ max is improved by more than 2.5 mL/kg/m$^2$, 3 mL/kg/m$^2$, 3.2 mL/kg/m$^2$, or 3.5 mL/kg/m$^2$ and the subject remains in the same NYHA functional class or has a reduced NYHA functional class following treatment.

In some embodiments, daily function and/or activity level of the subject is improved following treatment. Improved daily function and/or activity level may be measured, for example, by journaling or actigraphy, such as a FitBit or FitBit-like monitors.

In some embodiments, the subject has one or more of decreased shortness of breath, decreased chest pain, decreased arrhythmia burden, such as atrial fibrillation and ventricular arrhythmias, decreased incidence of heart failure, and decreased ventricular outflow obstruction following treatment.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/ or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use. In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders, diseases, or conditions.

The compounds and compositions described and/or disclosed herein may be combined with one or more other therapies to treat a heart disease, such as HCM or HFpEF. In some embodiments, the one or more therapies include therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors). In some embodiments, the one or more therapies include therapies that improve cardiac function by stimulating cardiac contractility (e.g., positive inotropic agents, such as the β-adrenergic agonist dobutamine or the phosphodiesterase inhibitor milrinone). In other embodiments, the one or more therapies include therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The compounds and compositions described and/or disclosed herein may be combined with one or more other therapies to treat HCM or HFpEF. In some embodiments, the compounds and/compositions may be combined with a β-blocker, verapamil, and/or disopyramide.

General Synthetic Methods

Compounds of Formula (I), (I-1), (I-2), (Ia), (Ia-1), (Ia-2), (Ib), (Ib-1), and (Ib-2) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (I-1), (I-2), (Ia), (Ia-1), (Ia-2), (Ib), (Ib-1), and (Ib-2).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (I-1), (I-2), (Ia), (Ia-1), (Ia-2), (Ib), (Ib-1), or (Ib-2), or any variation thereof. Other compounds described herein may be prepared by similar methods.

In some embodiments, compounds provided herein may be synthesized according to Scheme 1.

Scheme 1

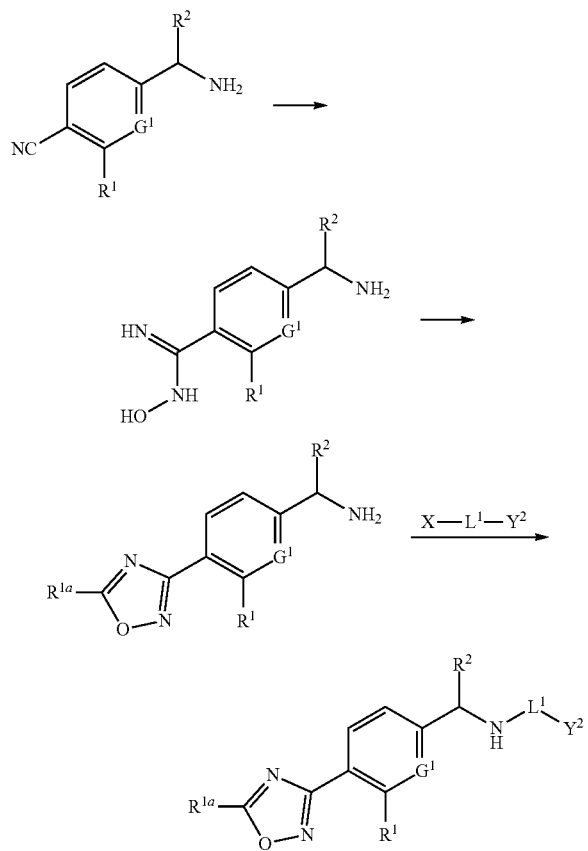

wherein $R^{1a}$, $R^1$, $R^2$, $L^1$, $Y^2$, and $G^1$ are as defined for Formula (I), or any variation thereof detailed herein, and X is a halogen.

An exemplary embodiment of the preparative method in Scheme 1 is shown in Scheme 1a.

Scheme 1a

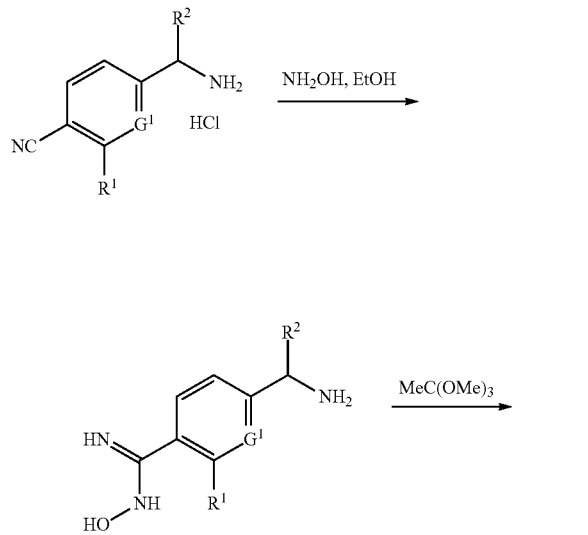

-continued

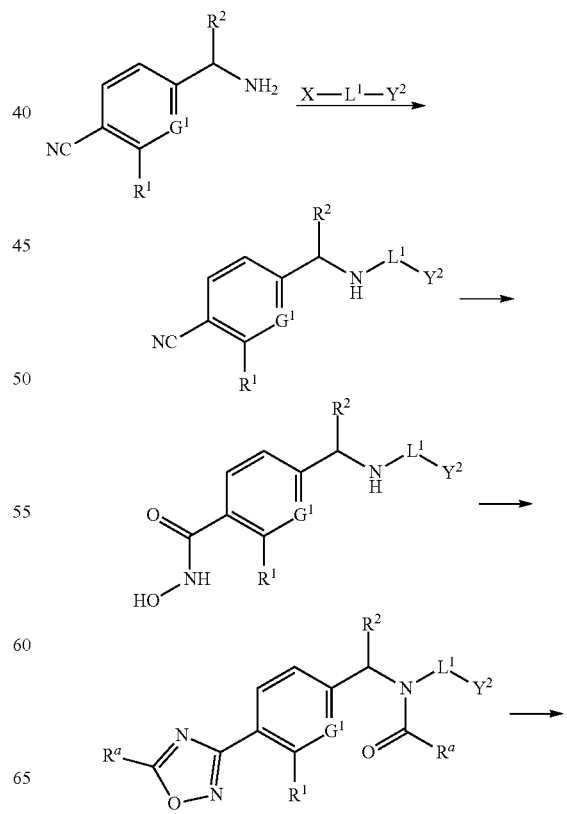

wherein $R^1$, $R^2$, $L^1$, $Y^2$, and $G^1$ are as defined for Formula (I), or any variation thereof detailed herein, and X is a halogen.

In some embodiments, compounds provided herein may be synthesized according to Scheme 2.

Scheme 2

-continued

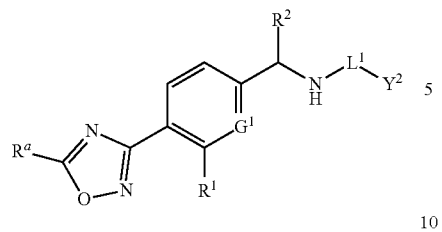

wherein $R^{1a}$, $R^1$, $R^2$, $L^1$, $Y^2$, and $G^1$ are as defined for Formula (I), or any variation thereof detailed herein, and X is a halogen.

An exemplary embodiment of the preparative method in Scheme 2 is shown in Scheme 2a.

Scheme 2a

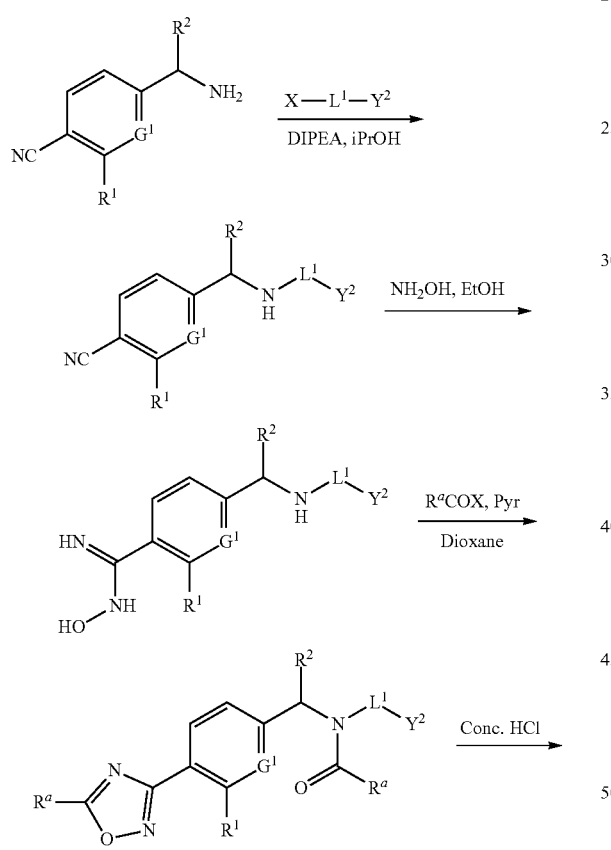

wherein $R^{1a}$, $R^1$, $R^2$, $L^1$, $Y^2$, and $G^1$ are as defined for Formula (I), or any variation thereof detailed herein, and X is a halogen.

In some embodiments, compounds provided herein may be synthesized according to Scheme 3.

Scheme 3

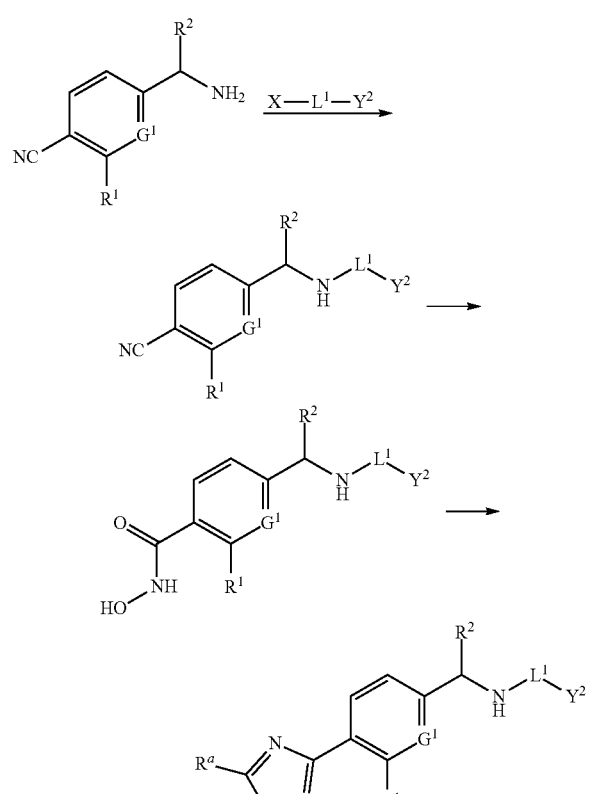

wherein $R^{1a}$, $R^1$, $R^2$, $L^1$, $Y^2$, and $G^1$ are as defined for Formula (I), or any variation thereof detailed herein, and X is a halogen.

An exemplary embodiment of the preparative method in Scheme 3 is shown in Scheme 3a.

Scheme 3a

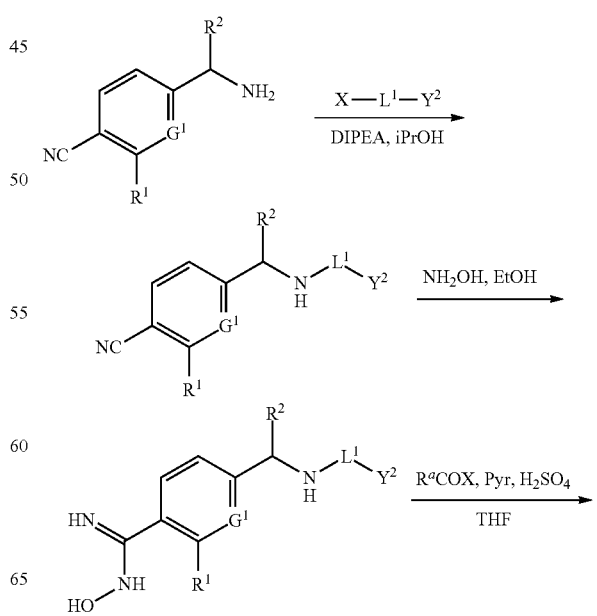

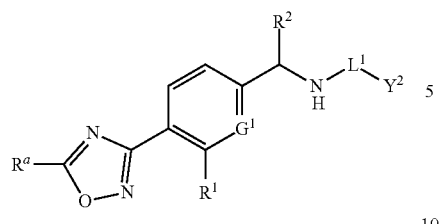

wherein $R^{1a}$, $R^1$, $R^2$, $L^1$, $Y^2$, and $G^1$ are as defined for Formula (I), or any variation thereof detailed herein, and X is a halogen.

In some embodiments, compounds provided herein may be synthesized according to Scheme 4.

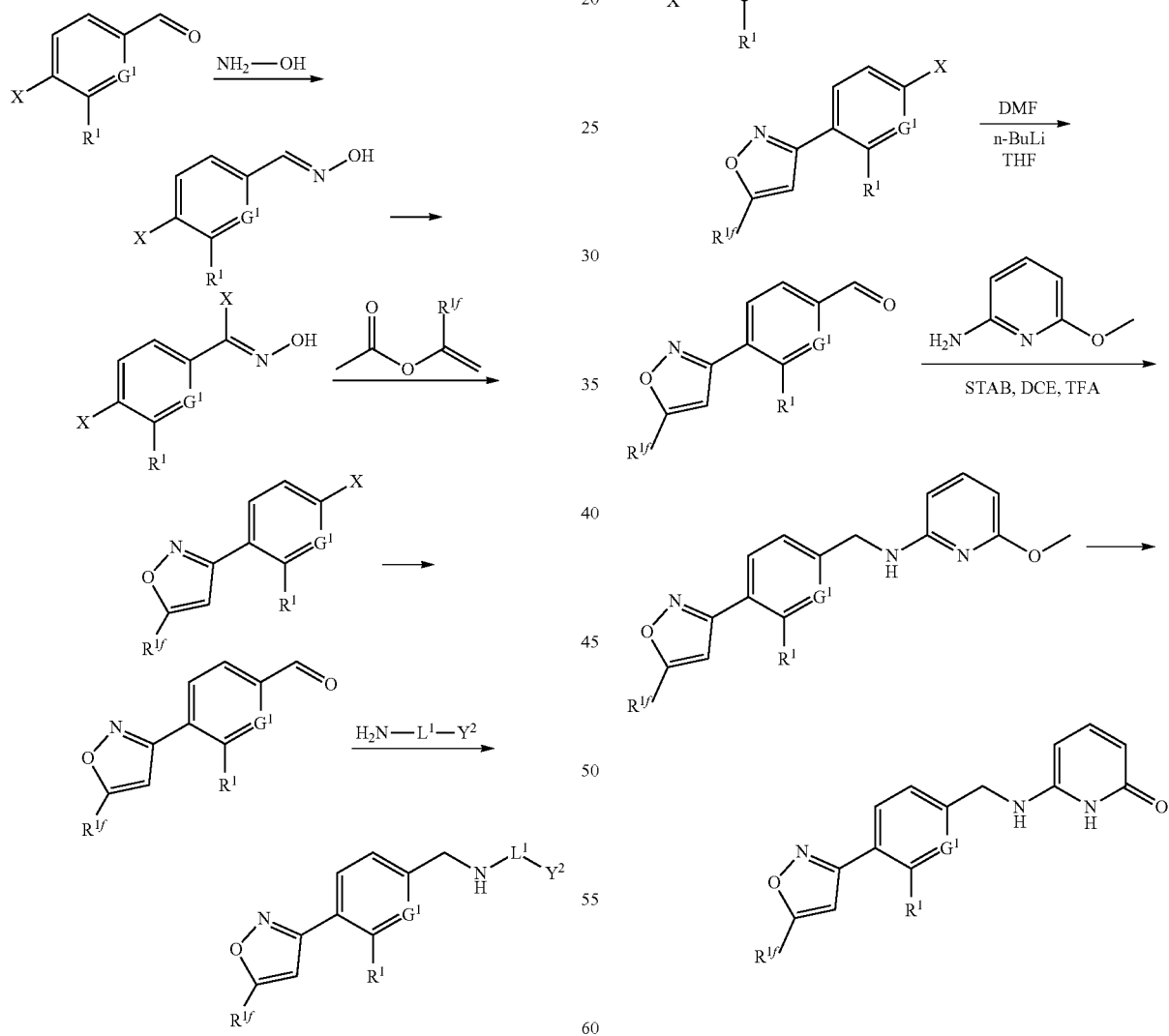

wherein $R^{1f}$, $R^1$, $L^1$, $Y^2$, and $G^1$ are as defined for Formula (I), or any variation thereof detailed herein, and each X is independently a halogen.

An exemplary embodiment of the preparative method in Scheme 4 is shown in Scheme 4a.

Scheme 4a

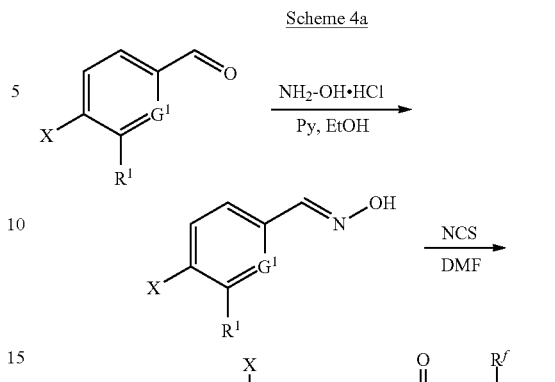

wherein $R^{1f}$, $R^1$, and $G^1$ are as defined for Formula (I), or any variation thereof detailed herein, and each X is independently a halogen.

In some embodiments, compounds provided herein may be synthesized according to Scheme 5.

Scheme 5

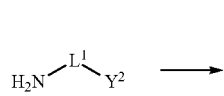

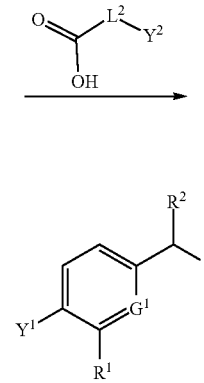

wherein $R^1$, $R^2$, $L^1$, $Y^1$, $Y^2$, and $G^1$ are as defined for Formula (I), or any variation thereof detailed herein.

An exemplary embodiment of the preparative method in Scheme 5 is shown in Scheme 5a.

Scheme 5a

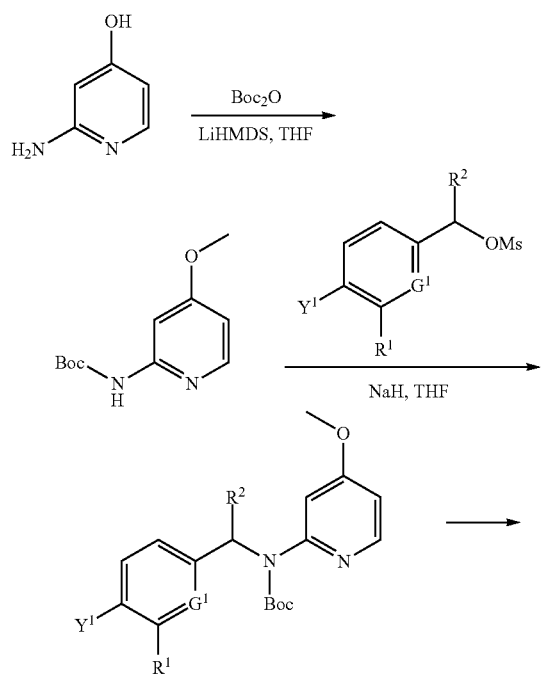

wherein $R^1$, $R^2$, $Y^1$, and $G^1$ are as defined for Formula (I), or any variation thereof detailed herein.

In some embodiments, compounds provided herein may be synthesized according to Scheme 6.

Scheme 6

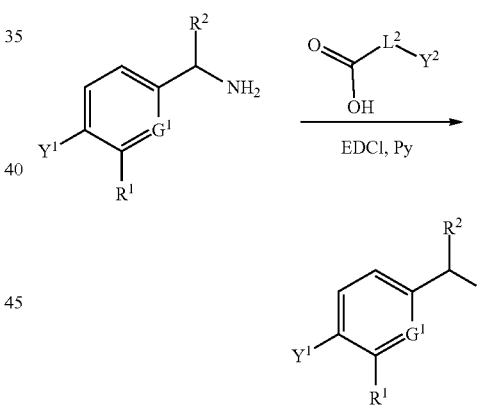

wherein $R^1$, $R^2$, $Y^1$, $Y^2$, $L^2$, and $G^1$ are as defined for Formula (I), or any variation thereof detailed herein.

An exemplary embodiment of the preparative method in Scheme 6 is shown in Scheme 6a.

Scheme 6a

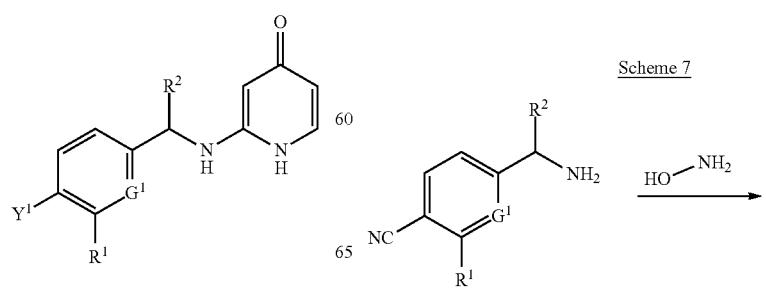

wherein $R^1$, $R^2$, $Y^1$, $Y^2$, $L^2$, and $G^1$ are as defined for Formula (I), or any variation thereof detailed herein.

In some embodiments, compounds provided herein may be synthesized according to Scheme 7.

Scheme 7

-continued

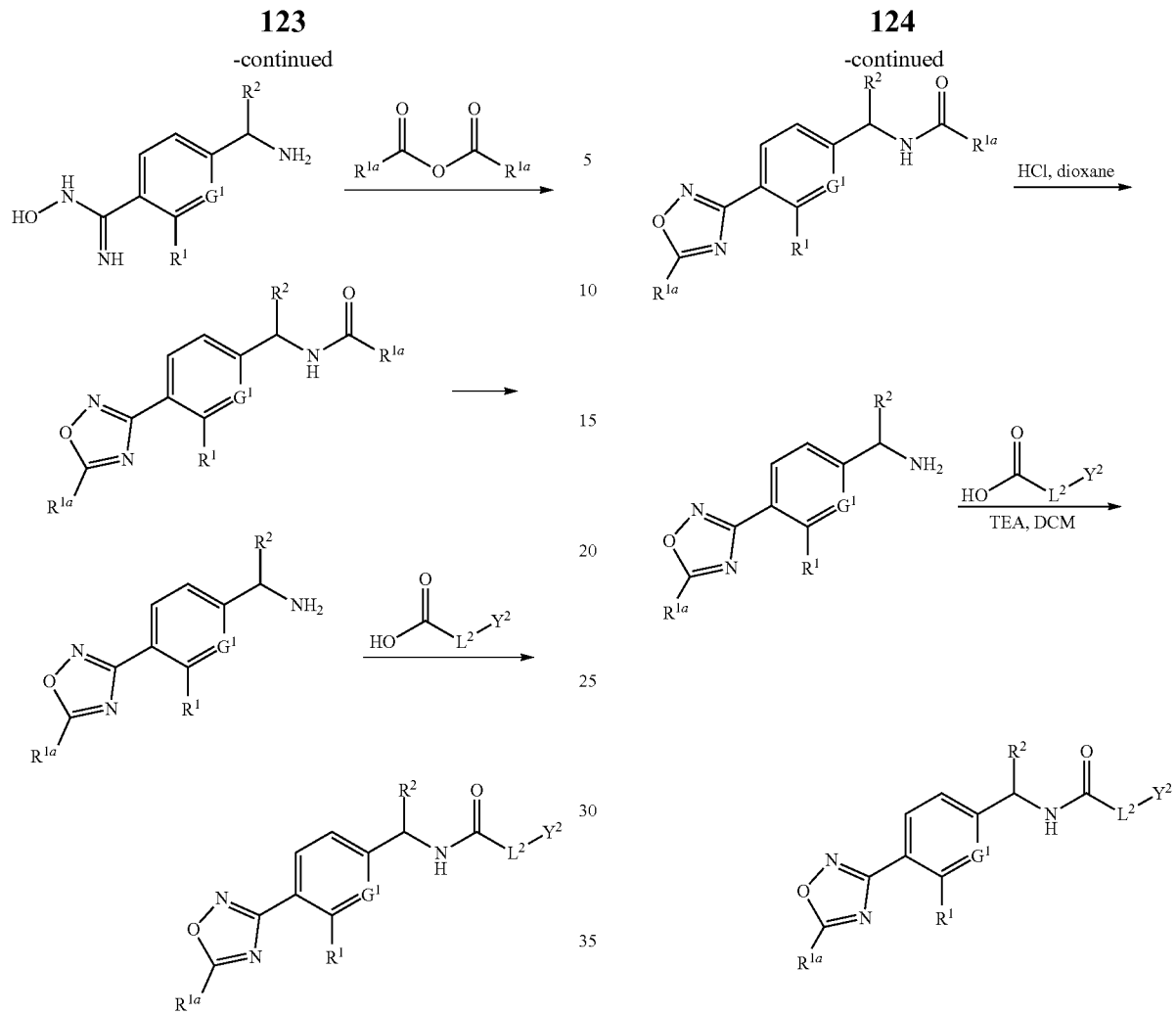

wherein $R^{1a}$, $R^1$, $R^2$, $L^2$, $Y^2$, and $G^1$ are as defined for Formula (I), or any variation thereof detailed herein.

An exemplary embodiment of the preparative method in Scheme 7 is shown in Scheme 7a.

Scheme 7a

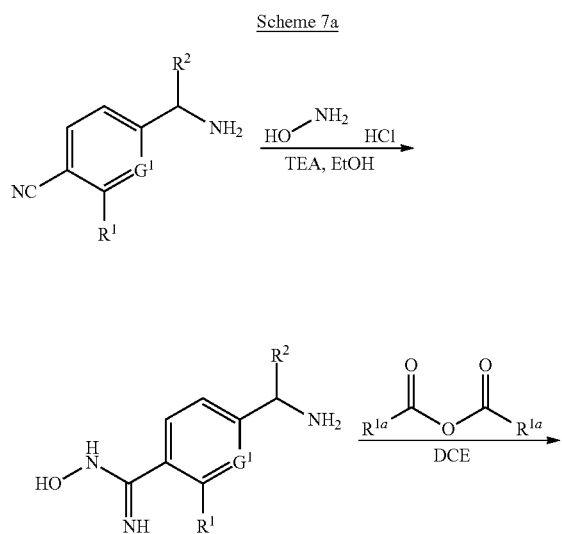

wherein $R^{1a}$, $R^1$, $R^2$, $L^2$, $Y^2$, and $G^1$ are as defined for Formula (I), or any variation thereof detailed herein.

Particular non-limiting examples are provided in the Example section below.

EXAMPLES

The following examples are offered to illustrate but not to limit the compositions, uses, and methods provided herein. The compounds are prepared using the general methods described above.

The following abbreviations are used throughout the Examples: TEA (trimethylamine), DCM (dichloromethane), (Boc)₂O (di-tert-butyl decarbonate), EA (Ethyl acetate), PE (Petroleum ether, DMF (N,N-dimethylformamide), DIEA (N-ethyl-N-isopropylpropan-2-amine), HATU (1-[Bis(dimethylamino)methylene]-1H-1,2,3-triazolo[4,5-b]pyridinium 3-oxid hexafluorophosphate), HOAt (1-Hydroxy-7-azabenzotriazole), HOBt (Hydroxybenzotriazole), EDCI (1-Ethyl-3-(3-dimethylaminopropyl)carbodiimide), MeOH (methanol), EtOH (ethanol), iPrOH (propan-2-ol), ACN (acetonitrile), TFA (trifluoroacetic acid), DPPA (Diphenylphosphoryl azide), DBU (1,8-Diazabicyclo(5.4.0)undec-7-ene), THF (tetrahydrofuran), PPh₃ (triphenylphosphane), SM (starting material), Hex (hexane), NCS (N-chlorosuccinimide), r.t. (room temperature), DCE (dichloroethane), FA (formic acid), CHCl₃ (Chloroform), BnBr (benzyl bromide), HCl (hydrogen chloride), equiv (equivalent), and DSC (bis(2,5-dioxopyrrolidin-1-yl) carbonate).

Example 1

Synthesis of Compound 4

1. Synthesis of Intermediate 1-2

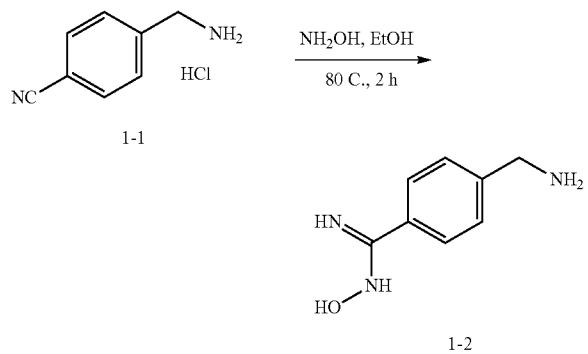

To a solution of 4-(Aminomethyl)benzonitrile hydrochloride (2.0 g, 11.9 mmol, 1.0 equiv) in EtOH (30 mL) was added hydroxylamine (5.0 mL, 50 wt % in water). The reaction was heated to 80° C. for 2 h and concentrated to provide 4-(aminomethyl)-N-hydroxybenzimidamide as a white solid. LRMS (ES) m/z 166.1 (M+H).

2. Synthesis of Intermediate 1-3

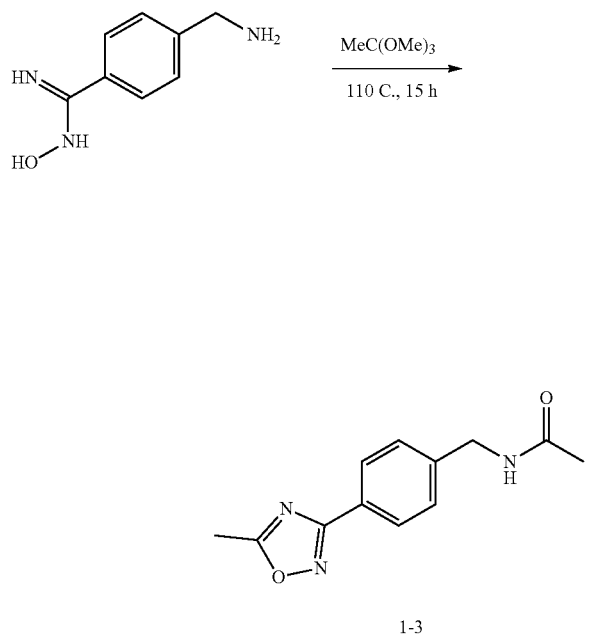

The intermediate product, 4-(aminomethyl)-N-hydroxybenzimidamide (11.9 mmol, 1.0 equiv) obtained from previous reaction was dissolved in 1,1,1-trimethoxyethane (20 mL), heated to reflux for 15 h, and concentrated to provide an intermediate product, N-(4-(5-methyl-1,2,4-oxadiazol-3-yl)benzyl)acetamide. LRMS (ES) m/z 232.1 (M+H).

3. Synthesis of Intermediate 1-4

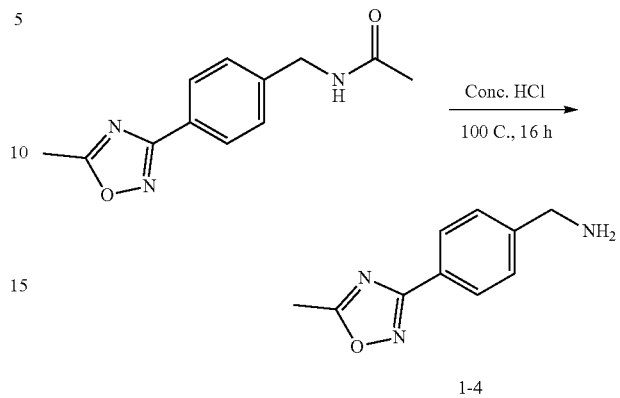

The intermediate product, N-(4-(5-Methyl-1,2,4-oxadiazol-3-yl)benzyl)acetamide (11.9 mmol, 1.0 equiv) in aqueous HCl (12 M, 50 mL) was heated to reflux for 16 h, concentrated under reduced pressure, and purified by silica gel chromatography (80 g column, 0-10% MeOH in DCM with 1% TEA) to provide 650 mg (29% over 3 steps) of (4-(5-methyl-1,2,4-oxadiazol-3-yl)phenyl)methanamine as an off-white solid. LRMS (ES) m/z 190.15 (M+H). $^1$H-NMR (Methanol-$d_4$, 400 MHz, ppm) δ 8.00 (d, J=8.4 Hz, 2H), 7.49 (d, J=8.4 Hz, 2H), 3.87 (s, 2H), 2.65 (s, 3H).

4. Synthesis of Compound 4

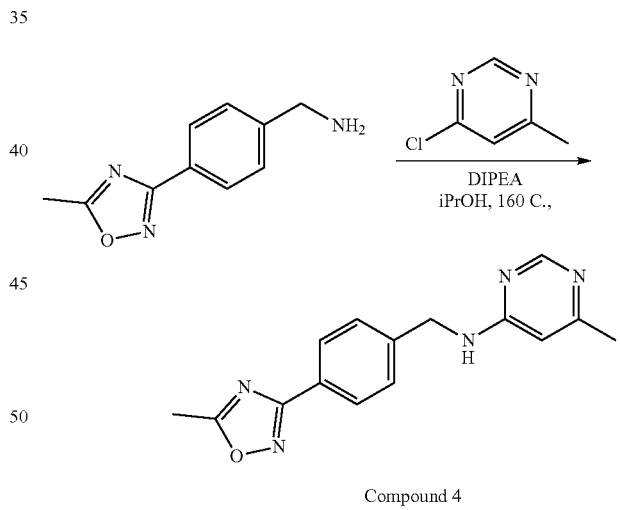

To a mixture of (4-(5-Methyl-1,2,4-oxadiazol-3-yl)phenyl)methanamine (40 mg, 0.21 mmol, 1.0 equiv) and IPA (3 mL) in a microwave vial were added 4-chloro-6-methylpyrimidine (33 mg, 0.25 mmol, 1.2 equiv) and DIPEA (88 uL, 0.51 mmol, 2.4 equiv). The vial was sealed and heated at 160° C. in a microwave reactor for 1 h. The reaction was concentrated and purified by RP-HPLC (Phenomenex, gemini 5u C18 150×21.2 mm, 10-100% ACN in water both with 0.1% formic acid gradient over 40 min) to provide 9.7 mg (16%) of 6-methyl-N-(4-(5-methyl-1,2,4-oxadiazol-3-yl)benzyl)pyrimidin-4-amine as an off-white solid. LRMS (ES) m/z 282.2 (M+H). $^1$H-NMR (Methanol-$d_4$, 400 MHz, ppm) δ 8.40 (s, 1H), 8.19 (s, 1H), 8.01 (d, J=8.3 Hz, 2H), 7.48 (d, J=7.9 Hz, 2H), 6.48 (s, 1H), 4.70 (s, 2H), 2.64 (s, 3H), 2.33 (s, 3H).

The following compounds were prepared by methods analogous to the method described for Compound 4:

| Compound No. | LRMS (ES) m/z |
|---|---|
| 1 | M + H = 302.1 |
| 2 | M + H = 268.2 |
| 3 | M + H = 268.2 |
| 4 | M + H = 336.2 |
| 5 | M + H = 308 |
| 6 | M + H = 293 |
| 7 | M + H = 296 |
| 9 | M + H = 302 |
| 10 | M + H = 293 |
| 12 | M + H = 302 |
| 13 | M + H = 302 |
| 14 | M + H = 292 |
| 14 | M + H = 292 |
| 15 | M + H = 292 |
| 16 | M + H = 336 |
| 18 | M + H = 302 |
| 19 | M + H = 310 |
| 20 | M + H = 301 |
| 26 | M + H = 282 |
| 42 | M + H = 340 |
| 44 | M + H = 301 |
| 45 | M + H = 340 |
| 47 | M + H = 312 |
| 59 | M + H = 308 |

Example 2

Synthesis of Compound 11

1. Synthesis of Intermediate 2-2

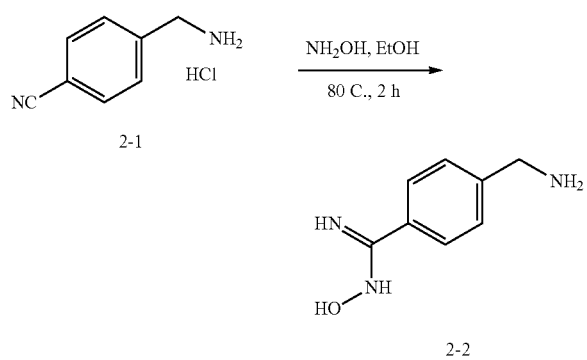

To a solution of 4-(Aminomethyl)benzonitrile hydrochloride (10 g, 59.3 mmol, 1.0 equiv) in EtOH (150 mL) was added hydroxylamine (50.0 mL, 50 wt % in water). The mixture was heated to 80° C. for 2 h and concentrated to provide 4-(aminomethyl)-N-hydroxybenzimidamide as a white solid. LRMS (ES) m/z 166.1 (M+H).

2. Synthesis of Intermediate 2-3

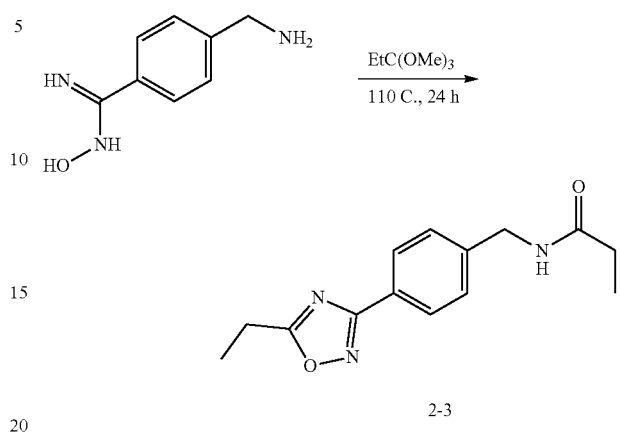

The intermediate product, 4-(aminomethyl)-N-hydroxybenzimidamide (1.0 g, 5.0 mmol, 1.0 equiv) obtained from previous reaction was dissolved in 1,1,1-trimethoxypropane (20 mL), heated to reflux for 24 h, and concentrated to provide an intermediate product, N-(4-(5-ethyl-1,2,4-oxadiazol-3-yl)benzyl)propionamide. LRMS (ES) m/z 260.1 (M+H).

3. Synthesis of Intermediate 2-4

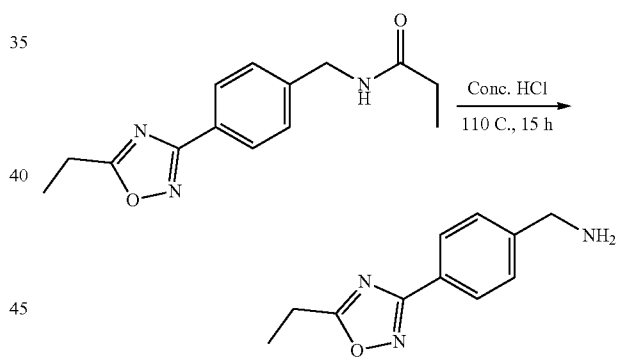

The intermediate product, N-(4-(5-Ethyl-1,2,4-oxadiazol-3-yl)benzyl)propionamide (5.0 mmol, 1.0 equiv) obtained from the previous reaction was dissolved in aqueous HCl (12 M, 30 mL), heated to reflux for 16 h, concentrated down the volume to approximately 3 mL, basified to pH 14 with aqueous NaOH (8 N), and diluted with water (100 mL) and DCM (100 mL). The aqueous layer was extracted with DCM twice. To the combined DCM layers was added 5 g of silica and the mixture was concentrated to dryness. The mixture was purified with silica gel chromatography (40 g column) eluting with MeOH and DCM (both contained with 1% TEA, gradient from 0-10%) to provide 0.3 g (25% over 2 steps) of (4-(5-ethyl-1,2,4-oxadiazol-3-yl)phenyl)methanamine as an off-white solid. LRMS (ES) m/z 204.1 (M+H). $^1$H-NMR (Methanol-$d_4$, 400 MHz, ppm) δ 8.02 (d, J=8.2 Hz, 2H), 7.50 (d, J=8.3 Hz, 2H), 3.87 (s, 2H), 3.01 (q, J=7.6 Hz, 2H), 1.44 (t, J=7.6 Hz, 3H).

4. Synthesis of Compound 11

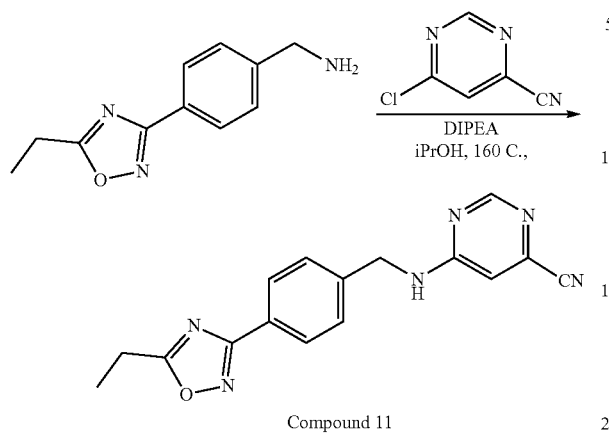

Compound 11

To a mixture of (4-(5-Ethyl-1,2,4-oxadiazol-3-yl)phenyl)methanamine (50 mg, 0.25 mmol, 1.0 equiv) and IPA (3 mL) in a microwave vial were added 6-chloropyrimidine-4-carbonitrile (41 mg, 0.30 mmol, 1.2 equiv) and DIPEA (103 uL, 0.59 mmol, 2.4 equiv). The vial was sealed and heated at 160° C. in a microwave reactor for 90 min. The mixture was concentrated and purified by RP-HPLC (Phenomenex, gemini 5u C18 150×21.2 mm, 10-100% ACN/water both with 0.1% formic acid gradient over 40 min) to provide 23 mg (31%) of 6-((4-(5-ethyl-1,2,4-oxadiazol-3-yl)benzyl)amino)pyrimidine-4-carbonitrile as a white solid. LRMS (ES) m/z 307.2 (M+H). $^1$H-NMR (Methanol-$d_4$, 400 MHz, ppm) δ 8.49 (s, 1H), 8.02 (d, J=7.9 Hz, 2H), 7.49 (d, J=7.8 Hz, 2H), 6.96 (s, 1H), 4.72 (s, 2H), 3.10-2.88 (m, 2H), 1.43 (t, J=7.6 Hz, 2H).

Example 3

Synthesis of Compound 17

1. Synthesis of Intermediate 3-2

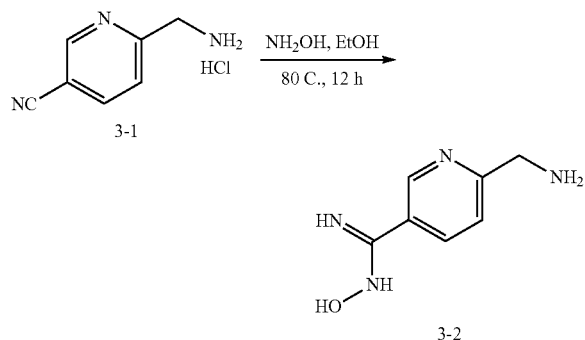

To a solution of 6-(Aminomethyl)nicotinonitrile hydrochloride (1.0 g, 5.9 mmol, 1.0 equiv) in EtOH (30 mL) was added hydroxylamine (5.0 mL, 50 wt % in water). The mixture was heated at 80° C. for 12 h and concentrated to provide an intermediate product, 6-(aminomethyl)-N-hydroxynicotinimidamide as a white solid. LRMS (ES) m/z 167.1 (M+H).

2. Synthesis of Intermediate 3-3

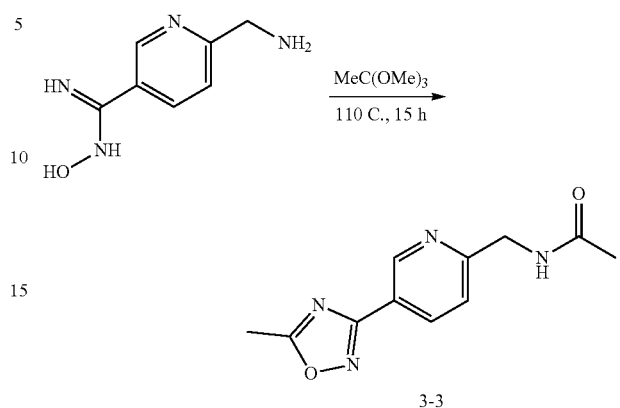

The intermediate product, 6-(Aminomethyl)-N-hydroxynicotinimidamide (5.9 mmol, 1.0 equiv) obtained from the previous reaction was dissolved in 1,1,1-trimethoxyethane (20 mL), refluxed for 15 h, and concentrated to provide an intermediate product, N-((5-(5-methyl-1,2,4-oxadiazol-3-yl)pyridin-2-yl)methyl)acetamide.

3. Synthesis of Intermediate 3-4

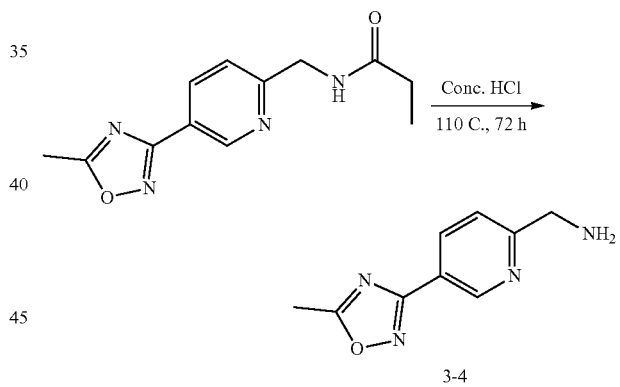

The intermediate product, N-((5-(5-Methyl-1,2,4-oxadiazol-3-yl)pyridin-2-yl)methyl)acetamide (5.9 mmol, 1.0 equiv) obtained from the previous reaction was dissolved in aqueous HCl (12 M, 50 mL), heated to reflux for 72 h, reduced the volume down to approximately 3 mL, basified to pH 14 with aqueous NaOH (8 N), and diluted with water (100 mL) and DCM (100 mL). The aqueous layer was extracted with DCM twice. To the combined DCM layers was added 5 g of silica and the mixture was concentrated to dryness. The mixture was purified with silica gel chromatography (40 g column) eluting with MeOH and DCM (both contained with 1% TEA, gradient from 0-10%) to provide 0.42 g (37% over 3 steps) of (5-(5-methyl-1,2,4-oxadiazol-3-yl)pyridin-2-yl)methanamine as an off-white solid. LRMS (ES) m/z 191.1 (M+H). $^1$H-NMR (Methanol-$d_4$, 400 MHz, ppm) δ 9.16 (d, J=2.1 Hz, 1H), 8.40 (dd, J=8.1, 2.1 Hz, 1H), 7.59 (dt, J=8.2, 1.0 Hz, 1H), 4.08 (s, 2H), 2.68 (s, 3H).

4. Synthesis of Compound 17

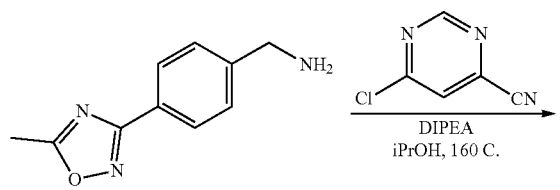

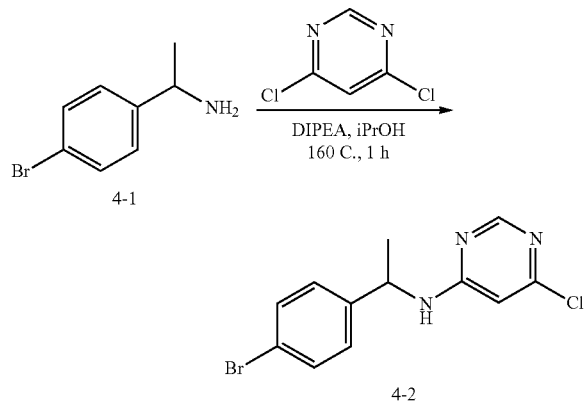

Compound 17

To a mixture of (5-(5-Methyl-1,2,4-oxadiazol-3-yl)pyridin-2-yl)methanamine (50 mg, 0.26 mmol, 1.0 equiv) and IPA (3 mL) in a microwave vial were added 6-chloro-4-cyanopyrimidine (44 mg, 0.32 mmol, 1.2 equiv) and DIPEA (110 uL, 0.63 mmol, 2.4 equiv). The vial was sealed and heated at 160° C. in a microwave reactor for 30 min. The mixture was concentrated and purified by reverse phase HPLC (Phenomenex, gemini 5u C18 150×21.2 mm, 10-100% ACN in water both with 0.1% formic acid gradient over 40 min) to provide 8.5 mg (11%) of 6-(((5-(5-methyl-1,2,4-oxadiazol-3-yl)pyridin-2-yl)methyl)amino)pyrimidine-4-carbonitrile as a white solid. LRMS (ES) m/z 294.2 (M+H). $^1$H-NMR (Methanol-$d_4$, 400 MHz, ppm) δ 9.14 (s, 1H), 8.47 (s, 1H), 8.38 (d, J=8.1 Hz, 1H), 7.56 (d, J=8.2 Hz, 1H), 7.07 (d, J=1.3 Hz, 1H), 4.84 (s, 2H), 2.68 (s, 3H).

Example 4

Synthesis of Compound 21

1. Synthesis of Intermediate 4-2

To a mixture of 1-(4-Bromophenyl)ethan-1-amine (1.0 g, 5.0 mmol, 1.0 equiv) and IPA (15 mL) in a microwave vial (20 mL) were added 4,6-dichloropyrimidine (0.89 g, 6.0 mmol, 1.2 equiv) and DIPEA (1.6 g, 12.0 mmol, 2.4 equiv). The vial was sealed and heated at 160° C. in a microwave reactor for 1 h. The mixture was concentrated onto 5 g of SiO$_2$ and purified by silica gel chromatography (80 g column, 0-10% MeOH in DCM with 1% TEA) to provide 1.1 g (70%) of N-(1-(4-bromophenyl)ethyl)-6-chloropyrimidin-4-amine as a white solid. LRMS (ES) m/z 312.0 (M+H). $^1$H-NMR (Chloroform-d, 400 MHz, ppm) δ 8.29 (s, 1H), 7.46 (d, J=8.4 Hz, 2H), 7.19 (d, J=8.4 Hz, 2H), 6.19 (s, 1H), 4.79 (bs, 1H), 1.54 (d, J=6.8 Hz, 3H).

2. Synthesis of Intermediate 4-3

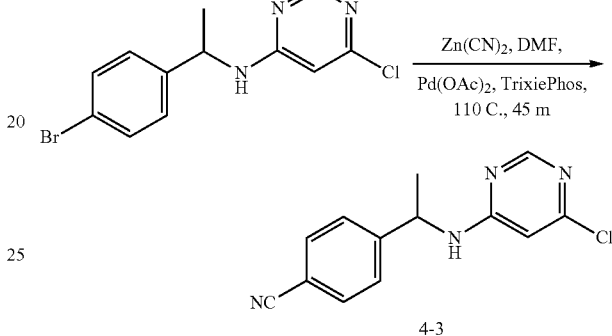

4-3

N-(1-(4-bromophenyl)ethyl)-6-chloropyrimidin-4-amine (61 mg, 0.20 mmol, 1.0 equiv), zinc cyanide (23 mg, 0.20 mmol, 1.0 equiv), palladium acetate (4.4 mg, 0.020 mmol, 0.1 equiv), and TrixiePhos (16 mg, 0.040 mmol, 0.2 equiv) were combined in a 100 mL round bottom flask and the flask was purged with nitrogen for 30 min. DMF (3 mL) and degassed by sparging with nitrogen for 30 min. The mixture was and then added to the reaction vessel with a syringe. The mixture was heated at 110° C. for 45 min, exposed to a stream of nitrogen to remove most of the DMF, added DMSO (1.5 mL), filtered, and purified with reverse phase HPLC (Phenomenex, gemini 5u C18 150×21.2 mm, 0-100% ACN in water both with 0.1% formic acid gradient over 40 min) to give 50 mg of 4-(1-((6-chloropyrimidin-4-yl)amino)ethyl)benzonitrile. LRMS (ES) m/z 259.0 (M+H).

3. Synthesis of Intermediate 4-4

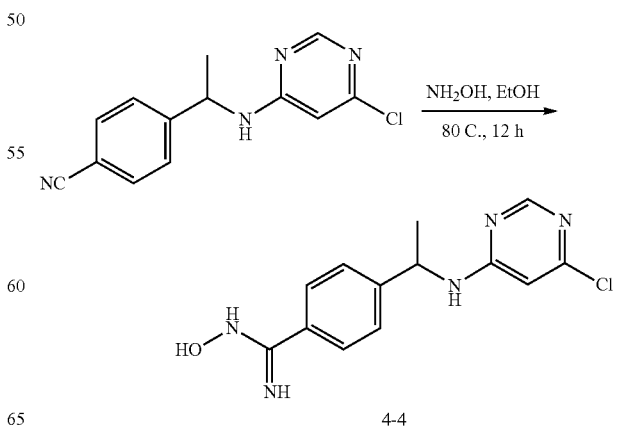

4-4

To a solution of 4-(1-((6-Chloropyrimidin-4-yl)amino) ethyl)benzonitrile (50 mg, 0.20 mmol, 1.0 equiv) in EtOH (30 mL) was added hydroxylamine (5.0 mL, 50 wt. % in water). The mixture was heated at 80° C. for 12 h and concentrated to provide an intermediate product, 4-(1-((6-chloropyrimidin-4-yl)amino)ethyl)-N-hydroxybenzimidamide.

4. Synthesis of Compound 21

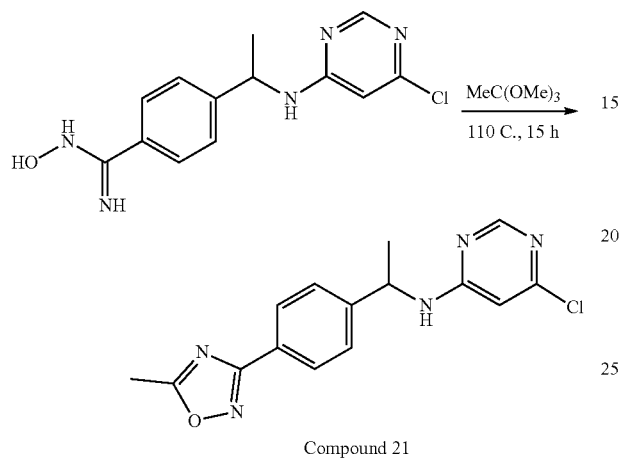

Compound 21

To a solution of 4-(1-((6-Chloropyrimidin-4-yl)amino) ethyl)-N-hydroxybenzimidamide (an intermediate mixture obtained from the previous step, 0.20 mmol, 1.0 equiv) in 1,1,1-trimethoxyethane (20 mL) was heated to reflux for 15 h. The reaction was concentrated and purified with RP-HPLC (Phenomenex, gemini 5u C18 150×21.2 mm, 0-100% ACN in water both with 0.1% formic acid gradient over 40 min) to provide 3.8 mg (6% over 3 steps) of 6-chloro-N-(1-(4-(5-methyl-1,2,4-oxadiazol-3-yl)phenyl)ethyl)pyrimidin-4-amine as a residue. LRMS (ES) m/z 316.1 (M+H). $^1$H-NMR (Methanol-$d_4$, 400 MHz, ppm) δ 8.19 (s, 1H), 8.00 (d, J=8.0 Hz, 2H), 7.50 (d, J=8.2 Hz, 2H), 6.55 (bs, 1H) 4.65-4.45 (m, 2H), 2.65 (s, 3H), 1.56 (d, J=7.0 Hz, 3H).

Example 5

Synthesis of Compound 22

1. Synthesis of Intermediate 5-2

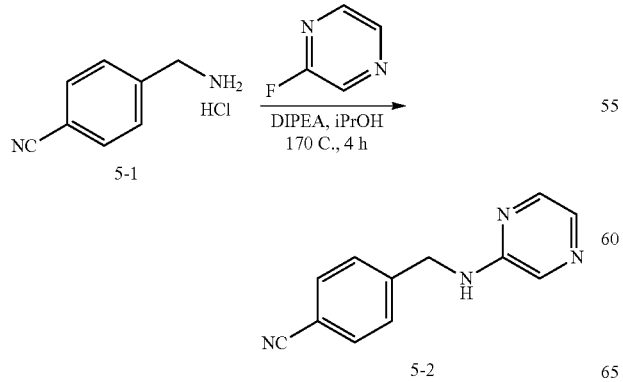

To a mixture of 4-(Aminomethyl)benzonitrile hydrochloride (1.6 g, 9.3 mmol, 1.0 equiv) and IPA (15.0 mL) in a microwave vial (20 mL) were added 2-fluoropyrazine (1.0 g, 10.2 mmol, 1.1 equiv) and DIPEA (2.9 g, 22.2 mmol, 2.4 equiv). The vial was sealed and heated at 170° C. in a microwave reactor for 4 h, concentrated onto 10 g of silica, and purified by silica gel chromatography (80 g column, 0-10% MeOH in DCM) to provide 1.2 g (62%) of 4-((pyrazin-2-ylamino)methyl)benzonitrile as a pale yellow solid. LRMS (ES) m/z 211.2 (M+H). $^1$H-NMR (Methanol-$d_4$, 400 MHz, ppm) δ 7.96-7.90 (m, 2H), 7.70-7.62 (m, 3H), 7.53-7.48 (m, 2H), 4.63 (s, 2H).

2. Synthesis of Intermediate 5-3

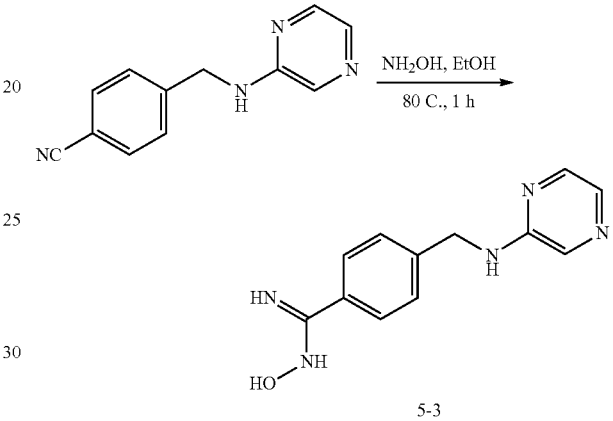

To a solution of 4-((Pyrazin-2-ylamino)methyl)benzonitrile (0.65 g, 3.1 mmol, 1.0 equiv) in EtOH (20 mL) was added hydroxylamine (5.0 mL, 50 wt % in water). The reaction was heated at 80° C. for 1 h and concentrated to provide 0.7 g (93%) of N-hydroxy-4-((pyrazin-2-ylamino) methyl)benzimidamide as a white powder. LRMS (ES) m/z 244.1 (M+H).

3. Synthesis of Intermediate 5-4

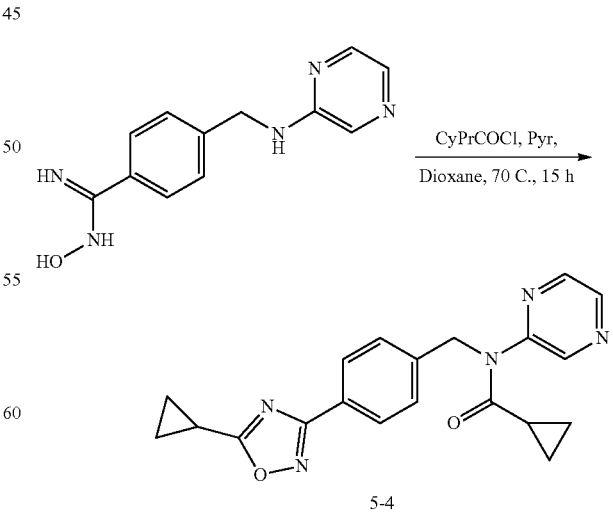

To N-hydroxy-4-((pyrazin-2-ylamino)methyl)benzimidamide (50 mg, 0.21 mmol, 1.0 equiv) in a mixture of dioxane (3 mL) and pyridine (1 mL) was added cyclopropanecarbonyl chloride (43 mg, 0.41 mmol, 2.0 equiv). The mixture was then heated at 70° C. for 16 h and concentrated to provide an intermediate product, N-(4-(5-cyclopropyl-1,2,4-oxadiazol-3-yl)benzyl)-N-(pyrazin-2-yl)cyclopropanecarboxamide. LRMS (ES) m/z 362.2 (M+H).

4. Synthesis of Compound 22

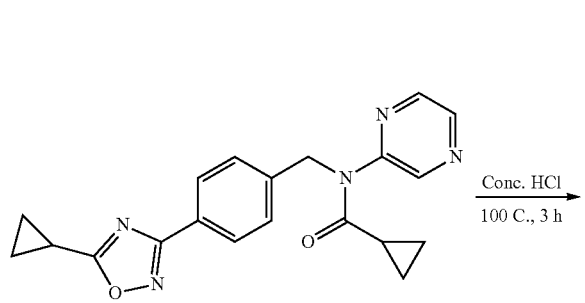

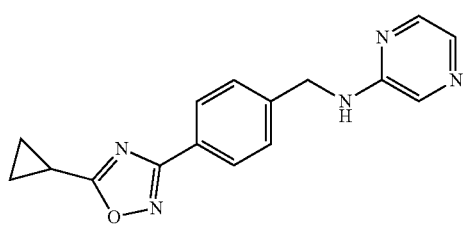

Compound 22

N-(4-(5-cyclopropyl-1,2,4-oxadiazol-3-yl)benzyl)-N-(pyrazin-2-yl)cyclopropanecarboxamide (0.21 mmol, 1.0 equiv) in aqueous HCl (12 M, 20 mL) was heated at 100° C. for 3 h, concentrated the volume down to approximately 3 mL, basified to pH 14 with aqueous NaOH (8 N), and diluted with water (100 mL) and DCM (100 mL). The aqueous layer was extracted with DCM twice. The combined DCM layers were concentrated and purified with RP-HPLC (Phenomenex, gemini 5u C18 150×21.2 mm, 10-100% acetonitrile in water both with 0.1% formic acid gradient over 40 min) to provide 3.7 mg (6% over 2 steps) of N-(4-(5-cyclopropyl-1,2,4-oxadiazol-3-yl)benzyl)pyrazin-2-amine. LRMS (ES) m/z 294.2 (M+H). $^1$H-NMR (Methanol-$d_4$, 400 MHz, ppm) δ 8.00-7.92 (m, 4H), 7.67 (d, J=2.9 Hz, 1H), 7.49 (d, J=8.0 Hz, 2H), 4.63 (s, 2H), 2.42-2.20 (m, 1H), 1.36-1.21 (m, 4H).

The following compounds were prepared by methods analogous to the method described for Compound 22:

| Compound No. | LRMS (ES) m/z |
|---|---|
| 23 | M + H = 308 |
| 24 | M + H = 304 |
| 25 | M + H = 286 |
| 30 | M + H = 312 |

Example 6

Synthesis of Compound 27

1. Synthesis of Intermediate 6-2

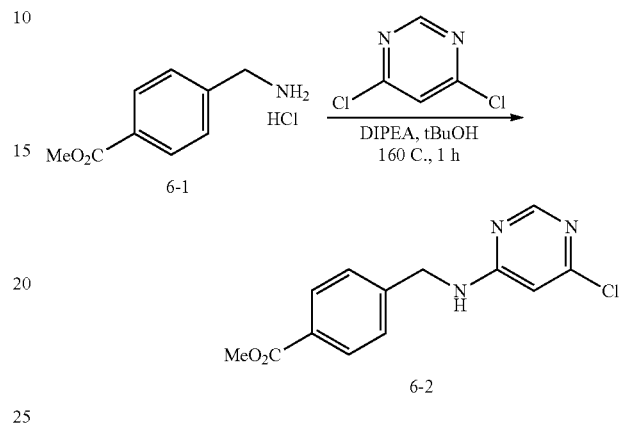

To a mixture of methyl 4-(aminomethyl)benzoate hydrochloride (0.92 g, 4.6 mmol, 1.0 equiv) and IPA (15 mL) in a microwave vial were added 4,6-dichloropyrimidine (1.4 g, 9.1 mmol, 2.0 equiv) and DIPEA (1.4 g, 11.0 mmol, 2.4 equiv). The vial was sealed and heated at 160° C. in a microwave reactor for 1 h. The mixture was concentrated and purified by silica gel chromatography (40 g column, 0-10% MeOH in DCM with 1% TEA) to provide 1.1 g (87%) of methyl 4-(((6-chloropyrimidin-4-yl)amino)methyl)benzoate. LRMS (ES) m/z 278.1 (M+H).

2. Synthesis of Intermediate 6-3

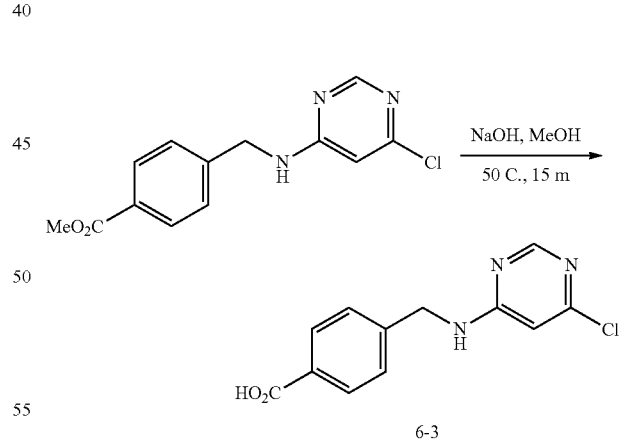

To a solution of methyl 4-(((6-chloropyrimidin-4-yl)amino)methyl)benzoate (0.50 g, 1.8 mmol, 1.0 equiv) in MeOH (5 mL) was added aqueous NaOH (8 N, 2.0 mL, 16 mmol, 8.9 equiv). The mixture was stirred at 50° C. for 15 min and added aqueous citric acid (10%, 100 mL). The solids were collected, washed with citric acid (10%, 50 mL) and hexanes (50 mL), and dried under vacuum to give 0.45 g (95%) of 4-(((6-chloropyrimidin-4-yl)amino)methyl)benzoic acid. LRMS (ES) m/z 264.1 (M+H).

3. Synthesis of Intermediate 6-4

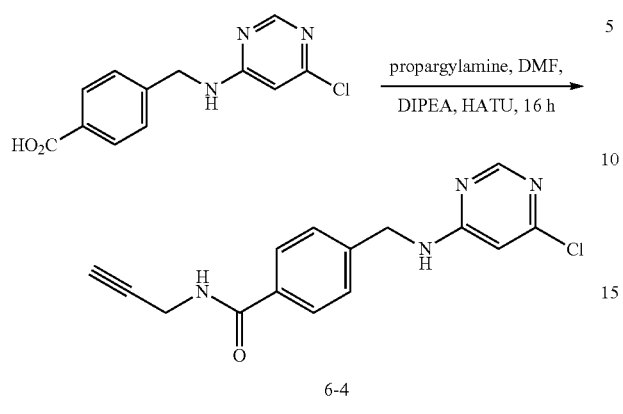

To a mixture of 4-(((6-chloropyrimidin-4-yl)amino)methyl)benzoic acid (70 mg, 0.27 mmol, 1.0 equiv), HATU (151 mg, 0.40 mmol, 1.5 equiv), and propargylamine (44 mg, 0.80 mmol, 3.0 equiv) combined in a vial (20 mL) were added DMF (2 mL) and DIPEA (139 uL, 0.80 mmol, 3.0 equiv). The mixture was stirred at r.t. for 16 h, filtered, and purified with RP-HPLC (Phenomenex, gemini 5u C18 150× 21.2 mm, 0-100% acetonitrile in water both with 0.1% formic acid gradient for 40 m) to provide 35 mg (44%) of 4-(((6-chloropyrimidin-4-yl)amino)methyl)-N-(prop-2-yn-1-yl)benzamide as a white solid. LRMS (ES) m/z 301.0 (M+H).

4. Synthesis of Compound 27

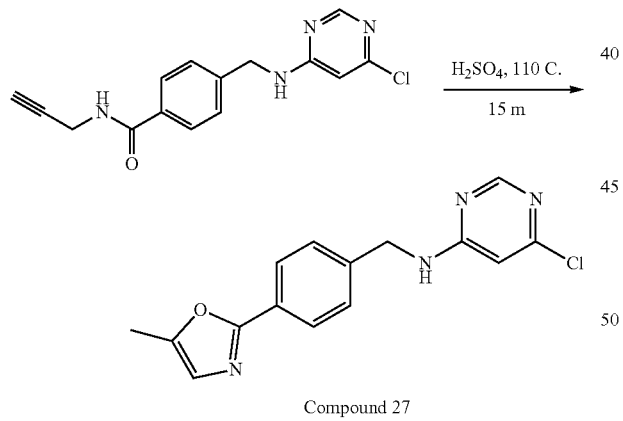

To 4-(((6-Chloropyrimidin-4-yl)amino)methyl)-N-(prop-2-yn-1-yl)benzamide (25 mg, 0.083 mmol, 1.0 equiv) in microwave vial with a stir bar was added neat $H_2SO_4$ (2.0 mL). The vial was sealed and heated at 110° C. in a microwave reactor for 15 min. The mixture was poured into water (50 mL), basified to pH 14 with aqueous NaOH (8 N), and extracted with DCM (50 mL) three times. The combined DCM layers were concentrated and purified by RP-HPLC (Phenomenex, gemini 5u C18 150×21.2 mm, 10-100% acetonitrile in water (both with 0.1% formic acid gradient over 40 min) to provide 7.4 mg (30%) of 6-chloro-N-(4-(5-methyloxazol-2-yl)benzyl)pyrimidin-4-amine as a white solid. LRMS (ES) m/z 301.1 (M+H). $^1$H-NMR (Methanol-$d_4$, 400 MHz, ppm) δ 8.25 (s, 1H), 7.93 (d, J=8.2 Hz, 2H), 7.45 (d, J=8.1 Hz, 2H), 6.90 (s, 1H), 6.57 (bs, 1H), 4.67 (bs, 2H), 2.41 (s, 3H).

Example 7

Synthesis of Compound 29

1. Synthesis of Intermediate 7-2

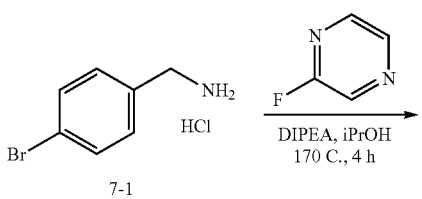

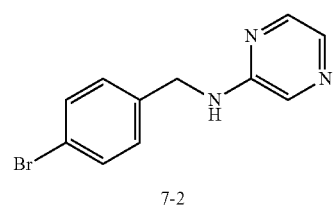

To a mixture of (4-bromophenyl)methanamine hydrochloride (2.2 g, 9.9 mmol, 1.0 equiv) and IPA (15 mL) in a microwave vial (20 mL) were added 2-fluoropyrazine (1.1 g, 10.9 mmol, 1.1 equiv) and DIPEA (3.1 g, 23.7 mmol, 2.4 equiv).). The vial was sealed and heated at 170° C. in a microwave reactor for 4 h. The mixture was concentrated onto 10 g of $SiO_2$ and purified by silica gel chromatography (80 g column, 0-10% MeOH in DCM) to provide 1.65 g (63%) of N-(4-bromobenzyl)pyrazin-2-amine as an off-white solid. LRMS (ES) m/z 264.0 (M+H).

2. Synthesis of Compound 29

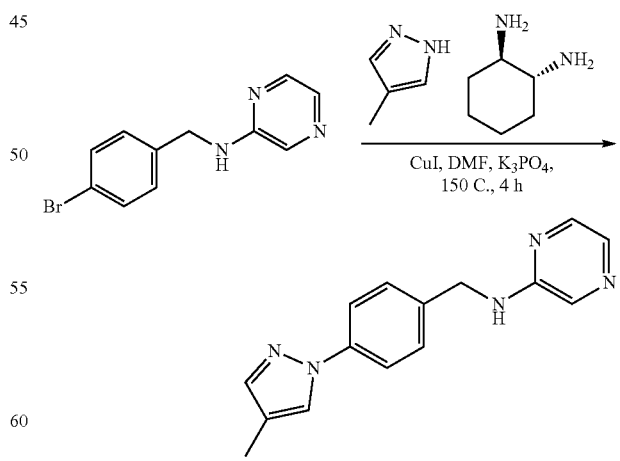

N-(4-Bromobenzyl)pyrazin-2-amine (75 mg, 0.28 mmol, 1.0 equiv), 4-methyl-1H-pyrazole (70 mg, 0.85 mmol, 3.0 equiv), copper(I) iodide (108 mg, 0.57 mmol, 2.0 equiv), potassium phosphate (151 mg, 0.71 mmol, 2.5 equiv), (1R,2R)-cyclohexane-1,2-diamine (6.5 mg, 0.057 mmol, 0.2 equiv), and DMF (4 mL) were combined in a microwave vial (6.0 mL). The mixture was heated to 150° C. for 4 h and partitioned between water (100 mL) and DCM (100 mL). The aqueous layer was extracted with DCM twice. The combined DCM layers were concentrated and purified with RP-HPLC (Phenomenex, gemini 5u C18 150×21.2 mm, 0-100% acetonitrile in water both with 0.1% formic acid gradient over 40 min) to provide 8.3 mg (11%) of N-(4-(4-methyl-1H-pyrazol-1-yl)benzyl)pyrazin-2-amine as a white solid. LRMS (ES) m/z 266.2 (M+H). $^1$H-NMR (Methanol-$d_4$, 400 MHz, ppm) δ 7.95 (bs, 3H), 7.66 (bs, 1H), 7.62 (d, J=8.6 Hz, 2H), 7.51 (s, 1H), 7.44 (d, J=8.6 Hz, 2H), 4.57 (s, 2H), 2.15 (s, 3H).

Example 8

Synthesis of Compound 31

1. Synthesis of Intermediate 8-2

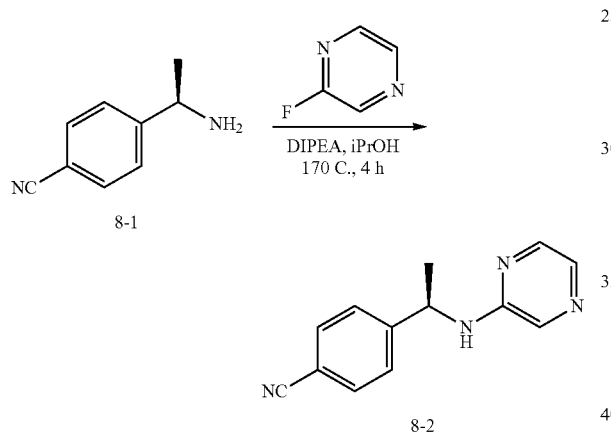

To a mixture of (R)-4-(1-aminoethyl)benzonitrile (1.0 g, 6.8 mmol, 1.0 equiv) and IPA (15 mL) in a microwave vial (20 mL) were added 2-fluoropyrazine (0.81 g, 8.2 mmol, 1.2 equiv) and DIPEA (2.1 g, 16.4 mmol, 2.4 equiv). The vial was sealed and heated at 170° C. in a microwave reactor for 4 h. The mixture was concentrated onto 5 g of SiO$_2$ and purified by silica gel chromatography (40 g column, 0-10% MeOH in DCM) to provide (R)-4-(1-(pyrazin-2-ylamino) ethyl)benzonitrile. LRMS (ES) m/z 225.1 (M+H). $^1$H-NMR (Methanol-$d_4$, 400 MHz, ppm) δ 7.92 (t, J=1.7 Hz, 1H), 7.85 (dd, J=2.9, 1.5 Hz, 1H), 7.70-7.63 (m, 2H), 7.61 (d, J=2.9 Hz, 1H), 7.58-7.52 (m, 2H), 5.08 (q, J=7.1 Hz, 1H), 1.54 (d, J=7.0 Hz, 3H).

2. Synthesis of Intermediate 8-3

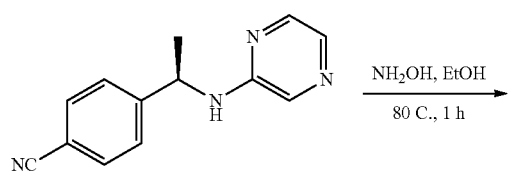

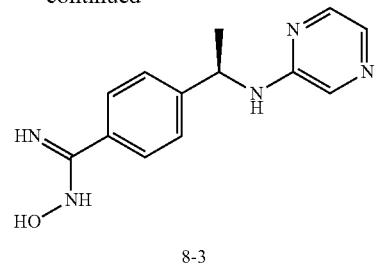

To a solution of (R)-4-(1-(pyrazin-2-ylamino)ethyl)benzonitrile (6.8 mmol, 1.0 equiv) in EtOH (20 mL) was added and hydroxylamine (5.0 mL, 50 wt. % in water). The mixture was heated at 80° C. for 1 h and concentrated to provide 1.2 g of (R)-N-hydroxy-4-(1-(pyrazin-2-ylamino) ethyl)benzimidamide as a white solid. LRMS (ES) m/z 258.15 (M+H).

3. Synthesis of Compound 31

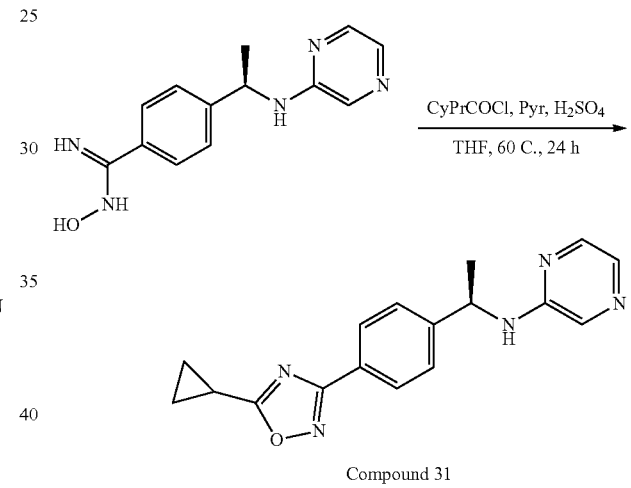

To (R)-N-hydroxy-4-(1-(pyrazin-2-ylamino)ethyl)benzimidamide (75 mg, 0.29 mmol, 1.0 equiv) in a mixture of THF (3 mL) and pyridine (1 mL) was added cyclopropanecarbonyl chloride (61 mg, 0.58 mmol, 2.0 equiv). The mixture was heated at 60° C. for 16 h, added conc. H$_2$SO$_4$ (6 drops), heated at 60° C. for 1 h, concentrated, and purified with RP-HPLC (Phenomenex, gemini 5u C18 150×21.2 mm, 10-100% acetonitrile in water both with 0.1% formic acid gradient over 40 min) to provide 33 mg (37%) of (R)-N-(1-(4-(5-cyclopropyl-1,2,4-oxadiazol-3-yl)phenyl) ethyl)pyrazin-2-amine as a white solid. LRMS (ES) m/z 308.2 (M+H). $^1$H-NMR (Methanol-$d_4$, 400 MHz, ppm) δ 7.97-7.86 (m, 4H), 7.60 (d, J=2.9 Hz, 1H), 7.50 (dd, J=8.5, 1.8 Hz, 2H), 5.08 (q, J=7.0 Hz, 1H), 2.40-2.22 (m, 1H), 1.55 (d, J=7.0 Hz, 3H), 1.37-1.18 (m, 4H).

The following compounds were prepared by methods analogous to the method described for Compound 31:

| Compound No. | LRMS (ES) m/z |
|---|---|
| 28 | M + H = 282 |
| 32 | M + H = 322 |

-continued

| Compound No. | LRMS (ES) m/z |
|---|---|
| 33 | M + H = 318 |
| 34 | M + H = 336 |
| 35 | M + H = 310 |
| 36 | M + H = 324 |
| 37 | M + H = 344 |
| 38 | M + H = 349 |
| 39 | M + H = 334 |
| 40 | M + H = 350 |
| 43 | M + H = 350 |

Example 9

Synthesis of Compound 41

1. Synthesis of Intermediate 9-2

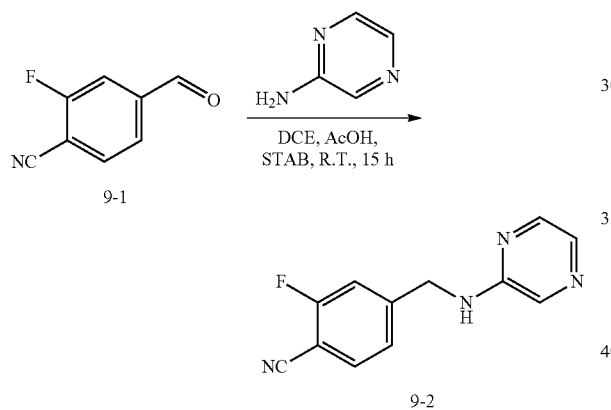

2-Fluoro-4-formylbenzonitrile (0.20 g, 1.3 mmol, 1.0 equiv), 2-aminopyrazine (0.14 g, 1.5 mmol, 1.1 equiv), DCE (5 mL), and AcOH (2 mL) were combined and stirred at r.t. for 30 min. To this mixture was added STAB (0.43 g, 2.0 mmol, 1.5 equiv). The mixture was stirred at r.t. overnight, added MeOH, concentrated directly onto 5 g of SiO$_2$, and purified by silica gel chromatography (24 g column, 0-100% EtOAc in hexanes) to provide 60 mg (20%) of 2-fluoro-4-((pyrazin-2-ylamino)methyl)benzonitrile. LRMS (ES) m/z 229.1 (M+H).

2. Synthesis of Intermediate 9-3

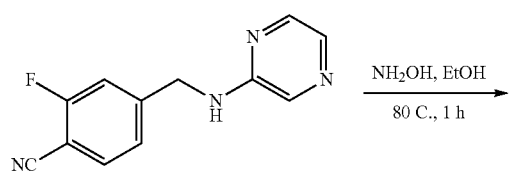

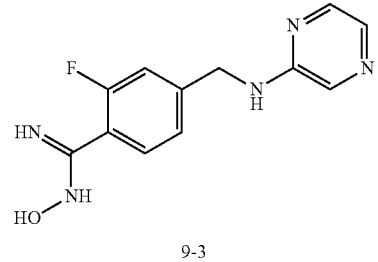

To a solution of 2-fluoro-4-((pyrazin-2-ylamino)methyl)benzonitrile (60 mg, 0.26 mmol, 1.0 equiv) in EtOH (20 mL) was added hydroxylamine (5.0 mL, 50 wt. % in water). The reaction was heated at 80° C. for 1 h and concentrated to provide 68 mg (99%) of 2-fluoro-N-hydroxy-4-((pyrazin-2-ylamino)methyl)benzimidamide. LRMS (ES) m/z 262.1 (M+H).

3. Synthesis of Compound 41

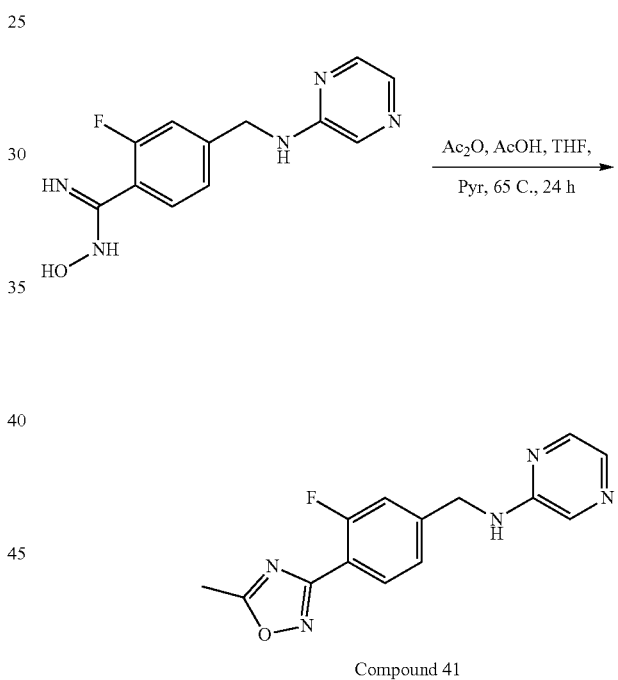

To 2-fluoro-N-hydroxy-4-((pyrazin-2-ylamino)methyl)benzimidamide (34 mg, 0.13 mmol, 1.0 equiv) in a mixture of THF (5 mL) and pyridine (0.3 mL) was added Ac$_2$O (27 mg, 0.26 mmol, 2.0 equiv). The mixture was heated at 65° C. for 1 h, added AcOH (0.1 mL), heated at 65° C. for an additional 4 h, added AcOH (0.1 mL), heated at 65° C. for 19 h, concentrated, and purified on RP-HPLC (Phenomenex, gemini 5u C18 150×21.2 mm, 10-100% acetonitrile in water both with 0.1% formic acid gradient over 40 min) to provide 24 mg (64%) of N-(3-fluoro-4-(5-methyl-1,2,4-oxadiazol-3-yl)benzyl)pyrazin-2-amine as a white solid. LRMS (ES) m/z 286.1 (M+H). $^1$H-NMR (Methanol-d$_4$, 400 MHz, ppm) δ 8.00-7.93 (m, 3H), 7.68 (dt, J=2.0, 0.9 Hz, 1H), 7.33 (ddt, J=8.1, 1.6, 0.8 Hz, 1H), 7.28 (dd, J=11.5, 1.6 Hz, 1H), 4.64 (s, 2H), 2.66 (s, 3H).

Example 10

Synthesis of Compound 46

1. Synthesis of Intermediate 10-2

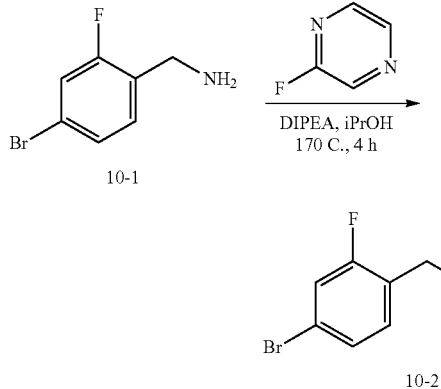

To a mixture of (4-bromo-2-fluorophenyl)methanamine (1.0 g, 4.9 mmol, 1.0 equiv) and IPA (15 mL) in a microwave vial (20 mL) were added 2-fluoropyrazine (0.58 g, 5.9 mmol, 1.2 equiv) and DIPEA (1.5 g, 11.8 mmol, 2.4 equiv). The vial was sealed and heated at 170° C. in a microwave reactor for 4 h. The mixture was concentrated onto silica (10 g) and purified by silica gel chromatography (40 g column, 20-100% EtOAc/hexanes) to provide 0.82 g (59%) of N-(4-bromo-2-fluorobenzyl)pyrazin-2-amine as a pale yellow solid. LRMS (ES) m/z 282.0 (M+H).

2. Synthesis of Intermediate 10-3

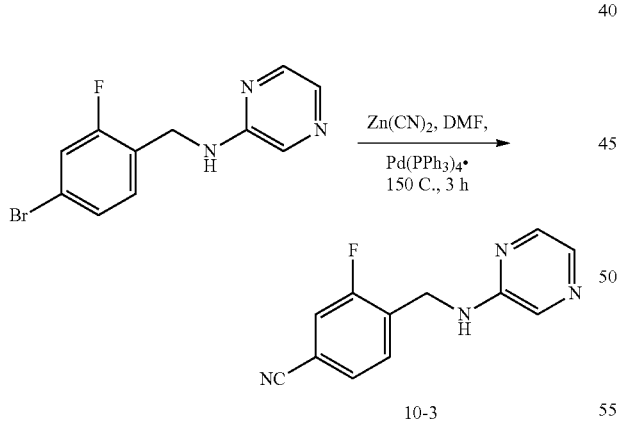

N-(4-bromo-2-fluorobenzyl)pyrazin-2-amine (0.32 g, 1.1 mmol, 1.0 equiv), zinc cyanide (0.39 g, 3.4 mmol, 3.0 equiv), tetrakis(triphenylphosphine)palladium(0) (258 mg, 0.22 mmol, 0.2 equiv), and DMF (4 mL) were combined and heated at 150° C. for 3 h. The reaction mixture was filtered and purified with RP-HPLC (Phenomenex, gemini 5u C18 150×21.2 mm, 0-100% acetonitrile in water both with 0.1% formic acid gradient over 40 min) to provide an intermediate mixture, 3-fluoro-4-((pyrazin-2-ylamino)methyl)benzonitrile. LRMS (ES) m/z 229.1 (M+H).

3. Synthesis of Intermediate 10-4

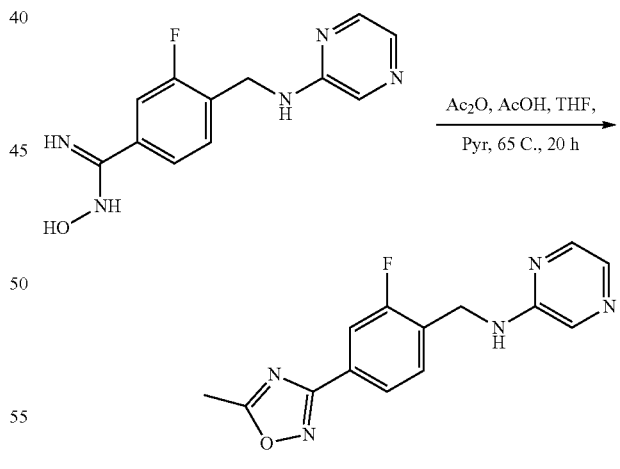

To a solution of 3-fluoro-4-((pyrazin-2-ylamino)methyl)benzonitrile (1.1 mmol, 1.0 equiv) in EtOH (20 mL) was added hydroxylamine (5.0 mL, 50 wt. % in water). The mixture was heated at 80° C. for 1 h, concentrated, purified with RP-HPLC (Phenomenex, gemini 5u C18 150×21.2 mm, 0-100% acetonitrile in water both with 0.1% formic acid gradient over 40 min) to provide 63 mg (22% over 2 steps) of 3-fluoro-N-hydroxy-4-((pyrazin-2-ylamino)methyl)benzimidamide. LRMS (ES) m/z 262.1 (M+H). $^1$H-NMR (Methanol-$d_4$, 400 MHz, ppm) δ 7.96-7.92 (m, 2H), 7.65 (dd, J=2.8, 1.1 Hz, 1H), 7.44-7.34 (m, 3H), 4.62 (s, 2H).

4. Synthesis of Compound 46

To 3-fluoro-N-hydroxy-4-((pyrazin-2-ylamino)methyl)benzimidamide (21 mg, 0.080 mmol, 1.0 equiv) in a mixture of THF (3 mL) and pyridine (0.1 mL) was added Ac$_2$O (16 mg, 0.16 mmol, 2.0 equiv). The mixture was heated at 65° C. for 16 h, added AcOH (0.3 mL), heated at 65° C. for 4 h, concentrated, and purified with RP-HPLC (Phenomenex, gemini 5u C18 150×21.2 mm, 10-100% acetonitrile in water both with 0.1% formic acid gradient over 40 min) to provide 8.6 mg (38% over 3 steps) of N-(2-fluoro-4-(5-methyl-1,2,4-oxadiazol-3-yl)benzyl)pyrazin-2-amine as a white solid. LRMS (ES) m/z 286.1 (M+H). $^1$H-NMR (Methanol-d$_4$, 400 MHz, ppm) δ 7.96 (s, 2H), 7.80 (dd, J=8.0, 1.5 Hz, 1H), 7.74 (dt, J=10.7, 1.3 Hz, 1H), 7.70-7.66 (m, 1H), 7.54 (t, J=7.7 Hz, 1H), 4.68 (s, 2H), 2.65 (s, 3H).

Example 11

Synthesis of Compound 48

1. Synthesis of Intermediate 11-2

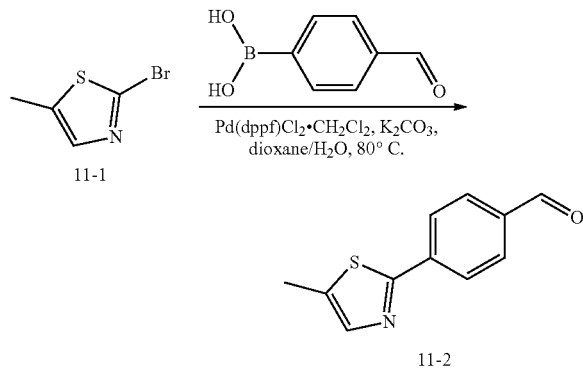

To a solution of 2-bromo-5-methyl-1,3-thiazole (300 mg, 1.68 mmol, 1.0 equiv) in a mixture of dioxane/water (50/10 mL) were added Pd(dppf)Cl$_2$·CH$_2$Cl$_2$ (138 mg, 0.17 mmol, 0.1 equiv) and potassium carbonate (465 mg, 3.36 mmol, 2.00 equiv) under nitrogen atmosphere. The mixture was stirred at 80° C. for 2 h, cooled to r.t, and added water (60 mL). The aqueous layer was extracted with ethyl acetate (30 mL) three times. The combined organic layers were dried over Na$_2$SO$_4$, concentrated under reduced pressure, and purified by silica gel column with ethyl acetate/petroleum ether (1/10) to give 330 mg (96%) of 4-(5-methyl-1,3-thiazol-2-yl)benzaldehyde as a yellow solid. LRMS (ES) m/z 204 (M+H).

2. Synthesis of Compound 48

To a solution of pyrazin-2-amine (113.5 mg, 1.19 mmol, 1.21 equiv) in DCE (20 mL) at r.t was added 4-(5-methyl-1,3-thiazol-2-yl)benzaldehyde (200 mg, 0.98 mmol, 1.00 equiv) and TFA (224.6 mg, 1.99 mmol, 2.02 equiv). The mixture was stirred for 30 min, added STAB (313.3 mg, 1.48 mmol, 1.50 equiv), stirred at r.t. overnight, concentrated under reduced pressure, and purified by silica gel column with ethyl acetate/petroleum ether (1/10) to give 31.2 mg (11%) of N-[[4-(5-methyl-1,3-thiazol-2-yl)phenyl]methyl]pyrazin-2-amine as a white solid. LRMS (ES) m/z 283 (M+H). $^1$H-NMR: (300 MHz, DMSO, ppm): 8.02 (s, 1H), 7.99 (m, 1H), 7.91 (m, 2H), 7.68 (m, 2H), 7.57 (m, 1H), 7.40 (m, 2H), 4.52 (m, 2H), 2.50 (s, 3H).

Example 12

Synthesis of Compound 49

1. Synthesis of Intermediate 12-2

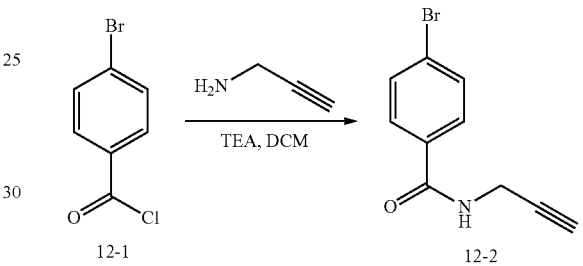

To a solution of 4-bromobenzoyl chloride (8 g, 36.45 mmol, 1.00 equiv) in DCM (80 mL) cooled to 0° C. were added prop-2-yn-1-amine (2 g, 36.3 mmol, 1.0 equiv) and TEA (7.35 g, 72.6 mmol, 2.0 equiv) dropwise. The mixture was stirred for 40 min at r.t., diluted with DCM (100 mL), washed with of brine (100 mL), dried over anhydrous sodium sulfate, and concentrated under reduced pressure to give 5.3 g (61%) of 4-bromo-N-(prop-2-yn-1-yl)benzamide as an off-white solid.

2. Synthesis of Intermediate 12-3

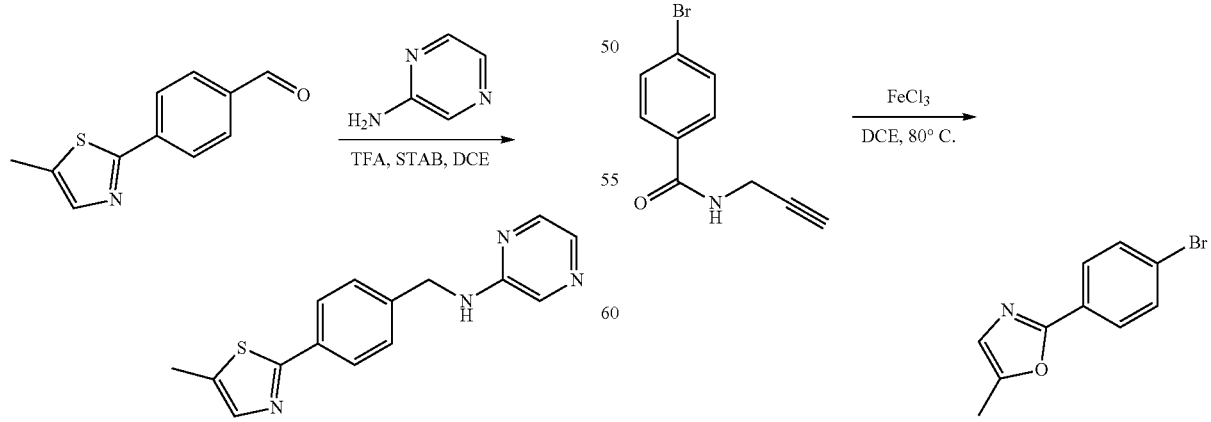

To a solution of 4-bromo-N-(prop-2-yn-1-yl)benzamide (2 g, 8.4 mmol, 1.0 equiv) in DCE (60 mL) at r.t. was added iron(III) chloride (680 mg, 4.2 mmol, 0.5 equiv). The mixture was stirred at 80° C. for 2 h, concentrated under reduced pressure, and purified by silica gel chromatography eluting with ethyl acetate/petroleum ether (1:10) to give 1.63 g (82%) of 2-(4-bromophenyl)-5-methyl-1,3-oxazole as a light yellow solid. LRMS (ES) m/z 238 (M+H).

2. Synthesis of Intermediate 12-4

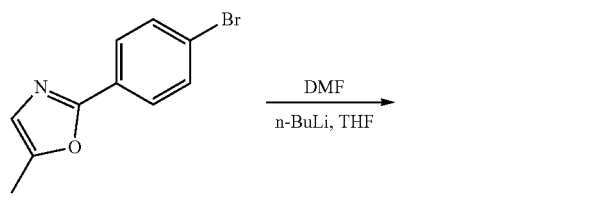

To a solution of 2-(4-bromophenyl)-5-methyl-1,3-oxazole (650 mg, 2.7 mmol, 1.0 equiv) in THF (18 mL) cooled to −78° C. was added n-BuLi (1.2 mL, 1.10 equiv) dropwise. The mixture was stirred at −78° C. for 30 min, added DMF (240 mg, 3.29 mmol, 1.20 equiv) dropwise, removed the ice bath, stirred at r.t. for 2 h, concentrated under reduced pressure, and purified by silica gel column eluting with ethyl acetate/petroleum ether (1:2) to give 80 mg (15%) of 2-(4-bromophenyl)-5-methyl-1,3-oxazole as a light yellow solid.

2. Synthesis of Compound 49

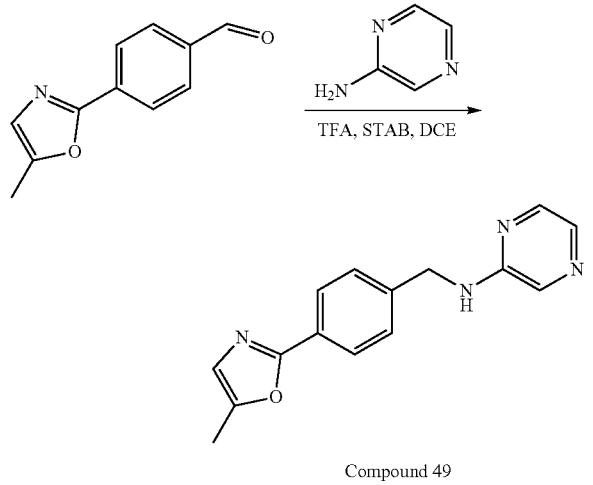

Compound 49

To a solution of 4-(5-methyl-1,3-oxazol-2-yl)benzaldehyde (80 mg, 0.43 mmol, 1.0 equiv) in DCE (6 mL) at r.t were added pyrazin-2-amine (61 mg, 0.64 mmol, 1.5 equiv) and TFA (98 mg, 0.87 mmol, 2.0 equiv) dropwise. The mixture was stirred at r.t. for 30 min, added STAB (136 mg, 0.64 mmol, 1.50 equiv), stirred overnight at r.t., concentrated under reduced pressure, and purified by C18 column with the following conditions (CombiFlash-1): Column, C18 silica gel; mobile phase, ACN/water=0/100 to ACN/water=4 5/55 gradient over 25 min; Detector, UV 254 nm) to give 32.3 mg (28%) of N-[[4-(5-methyl-1,3-oxazol-2-yl)phenyl]methyl]pyrazin-2-amine as a white solid. LCMS (ES) m/z 267 (M+H). $^1$H-NMR: (DMSO, ppm): δ 8.00 (1H, s), 7.99-7.86 (3H, m), 7.68-7.63 (2H, m), 7.46-7.43 (2H, d, J=8.1), 6.96 (1H, s), 4.55-4.53 (2H, d, J=6.0), 2.50 (3H, s).

Example 13

Synthesis of Compound 52

1. Synthesis of Intermediate 13-2

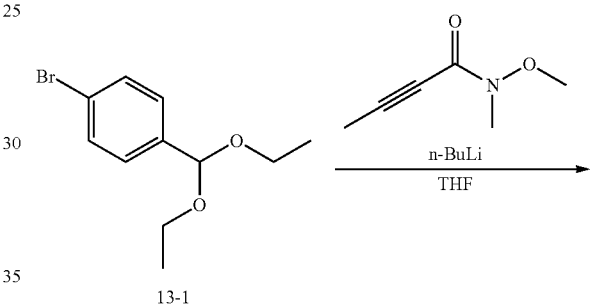

To a solution of 1-bromo-4-(diethoxymethyl)benzene (2.24 g, 8.65 mmol, 1.0 equiv.) in THF (20 mL) cooled to −78° C. was added BuLi (5.4 mL, 8.65 mmol, 1.6 M, 1.0 equiv.). The mixture was stirred at −78° C. for 5 min, added N-methoxy-N-methylbut-2-ynamide (1.1 g, 8.65 mmol, 1.0 equiv.), stirred for 30 min, quenched with aqueous NH$_4$Cl at −78° C., and warmed to r.t. The aqueous layer was extracted with EA three times. The combined organic layers were dried over Na$_2$SO$_4$, concentrated, and purified on silica gel using a EA and HE as eluent to give 465 mg (22%) of 1-(4-(diethoxymethyl)phenyl)but-2-yn-1-one.

2. Synthesis of Intermediate 13-3

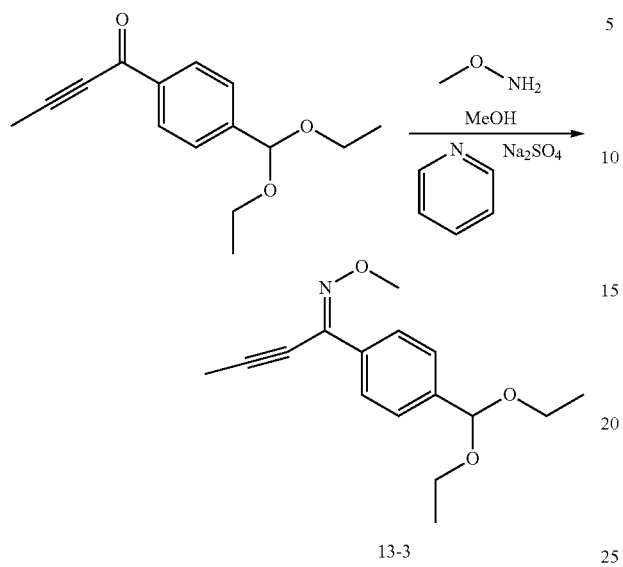

To a mixture of 1-(4-(diethoxymethyl)phenyl)but-2-yn-1-one (465 mg, 1.89 mmol, 1.0 equiv.), O-methyl oxime hydrochloride (315 mg, 3.78 mmol, 2.0 equiv.), and Na$_2$SO$_4$ (536 mg, 3.78 mmol, 2.0 equiv.) in anhydrous MeOH (10 mL) was added Py (299 mg, 3.78 mmol, 2.0 equiv.). The mixture was stirred at r.t. for 17 h, added water (10 mL), and extracted with EA (10 mL) three times. The combined organic layers were washed with brine, dried over anhydrous NaSO$_4$, concentrated under reduced pressure, and purified by column chromatography eluting with EA and HE give 519 mg (99.8%) of (E)-1-(4-(diethoxymethyl)phenyl)but-2-yn-1-one O-methyl oxime.

3. Synthesis of Intermediate 13-4

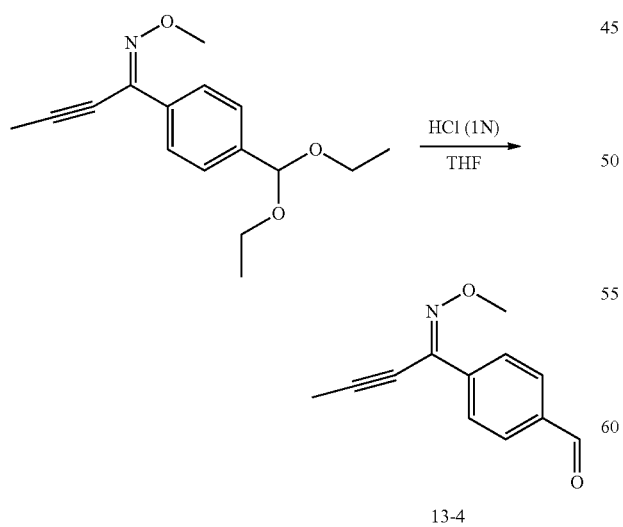

To a solution of (E)-1-(4-(diethoxymethyl)phenyl)but-2-yn-1-one O-methyl oxime (519 mg, 1.89 mmol, 1.0 equiv.) in THF (10 mL) was added aqueous HCl (1 N, 2 mL). The mixture was stirred at r.t. for 30 min and neutralized to pH 7-8 with saturated NaHCO$_3$ solution. The aqueous layer was extracted with EA three times. The combined organic layers were washed with brine, dried over anhydrous NaSO$_4$, and concentrated under reduced pressure to give 390 mg (80% pure) of (E)-4-(1-(methoxyimino)but-2-yn-1-yl)benzaldehyde. LRMS (ES) m/z 202.1 (M+H) as an intermediate mixture.

4. Synthesis of Intermediate 13-5

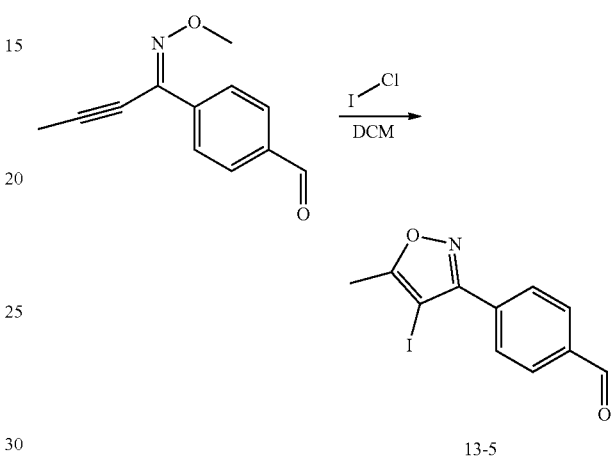

To a solution of (E)-4-(1-(methoxyimino)but-2-yn-1-yl)benzaldehyde (390 mg, 80% purity, 1.5 mmol, 1.0 equiv.) in DCM (20 mL) was added iodine chloride (368 mg, 2.26 mmol, 1.5 equiv.) in DCM (2.3 mL). The mixture was stirred at r.t. for 3 h, added aqueous Na$_2$S$_2$O$_3$ solution, stirred for 10 min, and separated the layers. The aqueous layer was extracted with DCM (15 mL) three times. The combined organic layers were dried over MgSO$_4$, concentrated under reduced pressure, and purified on silica gel eluting with EA/HE to give 180 mg (38%) of 4-(4-iodo-5-methylisoxazol-3-yl)benzaldehyde. LRMS (ES) m/z 314.0 (M+H).

5. Synthesis of Intermediate 13-6

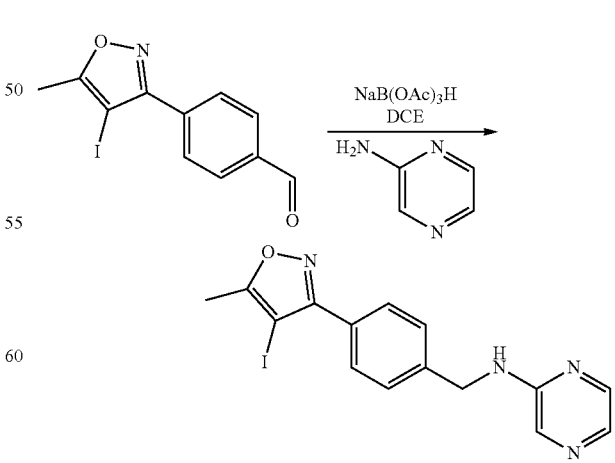

To a mixture of 4-(4-iodo-5-methylisoxazol-3-yl)benzaldehyde (180 mg, 0.58 mmol, 1.0 equiv.) and pyrazine-2-amine (60 mg, 0.63 mmol, 1.1 equiv.) in DCE (5.0 mL) stirred for 10 min at r.t. was added NaBH(OAc)$_3$ (243 mg, 1.15 mmol, 2.0 equiv.). The mixture was stirred at r.t. for 3 h, diluted with MeOH, concentrated, and purified with RP-HPLC eluting with ACN/water (both with 0.1% HCOOH) to give 70 mg (31%) of N-(4-(4-iodo-5-methylisoxazol-3-yl)benzyl)pyrazin-2-amine. LRMS (ES) m/z 393.0 (M+H). $^1$H NMR (400 MHz, Acetonitrile-d$_3$) δ 7.99 (d, J=1.5 Hz, 1H), 7.93 (dd, J=2.8, 1.5 Hz, 1H), 7.77-7.69 (m, 3H), 7.56-7.48 (m, 2H), 6.10 (br, 1H), 4.64 (d, J=6.2 Hz, 2H), 2.54 (s, 3H).

6. Synthesis of Compound 52

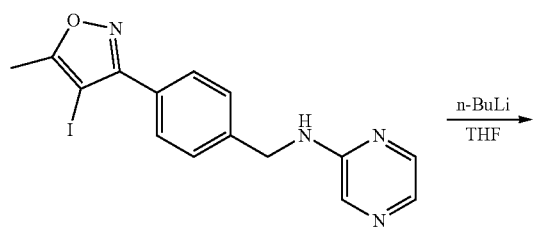

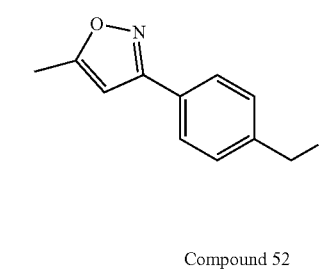

Compound 52

To a solution of N-(4-(4-iodo-5-methylisoxazol-3-yl)benzyl)pyrazin-2-amine (48 mg, 0.12 mmol) in THF (8.0 mL) cooled to −78° C. was added BuLi (0.23 mL, 0.37 mmol, 3.0 equiv.). The mixture was stirred at −78° C. for 5 min, added aqueous NH$_4$Cl solution, warmed to r.t., extracted with EA twice. The combined organic layers were dried over Na$_2$SO$_4$, concentrated under reduced pressure, and purified with RP-HPLC eluting with ACN/water (both with 0.1% HCOOH) to give 32 mg (98%) of N-(4-(5-methylisoxazol-3-yl)benzyl)pyrazin-2-amine. LRMS (ES) m/z 267.1 (M+H). $^1$H NMR (400 MHz, Methylene Chloride-d$_2$) δ 8.03-7.94 (m, 2H), 7.86-7.75 (m, 3H), 7.52-7.43 (m, 2H), 6.35 (q, J=0.9 Hz, 1H), 5.25 (s, 1H), 4.66 (d, J=5.1 Hz, 2H), 2.49 (d, J=0.9 Hz, 3H).

Example 14

Synthesis of Compound 55

1. Synthesis of Intermediate 14-2

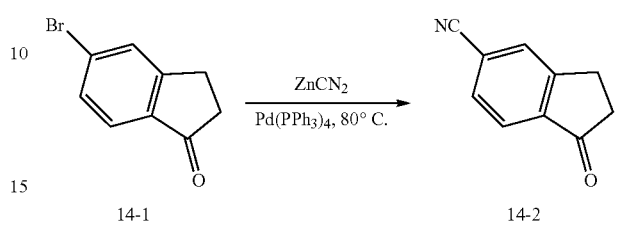

To a solution of 5-bromo-2,3-dihydro-1H-inden-1-one (80 g, 380.95 mmol, 1.00 equiv) in DMF (500 mL) at r.t were added Zn(CN)$_2$ (27.8 g, 237.61 mmol, 0.63 equiv) and Pd(PPh$_3$)$_4$ (15.8 g, 13.67 mmol, 0.036 equiv) under nitrogen. The mixture was stirred at 80° C. for 16 h, cooled to r.t., and filtered to remove solids. To the filtrate were added water (400 mL). The mixture was extracted with ethyl acetate (400 mL) twice. The combined organic layers were washed with brine (400 mL) three times, dried over Na$_2$SO$_4$ and concentrated under reduced pressure. The residue was purified by silica gel column eluting with ethyl acetate/petroleum ether (1/2) to give an intermediate product, which was triturated with 80 mL of PE/EA=10/1 to afford 48.3 g (80.7%) of 1-oxo-2,3-dihydro-1H-indene-5-carbonitrile as a yellow solid. LRMS (ES) m/z 158 (M+H).

2. Synthesis of Intermediate 14-3

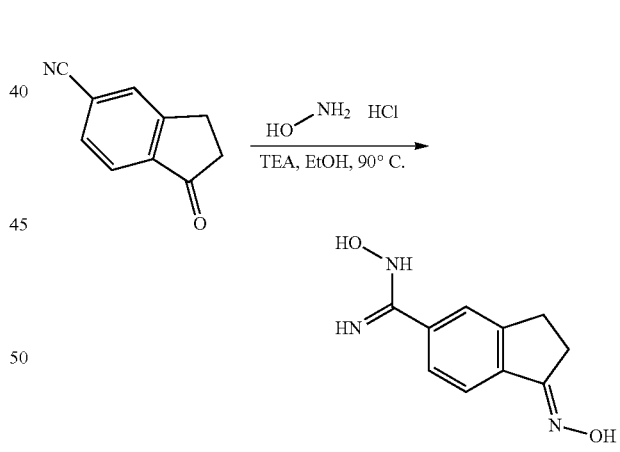

To a solution of 1-oxo-2,3-dihydro-1H-indene-5-carbonitrile (61.5 g, 391.3 mmol, 1.0 equiv) in ethanol (1.5 L) were added hydroxylamine hrdochloride (81.1 g, 1.2 mol, 3.0 equiv) and TEA (158.3 g, 1.6 mol, 4.0 equiv). The mixture was stirred at 85° C. for 2.5 h, concentrated under reduced pressure, purified by a silica gel column eluting with dichloromethane/methanol (10/1) give a mixture, which was triturated with PE (200 mL) to give 80 g of (1Z)-N-hydroxy-1-(hydroxyimino)-2,3-dihydro-1H-indene-5-carboximidamide as a yellow solid. LRMS (ES) m/z 206 (M+H).

3. Synthesis of Intermediate 14-4

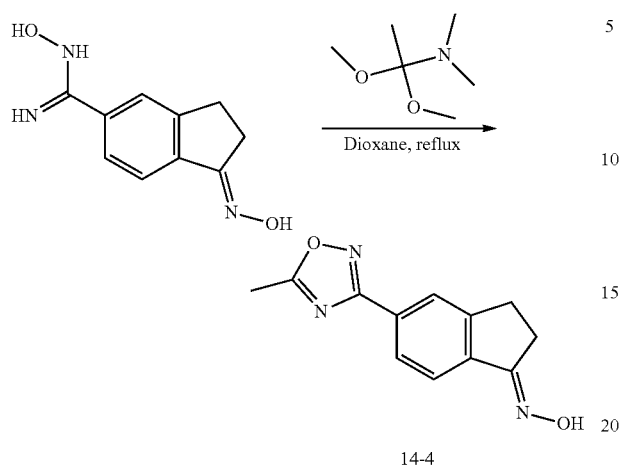

14-4

To a solution of (1Z)-N-hydroxy-1-(hydroxyimino)-2,3-dihydro-1H-indene-5-carboximidamide (30 g, 146.2 mmol, 1.0 equiv) in dioxane (60 mL) at r.t was added (1,1-dimethoxyethyl)dimethylamine (20 g, 150.2 mmol, 1.02 equiv). The mixture was stirred at 90° C. overnight, cooled to r.t, concentrated under reduced pressure, and purified by silica gel column eluting with ethyl acetate/petroleum ether (2:1) to provide 22 g (66%) of N-[(1Z)-5-(5-methyl-1,2,4-oxadiazol-3-yl)-2,3-dihydro-1H-inden-1-ylidene]hydroxylamine as a brown solid. LRMS (ES) m/z 230 (M+H).

4. Synthesis of Intermediate 14-5

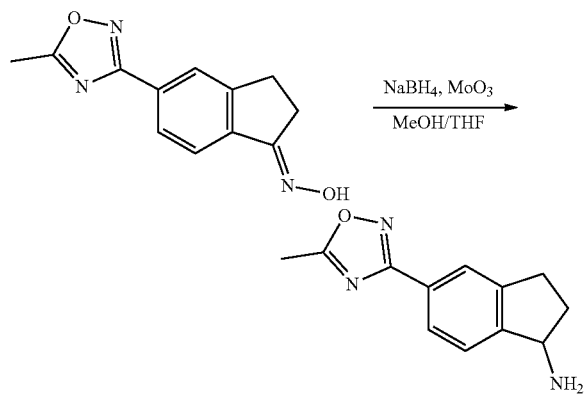

14-5

To a solution of N-[(1E)-5-(5-methyl-1,2,4-oxadiazol-3-yl)-2,3-dihydro-1H-inden-1-ylidene]hydroxylamine (15.6 g, 68.05 mmol, 1.0 equiv) in a mixture of MeOH and THF (1/1, 600 mL) were added $MoO_3$ (19.8 g, 2.00 equiv) and $NaBH_4$ (10.4 g, 274.91 mmol, 4.00 equiv) in portions at r.t. The mixture was stirred at r.t. overnight, quenched with sat·$NH_4Cl$ (50 mL) dropwise slowly, concentrated under reduced pressure, and purified by silica gel column with DCM/MeOH (10:1) as eluent to give a mixture which was triturated in a mixture of EA:PE (1:10) to afford 11 g (75%) of 5-(5-methyl-1,2,4-oxadiazol-3-yl)-2,3-dihydro-1H-inden-1-amine as an off-white solid. LRMS (ES) m/z 199 [M+H-$NH_3$].

5. Synthesis of Compound 55

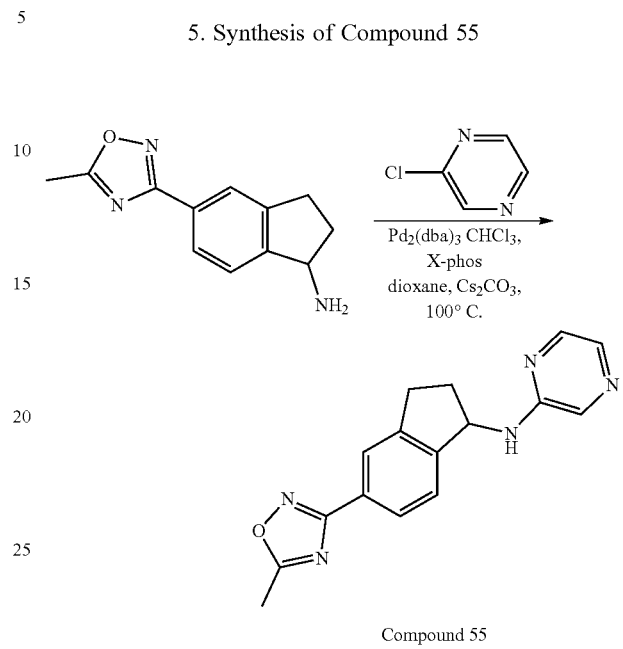

Compound 55

To a solution of 5-(5-methyl-1,2,4-oxadiazol-3-yl)-2,3-dihydro-1H-inden-1-amine (120 mg, 0.56 mmol, 1.0 equiv) in dioxane (8 mL) were added 2-chloropyrazine (127 mg, 1.1 mmol, 2.0 equiv), $Pd_2(dba)_3CHCl_3$ (58 mg, 0.06 mmol, 0.1 equiv), X-phos (12 mg, 0.03 mmol, 0.05 equiv) and $Cs_2CO_3$ (546 mg, 1.68 mmol, 3.0 equiv) at r.t. The mixture was heated at 100° C. for 16 h under nitrogen, cooled to r.t, added EA (50 mL), washed with brine (20 ml) twice, dried over $Na_2SO_4$, concentrated under reduced pressure, and purified by Prep-HPLC with the following condition (Column, X-Bridge, C18, Shield RP, 19*150 mm Sum; mobile phase, water with 0.05% $NH_3H_2O$ and ACN (32.0% CH3CN gradient up to 62.0% over 8 min) to give 20.7 mg (13%) of N-[5-(5-methyl-1,2,4-oxadiazol-3-yl)-2,3-dihydro-1H-inden-1-yl]pyrazin-2-amine as a white solid. LRMS (ES) m/z 294 (M+H). $^1$H-NMR: (300 MHz, DMSO, ppm): δ 7.93 (m, 2H), 7.89 (m, 1H), 7.81 (m, 1H), 7.70 (m, 1H), 7.52 (m, 1H), 7.40 (m, 1H), 5.53 (m, 1H), 3.09 (m, 1H), 2.91 (m, 1H), 2.65 (m, 3H), 2.52 (m, 1H), 1.89 (m, 1H).

Example 15

Synthesis of Compound 56

1. Synthesis of Intermediate 15-2

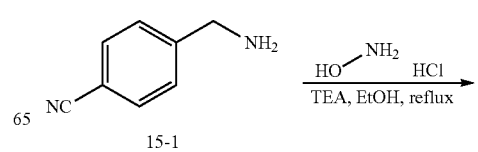

15-1

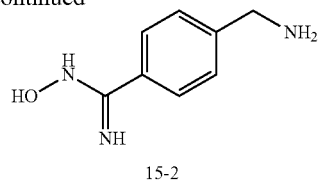

15-2

To a solution of 4-(aminomethyl)benzonitrile (2 g, 15.13 mmol, 1.0 equiv) in ethanol (30 mL) were added TEA (4.6 g, 45.5 mmol, 3.0 equiv) and hydroxylamine hydrogen chloride (2.6 g, 37.7 mmol, 2.5 equiv) at r.t. The mixture was heated at 80° C. overnight, concentrated under reduced pressure, purified by silica gel column eluting with ethyl acetate/petroleum ether to give 2.4 g of 4-(aminomethyl)-N-hydroxybenzene-1-carboximidamide as a white solid. LRMS (ES) m/z 166 (M+H).

2. Synthesis of Intermediate 15-3

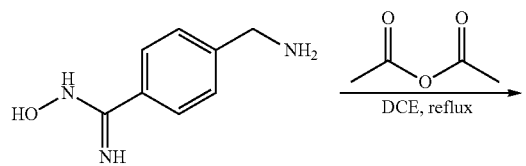

15-3

To a solution of 4-(aminomethyl)-N-hydroxybenzene-1-carboximidamide (2.49 g, 15.1 mmol, 1.0 equiv) in DCE (100 mL) was added acetyl acetate (3.1 g, 30.37 mmol, 2.00 equiv) at r.t. The mixture was heated at 75° C. overnight, concentrated under reduced pressure, purified by silica gel chromatography eluting with ethyl acetate/petroleum ether to give a mixture, which was purified again by Prep-HPLC with the following conditions (2 #-AnalyseHPLC-SHIMADZU(HPLC-10)): Column, XBridge Prep OBD C18 Column, 19*250 mm, 5 um; mobile phase, water (0.05% NH$_3$H$_2$O) and ACN 18.0% ACN to 43.0% gradient over 8 min; Detector, UV 254 nm to give 2.3 g (66%) of N-[[4-(5-methyl-1,2,4-oxadiazol-3-yl)phenyl]methyl]acetamide as a white solid. LRMS (ES) m/z 232 (M+H).

3. Synthesis of Intermediate 15-4

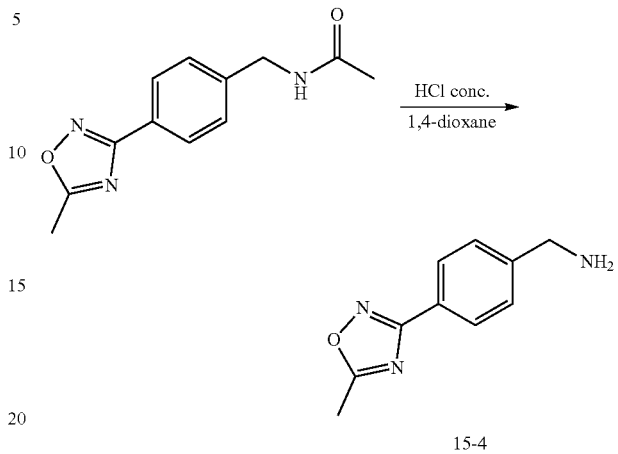

15-4

To a solution of N-[[4-(5-methyl-1,2,4-oxadiazol-3-yl)phenyl]methyl]acetamide (6.7 g, 28.97 mmol, 1.0 equiv) in 1,4-dioxane (100 mL) was added conc. HCl (100 mL) at r.t. The mixture was heated at 100° C. overnight, cooled to r.t, adjusted the pH to 10 with sodium hydroxide (1 N), and extracted with ethyl acetate (200 mL) twice. The combined organic layers were concentrated under reduced pressure and purified by silica gel chromatography eluting with dichloromethane/methanol (20:1) to give 3 g (55%) of [4-(5-methyl-1,2,4-oxadiazol-3-yl)phenyl]methanamine as a off-white solid. LRMS (ES) m/z 190 (M+H).

4. Synthesis of Compound 56

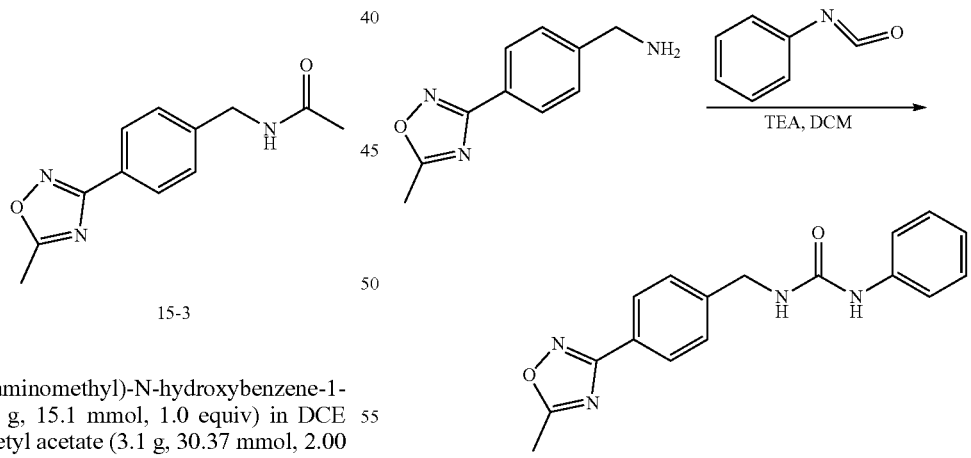

Compound 56

To a solution of [4-(5-methyl-1,2,4-oxadiazol-3-yl)phenyl]methanamine (100 mg, 0.53 mmol, 1.0 equiv) in DCM (4 mL) were added TEA (106 mg, 1.05 mmol, 2.00 equiv) and isocyanatobenzene (125 mg, 1.05 mmol, 2.00 equiv) at r.t. The mixture was stirred at r.t. for 1 h, concentrated under reduced pressure, and purified by Prep-HPLC with the following conditions (2 #-AnalyseHPLC-SHIMADZU (HPLC-10)): Column, XBridge Prep OBD C18 Column, 19*250 mm, 5 um; mobile phase, water (0.05% NH$_3$H$_2$O) and ACN gradient from 37.0% ACN to 53.0% over 8 min; Detector, UV 220 nm to give 105.7 mg (65%) of 3-[[4-(5-methyl-1,2,4-oxadiazol-3-yl)phenyl]methyl]-1-phenylurea as a white solid. LRMS (ES) m/z 309 (M+H). $^1$H-NMR: (DMSO, ppm): δ 8.62 (1H, s), 7.97-7.95 (2H, d, J=8.4), 7.48-7.39 (4H, m), 7.24-7.19 (2H, t, J=7.5), 6.92-6.87 (1H, t, J=7.2), 6.73-6.69 (1H, t, J=5.7), 4.38-4.36 (2H, d, J=6.0), 2.65 (3H, s).

The following compounds were prepared by methods analogous to the method described for Compound 56:

| Compound No. | LRMS (ES) m/z |
| --- | --- |
| 54 | M + H = 248 |
| 57 | M + H = 324.2 |
| 59 | M − H = 308.2 |

Example 16

Synthesis of Compound 60

1. Synthesis of Intermediate 16-2

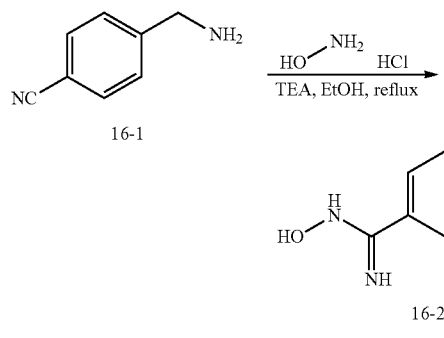

16-1

16-2

To a solution of 4-(aminomethyl)benzonitrile (2 g, 15.1 mmol, 1.00 equiv) in EtOH (30 mL) were added TEA (4.6 g, 45.5 mmol, 3.0 equiv) and hydroxylamine hydrogen chloride (2.6 g, 37.7 mmol, 2.5 equiv) at r.t. The mixture was heated at 80° C. for 15 h, concentrated under reduced pressure, and purified by silica gel chromatography (100% EA) to give 2.4 g of 4-(aminomethyl)-N-hydroxybenzene-1-carboximidamide as a white solid.

2. Synthesis of Intermediate 16-3

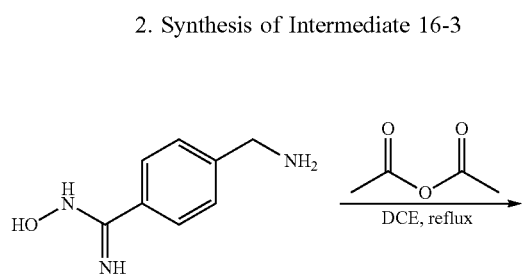

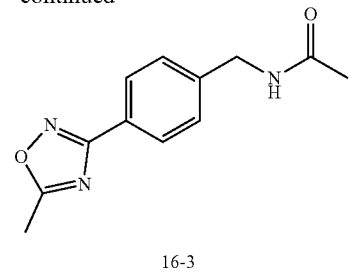

16-3

To a solution of 4-(aminomethyl)-N-hydroxybenzene-1-carboximidamide (2.49 g, 15.1 mmol, 1.00 equiv) in DCE (100 mL) was added acetyl acetate (3.1 g, 30.4 mmol, 2.00 equiv) at r.t. The mixture was heated at 75° C. for 15 h, concentrated under reduced pressure, and purified by silica gel chromatography eluting with EA to give a mixture, which was purified again by Prep-HPLC with the following conditions: (2 #-AnalyseHPLC-SHIMADZU(HPLC-10)): Column, XBridge Prep OBD C18 Column, 19*250 mm, 5 um; mobile phase, Water (0.05% NH$_3$H$_2$O) and ACN (18.0% ACN up to 43.0% in 8 min); Detector, UV 254 nm) to afford 2.3 g (66%) of N-[[4-(5-methyl-1,2,4-oxadiazol-3-yl)phenyl]methyl]acetamide as a white solid. LRMS (ES) m/z 232 (M+H). $^1$H-NMR: (DMSO, ppm): δ 8.44-8.41 (1H, m), 7.95-7.93 (2H, d, J=8.1), 7.43-7.40 (2H, d, J=8.1), 4.33-4.31 (2H, d, J=6.0), 2.65 (3H, s), 1.89 (3H, s).

3. Synthesis of Intermediate 16-4

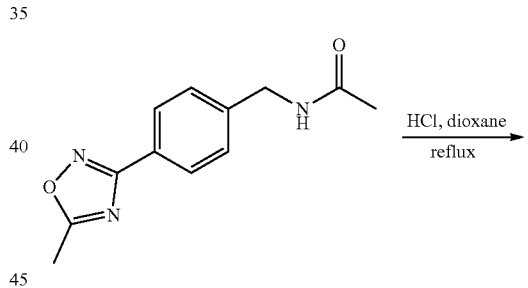

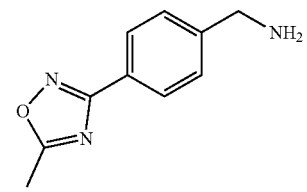

16-4

To a solution of N-[[4-(5-methyl-1,2,4-oxadiazol-3-yl)phenyl]methyl]acetamide (2.1 g, 9.08 mmol, 1.00 equiv) in dioxane (30 mL) was added concentrated HCl (30 mL) dropwise at r.t. The mixture was heated at 100° C. for 15 h, concentrated under reduced pressure, and purified by silica gel chromatography with DCM/MeOH (15/1) to give 1.2 g (70%) of [4-(5-methyl-1,2,4-oxadiazol-3-yl)phenyl]methanamine as a white solid.

4. Synthesis of Compound 60

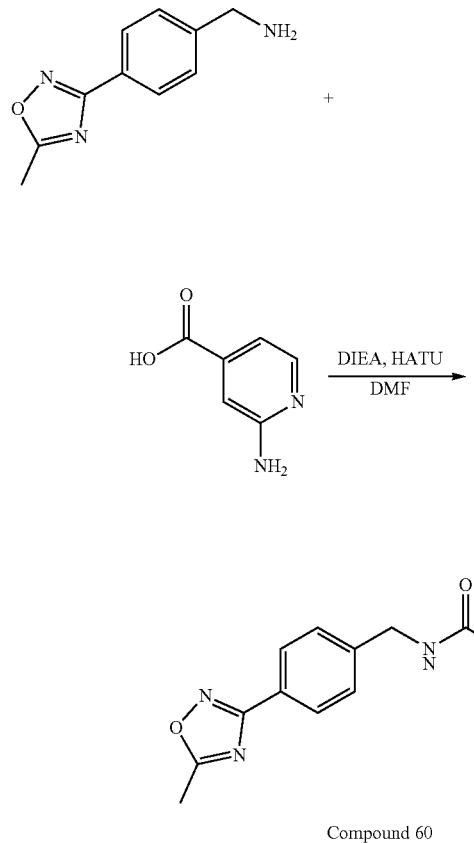

Compound 60

To a solution of [4-(5-methyl-1,2,4-oxadiazol-3-yl)phenyl]methanamine (95 mg, 0.50 mmol, 1.00 equiv) in DMF (4 mL) were added 2-aminopyridine-4-carboxylic acid (69.5 mg, 0.50 mmol, 1.00 equiv) and DIPEA (100 mg, 0.77 mmol, 1.50 equiv) at r.t. The mixture was stirred at r.t. for 10 min, added HATU (230 mg, 0.60 mmol, 1.20 equiv), stirred for 15 ht., filtered, concentrated, and purified by Prep-HPLC with the following conditions: (2 #-AnalyseHPLC-SHIMADZU(HPLC-10)): Column, Gemini-NX C18 AXAI Packed, 21.2*150 mm 5 um; mobile phase, water (0.05% NH$_3$H$_2$O) and ACN (33.0% ACN up to 41.0% in 5 min); Detector, uv 254 nm. to afford 6.9 mg (4%) of 2-amino-N-[[4-(5-methyl-1,2,4-oxadiazol-3-yl)phenyl]methyl]pyridine-4-carboxamide as a white solid. LRMS (ES) m/z 310 (M+H). $^1$H-NMR: (DMSO, 400 MHz, ppm): δ 9.14-9.11 (1H, t, J=6.0), 7.99-7.93 (3H, m), 7.46-7.44 (2H, d, J=8.0), 6.86-6.83 (2H, m), 7.54-7.47 (3H, m), 6.14 (2H, s), 4.50-4.48 (2H, d, J=6.0), 2.80 (1H, s), 2.63 (3H, s).

The following compounds were prepared by methods analogous to the method described for Compound 60:

| Compound No. | LRMS (ES) m/z |
|---|---|
| 50 | M + H = 294.1 |
| 63 | M + H = 310.31 |

Example 17

Synthesis of Compounds 61 and 71

1. Synthesis of Intermediate 17-2

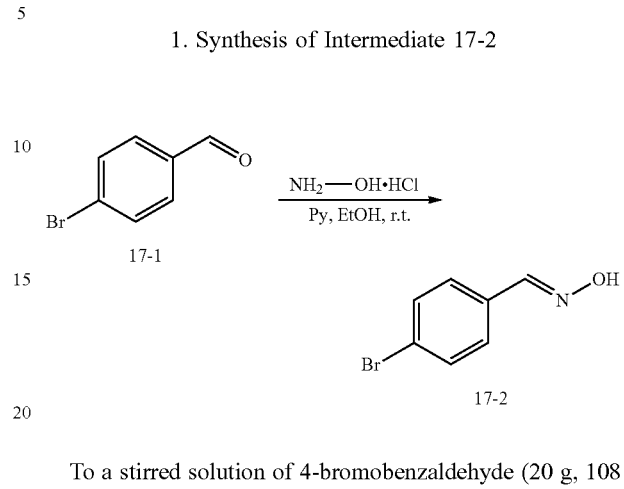

To a stirred solution of 4-bromobenzaldehyde (20 g, 108 mmol, 1.0 equiv) in EtOH (100 mL) were added hydroxylamine hydrochloride (8.4 g, 122 mmol, 1.1 equiv) and pyridine (50 mL) at r.t. The mixture was stirred for 3 h at r.t. and concentrated under reduced pressure to give 22 g of (E)-N-[(4-bromophenyl)methylidene]hydroxylamine as a white solid.

2. Synthesis of Intermediate 17-3

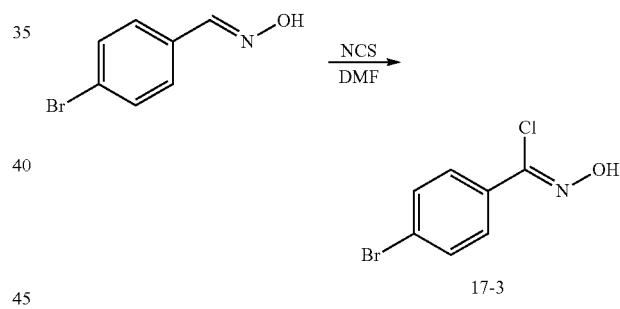

To a stirred solution of (E)-N-[(4-bromophenyl)methylidene]hydroxylamine (22 g, 110 mmol, 1.0 equiv) in DMF (100 mL) was added NCS (18 g, 135 mmol, 1.2 equiv) at r.t. The mixture was stirred at room temperature for 12 h, added water (500 mL), collected the solid by filtration, and dried in an oven under reduced pressure to give 27 g of (Z)-4-bromo-N-hydroxybenzene-1-carbonimidoyl chloride as a yellow solid.

3. Synthesis of Intermediate 17-4

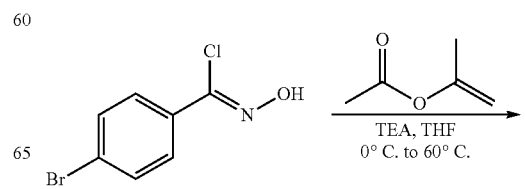

-continued

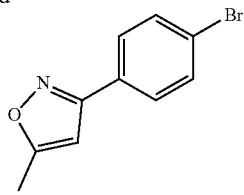

17-4

To a stirred solution of (Z)-4-bromo-N-hydroxybenzene-1-carbonimidoyl chloride (27 g, 115 mmol, 1.0 equiv) cooled to 0° C. in THF (500 mL) were added prop-1-en-2-yl acetate (35 g, 345 mmol, 3.0 equiv) and TEA (24 g, 237 mmol, 2.1 equiv) dropwise. The mixture was stirred at r.t. for 2 h, heated at 60° C. for 2 h, concentrated under reduced pressure, and purified by silica gel chromatography eluting with EA/PE (1/100) to give a mixture, which was triturated with a mixture of ether/HE (1/5) to afford 6 g (22%) of 3-(4-bromophenyl)-5-methyl-1,2-oxazole as an white solid.

4. Synthesis of Intermediate 17-5

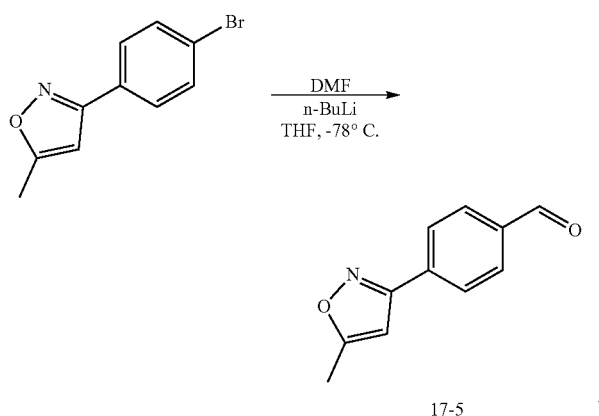

17-5

To a stirred solution of 3-(4-bromophenyl)-5-methyl-1,2-oxazole (9.68 g, 40.7 mmol, 1.0 equiv) in THF (400 mL) cooled to −78° C. was added n-BuLi (2.5M in hexane, 20 mL, 1.20 equiv) dropwise. The mixture was stirred at −78° C. for 30 min, added DMF (8 mL) dropwise at −78° C., stirred for 2 h at r.t, quenched with saturated aqueous NH₄Cl solution (50 mL), and extracted with EA (400 mL) four times. The combined organic layers were washed with brine (500 mL), dried over anhydrous sodium sulfate, concentrated under reduced, and purified by silica gel chromatography eluting with EA/PE (1/3) to afford 4 g (53%) of 4-(5-methyl-1,2-oxazol-3-yl)benzaldehyde as a yellow solid.

5. Synthesis of Compound 71

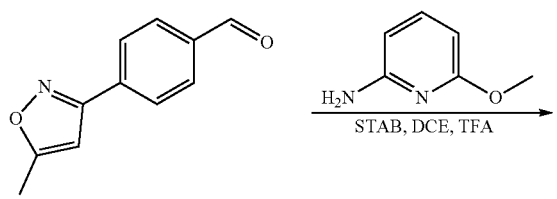

-continued

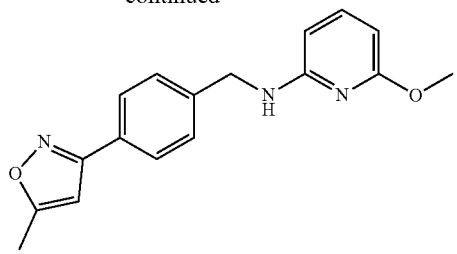

Compund 71

To a solution of 4-(5-methyl-1,2-oxazol-3-yl)benzaldehyde (150 mg, 0.80 mmol, 1.00 equiv) in DCE (10 mL) were added 6-methoxypyridin-2-amine (199 mg, 1.60 mmol, 2.0 equiv), trifluoroacetic acid (39 mg, 0.35 mmol, 0.5 equiv), and STAB (510 mg, 2.41 mmol, 3.0 equiv). The mixture was stirred for 2 h at r.t, concentrated under reduced pressure, dissolved in EA (50 mL), washed with brine (20 mL) twice, dried over Na₂SO₄, and concentrated under reduced pressure to give 150 mg (63%) of 6-methoxy-N-[[4-(5-methyl-1,2-oxazol-3-yl)phenyl]methyl]pyridin-2-amine as an off-white solid. ¹H-NMR: (300 MHz, CD₃OD, ppm): δ 7.70 (d, J=9 Hz, 2H), 7.42 (d, J=9 Hz, 2H), 7.13 (t, J=7.8 Hz, 1H), 6.49 (s, 1H), 6.00 (d, J=7.8 Hz 1H), 5.88 (d, J=7.8 Hz, 1H), 4.51 (s, 2H), 3.72 (s, 3H), 2.44 (s, 3H). LRMS (ES) m/z 296 (M+H).

6. Synthesis of Compound 61

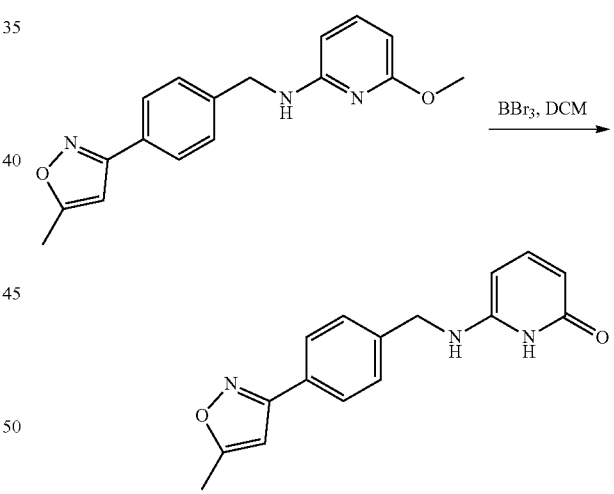

Compound 61

To a solution of 6-methoxy-N-[[4-(5-methyl-1,2-oxazol-3-yl)phenyl]methyl]pyridin-2-amine (60 mg, 0.20 mmol, 1.0 equiv) in DCM (5 mL) cooled to 0° C. was added BBr₃ (0.5 mL) dropwise. The mixture was stirred at r.t. for 15 h, quenched with MeOH (2 mL), concentrated under reduced pressure, and purified by Prep-HPLC with the following conditions: Column, X-Bridge, C18, Shield RP, 19*150 mm 5um; mobile phase, water with 0.05% NH₃H₂O and ACN (20.0% ACN up to 32.0% in 6 min, up to 100.0% in 5 min, down to 0% in 1 min); Detector, Waters 2767 254 nm to afford 5 mg (9%) of 6-([[4-(5-methyl-1,2-oxazol-3-yl)phenyl]methyl]amino)-1,2-dihydropyridin-2-one as a white solid. LRMS (ES) m/z 282 (M+H). $^1$H-NMR: (300 MHz, DMSO, ppm): δ 7.80 (m, 2H), 7.45 (m, 2H), 7.13 (m, 1H), 6.93 (m, 1H), 6.70 (m, 1H), 5.52 (m, 2H), 4.37 (m, 2H), 2.45 (m, 3H).

The following compounds were prepared by methods analogous to the method described for Compound 61:

| Compound No. | LRMS (ES) m/z |
|---|---|
| 53 | M + H = 267 |
| 62 | M + H = 255 |
| 64 | M + H = 269 |
| 65 | M + H = 283 |
| 66 | M + H = 297 |

Example 18

Synthesis of Compound 68

1. Synthesis of Intermediate 18-2

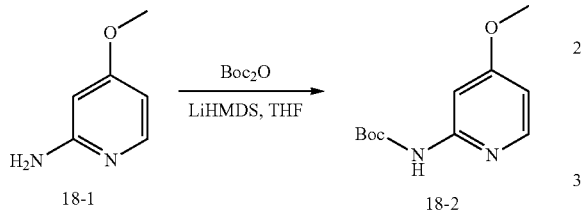

To a solution of 4-methoxypyridin-2-amine (250 mg, 2.01 mmol, 1.00 equiv) in THF (10 mL) cooled down to 0° C. were added LHMDS (1 M in THF, 4.4 mL, 2.2 equiv) and di-tert-butyl dicarbonate (461 mg, 2.11 mmol, 1.05 equiv). The mixture was stirred at r.t. for 3 h. added saturated aqueous NH$_4$Cl solution (20 mL), and extracted with EA (30 mL) three times. The combined organic layers were washed with brine (20 mL), dried over anhydrous sodium sulfate, concentrated under reduced pressure, and purified by Prep-TLC eluting with DCM/MeOH (25/1) to give 190 mg (42%) of tert-butyl N-(4-methoxypyridin-2-yl)carbamate as a white solid.

2. Synthesis of Intermediate 18-4

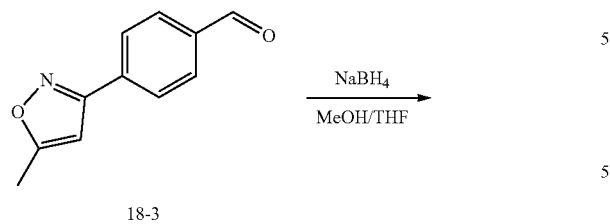

To a solution of 4-(5-methyl-1,2-oxazol-3-yl)benzaldehyde (500 mg, 2.67 mmol, 1.00 equiv) in a mixture of THF/methanol (1/1, 10 mL) cooled down to 0° C. was added NaBH$_4$ (203 mg, 5.37 mmol, 1.00 equiv) in portions. The mixture was stirred at r.t. for 1 h, quenched with saturated aqueous NH$_4$Cl (20 mL), and extracted with ethyl acetate (30 mL) three times. The combined organic layers were concentrated under reduced pressure to give 460 mg of [4-(5-methyl-1,2-oxazol-3-yl)phenyl]methanol as an off-white solid.

3. Synthesis of Intermediate 18-5

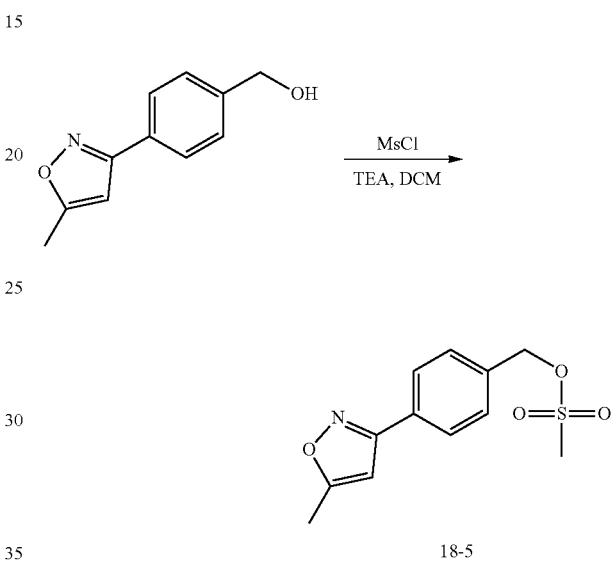

To a solution of [4-(5-methyl-1,2-oxazol-3-yl)phenyl]methanol (460 mg, 2.43 mmol, 1.00 equiv) in DCM (40 mL) cooled down to 0° C. were added TEA (490 mg, 4.84 mmol, 1.99 equiv) and MsCl (460 mg, 4.04 mmol, 1.66 equiv) dropwise. The mixture was stirred at r.t. for 1 h and added water (20 mL). The aqueous layer was extracted with DCM (20 mL) three times. The combined organic layers were dried over anhydrous sodium sulfate, concentrated under reduced pressure, and purified by Prep-TLC eluting with PE/EA (1/4) to give 95 mg (15%) of [4-(5-methyl-1,2-oxazol-3-yl)phenyl]methyl methanesulfonate as a light yellow solid.

4. Synthesis of Intermediate 18-6

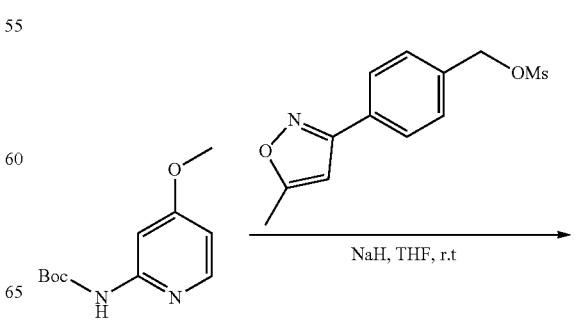

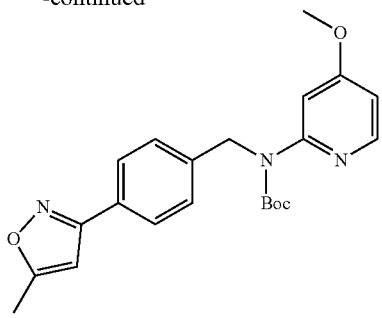

18-6

To a solution of tert-butyl N-(4-methoxypyridin-2-yl) carbamate (80 mg, 0.36 mmol, 1.00 equiv) in THF (20 mL) were added sodium hydride (21 mg, 0.53 mmol, 1.50 equiv, 60%) and [4-(5-methyl-1,2-oxazol-3-yl)phenyl]methyl methanesulfonate (100 mg, 0.37 mmol, 1.00 equiv) at r.t. The mixture was stirred at r.t. for 1 h, concentrated under reduced pressure, and purified by Prep-TLC (PE/EA, 1/2) to give 160 mg of tert-butyl N-(4-methoxypyridin-2-yl)-N-[[4-(5-methyl-1,2-oxazol-3-yl)phenyl]methyl]carbamate as an off-white solid. LRMS (ES) m/z 396 (M+H).

5. Synthesis of Compound 68

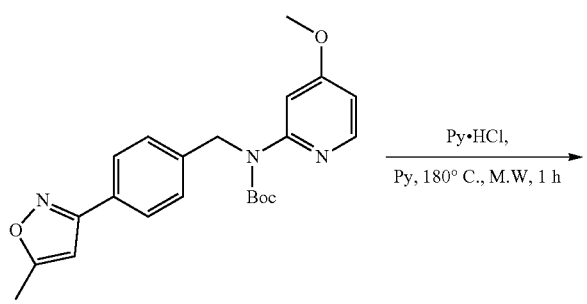

Compound 68

To a solution of tert-butyl N-(4-methoxypyridin-2-yl)-N-[[4-(5-methyl-1,2-oxazol-3-yl)phenyl]methyl]carbamate (90 mg, 0.23 mmol, 1.00 equiv) in pyridine (6 mL) was added pyridine hydrochloride (262 mg, 2.27 mmol, 10 equiv). The mixture was heated at 180° C. for 1 h under microwave radiation, concentrated under reduced pressure, and purified by Prep-HPLC with the following conditions: (2 #-AnalyseHPLC-SHIMADZU(HPLC-10)): Column, XBridge C18 OBD Prep Column, 10 μm, 19 mm×250 mm; mobile phase, water (0.05% NH₃H₂O) and ACN (10.0% ACN up to 40.0% in 8 min); Detector, UV 220 nm. This purification afforded 16.9 mg (26%) of 2-([[4-(5-methyl-1,2-oxazol-3-yl)phenyl]methyl]amino)-1,4-dihydropyridin-4-one as a white solid. LRMS (ES) m/z 282 (M+H). ¹H-NMR: (DMSO, 300 MHz, ppm): δ 9.84 (1H, s), 7.76-7.74 (2H, d, J=8.1), 7.67-7.66 (1H, s), 7.58-7.52 (2H, m), 6.83 (1H, s), 6.72 (1H, s), 5.99 (1H, s), 5.85 (1H, s), 4.46-4.44 (2H, d, J=5.4), 2.44 (3H, s).

Example 19

Synthesis of Compound 69

1. Synthesis of Intermediate 19-2

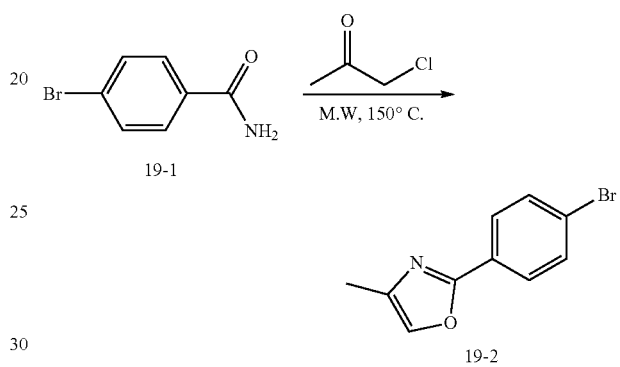

To a solution of 4-bromobenzamide (300 mg, 1.50 mmol, 1.0 equiv) in ethanol (7 mL) was added 1-chloropropan-2-one (276 mg, 3.0 mmol, 2.0 equiv) at r.t. The mixture was heated at 150° C. in a microwave reactor for 1 h, concentrated under reduced pressure, and purified by silica gel column eluting with EA/PE (1:3) to give 290 mg (81%) of 4-(4-methyl-1,3-oxazol-2-yl)benzaldehyde as a white solid. LRMS (ES) m/z 238 (M+H).

2. Synthesis of Intermediate 19-3

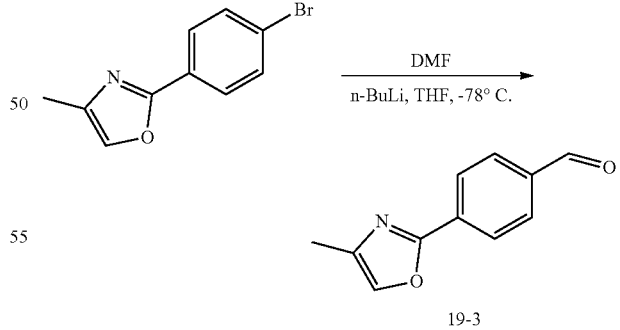

To a solution of 2-(4-bromophenyl)-4-methyl-1,3-oxazole (290 mg, 1.22 mmol, 1.0 equiv) in THF (5 mL) at −78° C. was added n-BuLi (0.6 mL, 1.20 equiv) dropwise. The mixture was stirred at −78° C. for 30 min, added DMF (180 mg, 2.00 equiv) dropwise at −78° C., stirred at r.t. for 2 h, concentrated under reduced pressure, and purified by silica gel column eluting with ethyl acetate/petroleum ether (1:5)

to give 126 mg (55%) of 4-(4-methyl-1,3-oxazol-2-yl)benzaldehyde as a light yellow solid. LRMS (ES) m/z 188 (M+H).

3. Synthesis of Compound 69

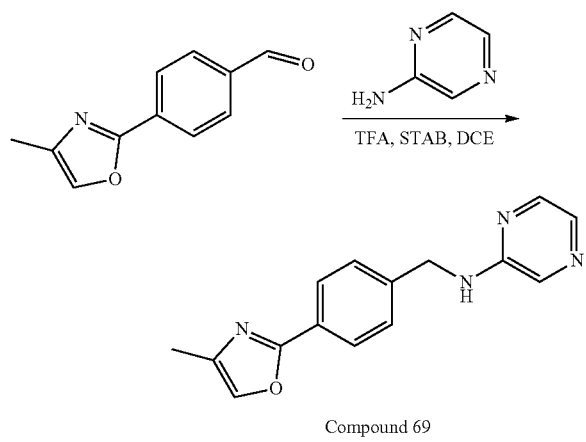

Compound 69

To a solution of 4-(4-methyl-1,3-oxazol-2-yl)benzaldehyde (100 mg, 0.53 mmol, 1.0 equiv) in DCE (7 mL) were added pyrazin-2-amine (76 mg, 0.80 mmol, 1.50 equiv) and trifluoroacetic acid (122 mg, 1.08 mmol, 2.0 equiv) at r.t. The mixture was stirred at r.t for 30 min, added STAB (227 mg, 1.07 mmol, 2.0 equiv), stirred at r.t. for 3 h, concentrated under reduced pressure, and purified by Prep-HPLC with the following conditions (2 #-AnalyseHPLC-SHIMADZU (HPLC-10)): Column, XBridge Prep OBD C18 Column, 19*250 mm, 5 um; mobile phase, water (0.05% $NH_3H_2O$) and ACN (31.0% ACN to 61.0% gradient over 8 min); Detector, UV 254 nm) to give 19.1 mg (13%) of N-[[4-(4-methyl-1,3-oxazol-2-yl)phenyl]methyl]pyrazin-2-amine as a white solid. LRMS (ES) m/z 267 [M+H]. $^1$H-NMR: (CD$_3$OD, ppm): δ 7.92-7.90 (4H, m), 7.63 (2H, s), 7.46-7.44 (2H, m), 4.58 (2H, s), 2.18 (3H, s).

Other compounds described herein are prepared. Characterization data for other prepared compounds are provided below:

| Compound No. | LRMS (ES) m/z |
|---|---|
| 11 | M + H = 307.2 |
| 27 | M + H = 301 |
| 29 | M + H = 266 |
| 51 | M + H = 393.1 |
| 52 | M + H = 267.1 |
| 67 | M + H = 297 |

Biological Example B-1

Myofibril Assays

To evaluate the effect of compounds on the ATPase activity of full-length cardiac myosin in the context of the native sarcomere, skinned myofibril assays were performed. Bovine cardiac myofibrils were obtained by homogenizing bovine cardiac left ventricular tissue in the presence of a detergent such as triton X-100. Such treatment removes membranes and a majority of the soluble cytoplasmic proteins but leaves intact the cardiac sarcomeric acto-myosin apparatus. Myofibril preparations retain the ability to hydrolyze ATP in an $Ca^{2+}$ regulated manner. ATPase activities of such myofibril preparations in the presence and absence of compounds were assayed at $Ca^{2+}$ concentrations activating to a defined fraction of the maximal rate (i.e., 25%, 75%). Small molecule agents were assessed for their ability to inhibit the steady-state ATPase activity of bovine cardiac myofibrils using pyruvate kinase and lactate dehydrogenase (PK/LDH)-coupled enzyme system. This assay regenerates myosin-produced ADP into ATP by oxidizing NADH, producing an absorbance change at 340 nm. Prior to testing small molecule agents, the bovine cardiac myofibrils were assessed for their calcium responsiveness and the calcium concentration that achieves either a 50% (pCa$_{50}$) or 75% (pCa$_{75}$) activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM 12 buffer). Final assay conditions were 1 mg/mL of bovine cardiac myofibrils, 4 U/mL pyruvate kinase, 6 U/mL lactate dehydrogenase, 50 μM ATP, 0.1 mg/mL BSA (bovine serum albumin), 10 ppm antifoam, 1 mM DTT, 0.5 mM NADH, 1.5 mM PEP, 0.6 mM EGTA, and an amount of CaCl$_2$ sufficient to achieve either 50% or 75% activation of the myofibril ATPase activity. Results for compounds tested are provided in Table A. Compounds tested were prepared in accordance with the synthetic procedures described herein.

TABLE A

| Cmpd No. | CDMF75 IC$_{15}$ (μM) | CDMF75 IC$_{50}$ (μM) |
|---|---|---|
| 1 | 1.4 | 8.1 |
| 2 | 0.8 | 4.3 |
| 3 | 3.6 | 27.7 |
| 4 | 1.9 | 6.6 |
| 5 | 1.0 | 3.7 |
| 6 | 5.6 | 27.0 |
| 7 | 0.4 | 1.8 |
| 8 | 3.1 | 16.6 |
| 9 | 0.3 | 1.2 |
| 10 | 1.3 | 7.6 |
| 11 | 0.2 | 0.7 |
| 12 | 2.5 | 9.8 |
| 13 | 0.3 | 1.5 |
| 14 | 4.6 | 20.9 |
| 15 | 1.0 | 5.5 |
| 16 | 3.1 | 17.3 |
| 17 | 2.9 | 18.9 |
| 18 | 0.4 | 2.1 |
| 19 | 1.2 | 4.3 |
| 20 | 1.5 | 5.2 |
| 21 | 2.2 | 12.8 |
| 22 | 0.4 | 1.8 |
| 23 | 0.3 | 1.4 |
| 24 | 0.8 | 3.1 |
| 25 | 1.1 | 4.5 |
| 26 | 1.1 | 5.6 |
| 27 | 1.2 | 8.9 |
| 28 | 0.6 | 2.6 |
| 29 | 8.1 | 38.9 |
| 30 | 0.5 | 2.6 |
| 31 | 0.4 | 1.51 |
| 32 | 0.3 | 1.4 |
| 33 | 0.3 | 1.5 |
| 34 | 0.5 | 2.3 |
| 35 | 0.7 | 3.0 |
| 36 | 7.1 | 36.5 |
| 37 | 1.3 | 5.6 |
| 38 | 3.0 | 19.1 |

TABLE A-continued

| Cmpd No. | CDMF75 IC$_{15}$ (µM) | CDMF75 IC$_{50}$ (µM) |
|---|---|---|
| 39 | 0.2 | 0.9 |
| 40 | 0.3 | 1.1 |
| 41 | 0.7 | 3.9 |
| 42 | 0.8 | 4.8 |
| 43 | 0.4 | 1.7 |
| 44 | 2.2 | 10.9 |
| 45 | 0.9 | 4.0 |
| 46 | 0.4 | 2.2 |
| 47 | 0.3 | 1.7 |
| 48 | 4.0 | 19.0 |
| 49 | 0.3 | 28.6 |
| 50 | 3.4 | 15.1 |
| 51 | 0.2 | 0.9 |
| 52 | 0.2 | 1.0 |
| 53 | 2.1 | 9.4 |
| 54 | 6.0 | 25.8 |
| 55 | 0.4 | 1.3 |
| 56 | 1.2 | 4.7 |
| 57 | 3.1 | 19.3 |
| 58 | 2.3 | 11.4 |
| 59 | 0.7 | 2.2 |
| 60 | 7.7 | 30.8 |
| 61 | 2.4 | 10.2 |
| 62 | 5.0 | 23.0 |
| 63 | 22.8 | >39.2 |
| 64 | 7.7 | >39.2 |
| 65 | 7.6 | >39.2 |
| 66 | 0.3 | 1.7 |
| 67 | 0.4 | 2.2 |
| 68 | >39.2 | >39.2 |
| 69 | 18.4 | >39.2 |
| 70 | 0.8 | 4.1 |
| 71 | >39.2 | >39.2 |

Biological Example B-2

Myocyte Assays (i) Preparation of Adult Cardiac Ventricular Rat Myocytes

Adult male Sprague-Dawley rats were anesthetized and the hearts were quickly excised, rinsed and the ascending aorta was cannulated. Continuous retrograde perfusion was initiated on the hearts at a perfusion pressure of 60 cm H$_2$O. Hearts were first perfused with a nominally Ca$^{2+}$-free modified Krebs solution of the following composition: 113 mM NaCl, 4.7 mM KCl, 0.6 mM KH$_2$PO$_4$, 0.6 mM Na$_2$HPO$_4$, 1.2 mM MgSO$_4$, 12 mM NaHCO$_3$, 10 mM KHCO$_3$, 30 mM taurine, 5.5 mM glucose and 10 mM Hepes (all Sigma). This medium is not recirculated and is continually aerated with a 95% O$_2$/5% CO$_2$ mixture. After approximately 3 minutes, the heart was perfused with a modified Krebs buffer supplemented with collagenase (Worthington) and 12.5 µM final calcium concentration. The heart was removed from the cannulae after the heart appeared blanched and soft in appearance. The atria and vessels were removed, and the ventricles were gently dissected into smaller pieces with forceps. The tissue was homogenized by repeated pipette trituration, and the collagenase reaction was stopped by 10% bovine calf serum (BCS), sedimentation and resuspension in perfusion buffer containing 5% BCS and 12.5 uM CaCl$_2$. Myocytes were made calcium tolerant by stepwise addition of a CaCl$_2$ solution to a final concentration of 1.2 mM. Cells were then washed and resuspended in Tyrode's buffer (137 mM NaCl, 3.7 mM KCl, 0.5 mM MgCl, 11 mM glucose, 4 mM Hepes, and 1.2 mM CaCl$_2$, pH 7.4). Cells were kept for 60 min at 37° C. prior to initiating experiments and used within 5 hrs of isolation. Preparations of cells were used only if cells first passed QC criteria by demonstrating a contractile response to standard (>150% of basal) and isoproterenol (ISO; >250% of basal) treatment. Additionally, only cells whose basal contractility was between 3 and 8% were used in subsequent experiments with compounds.

(ii) Adult Ventricular Myocyte Contractility Experiments

Aliquots of myocytes in Tyrode's buffer were placed in perfusion chambers (series 20 RC-27NE; Warner Instruments) complete with heating platforms. Myocytes were allowed to attach, the chambers were heated to 37° C., and the cells were perfused with 37° C. Tyrode's buffer. Myocytes were field stimulated at 1 Hz in with platinum electrodes (20% above threshold). Only cells that had clear striations and were quiescent prior to pacing were used for contractility experiments. To determine basal contractility, myocytes were imaged through a 40× objective. Using a variable frame rate (60-240 Hz) charge-coupled device camera, the images were digitized and displayed on a computer screen at a sampling speed of 240 Hz (IonOptix Milton, MA). Once cell contraction was stable over time, test compounds (0.01-15 µM) were perfused into the chambers on the myocytes for 5 minutes. Contractility of the myocytes and contraction and relaxation velocities were then recorded using edge detection.

(III) Contractility Analysis

Five or more individual myocytes were tested per compound from two or more different myocyte preparations. For each cell, twenty or more contractility transients at basal (defined as 1 min prior to compound infusion) and after compound addition (defined as 5 min after starting compound perfusion), were averaged and compared. These average transients were analyzed using the IonWizard software (IonOptix) to determine changes in diastolic length and fractional shortening. Fractional shortening was calculated as: ((resting length −length at peak contraction) divided by the resting length). The percent change in fractional shortening from baseline was calculated as: ((post-dose fractional shortening/basal fractional shortening)*100). The percent reduction in fractional shortening from baseline was calculated as: (100−percent change in fractional shortening from baseline). Maximum contraction and relaxation velocities (um/sec) was also determined. Results from individual cells were averaged and the SEM was calculated.

The effect of the compounds on the fractional shortening (FS) of the myocytes is shown in Table B.

TABLE B

| Compound No. | Concentration (µM) | % FS (% reduction from baseline) ± SEM | # of cells tested |
|---|---|---|---|
| 19 | 10 | 14.4 ± 3.4 | 5 |
| 28 | 5 | 43.6 ± 9.3 | 5 |
| 34 | 5 | 30.7 ± 5.0 | 5 |
| 52 | 1 | 17.4 ± 6.8 | 5 |

% FS = Average of each cell's (post baseline percent peak height/pre-baseline percent peak height) × 100

Biological Example B-3

Echocardiography assessment of acute pharmacodynamic effect in rat cardiac contractility.

Assessment of in vivo cardiac function by echocardiography was performed in male Sprague Dawley rats under isoflurane (1-3%) anesthesia. 2-D M-mode images of the left ventricle were acquired in the parasternal long-axis view before and during administration of compounds by continuous IV infusion. In vivo fractional shortening was determined by M-mode image analysis with the following calculation: ((End diastolic diameter−end systolic diameter)/end diastolic diameter×100). For continuous IV infusion experiments, three pre-dose baseline M-mode images were taken at 1 minute intervals prior to infusion of compound. Compounds were formulated in 50% Propylene Glycol (PG): 16% Cavitron: 10% dimethylacetamide (DMA) and delivered via a jugular vein catheter at the rate of 1 mL/kg/h. An estimated loading and maintenance IV infusion dose was administered to establish a steady state plasma concentration that produced a sustained, 20% relative reduction in cardiac fractional shortening for 60 minutes. During infusion, M-mode images were taken at 5 minute intervals for 60 minutes. Blood samples were taken to determine the plasma concentration of the compounds. Data were reported as an estimated $IC_{20}$ value, which is the concentration at which fractional shortening is 20% of the pre-dose baseline contractility. The $IC_{20}$ results are summarized Table C.

TABLE C

| Compound No. | Loading + Maintenance IV dose (mg/kg) | $IC_{20}$ (µM) |
|---|---|---|
| 28 | 0.5 + 1.5 | 0.8 |

For oral dosing studies, three pre-dose baseline M-Mode images are taken at 1 minute intervals prior to compound administration. Compounds are formulated in a 0.5% hydroxypropyl methylcellulose 2910 (HPMC 2910): 0.1% Tween 80 suspension and delivered as a single dose (5 mL/kg) by oral gavage. At one and four hours post-dose, rats are lightly anesthetized for M-mode echocardiography measurement. The compound effect on cardiac fractional shortening may be presented as a percent reduction of baseline fractional shortening (=100%).

Concurrent with echocardiography measurements, blood samples are taken to determine the corresponding compound plasma concentration, which may be represented as $IC_{50}$ and $IC_{10}$ values, which is the concentration at which fractional shortening is 50% and 10% of the pre-dose baseline contractility, respectively.

Biological Example B-4

Longitudinal Echocardiography Assessment of Mouse Model of HCM

Assessment over time of in vivo cardiac function by echocardiography is performed using a previously reported mouse model of familial hypertrophic cardiomyopathy, which is generated by an arginine to glutamine mutation at residue 403 (R403Q) of the alpha cardiac myosin heavy chain (MHC) gene (Geisterfer-Lowrance et al., Science. 1996 May 3; 272(5262):731-4). Cardiac dysfunction, fibrosis, and measures of cardiac hypertrophy (including ventricular wall thickness) increase with age in this mouse model (Geisterfer-Lowrance, supra; Jiang et al., Science. 2013, 342(6154):111-4).

R403Q mice receive vehicle or test compound formulated in chow for 24 weeks. Longitudinal echocardiography measurements are performed every 4 weeks. Echocardiography measurements are taken with mice under isoflurane (1-3%) anesthesia. 2-D M-mode images of the left ventricle are acquired in short-axis view. In vivo fractional shortening is determined by M-Mode image analysis with the following calculation: ((End diastolic diameter−end systolic diameter)/end diastolic diameter×100).

Biological Example B-5

Fibrosis Reduction in a Rat Model of Cardiac Hypertrophy

Assessment of fibrosis reduction is performed using Dahl Salt Sensitive (DSS) rats, a previously reported hypertension-induced rat model of heart failure with preserved ejection fraction (Fillmore et al., Mol Med. 2018, 24(1):3; Dahl et al., J Exp Med. 1962, 115:1173-90). DSS rats fed a high salt diet demonstrate progressive cardiovascular dysfunction, including increased systolic blood pressure, diastolic dysfunction, cardiac hypertrophy, and cardiac fibrosis (Fillmore, supra; Dahl, supra; Sakata et al., J Am Coll Cardiol. 2001 January; 37(1):293-9; Kim-Mitsuyama et al., Hypertens Res. 2004 October; 27(10):771-9).

DSS rats receive vehicle or test compound formulated in low or high salt chow for 6 weeks. Perivascular and interstitial cardiac tissue samples are imaged and assayed for % cardiac fibrosis.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The invention claimed is:

1. A compound of Formula (I):

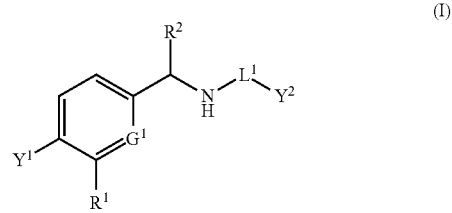

or a pharmaceutically acceptable salt thereof, wherein:

$R^1$ is H or halo;

$G^1$ is —N— or —C($R^b$)—, wherein $R^b$ is H or halo;

$R^2$ is H or —$CH_3$;

$L^1$, $Y^1$, and $Y^2$ are defined by (i) or (ii):

(i) $L^1$ is absent;
   $Y^1$ is $R^x$; and
   $Y^2$ is $R^z$;
or (ii) $L^1$

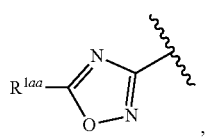, wherein $L^2$ is absent, —O—, —NH—, or —OCH$_2$—*, and wherein * indicates the attachment to $Y^2$;

$Y^1$ is

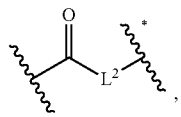, wherein $R^{1aa}$ is H, alkyl, cycloalkyl, cycloalkenyl, heterocycloalkyl, heterocycloalkenyl, aryl, or heteroaryl; and $Y^2$ is —CH$_3$, phenyl, or $R^z$;

$R^x$ is

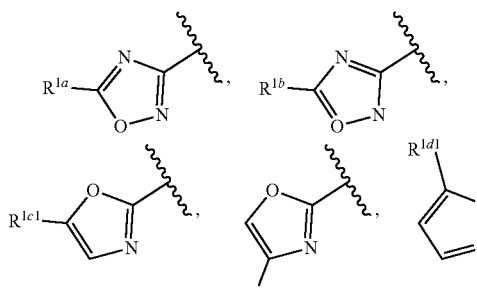

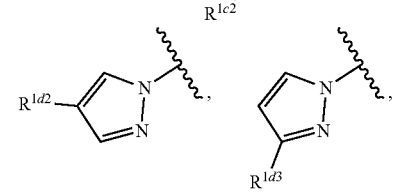

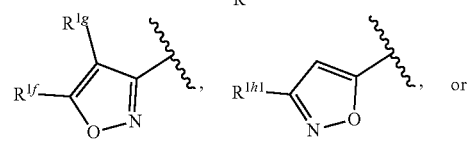, or

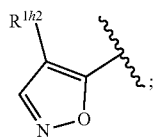;

$R^{1a}$, $R^{1b}$, $R^{1c1}$, $R^{1c2}$, $R^{1f}$, $R^{1g}$, $R^{1h1}$, and $R^{1h2}$ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl;

$R^{1d1}$, $R^{1d2}$, and $R^{1d3}$ are each independently alkyl, alkenyl, alkynyl, —C(O)O— alkyl, cycloalkyl, cycloalkenyl, cycloalkynyl, heterocycloalkyl, heterocycloalkenyl, aryl, or heteroaryl;

$R^{1e1}$ and $R^{1e2}$ are each independently H, alkyl, alkenyl, alkynyl, haloalkyl, —C(O)O-alkyl, or a cycloalkyl, cycloalkenyl, cycloalkynyl, heterocycloalkyl, heterocycloalkenyl, or heteroaryl ring;

$R^z$ is

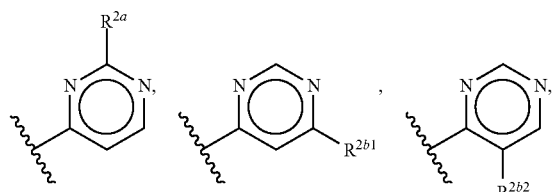

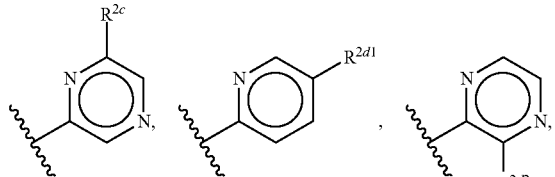

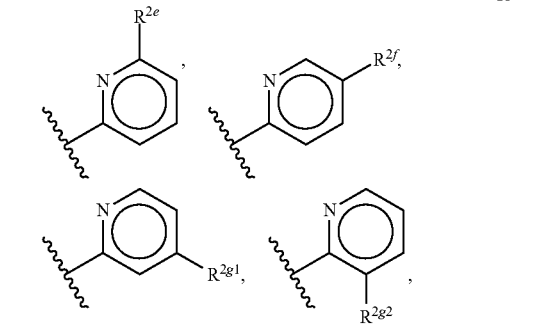

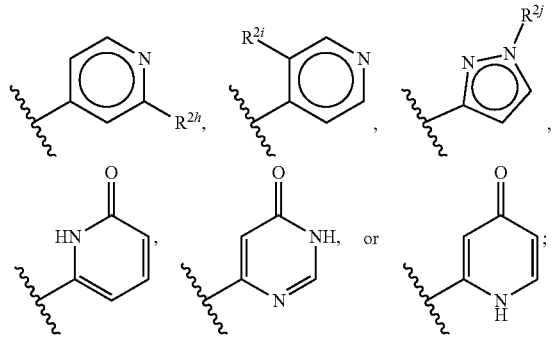

$R^{2a}$, $R^{2b1}$, $R^{2b2}$, $R^{2c}$, $R^{2d1}$, $R^{2g2}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$;

R$^{2e}$, R$^{2f}$, R$^{2g1}$, and R$^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and R$^c$ and R$^d$ are each independently H or alkyl;

wherein, when Y$^1$ is

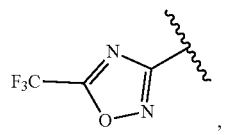 [SMILES: *c1noc(C(F)(F)F)n1]

at least one of (a)-(c) applies:
(a) R$^2$ is —CH$_3$;
(b) R$^1$ is halo; and
(c) G$^1$ is —C(R$^b$)—, wherein R$^b$ is halo; and when Y$^1$ is

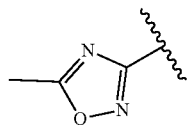 [SMILES: *c1noc(C)n1]

and Y$^2$ is

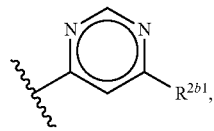

R$^{2b1}$ is selected from the group consisting of H, halo, —OH, —CN, —NR$^c$R$^d$, alkyl, alkenyl, alkynyl, —O—C$_2$-C$_6$alkyl, haloalkyl, cycloalkyl, and —C(O)NR$^c$R$^d$.

2. The compound of claim 1, wherein the compound is of Formula (Ia):

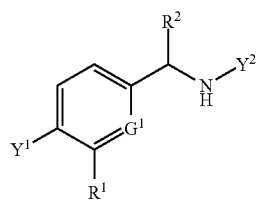

or a pharmaceutically acceptable salt thereof, wherein:
R$^1$ is H or halo;
G$^1$ is —N— or —C(R$^b$)—, wherein R$^b$ is H or halo;
R$^2$ is H or —CH$_3$;
Y$^1$ is R$^x$;

R$^x$ is

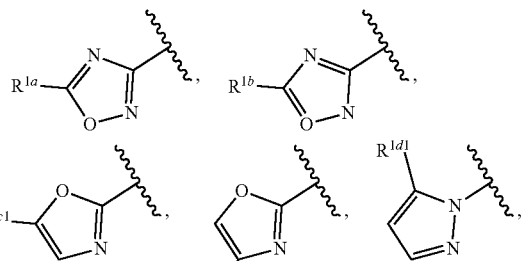

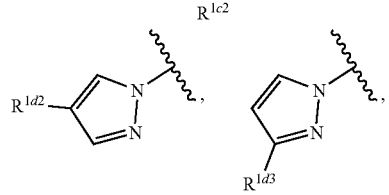

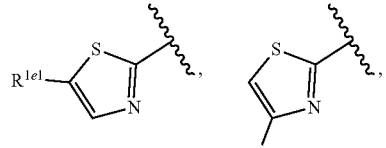

R$^{1a}$, R$^{1b}$, R$^{1c1}$, R$^{1c2}$, R$^{1f}$, R$^{1g}$, R$^{1h1}$, and R$^{1h2}$ are each independently H, alkyl, alkenyl, alkynyl, —C(O)O-alkyl, cycloalkyl, cycloalkenyl, cycloalkynyl, heterocycloalkyl, heterocycloalkenyl, aryl, or heteroaryl;

R$^{1d1}$, R$^{1d2}$, and R$^{1d3}$ are each independently alkyl, alkenyl, alkynyl, —C(O)O— alkyl, cycloalkyl, cycloalkenyl, cycloalkynyl, heterocycloalkyl, heterocycloalkenyl, aryl, or heteroaryl;

R$^{1e1}$ and R$^{1e2}$ are each independently H, alkyl, alkenyl, alkynyl, haloalkyl, —C(O)O-alkyl, or a cycloalkyl, cycloalkenyl, cycloalkynyl, heterocycloalkyl, heterocycloalkenyl, or heteroaryl ring;

Y$^2$ is R$^z$;

R$^z$ is

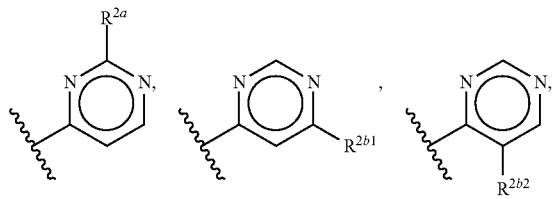

-continued

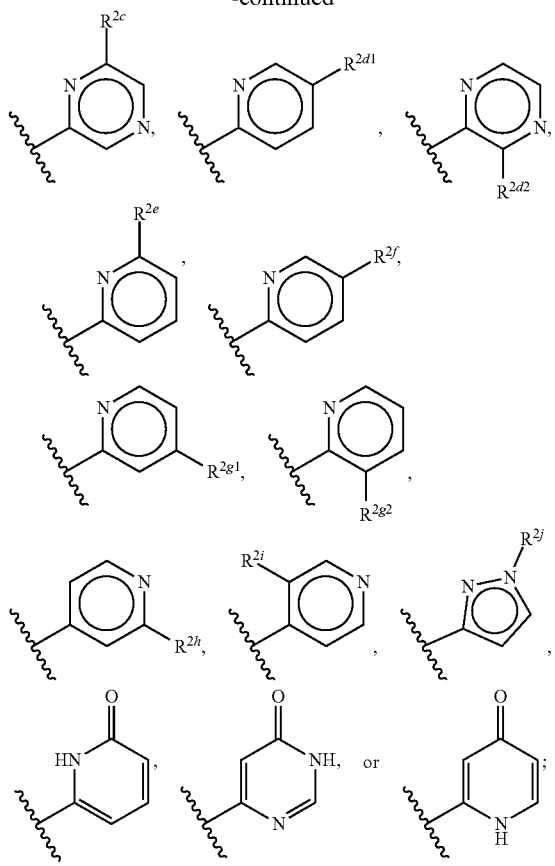

$R^{2a}$, $R^{2b1}$, $R^{2b2}$, $R^{2c}$, $R^{2d1}$, $R^{2d2}$, $R^{2h}$, $R^{2i}$, and $R^{2j}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$;

$R^{2e}$, $R^{2f}$, $R^{2g}$, and $R^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$; and R$^c$ and R$^d$ are each independently H or alkyl; wherein, when Y$^1$ is

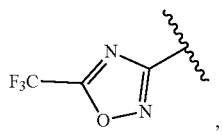

at least one of (a)-(c) applies:
(a) R$^2$ is —CH$_3$;
(b) R$^1$ is halo; and
(c) G$^1$ is —C(R$^b$)—, wherein R$^b$ is halo; and when Y$^1$ is

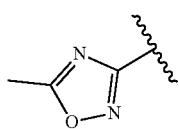 [SMILES: *c1noc(C)n1]

and Y$^2$ is

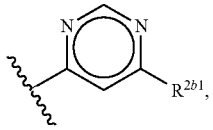

R$^{2b1}$ is selected from the group consisting of H, halo, —OH, —CN, —NR$^c$R$^d$, alkyl, alkenyl, alkynyl, —O—C$_2$-C$_6$alkyl, haloalkyl, cycloalkyl, and —C(O)NR$^c$R$^d$.

3. The compound of claim 1, wherein the compound is of Formula (Ib):

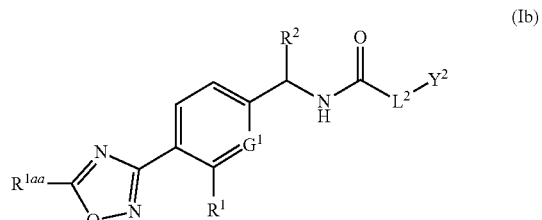

(Ib)

or a pharmaceutically acceptable salt thereof, wherein:
R$^{1aa}$ is H, alkyl, cycloalkyl, cycloalkenyl, heterocycloalkyl, heterocycloalkenyl, aryl, or heteroaryl;
R$^1$ is H or halo;
G$^1$ is —N— or —C(R$^b$)—, wherein R$^b$ is H or halo;
R$^2$ is H or —CH$_3$;
L$^2$ is absent, —O—, —NH—, or —OCH$_2$—*;
wherein * indicates the attachment to Y$^2$;
Y$^2$ is CH$_3$, phenyl, or R$^z$;
R$^z$ is

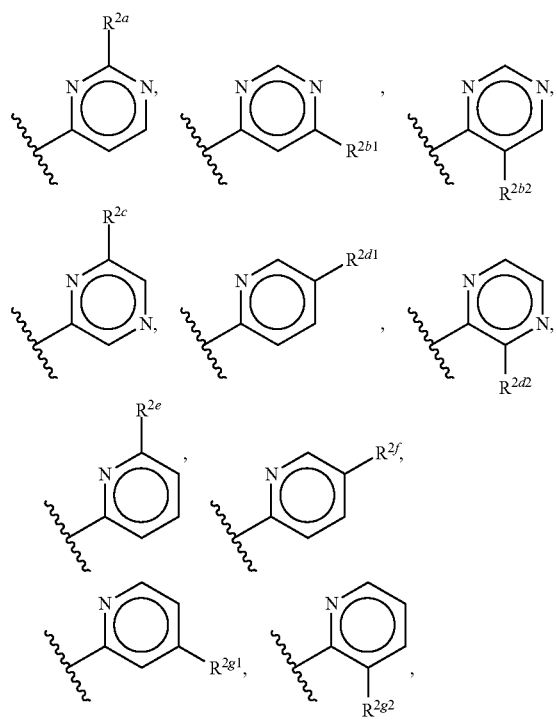

-continued

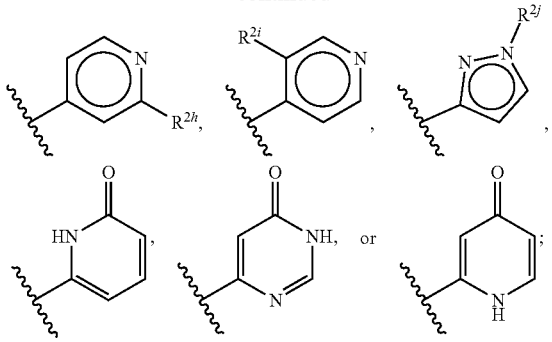

R²ᵃ, R²ᵇ¹, R²ᵇ², R²ᶜ, R²ᵈ¹, R²ᵍ², R²ʰ, R²ⁱ, and R²ʲ are each independently selected from the group consisting of H, halo, —OH, —CN, —NRᶜRᵈ, alkyl, alkenyl, alkynyl, —O-alkyl, haloalkyl, cycloalkyl, and —C(O)NRᶜRᵈ;

R²ᵉ, R²ᶠ, R²ᵍ¹, and R²ᵍ² are each independently selected from the group consisting of halo, —OH, —CN, —NRᶜRᵈ, alkyl, alkenyl, alkynyl, —O-alkyl, haloalkyl, cycloalkyl, and —C(O)NRᶜRᵈ; and Rᶜ and Rᵈ are each independently H or alkyl.

4. The compound of claim 1, or a pharmaceutically acceptable salt thereof, wherein R¹ is H.

5. The compound of claim 1, or a pharmaceutically acceptable salt thereof, wherein R¹ is halo.

6. The compound of claim 1, or a pharmaceutically acceptable salt thereof, wherein G¹ is —N—.

7. The compound of claim 1, or a pharmaceutically acceptable salt thereof, wherein G¹ is —C(Rᵇ)—, and Rᵇ is H or halo.

8. The compound of claim 1, or a pharmaceutically acceptable salt thereof, wherein R² is H.

9. The compound of claim 1, or a pharmaceutically acceptable salt thereof, wherein R² is —CH₃.

10. The compound of claim 1, or a pharmaceutically acceptable salt thereof, wherein Y¹ is

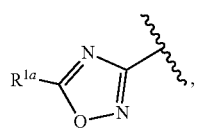

and R¹ᵃ is H, alkyl, haloalkyl, —C(O)O-alkyl, cycloalkyl, cycloalkenyl, heterocycloalkyl, heterocycloalkenyl, aryl, or heteroaryl.

11. The compound of claim 1, or a pharmaceutically acceptable salt thereof, wherein Y¹ is

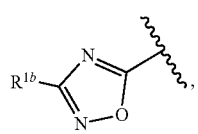

and R¹ᵇ is H, alkyl, haloalkyl, —C(O)O-alkyl, cycloalkyl, cycloalkenyl, heterocycloalkyl, heterocycloalkenyl, aryl, or heteroaryl.

12. The compound of claim 1, or a pharmaceutically acceptable salt thereof, wherein Y¹ is

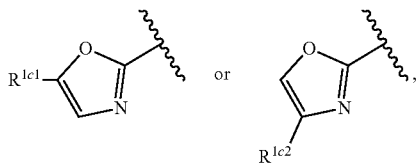

and R¹ᶜ¹ and R¹ᶜ² are each independently H, alkyl, haloalkyl, —C(O)O-alkyl, cycloalkyl, cycloalkenyl, heterocycloalkyl, heterocycloalkenyl, aryl, or heteroaryl.

13. The compound of claim 1, or a pharmaceutically acceptable salt thereof, wherein Y¹ is

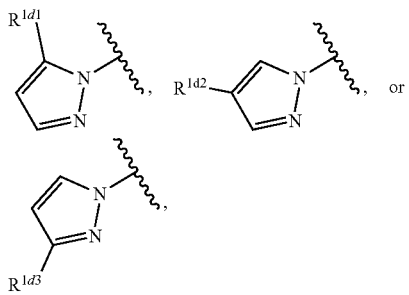

and R¹ᵈ¹, R¹ᵈ², and R¹ᵈ³ are each independently alkyl, alkenyl, alkynyl, —C(O)O-alkyl, cycloalkyl, cycloalkenyl, cycloalkynyl, heterocycloalkyl, heterocycloalkenyl, aryl, or heteroaryl.

14. The compound of claim 1, or a pharmaceutically acceptable salt thereof, wherein Y¹ is

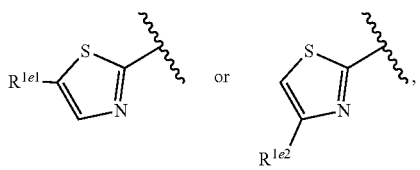

and R¹ᵉ¹ and R¹ᵉ² are each independently H, alkyl, alkenyl, alkynyl, haloalkyl, —C(O)O-alkyl, cycloalkyl, cycloalkenyl, cycloalkynyl, heterocycloalkyl, heterocycloalkenyl, or heteroaryl.

15. The compound of claim 1, or a pharmaceutically acceptable salt thereof, wherein Y¹ is

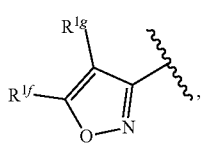

and R¹ᶠ and R¹ᵍ are each independently H, alkyl, alkenyl, alkynyl, haloalkyl, —C(O)O-alkyl, cycloalkyl, cycloalkenyl, cycloalkynyl, heterocycloalkyl, heterocycloalkenyl, aryl, or heteroaryl.

16. The compound of claim 1, or a pharmaceutically acceptable salt thereof, wherein $Y^1$ is

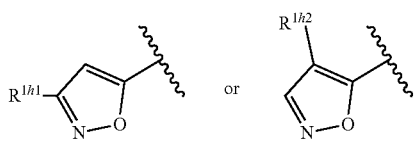

and $R^{1h1}$ and $R^{1h2}$ are each independently H, alkyl, haloalkyl, —C(O)O-alkyl, cycloalkyl, cycloalkenyl, heterocycloalkyl, heterocycloalkenyl, aryl, or heteroaryl.

17. The compound of claim 1, or a pharmaceutically acceptable salt thereof, wherein $Y^1$ is selected from the group consisting of

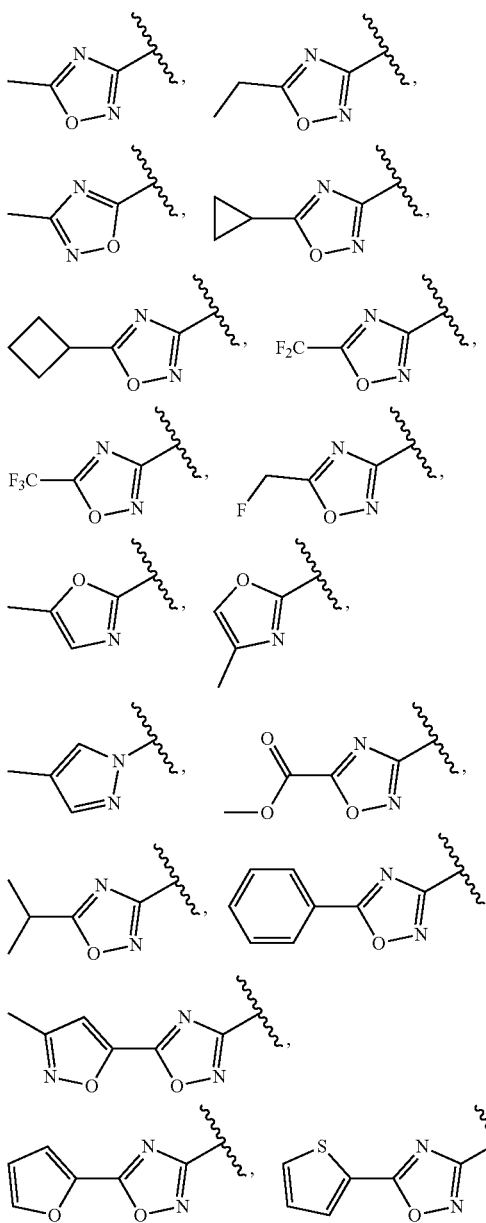

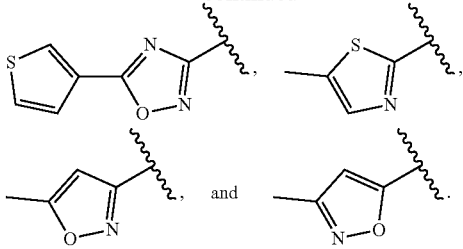

18. The compound of claim 1, or a pharmaceutically acceptable salt thereof, wherein $Y^1$ is

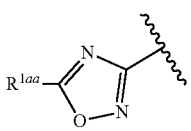

and $R^{1aa}$ is alkyl.

19. The compound of claim 1, or a pharmaceutically acceptable salt thereof, wherein $L^2$ is absent.

20. The compound of claim 1, or a pharmaceutically acceptable salt thereof, wherein $L^2$ is —O—.

21. The compound of claim 1, or a pharmaceutically acceptable salt thereof, wherein $L^2$ is —NH—.

22. The compound of claim 1, or a pharmaceutically acceptable salt thereof, wherein $L^2$ is —OCH$_2$—*, wherein * indicates the attachment to $Y^2$.

23. The compound of claim 1, or a pharmaceutically acceptable salt thereof, wherein $Y^2$ is

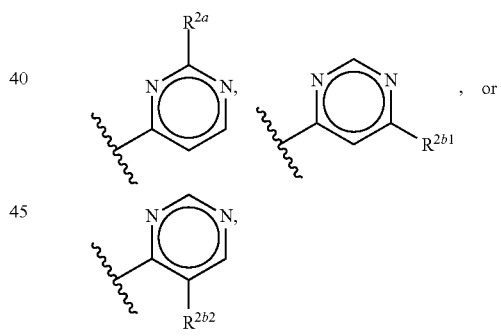

and $R^{2a}$, $R^{2b1}$, and $R^{2b2}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$.

24. The compound of claim 1, or a pharmaceutically acceptable salt thereof, wherein $Y^2$ is

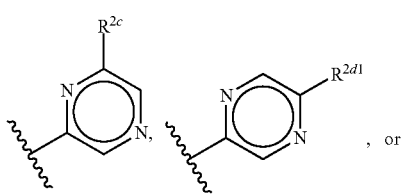

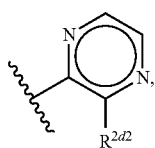

and R$^{2c}$, R$^{2d1}$, and R$^{2d2}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$.

25. The compound of claim 1, or a pharmaceutically acceptable salt thereof, wherein Y$^2$ is

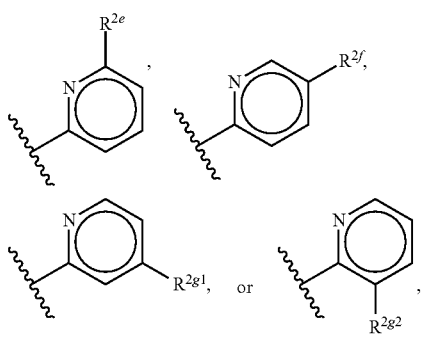

and R$^{2e}$, R$^{2f}$, R$^{2g1}$, and R$^{2g2}$ are each independently selected from the group consisting of halo, —OH, —CN, —NR$^c$R$^d$, alkyl, alkenyl, alkynyl, —O-alkyl, haloalkyl, cycloalkyl, and —C(O)NR$^c$R$^d$.

26. The compound of claim 1, or a pharmaceutically acceptable salt thereof, wherein Y$^2$ is

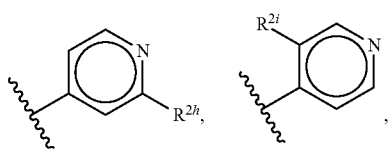

and R$^{2h}$ and R$^{2i}$ are each independently selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$.

27. The compound of claim 1, or a pharmaceutically acceptable salt thereof, wherein Y$^2$ is

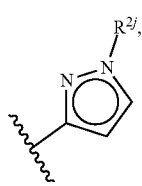

and R$^{2j}$ is selected from the group consisting of H, halo, —OH, —CN, —NR$^c$R$^d$, alkyl, alkenyl, alkynyl, —O-alkyl, haloalkyl, cycloalkyl, and —C(O)NR$^c$R$^d$.

28. The compound of claim 1, or a pharmaceutically acceptable salt thereof, wherein Y$^2$ is selected from the group consisting of

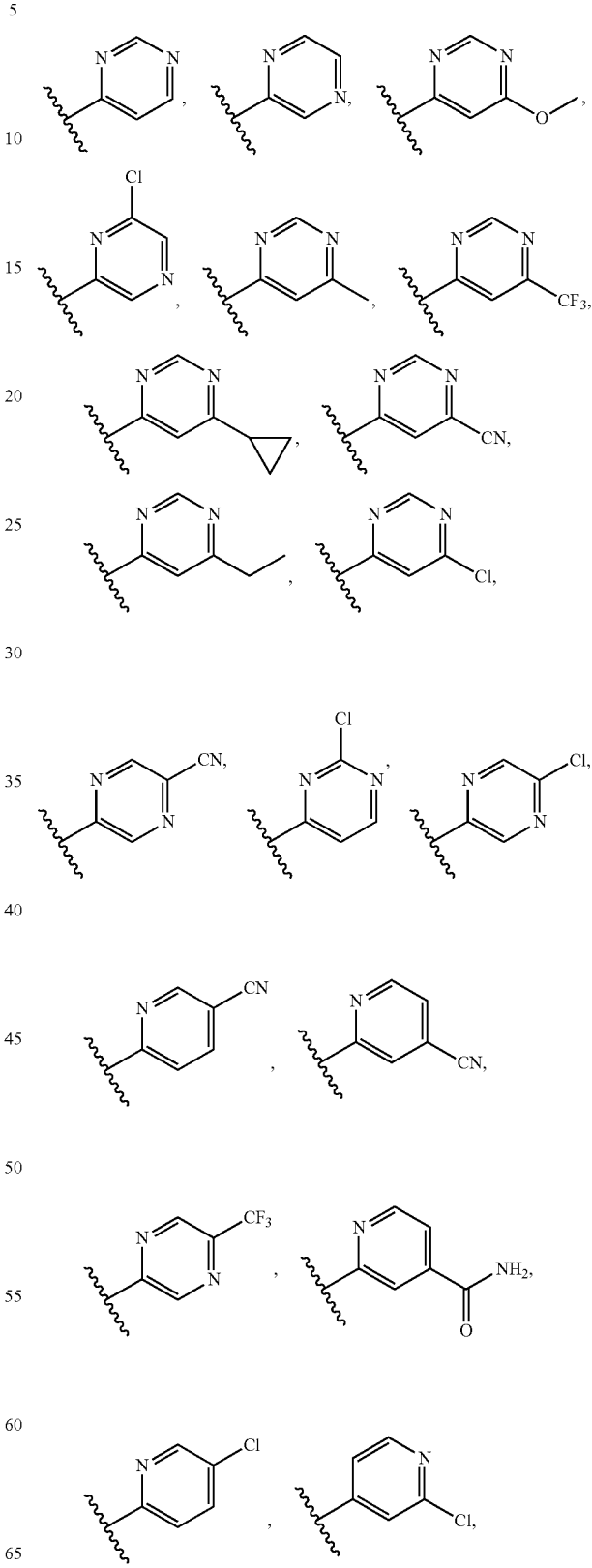

-continued
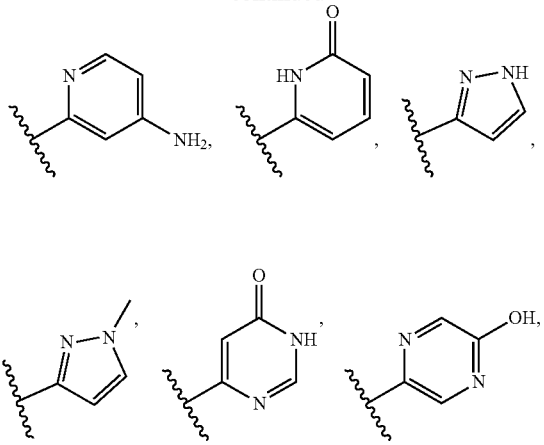
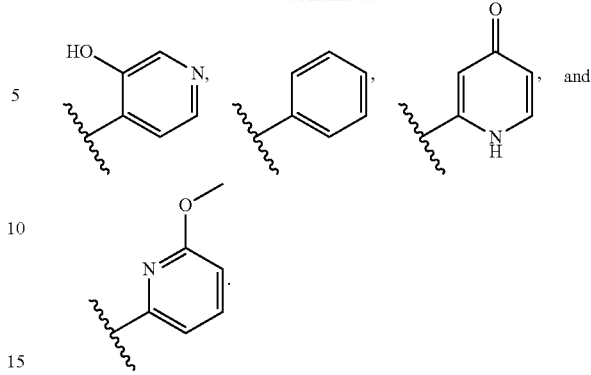
29. The compound of claim 1, or a pharmaceutically acceptable salt thereof, wherein $Y^2$ is $CH_3$ or phenyl.
30. A compound selected from the group consisting of
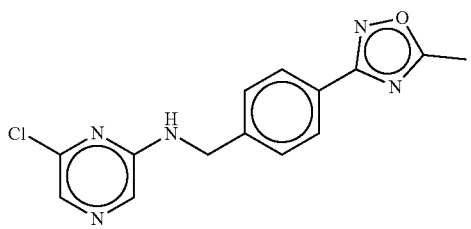
6-chloro-N-(4-(5-methyl-1,2,4-oxadiazol-3-yl)benzyl)pyrazin-2-amine;
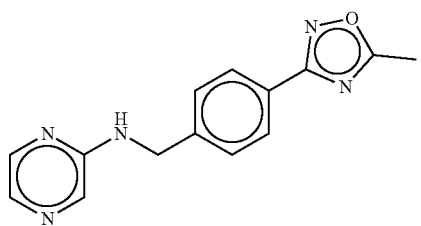
N-(4-(5-methyl-1,2,4-oxadiazol-3-yl)benzyl)pyrazin-2-amine;
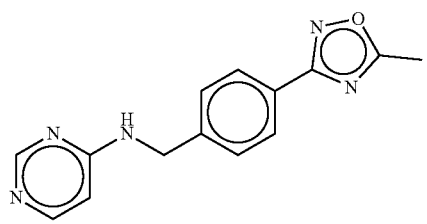
N-(4-(5-methyl-1,2,4-oxadiazol-3-yl)benzyl)pyrimidin-4-amine;
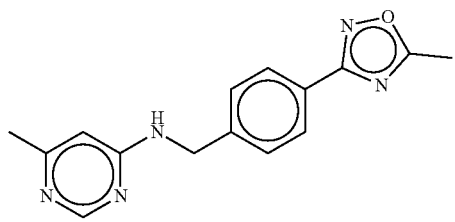
6-methyl-N-(4-(5-methyl-1,2,4-oxadiazol-3-yl)benzyl)pyrimidin-4-amine;

-continued

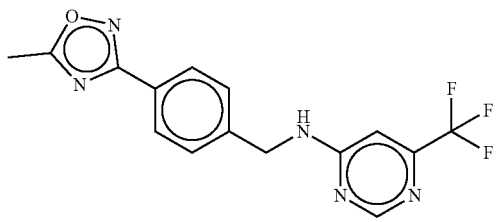

N-(4-(5-methyl-1,2,4-oxadiazol-3-yl)benzyl)-6-(trifluoromethyl)pyrimidin-4-amine;

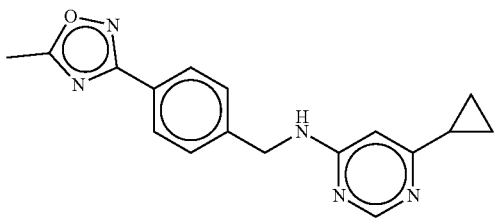

6-cyclopropyl-N-(4-(5-methyl-1,2,4-oxadiazol-3-yl)benzyl)pyrimidin-4-amine;

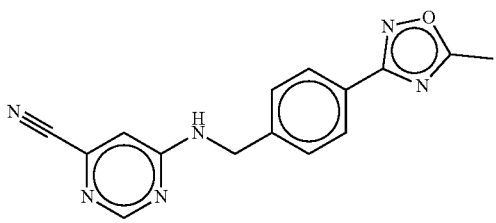

6-((4-(5-methyl-1,2,4-oxadiazol-3-yl)benzyl)amino)pyrimidine-4-carbonitrile;

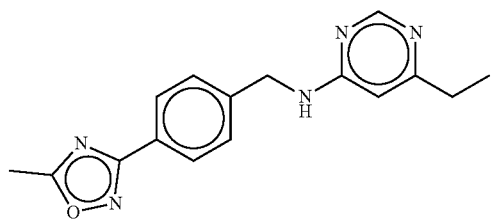

6-ethyl-N-(4-(5-methyl-1,2,4-oxadiazol-3-yl)benzyl)pyrimidin-4-amine;

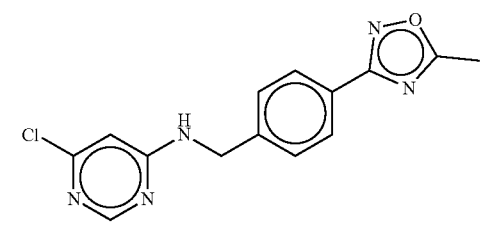

6-chloro-N-(4-(5-methyl-1,2,4-oxadiazol-3-yl)benzyl)pyrimidin-4-amine;

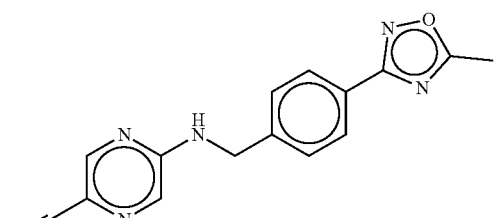

5-((4-(5-methyl-1,2,4-oxadiazol-3-yl)benzyl)amino)pyrazine-2-carbonitrile;

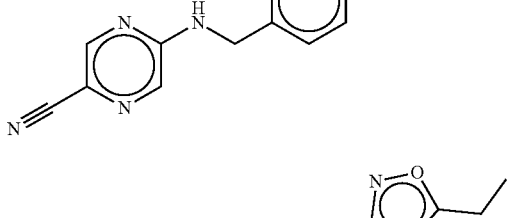

6-((4-(5-ethyl-1,2,4-oxadiazol-3-yl)benzyl)amino)pyrimidine-4-carbonitrile;

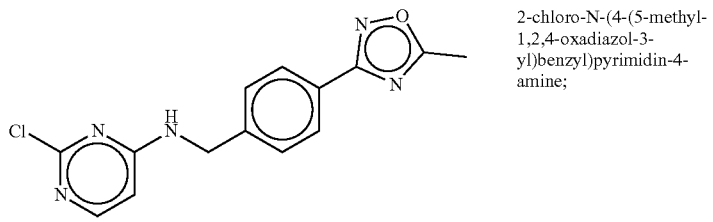 2-chloro-N-(4-(5-methyl-1,2,4-oxadiazol-3-yl)benzyl)pyrimidin-4-amine;
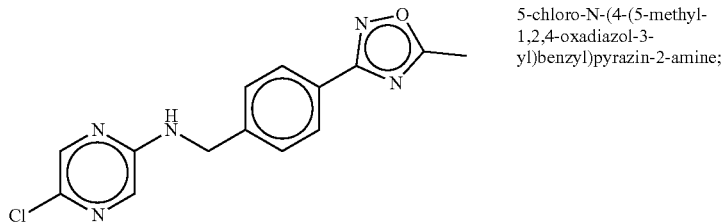 5-chloro-N-(4-(5-methyl-1,2,4-oxadiazol-3-yl)benzyl)pyrazin-2-amine;
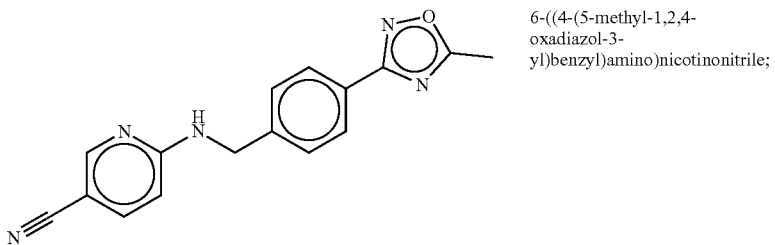 6-((4-(5-methyl-1,2,4-oxadiazol-3-yl)benzyl)amino)nicotinonitrile;
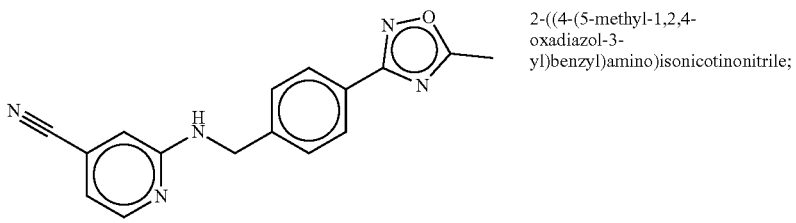 2-((4-(5-methyl-1,2,4-oxadiazol-3-yl)benzyl)amino)isonicotinonitrile;
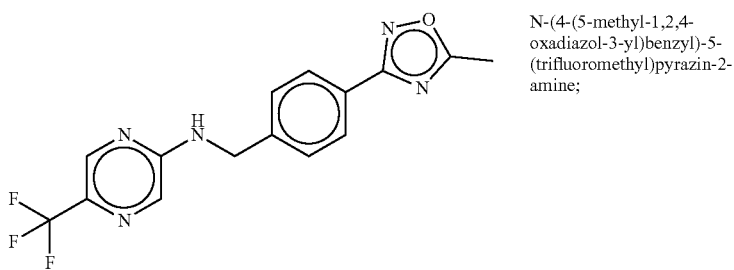 N-(4-(5-methyl-1,2,4-oxadiazol-3-yl)benzyl)-5-(trifluoromethyl)pyrazin-2-amine;
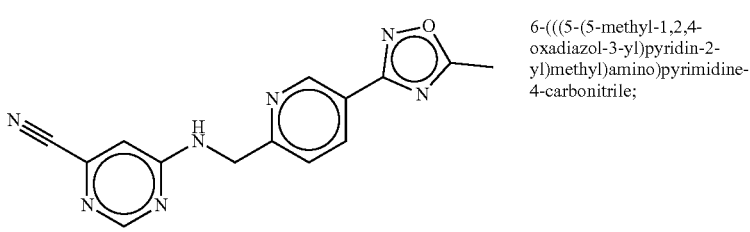 6-(((5-(5-methyl-1,2,4-oxadiazol-3-yl)pyridin-2-yl)methyl)amino)pyrimidine-4-carbonitrile;

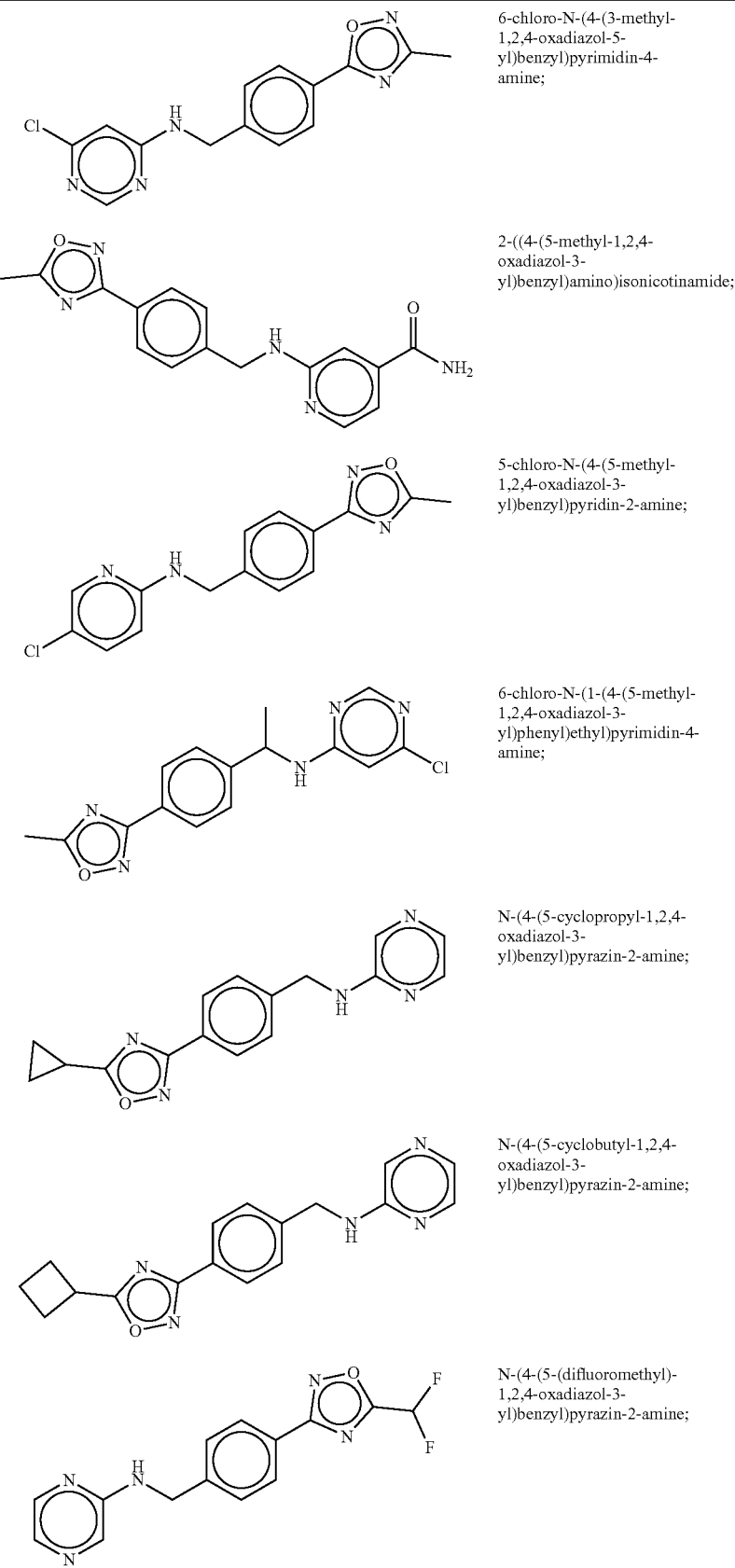

6-chloro-N-(4-(3-methyl-1,2,4-oxadiazol-5-yl)benzyl)pyrimidin-4-amine;

2-((4-(5-methyl-1,2,4-oxadiazol-3-yl)benzyl)amino)isonicotinamide;

5-chloro-N-(4-(5-methyl-1,2,4-oxadiazol-3-yl)benzyl)pyridin-2-amine;

6-chloro-N-(1-(4-(5-methyl-1,2,4-oxadiazol-3-yl)phenyl)ethyl)pyrimidin-4-amine;

N-(4-(5-cyclopropyl-1,2,4-oxadiazol-3-yl)benzyl)pyrazin-2-amine;

N-(4-(5-cyclobutyl-1,2,4-oxadiazol-3-yl)benzyl)pyrazin-2-amine;

N-(4-(5-(difluoromethyl)-1,2,4-oxadiazol-3-yl)benzyl)pyrazin-2-amine;

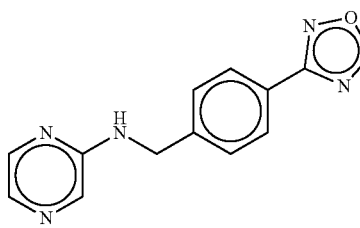 N-(4-(5-(fluoromethyl)-1,2,4-oxadiazol-3-yl)benzyl)pyrazin-2-amine;

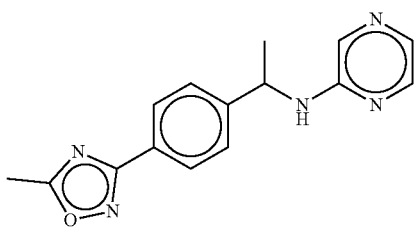 N-(1-(4-(5-methyl-1,2,4-oxadiazol-3-yl)phenyl)ethyl)pyrazin-2-amine;

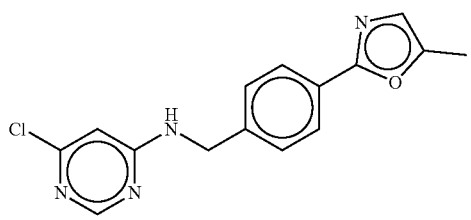 6-chloro-N-(4-(5-methyloxazol-2-yl)benzyl)pyrimidin-4-amine;

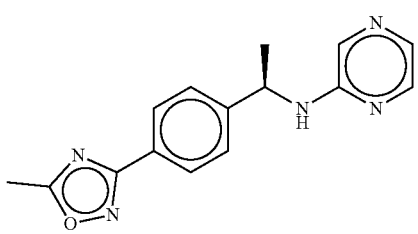 (R)-N-(1-(4-(5-methyl-1,2,4-oxadiazol-3-yl)phenyl)ethyl)pyrazin-2-amine;

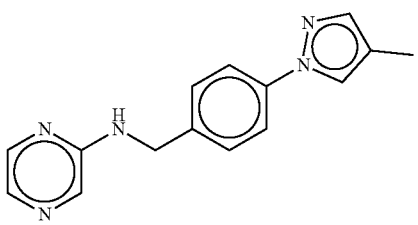 N-(4-(4-methyl-1H-pyrazol-1-yl)benzyl)pyrazin-2-amine;

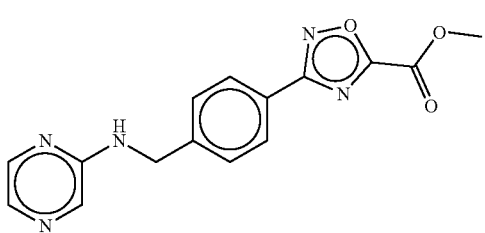 methyl 3-(4-((pyrazin-2-ylamino)methyl)phenyl)-1,2,4-oxadiazole-5-carboxylate;

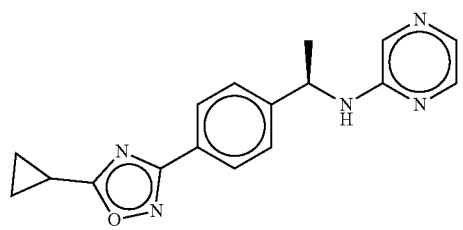 (R)-N-(1-(4-(5-cyclopropyl-1,2,4-oxadiazol-3-yl)phenyl)ethyl)pyrazin-2-amine;

-continued

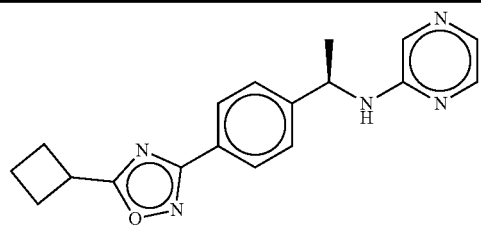 (R)-N-(1-(4-(5-cyclobutyl-1,2,4-oxadiazol-3-yl)phenyl)ethyl)pyrazin-2-amine;

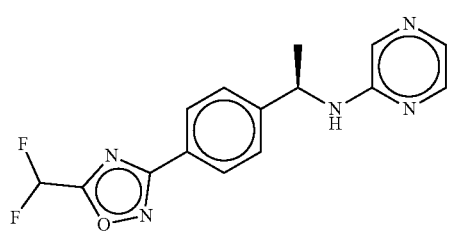 (R)-N-(1-(4-(5-(difluoromethyl)-1,2,4-oxadiazol-3-yl)phenyl)ethyl)pyrazin-2-amine;

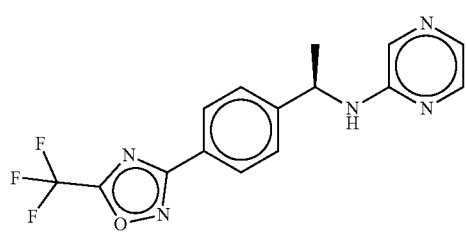 (R)-N-(1-(4-(5-(trifluoromethyl)-1,2,4-oxadiazol-3-yl)phenyl)ethyl)pyrazin-2-amine;

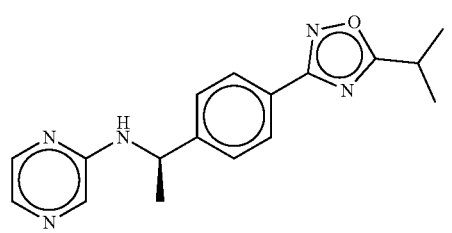 (R)-N-(1-(4-(5-isopropyl-1,2,4-oxadiazol-3-yl)phenyl)ethyl)pyrazin-2-amine;

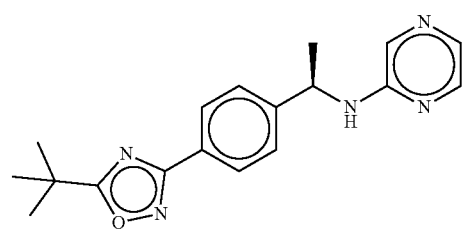 (R)-N-(1-(4-(5-(tert-butyl)-1,2,4-oxadiazol-3-yl)phenyl)ethyl)pyrazin-2-amine;

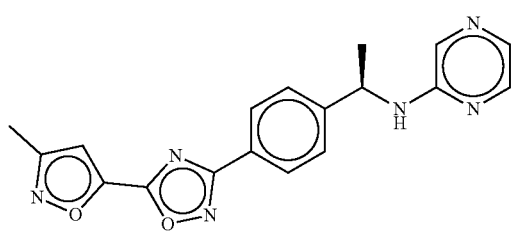 (R)-N-(1-(4-(5-(3-methylisoxazol-5-yl)-1,2,4-oxadiazol-3-yl)phenyl)ethyl)pyrazin-2-amine;

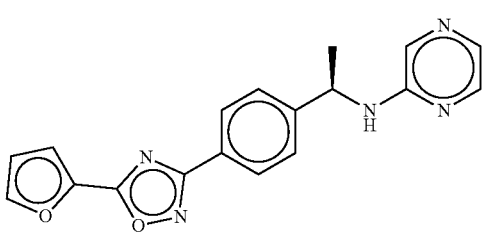 (R)-N-(1-(4-(5-(furan-2-yl)-1,2,4-oxadiazol-3-yl)phenyl)ethyl)pyrazin-2-amine;

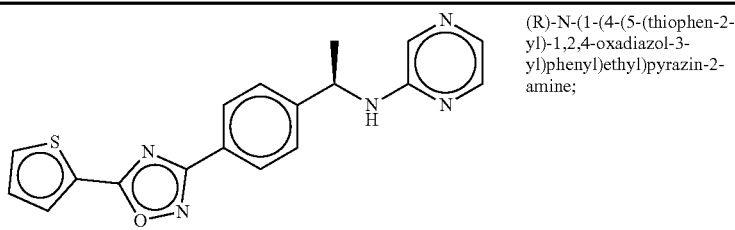
(R)-N-(1-(4-(5-(thiophen-2-yl)-1,2,4-oxadiazol-3-yl)phenyl)ethyl)pyrazin-2-amine;

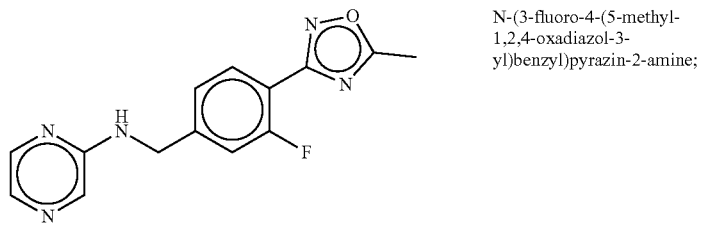
N-(3-fluoro-4-(5-methyl-1,2,4-oxadiazol-3-yl)benzyl)pyrazin-2-amine;

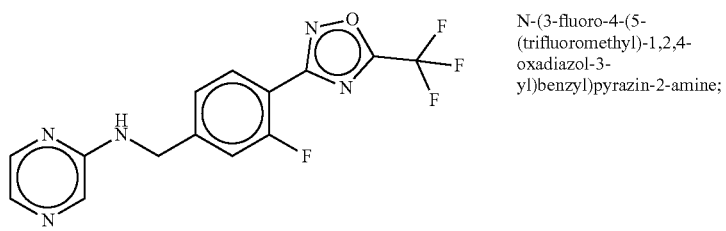
N-(3-fluoro-4-(5-(trifluoromethyl)-1,2,4-oxadiazol-3-yl)benzyl)pyrazin-2-amine;

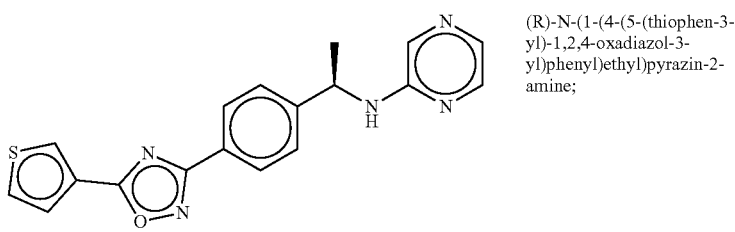
(R)-N-(1-(4-(5-(thiophen-3-yl)-1,2,4-oxadiazol-3-yl)phenyl)ethyl)pyrazin-2-amine;

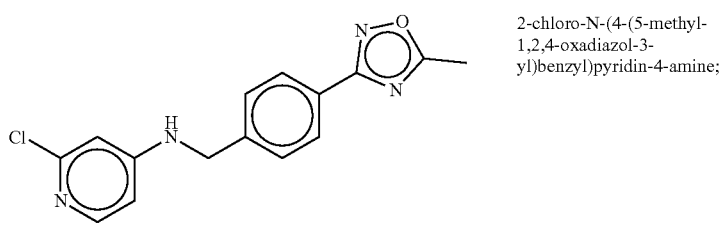
2-chloro-N-(4-(5-methyl-1,2,4-oxadiazol-3-yl)benzyl)pyridin-4-amine;

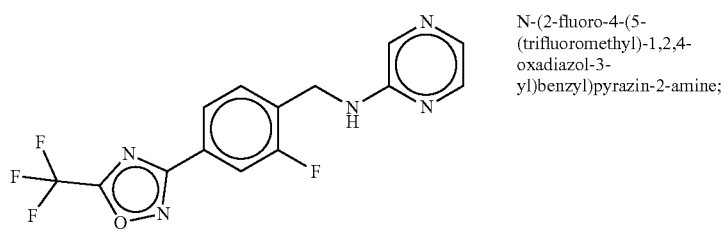
N-(2-fluoro-4-(5-(trifluoromethyl)-1,2,4-oxadiazol-3-yl)benzyl)pyrazin-2-amine;

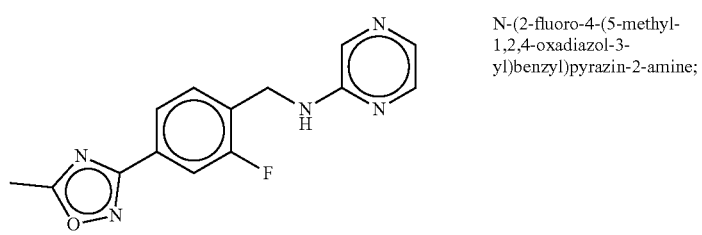
N-(2-fluoro-4-(5-methyl-1,2,4-oxadiazol-3-yl)benzyl)pyrazin-2-amine;

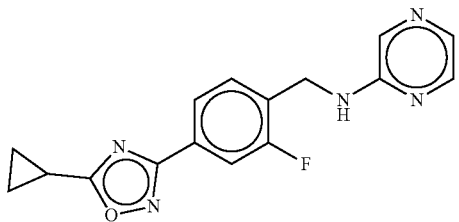 N-(4-(5-cyclopropyl-1,2,4-oxadiazol-3-yl)-2-fluorobenzyl)pyrazin-2-amine;
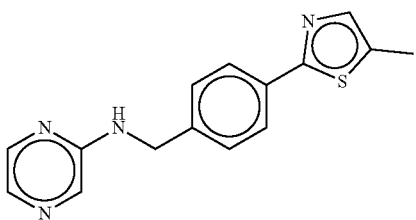 N-(4-(5-methylthiazol-2-yl)benzyl)pyrazin-2-amine;
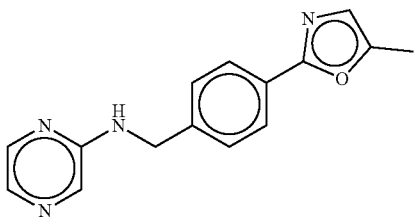 N-(4-(5-methyloxazol-2-yl)benzyl)pyrazin-2-amine;
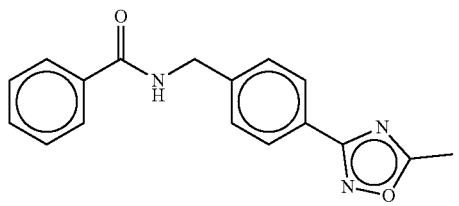 N-(4-(5-methyl-1,2,4-oxadiazol-3-yl)benzyl)benzamide;
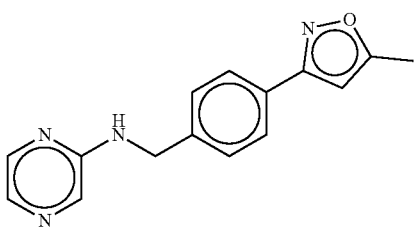 N-(4-(5-methylisoxazol-3-yl)benzyl)pyrazin-2-amine;
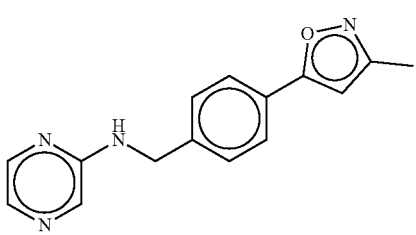 N-(4-(3-methylisoxazol-5-yl)benzyl)pyrazin-2-amine;
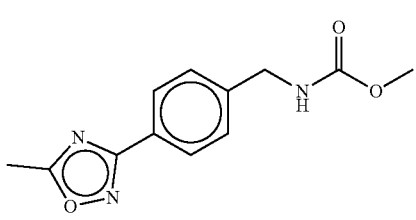 methyl (4-(5-methyl-1,2,4-oxadiazol-3-yl)benzyl)carbamate;

-continued
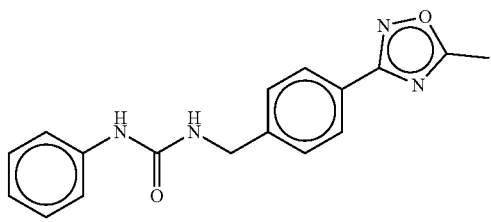
1-(4-(5-methyl-1,2,4-oxadiazol-3-yl)benzyl)-3-phenylurea;
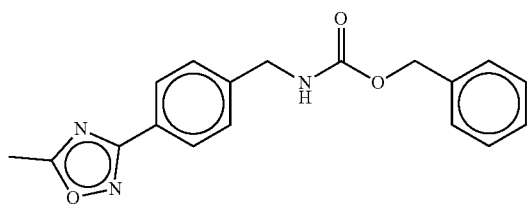
benzyl (4-(5-methyl-1,2,4-oxadiazol-3-yl)benzyl)carbamate;
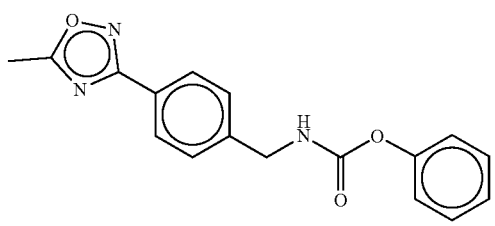
phenyl (4-(5-methyl-1,2,4-oxadiazol-3-yl)benzyl)carbamate;
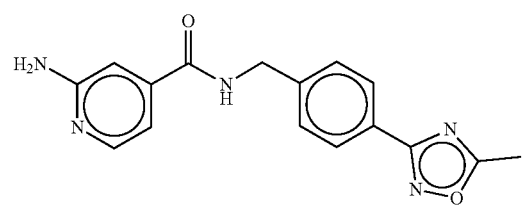
2-amino-N-(4-(5-methyl-1,2,4-oxadiazol-3-yl)benzyl)isonicotinamide;
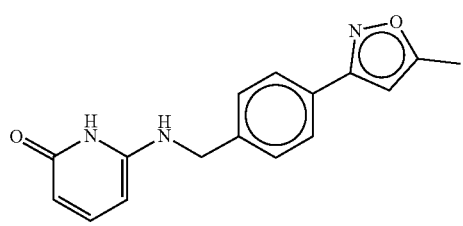
6-((4-(5-methylisoxazol-3-yl)benzyl)amino)pyridin-2(1H)-one;
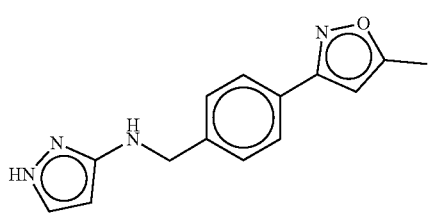
N-(4-(5-methylisoxazol-3-yl)benzyl)-1H-pyrazol-3-amine;
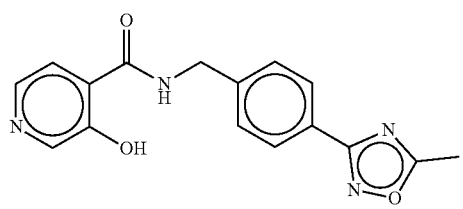
3-hydroxy-N-(4-(5-methyl-1,2,4-oxadiazol-3-yl)benzyl)isonicotinamide;

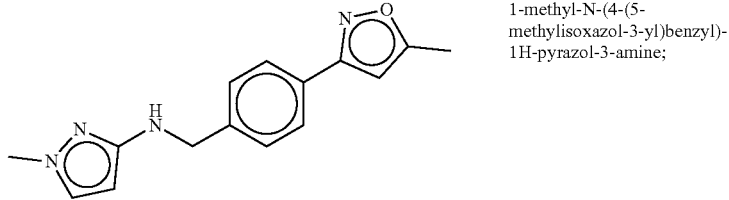
1-methyl-N-(4-(5-methylisoxazol-3-yl)benzyl)-1H-pyrazol-3-amine;
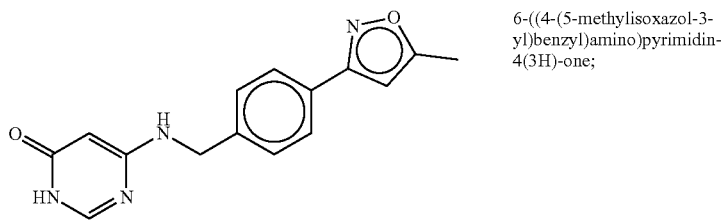
6-((4-(5-methylisoxazol-3-yl)benzyl)amino)pyrimidin-4(3H)-one;
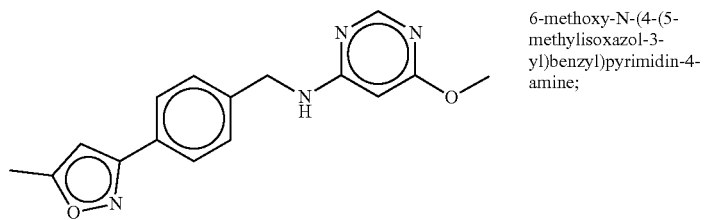
6-methoxy-N-(4-(5-methylisoxazol-3-yl)benzyl)pyrimidin-4-amine;
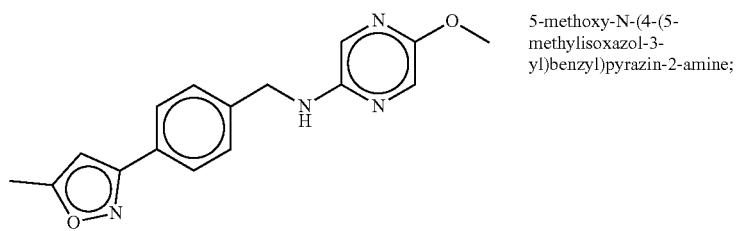
5-methoxy-N-(4-(5-methylisoxazol-3-yl)benzyl)pyrazin-2-amine;
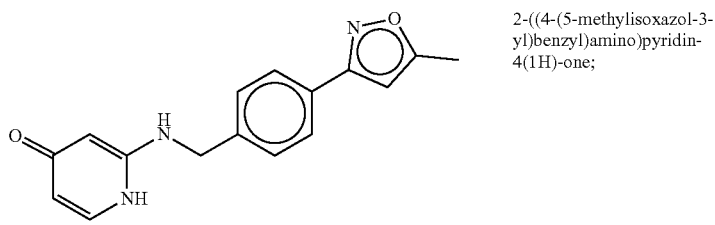
2-((4-(5-methylisoxazol-3-yl)benzyl)amino)pyridin-4(1H)-one;
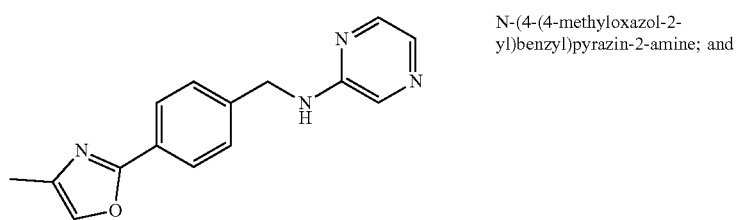
N-(4-(4-methyloxazol-2-yl)benzyl)pyrazin-2-amine; and

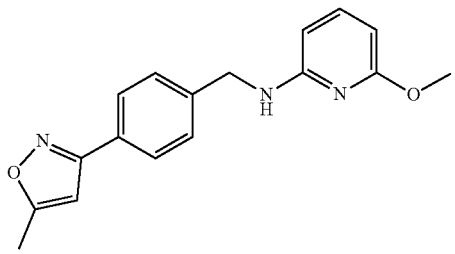 [SMILES: COc1cccc(NCc2ccc(-c3cc(C)on3)cc2)n1] 6-methoxy-N-[[4-(5-methyl-1,2-oxazol-3-yl)phenyl]methyl]pyridin-2-amine;

or a pharmaceutically acceptable salt thereof.

31. A pharmaceutical composition comprising a compound according to claim 1, or a pharmaceutically acceptable salt thereof, and a pharmaceutically acceptable excipient.

32. A method of treating heart disease in a subject in need thereof, comprising administering to the subject a compound of claim 1, or a pharmaceutically acceptable salt thereof.

33. The method of claim 32, wherein the heart disease is hypertrophic cardiomyopathy.

34. The method of claim 33, wherein the hypertrophic cardiomyopathy is obstructive or nonobstructive or is caused by sarcomeric and/or non-sarcomeric mutations.

35. The method of claim 32, wherein the heart disease is heart failure with preserved ejection fraction.

36. The method of claim 32, wherein the heart disease is selected from the group consisting of diastolic dysfunction, primary or secondary restrictive cardiomyopathy, myocardial infarction and angina pectoris, left ventricular outflow tract obstruction, hypertensive heart disease, congenital heart disease, cardiac ischemia, coronary heart disease, diabetic heart disease, congestive heart failure, right heart failure, cardiorenal syndrome, and infiltrative cardiomyopathy.

37. The method of claim 32, wherein the heart disease is or is related to one or more conditions selected from the group consisting of cardiac senescence, diastolic dysfunction due to aging, left ventricular hypertrophy and concentric left ventricular remodeling.

38. A method of treating a disease or condition that is associated with small left ventricular cavity, cavity obliteration, hyperdynamic left ventricular contraction, myocardial ischemia, or cardiac fibrosis in a subject in need thereof, comprising administering to the subject a compound of claim 1, or a pharmaceutically acceptable salt thereof.

39. A method of inhibiting the cardiac sarcomere, comprising contacting the cardiac sarcomere with a compound of claim 1, or a pharmaceutically acceptable salt thereof.

* * * * *